US009528094B2

(12) United States Patent
Borca et al.

(10) Patent No.: US 9,528,094 B2
(45) Date of Patent: Dec. 27, 2016

(54) ATTENUATED AFRICAN SWINE FEVER VIRUS VACCINE BASED IN THE DELETION OF MGF GENES

(71) Applicants: The United States of America, as Represented by the Secretary of Agriculture, Washington, DC (US); The University of Connecticut, Storrs, CT (US)

(72) Inventors: Manuel V. Borca, Westbrook, CT (US); Lauren G. Holinka-Patterson, Deep River, CT (US); Vivian K. O'Donnell, Old Saybrook, CT (US); Guillermo S. Risatti, Westbrook, CT (US); Douglas Gladu, Guilford, CT (US)

(73) Assignees: The United States of America, as Represented by the Secretary of Agriculture, Washington, DC (US); The University of Connecticut, Storrs, CT (US)

( * ) Notice: Subject to any disclaimer, the term of this patent is extended or adjusted under 35 U.S.C. 154(b) by 37 days.

(21) Appl. No.: 14/537,248

(22) Filed: Nov. 10, 2014

(65) Prior Publication Data
US 2016/0130562 A1    May 12, 2016

(51) Int. Cl.
*A61K 39/12*    (2006.01)
*C12N 7/00*    (2006.01)
*C12Q 1/70*    (2006.01)

(52) U.S. Cl.
CPC .............. *C12N 7/00* (2013.01); *A61K 39/12* (2013.01); *C12Q 1/701* (2013.01); *C12N 2710/12034* (2013.01); *C12N 2710/12062* (2013.01)

(58) Field of Classification Search
None
See application file for complete search history.

*Primary Examiner* — Stacy B Chen
(74) *Attorney, Agent, or Firm* — John D. Fado; Evelyn M. Rabin

(57) ABSTRACT

African swine fever virus (ASFV) is the etiological agent of a contagious and often lethal viral disease of domestic pigs. Control of ASF has been hampered by the unavailability of vaccines. Experimental vaccines have been derived from naturally occurring, cell culture-adapted, or genetically modified live attenuated ASFVs; however, these vaccines are only successful when protecting against homologous viruses. Among viral genes reported to be involved in virulence are components of the multi gene family (MGF). Here we report the construction of a recombinant ΔMGF virus derived from the highly virulent ASFV Georgia 2007 (ASFV-G) isolate. In vivo, ASFV-G ΔMGF administered intramuscularly (IM) to swine at either $10^2$ or $10^4$ HAD$_{50}$ are completely attenuated; the inoculated animals are completely asymptomatic. Animals infected with $10^2$ or $10^4$ HAD50 of ASFV-G ΔMGF are protected against the presentation of clinical disease when challenged at 28 days post infection with the virulent parental strain Georgia 2007.

4 Claims, 3 Drawing Sheets
(2 of 3 Drawing Sheet(s) Filed in Color)

ATTENUATED AFRICAN SWINE FEVER VIRUS VACCINE BASED IN THE DELETION OF MGF GENES

BACKGROUND OF THE INVENTION

Field of the Invention

This invention relates to the construction of a recombinant African Swine Fever Virus (ASFV) live attenuated candidate strain vaccine for the highly virulent Georgia 2007 isolate ASFV-G. The vaccine comprises the ASFV-G ΔMGF, a recombinant ASFV-G modified by deleting a large portion of the MGF (Multi Gene Family) genes.

Description of the Relevant Art

African Swine Fever (ASF) is a contagious viral disease of swine. The causative agent, ASF virus (ASFV), is a large enveloped virus containing a double-stranded DNA genome of approximately 190 kilobase pairs. ASFV shares aspects of genome structure and replication strategy with other large double-stranded DNA viruses, including the *Poxviridae, Iridoviridae* and *Phycodnaviridae* (Costard et al. 2009. *Phil. Trans. Royal Soc. B* 364:2683-2696). ASFV infections in domestic pigs are often fatal and are characterized by fever, hemorrhages, ataxia and severe depression. However, the course of infection varies, ranging from highly lethal to sub-clinical, depending on host characteristics and the particular virus strain (Tulman et al. 2009. *Curr. Top. Microbiol. Immunol.* 328:43-87).

Currently, the disease is endemic in more than twenty sub-Saharan African countries. In Europe, ASF is still endemic on the island of Sardinia (Italy) and new outbreaks have been declared in the Caucasus region since 2007, affecting Georgia, Armenia, Azerbaijan and Russia. Isolated outbreaks have been recently reported in Ukraine, Belarus, Lithuania, Latvia and Poland, posing the risk of further dissemination into neighbouring countries. The epidemic virus, ASFV Georgia 2007/1, is a highly virulent isolate belonging to the genotype II (Chapman et al. 2011. *Emerging Infect. Dis.* 17:599-605).

At present, there is no vaccine available for ASF and disease outbreaks are controlled by animal quarantine and slaughter. Attempts to vaccinate animals using infected cell extracts, supernatants of infected pig peripheral blood leukocytes, purified and inactivated virions, infected glutaraldehyde-fixed macrophages, or detergent-treated infected alveolar macrophages failed to induce protective immunity (Coggins, L. 1974. *Prog. Med. Virol.* 18:48-63; Forman et al. 1982. *Arch. Virol.* 74:91-100; Kihm et al. 1987. In: *African Swine Fever*, Becker, Y. (ed), Martinus Nijhoff, Boston, pp 127-144; Mebus, C. A. 1988. *Adv. Virus Res.* 35:251-269). Homologous protective immunity does develop in pigs surviving viral infection. Pigs surviving acute infection with moderately virulent or attenuated variants of ASFV develop long-term resistance to homologous, but rarely to heterologous, virus challenge (Hamdy and Dardiri. 1984. *Am. J. Vet. Res.* 45:711-714; Ruiz-Gonzalvo et al. 1981. In: *FAO/CEC Expert Consultation in ASF Research*, Wilkinson, P. J. (ed), Rome, pp 206-216). Pigs immunized with live attenuated ASF viruses containing engineered deletions of specific ASFV virulence-associated genes were protected when challenged with homologous parental virus. Specifically, individual deletion of UK (DP69R), 23-NL (DP71L), TK (A240L) or 9GL (B119L) genes from the genomes of pathogenic ASF viruses (Malawi Lil-20/1, Pretoriuskop/96/4, and E70) markedly attenuated the virus in swine and the animals immunized with these attenuated viruses were protected against challenge with homologous virus (Moore et al. 1998. *J. Virol.* 72:10310-10315; Lewis et al. 2000. *J. Virol.* 74:1275-1285; Zsak et al. 1996. *J. Virol.* 70:8865-8871; Zsak et al. 1998. *J. Virol.* 72:1028-1035). These observations constitute the only experimental evidence describing the rational development of an effective live attenuated virus against ASFV.

Variations in genome size and restriction fragment patterns are observed among different ASFV isolates and this diversity resides in the terminal genomic regions. These ASFV variable regions comprise the left 35-kb and the right 15-kb ends of the genome and contain at least five multigene families (MGFs): MGF 100, MGF 110, MGF 300, MGF 360, and MGF 505 (Neilan et al. 2002. *J. Virology* 76:3095-3104). These genes are grouped in these MGFs because the share sequence and structural identity. The functions of these genes are not completely understood, but they have been correlated with macrophage host range, modulation of the innate host immune response and virulence (Zsak et al. 2001. *J. Virol.* 75:3066-3076; Afonso et al. 2004. *J. Virol.* 78:1858-1864; Neilan et al. 2002, supra).

Deletions of several MGF genes in association with the deletion of the NL gene (resulting in the deletion of a total of 7,559 nucleotides) have been used to attenuate the virulent isolate Malawi already having deleted its NL gene (Neilan et al. 2002, supra). However, the resulting attenuated Malawi-ΔNL-ΔMGF ASFV was not tested as an experimental vaccine to assess its ability to prevent disease when challenged with the virulent parental virus. Nor was the effect of the modified virus against heterologous ASFV strains determined. Thus, there is a need for an effective live attenuated vaccine for the highly virulent ASFV Georgia 2007 isolate, ASFV-G, for which there is no vaccine candidate.

SUMMARY OF THE INVENTION

We have developed the novel recombinant mutant ASFV-G ΔMGF virus, a modification of the ASFV-G (African Swine Fever Virus-Georgia 2007 isolate).

In accordance with this discovery, it is an object of the invention to provide the novel mutant ASFV-G ΔMGF virus, resulting from the deletion of a large portion of the MGF genes of the parental ASFV-G. The nucleotide sequence of ASFV-G ΔMGF (SEQ ID NO:2) differs from the nucleotide sequence encoding the ASFV-G (SEQ ID NO:1). While the nucleotide sequence of ASFV-G (SEQ ID NO:1) encodes the wild-type MGF proteins: MGF 100, MGF 110, MGF 300, MGF 360 and MGF 505, the nucleotide sequence of ASFV-G ΔMGF (SEQ ID NO:2) present a deletion of MGF 360 genes 12L, 13, and 14L and the MGF505 1R, 2R and 3R resulting in a 7,559 nucleotide deletion from nucleotide 27,928 through nucleotide 35,487 (of the wild-type ASFV-G genome.

An added object of the invention is to provide immunogenic compositions comprising a viable ASFV-G ΔMGF virus.

An additional object of the invention is to provide a rationally designed live attenuated ASFV-G ΔMGF vaccine effective to protect an animal from clinical ASF disease when challenged with pathogenic ASFV-G.

A further object of the invention is to provide a genetic marker vaccine which can potentially distinguish between vaccinated animals and animals infected with ASFV-G.

Another object of the invention is to provide a method for protecting an animal against ASFV-G by administering an effective amount of rationally designed live attenuated ASFV-G ΔMGF vaccine.

An additional object of the invention is to provide a method for distinguishing animals infected with ASFV-G from animals vaccinated with said rationally designed live attenuated ASFV-G ΔMGF vaccine, comprising a genetic DIVA strategy for differentiating vaccinated animals from wild-type infected animals.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

Figures 1A, 1B:
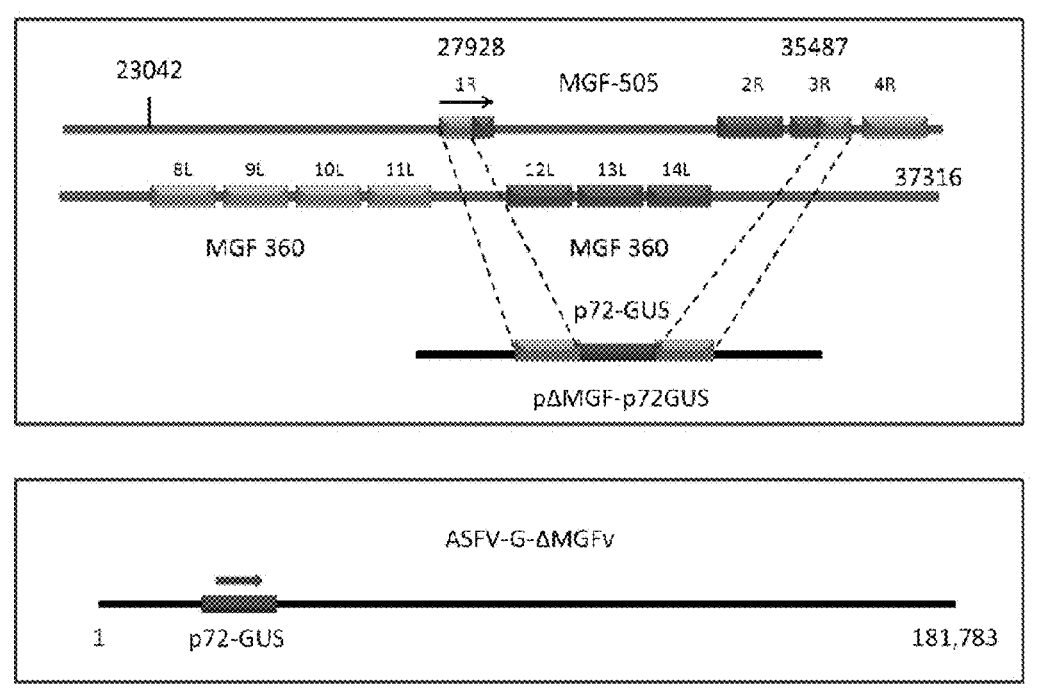

FIG. 1A (Top Panel) is a diagram depicting the area of the ASFV-G genome deleted during the construction of ASFV-G-ΔMGF. The nucleotide position of the deleted MGF genes the in the ASFV-G genome are indicated as well as the location of the βGus cassette. FIG. 1B (Bottom Panel) is a diagram representing the location of the area where recombination occurs within the ASFV-G genome.

FIG. 3 shows the in vitro growth kinetics of ASFV-G-ΔMGF and parental ASFV-G viruses. Primary swine macrophage cell cultures were infected (MOI=0.1 or 0.01) with either ASFV-G-ΔMGF or parental ASFV-G viruses, and virus yield obtained at the indicated times post-infection were titrated in primary swine macrophage cell cultures. Data represent means and standard deviations from two independent experiments. Sensitivity of virus detection: ≥1.8 $TCID_{50}$/ml.

DETAILED DESCRIPTION OF THE INVENTION

Figure 2:
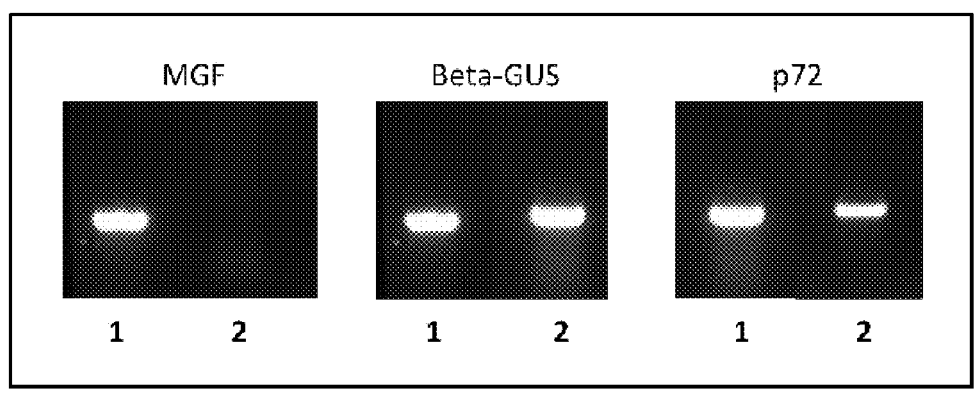
FIG. 2 depicts the assessment of the purity of the ASFV-G-ΔMGF virus stock by PCR. PCR analysis of ASFV-G-ΔMGF DNA was carried out using specific primers targeting MGFs, p72 (B6460), or βGus genes. Lane 1: ASFV-G; Lane 2: ASFV-G-ΔMGF.

We have developed an attenuated virus that can be used as a vaccine candidate through the approach of targeting the multi gene family (MGF) for genetic modifications. MGF genes are a group of viral genes that have partial sequence and structural identity, and are reported to be involved in virulence. Here we report the construction of a recombinant ΔMGF virus derived from the highly virulent ASFV Georgia 2007 isolate (ASFV-G) by specifically deleting genes of the MGF 360 and MGF 500 (ASFV-G-ΔMGF). ASFV-G ΔMGF when administered intramuscularly (IM) to swine at either $10^2$ or $10^4$ $HAD_{50}$ are completely attenuated. In addition, animals infected with ASFV-G ΔMGF were protected against the presentation of clinical disease when challenged at 28 days post infection with the virulent parental strain Georgia 2007.

No vaccines are available to prevent ASFV infection. Only live attenuated virus strains have been useful in protecting pigs against challenge with homologous virulent isolates. These attenuated viruses have been regularly produced by sequential passages in cell cultures and, more recently, by genetic manipulation. Naturally occurring attenuated viruses have been used as live vaccine candidates. Attenuated viruses obtained by genetic manipulation involve the deletion of specific genes by a process of homologous recombination. Independent deletion of four different genes from ASFV has been shown to attenuate virulent viruses. Independent deletions of the NL (DP71L) (Zsak et al. 1996, supra) or the UK (DP69R) (Zsak et al. 1998, supra) genes from ASFV E75, deletion of the TK (A240L) gene (Moore et al., supra) from ASFV adapted to Vero cells, Malawi Lil-20/1 and Haiti, and deletion of the 9GL (B119L) gene also from Malawi Lil-20/1 (Lewis et al., supra) and Pretoriuskop/96/4 (Neilan et al., supra) isolates rendered recombinant deletion mutant viruses with significantly reduced virulence in swine. In all these cases, animals inoculated with each of these genetically modified viruses survived the infection and became protected against ASFV when challenged with the corresponding virulent parental virus (homologous challenge) (Lewis et al., supra; Moore et al., supra; Neilan et al., supra; Zsak et al. 1996, supra; Zsak et al. 1998, supra). Those findings suggest that development of attenuated ASFV recombinant viruses by genetic manipulations of target genes is an effective approach for vaccine development.

The NL (DP71L) gene product exists in two different forms, a long (184 amino acids as in 23-NL) or a short form (70 to 72 amino acids) depending on the ASFV isolate (Zsak et al. 1996, supra). Although deletion of this gene in ASFV E70 isolate (short form) rendered an attenuated virus, the deletion of the NL (DP71L) gene from ASFV Malawi Lil-20/1 (long form) or Pretoriuskop/96/4 (short form) did not result in attenuation of the virus (Afonso et al. 1998. *J. Gen. Virol.* 79 (Pt. 10):2543-2547). The NL proteins encoded by E70 (short form) and Malawi Lil-20/1 (long form) differ significantly and that may explain the phenotypic differences observed in swine inoculated with the respective deletion mutant viruses. Interestingly, when the genome of the virulent ASFV Malawi Lil-20/1-ΔNL (Afonso et al. 1998, supra) strain was genetically manipulated to include a deletion in the MGF 360/MGF 505 area, the resulting virus showed an attenuated phenotype in swine (Neilan et al. 2002, supra). As claimed by the authors, deletion of the MGF genes acted by complementing ΔNL function. There was no report indicating that the deletion of the MGF genes, which resulted in the ASFV Malawi Lil-20/1 lacking both NL and MGF genes, caused, by itself, a complete attenuation of ASFV in swine.

In addition, the ASFV Malawi Lil-20/1 lacking NL and MGF genes reported by Neilan et al. (2002) was never tested as an experimental vaccine to assess its ability to protect swine when challenged with any virulent ASFV strain. Conversely, it is demonstrated here that ASFV-G-ΔMGF is able to induce an effective protection against the presentation of clinical disease after the challenge with homologous parental virus ASFV-G.

In summary, here we present evidence that deletion of some of the MGF genes that have been associated with virus virulence entirely protects pigs against challenge with the virulent parental ASFV-G.

A vaccine is defined herein as a biological agent which is capable of providing a protective response in an animal to which the vaccine has been delivered and is incapable of causing severe disease. Administration of the vaccine results in immunity from a disease; the vaccine stimulates antibody production or cellular immunity against the pathogen causing the disease. Immunity is defined herein as the induction of a significant higher level of protection in a population of swine against mortality and clinical symptoms after vaccination compared to an unvaccinated group. In particular, the vaccine according to the invention protects a large proportion of vaccinated animals against the occurrence of clinical symptoms of the disease and mortality. The vaccine of the invention herein is a genetically engineered mutant virus vaccine. A genetic marker vaccine is defined as a vaccine that, in conjunction with a diagnostic test, enables genetic differentiation of vaccinated animals from infected animals. A deletion mutation can be used to differentiate infected from vaccinated animals. A mutation is understood to be a change in the genetic information of "wild-type" or unmodified MGF genes of a parent ASFV-G strain. The ASFV-G ΔMGF mutant virus is changed: six MGF genes are deleted from the native ASFV-G. Thus, ASFV-G ΔMGF has fewer nucleotides than the wild-type ASFV-G, as a result of nucleotides 27,928 to 35,487 being deleted from the native ASFV-G. The ASFV-G ΔMGF recombinant mutant comprises a mutant cDNA encoding a mutation in the ASFV-G MGF genes, wherein said recombinant ASFV-G mutant (ASFV-G ΔMGF) is a live attenuated ASFV-G vaccine when used at IM inoculation doses of $10^2$-$10^4$ $HAD_{50}$.

A vaccine against ASFV-G is provided that comprises a ASFV-G ΔMGF virus mutant as defined above in a live form, and a pharmaceutically acceptable carrier or diluent. The vaccine according to the invention containing the live virus can be prepared and marketed in the form of a suspension or in a lyophilized form and additionally contains a pharmaceutically acceptable carrier or diluent customary used for such compositions. Carriers include stabilizers, preservatives and buffers. Suitable stabilizers are, for example SPGA (sucrose, phosphate, glutamate, and human. albumin), carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are well known in the art. Furthermore, nucleic acid sequences encoding polypeptides for pharmaceutical or diagnostic applications, in particular immunomodulators such as lymphokines, interferons or cytokines, may be incorporated into the vaccine.

A vaccine according to the invention can be prepared by conventional methods such as those commonly used for the commercially available live attenuated ASFV vaccines. Briefly, a susceptible substrate is inoculated with the ASFV-G ΔMGF mutant and propagated until the virus has replicated to a desired titer after which ASFV-G ΔMGF-containing material is harvested. Subsequently, the harvested material is formulated into a pharmaceutical preparation with immunizing properties.

Every substrate which is able to support the replication of ASFV-G ΔMGF viruses can be used in the present invention, including primary cultures of swine peripheral blood macrophages.

The vaccine may be administered by intramuscular, subcutaneous or intranasal inoculation or injection in an amount which is effective to protect the animal against challenge by a virulent strain of ASFV-G. This amount may vary according to the animal being inoculated, taking into consideration the size and weight of the animal. The vaccine according to the invention comprises an effective dosage of the ASFV-G ΔMGF mutant as the active component, i.e. an amount of immunizing ASFV-G ΔMGF material that will induce immunity in the vaccinated animals, swine, against challenge by a virulent ASFV-G. Immunity is defined herein as the induction of a significant higher level of protection in a population of swine against mortality and clinical symptoms after vaccination compared to an unvaccinated group. In particular, the vaccine according to the invention prevents a large proportion of vaccinated animals against the occurrence of clinical symptoms of the disease and mortality. Typically, the live vaccine can be administered in a dose of $10^2$-$10^4$ $HAD_{50}$. Effective amounts may be experimentally determined as necessary by those of skill in the art by following the guidance provided, for example, by Example 6.

In addition to the ASFV-G ΔMGF mutant, the invention can also include combination vaccines comprising a vaccine strain capable of inducing protection against another porcine pathogen.

The ASFV-G ΔMGF vaccine described above, in conjunction with a diagnostic method, has the potential of distinguishing between animals that are vaccinated with it and animals that are infected with naturally occurring ASFV-G strains or vaccinated with conventional ASFV-G vaccines.

The present invention also provides an invaluable tool to monitor ASFV-G control measures that may lead to eradication of ASFV-G if applied in large scale stamping out programs. This tool concerns a method for determining ASFV-G infection in swine comprising the step of examining a sample of the animal for the presence of nucleotides encoding the wild-type ASFV-G MGF protein versus the polynucleotide encoding the shorter ASFV-G ΔMGF polypeptide due to deletions in the MGF genes of ASFV-G ΔMGF. The sample of the animal used in this method may be any sample in which ASFV-G versus ASFV-G ΔMGF genetic differences allowing for differentiating of natural infection versus vaccination can be detected by genetic DIVA.

EXAMPLES

Having now generally described this invention, the same will be better understood by reference to certain specific examples, which are included herein only to further illustrate the invention and are not intended to limit the scope of the invention as defined by the claims.

Example 1

Cell Cultures and Viruses

Primary swine macrophage cell cultures were prepared from defibrinated swine blood as previously described by Zsak et al. (1996, supra). Briefly, heparin-treated swine blood was incubated at 37° C. for 1 hour to allow sedimentation of the erythrocyte fraction. Mononuclear leukocytes were separated by flotation over a Ficoll-Paque (Pharmacia, Piscataway, N.J.) density gradient (specific gravity, 1.079). The monocyte/macrophage cell fraction was cultured in plastic Primaria (Falcon; Becton Dickinson Labware, Franklin Lakes, N.J.) tissue culture flasks containing macrophage media, composed of RPMI 1640 Medium (Life Technologies, Grand Island, N.Y.) with 30% L929 supernatant and 20% fetal bovine serum (HI-FBS, Thermo Scientific, Waltham, Mass.) for 48 hours at 37° C. under 5% $CO_2$. Adherent cells were detached from the plastic by using 10 mM EDTA in phosphate buffered saline (PBS) and were then reseeded into Primaria T25, 6- or 96-well dishes at a density of $5\times10^6$ cells per ml for use in assays 24 hours later.

ASFV Georgia (ASFV-G) was a field isolate kindly provided by Dr. Nino Vepkhvadze, from the Laboratory of the Ministry of Agriculture (LMA) in Tbilisi, Republic of Georgia.

Comparative growth curves between ASFV-G and ASFV-G ΔMGF viruses were performed in primary swine macrophage cell cultures. Preformed monolayers were prepared in 24-well plates and infected at MOI of 0.1 and 0.01 (based on $HAD_{50}$ previously determined in primary swine macrophage cell cultures). After 1 hour of adsorption at 37° C. under 5% $CO_2$ the inoculum was removed and the cells were rinsed two times with PBS. The monolayers were then rinsed with macrophage media and incubated for 2, 24, 48, 72 and 96 hours at 37° C. under 5% $CO_2$. At appropriate times post-infection, the cells were frozen at −70° C. and the thawed lysates were used to determine titers by $HAID_{50}$/ml in primary swine macrophage cell cultures. All samples were run simultaneously to avoid inter-assay variability.

Virus titration was performed on primary swine macrophage cell cultures in 96-well plates. Virus dilutions and cultures were performed using macrophage medium. Presence of virus was assessed by hemadsorption (HA) and virus titers were calculated by the Reed and Muench method (1938. *Amer. J. Hygiene* 27:493-497).

Example 2

Construction of the Recombinant ASFV-G-ΔMGF

ASFV-G ΔMGF was constructed from the highly pathogenic ASFV Georgia 2007 isolate (ASFV-G). Recombinant ASFVs were generated by homologous recombination between the parental ASFV genome and a recombination transfer vector following infection and transfection of swine macrophage cell cultures (Neilan et al., supra; Zsak et al. 1996, supra). Recombinant transfer vector (p72GUSΔMGF) contained flanking genomic regions to MGF500 1R, and 3R genes, which included portions of MGF mapping to the left (3.3 kbp) and right (1 kbp) of the MGF500 1R, and 3R genes and a reporter gene cassette containing the β-glucuronidase (GUS) gene with the ASFV p72 late gene promoter, p72GUS (45) (FIG. 1). This construction created a 7,559-nucleotide deletion including a partial deletion of MGF500 1R, and 3R genes and complete deletion of ASFV MGF 360 genes 12L, 13, and 14L along with MGF500 2R) (FIG. 1). Recombinant transfer vector p72GUSΔMGF was obtained by DNA synthesis (GenScript, Piscataway, N.J., USA). Macrophage cell cultures were infected with ASFV-G and transfected with p72GUSΔMGF. Recombinant viruses representing independent primary plaques were purified to homogeneity by successive rounds of plaque assay purification.

ASFV-G-ΔMGF was constructed from the highly pathogenic ASFV Georgia 2007 isolate (ASFV-G). A 7,559-nucleotide region, encompassing nucleotide positions 27,928-35,487 in the virus genome (FIG. 1) was deleted from ASFV-G virus and replaced with a cassette containing the p72GUS reporter gene cassette by homologous recombination (see Material and Methods). The recombinant virus was obtained after 8 successive plaque purification events on monolayers of primary swine macrophage cell cultures. The virus population obtained from the last round of plaque purification was amplified in primary swine macrophage cell cultures to obtain a virus stock. To ensure the absence of parental ASFV-G, virus DNA was extracted from the virus stock and analyzed by PCR using primers targeting genes p72 (B646L), MGF and β-Gus. Only amplicons for p72 (B646L) and β-Gus genes were detected in DNA extracted from the virus stock; whereas no amplicons were generated with primers targeting the MGF gene indicating the lack of contamination of the ASFV-G-ΔMGF stock with ASFV-G.

Example 3

Polymerase Chain Reaction (PCR)

The extent of purity of ASFV-G ΔMGF in the virus stock as well as in virus isolated from infected animals was assessed by PCR. Detection of the MGF genes was performed using the following pair of primers: forward 5' CATGGAACTATTCAACGA GCAGGA 3'(SEQ ID NO:3); reverse 5' CGCTGATCAATTCCACAGTT 3' (SEQ ID NO:4). Detection of the β-Gus gene was performed using the following pair of primers: forward 5'GACGGCCT-GTGGGCATT3' (SEQ ID NO:5); reverse 5'GCGATG-GATTC CGGCAT3' (SEQ ID NO:6). Detection of the p72 (86460 gene was performed using the following pair of primers: forward 5'GTCTTATTGCTAACGATGGGAAG3' (SEQ ID NO:7); reverse 5'CCAAAGGTAAGCTTGTTTC-CCAA3' (SEQ ID NO:8).

PCR products were sequenced using the dideoxynucleotide chain-termination method (Sanger et al. 1977. *Proc. Natl. Acad. Sci. USA* 74:5463-5467). Sequencing reactions were prepared with the Dye Terminator Cycle Sequencing Kit (Applied Biosystems, Foster City, Calif.). Reaction products were sequenced on a PRISM 3730xl automated DNA sequencer (Applied Biosystems). Sequence data were assembled with the Phrap software program (Retrieved from the Internet: phrap.org), with confirmatory assemblies performed using CAP3 (Huang and Madan. 1999. *Genome Res.* 9:868-877). The final DNA consensus sequence represented an average five-fold redundancy at each base position. Sequence comparisons were conducted using BioEdit software (Tom Hall, Ibis Biosciences Carlsbad, Calif., Copyright 1997-2013).

Example 4

Next Generation Sequencing (NGS) of ASFV Genomes

To evaluate the accuracy of the genetic modification and the integrity of the genome of the recombinant virus, full genome sequences of ASFV-G ΔMGF and parental ASFV-G were obtained using Next Generation Sequencing (NGS) and compared. ASFV DNA was obtained from the cytoplasm of infected cells using the Trizol method (Life Technologies, Grand Island, N.Y., USA). DNA concentration was determined using the Qubit® dsDNA HS assay kit (Life Technologies) and read on a Qubit® 2 Flourometer (Life Technologies). One microgram of virus DNA was enzymatically fragmented to obtain blunt end fragments in a length range of 200-300 bp using the Ion Shear™ Plus reagent kit (Life Technologies) and incubated at 37° C. in a Peltier Thermal Cycler DNA Engine Tetrad 2. After shearing, the fragmented DNA library was loaded onto a DNA chip (Agilent, Santa Clara, Calif., USA) and analyzed using a 2100 Bioanalyzer (Agilent) to assess DNA size distribution and size range. Fragmented DNA was ligated to Ion-compatible adapters and library barcodes, followed by nick-repair to complete the linkage between adapters and DNA inserts using the Ion Plus Fragment Library kit (Life Technologies). The adapter-ligated library was size-selected for optimum length on 2% Agarose Gel Cassettes (Sage Science, Beverly, Mass., USA) using the Pippin Prep™ instrument (Sage Science). Library concentration was normalized using the Ion Library Equalizer™ Kit (Life Technologies). Next, the DNA library was clonally amplified onto Ion Sphere™ Particles generating template-positive ISPs using the Ion PGM™ Template OneTouch™ 2 200 Kit (Life Technologies) with the Ion OneTouch™ 2 Instrument (Life Technologies). Before proceeding to enrichment, quality assessment of non-enriched template-positive ISPs was performed using the Ion Sphere™ Quality Control assay kit (Life Technologies) and a Qubit® 2 Flourometer instrument. The template-positive ISPs were then enriched using the Ion PGM™ Template OneTouch™ 2 200 Kit (Life Technologies) and Ion OneTouch™ ES instrument (Life Technologies) to eliminate template-negative ISPs and to denature DNA on template-positive ISPs. Using the Ion PGM™ 200 Sequencing v2 Kit (Life Technologies), enriched template ISPs were prepared for sequencing and loaded onto either Ion 314™ or Ion 316™ Chip v2 (Life Technologies) and run on the Ion PGM™ Sequencer (Life Technologies). Obtained sequences were then trimmed using Galaxy (Retrieved from the Internet: usegalaxy.org/) NGS QC and Manipulation tools. Sequences were aligned and analyzed using Sequencher 5.2.2 (Genecodes) and CLC Genomics Workbench (CLCBio) software.

The following differences were observed between these two viruses (nucleotide positions are provided based on ASFV Georgia 2007/1, GenBank accession FR682468): (i) two nucleotide insertions, T at position 433 and A at position 441 in a non-coding segment of the genome; (ii) two nucleotide deletions, T at position 1602 and T at position 1603 in the MGF 360-1 L gene ORF resulting in a frameshift; (iii) a nucleotide deletion, T at position 1620 in the MGF 360-1 L gene ORF resulting in a frameshift; (iv) a nucleotide mutation, A to G at position 97391 resulting in a silent mutation in ORF B438L; (v) a nucleotide mutation, C to G at position 166192 resulting in a residue substitution (Ala to Pro) at residue position 85 in ORF E199L; and (vi) a nucleotide insertion, T at position 183303, a non-coding segment of the genome (Table 1). Second, a full-length genome comparison between ASFV ΔMGF and parental ASFV-G was performed. The DNA sequence assemblies of ASFV ΔMGF and ASFV-G revealed a deletion of 7,559 nucleotides between nucleotide positions 27,928-35,487 of the ASFV genome corresponding with the introduced modification. The consensus sequence of the ASFV-G-ΔMGF genome showed an insertion of 2,324 nucleotides corresponding to the p72-βGUS cassette sequence. Besides the insertion of the cassette, no additional difference was observed between ASFV-G-ΔMGF and ASFV-G genomes. In summary, ASFV-G-ΔMGF virus did not accumulate any significant mutations during the process of homologous recombination and plaque purification.

TABLE 1

Summary of genetic changes in ASFV-G and ASFV-G-MGF compared with ASFV Georgia07/1 sequence.

| NPN* | Gene | Variant | Amino Acid Change | Virus ASFV-G | ASFV-G ΔMGF |
|---|---|---|---|---|---|
| 434 | Non coding | Insertion - T | | + | + |
| 441 | Non coding | Insertion - A | | + | + |
| 1602 | MGF 360 1L | Deletion - TT | Frame Shift | + | + |
| 1620 | MGF 360 1L | Insertion - T | Frame Shift | + | + |
| 97391 | B438L | A - G | Conserved | + | + |
| 166192 | E199L | C - G | Ala 85 Pro | + | + |
| 183303 | Non coding | Insertion of T | | + | + |

*Nucleotide Position Number (based on the sequence of ASFV Georgia 2007/1 isolate published by Chapman et al. 2011)

Example 5

Replication of ASFV-G ΔMGF in Primary Swine Macrophages

Figure 3:
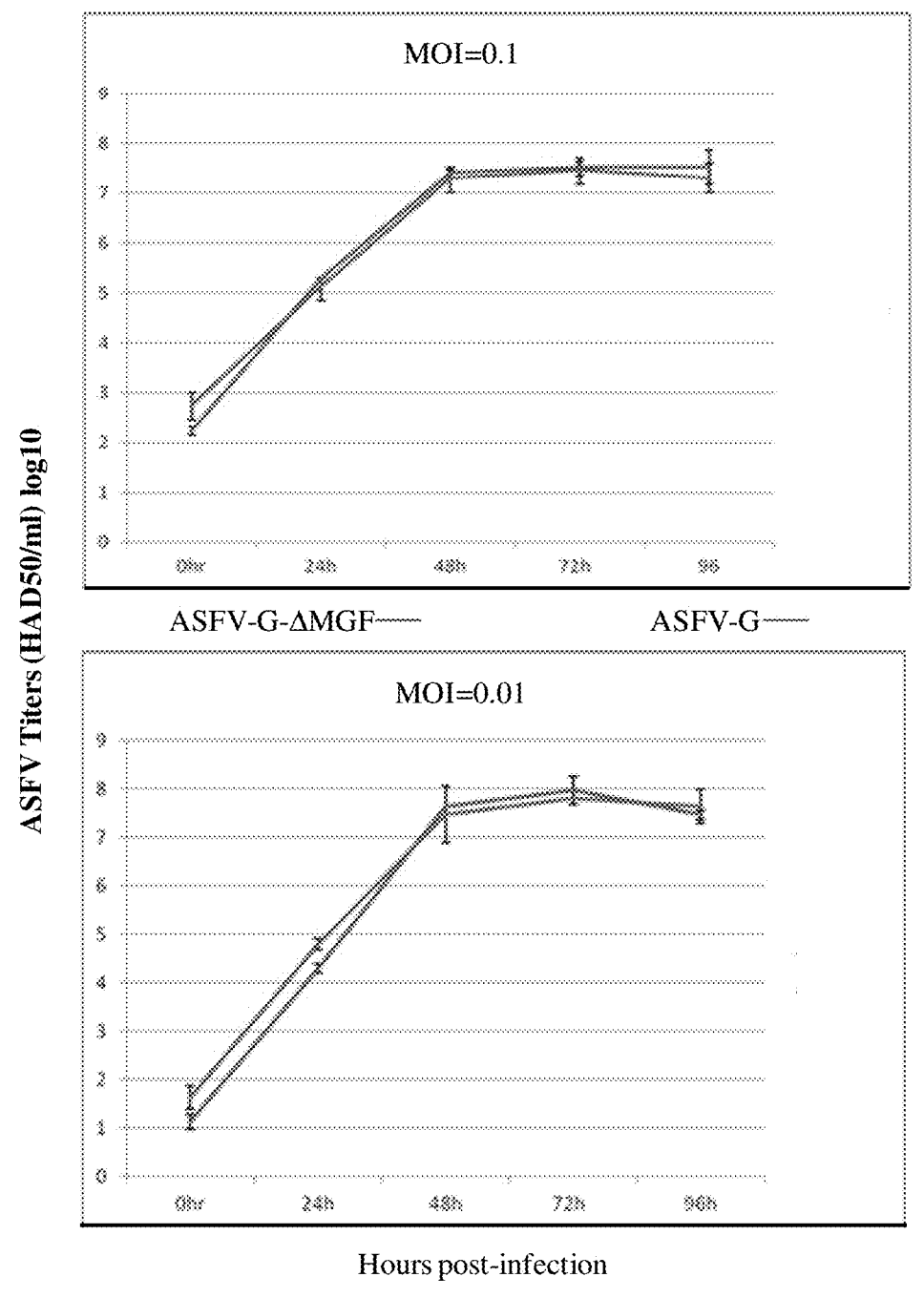

In vitro growth characteristics of ASFV-G-ΔMGF were evaluated in primary swine macrophage cell cultures, the primary cell targeted by ASFV during infection in swine, and compared relative to parental ASFV-G in a multistep growth curve (FIG. 3). Cell cultures were infected at a MOI of either 0.1 or 0.01 and samples were collected at 2, 24, 48, 72 and 96 hours post-infection (hpi). ASFV-G-ΔMGF virus displayed a growth kinetic indistinguishable from that of the parental ASFV-G virus (FIG. 3). Therefore, deletion of these MGF genes does not significantly affect the ability of the virus to replicate in vitro in primary swine macrophage cell cultures.

Example 6

Assessment of ASFV-G ΔMGF Virulence in Swine; Protective Efficacy of ASFV-G ΔMGF Against Challenge with Parental ASFV-G Animal experiments were performed under biosafety level 3 conditions in the animal facilities at PIADC following a protocol approved by the Institutional Animal Care and Use Committee.

ASFV-G ΔMGF was assessed for its virulence phenotype relative to the virulent parental ASFV-G virus using 80-90 pound commercially bred swine. Five pigs were inoculated intramuscularly (IM) either with $10^2$ or $10^4$ $HAD_{50}$ of either ASFV-G ΔMGF or ASFV-G virus. Clinical signs (anorexia, depression, fever, purple skin discoloration, staggering gait, diarrhea and cough) and changes in body temperature were recorded daily throughout the experiment.

Here, 80-90 pound pigs inoculated via IM with either $10^2$ or $10^4$ $HAD_{50}$ of ASFV-G exhibited increased body temperature (>104° F.) by 3 to 4 days post-infection (Table 2). Pigs presented clinical signs associated with the disease including anorexia, depression, purple skin discoloration, staggering gait, and diarrhea. Signs of the disease aggravated progressively over time and animals either died or were euthanized in extremis by days 7 or 8 post-infection. Interestingly, animals inoculated via IM with either $10^2$ or $10^4$ $HAD_{50}$ of ASFV-G-ΔMGF did not develop any ASF-associated clinical sign. Therefore, deletion of the selected six genes of the MGF 360 and 505 completely attenuated the highly virulent ASFV-G.

TABLE 2

Effect of ASFV-G ΔMGF and ASFV-G infection on swine survival and fever.

| | | | Fever | | |
|---|---|---|---|---|---|
| Virus | No. of Survivors/ Total | Mean Time to death (Days ± SD) | No. of Days to onset (Days ± SD) | Duration No. of Days (Days ± SD) | Maximum Daily Temp (° F. ± SD) |
| ASFV-G $10^2$ HAD$_{50}$ | 0/5 | 9.2 (0.45) | 7.2 (0.84) | 2 (0.71) | 106.4 (0.67) |
| ASFV-G ΔMGF $10^2$ HAD$_{50}$ | 5/10 | — | — | — | 103.0 (0.17) |
| ASFV-G $10^4$ HAD$_{50}$ | 0/5 | 7.4 (0.55) | 3.6 (0.89) | 3.8 (1.1) | 106.9 (0.51) |
| ASFV-G ΔMGF $10^4$ HAD$_{50}$ | 5/5 | — | — | — | 103.0 (0.17) |

Viremia in experimentally inoculated animals was quantified at day 7 post-infection. Pigs inoculated with either $10^2$ or $10^4$ HAD$_{50}$ of virulent parental ASFV-G had virus titers in blood averaging 7.70 (SD=0.27) and 8.78 (SD=0.12) HAD$_{50}$/ml, respectively. Pigs inoculated with $10^4$ HAD$_{50}$ of mutant ASFV-G-ΔMGF had virus titers in blood averaging 3.88 (SD=0.76) HAD$_{50}$/ml, whereas pigs inoculated with $10^2$ HAD$_{50}$ of mutant ASFV-G ΔMGF presented undetectable virus titers in blood.

Deletion of the six genes belonging to MGF360 and MGF505 (together with the deletion of NL genes) from the genome of the recombinant ASFV isolate Malawi ΔNL had been shown to reduce virulence in swine (Neilan et al., supra). In those reports, IM inoculation of $10^3$ TCID$_{50}$ of ASFV isolate Malawi ΔNL-ΔMGF only induced a transient rise in body temperature. No reference was presented to the effect of the deletion of the six MGF genes alone; no challenge data were presented.

Pigs which had been inoculated via IM with either $10^2$ or $10^4$ HAD$_{50}$ of ASFV-G-ΔMGF and had survived the infection without signs of the disease, were challenged via IM with $10^3$ HAD$_{50}$ of virulent parental ASFV-Georgia 2007 at day 28 post-inoculation. Five naïve animals that were challenged using same route and dose served as non-inoculated/challenged control group. All ASFV-G-ΔMGF inoculated and challenged animals remained completely asymptomatic during all the observational period (21 days) (Table 3). All the animals in the non-inoculated/challenged control group developed disease with a clinical course similar to that observed in animals inoculated with $10^2$ or $10^4$ HAD$_{50}$ of ASFV-G (see above). Therefore, ASFV-G-ΔMGF is able to induce protection against the presentation of clinical disease when challenged with the highly virulent parental virus.

Example 7

Genetic DIVA Strategy—Real-Time RT-PCR

Total DNA was extracted from blood, serum and organ samples using the DNeasy mini kit (Qiagen), following the manufacturer's recommendations. Extracted DNA was subject to real time-PCR assay for detection and differentiation of ASFV-G and ASFV-GΔMGF. The highly conserved full-length MGF genes are present in the genome of wild-type ASFV-G and is detected in organs, blood and serum of infected pigs whereas the gene is not detected in pigs vaccinated with the vaccine comprising ASFV-GΔMGF where a portion of the MGF has been deleted.

ASFV-G DNA is detected by Sybr Green real time PCR using primer set: MGF For-191 5'GTAAGATAC-GAAAAGGCGTG3' (SEQ ID NO:9) and 9GL-Rev-297 5'GACGCTCCTAGCTGGAA3' (SEQ ID NO:10); ASFV-GΔ9GL is not detected. Modifications in ASFV-GΔ9GL DNA is detected by Sybr Green real time PCR using primer set: 9GL-For-127 5'GTTGTTATGGAACGCGAAG3' (SEQ ID NO:11) and GUS-Rev-366 5'GGGTTTCTACAGGACG-TAACA3' (SEQ ID NO:12) or primer set: GUS-TT-For 5'CTGTTGAATTACGTTAAGCATG3' (SEQ ID NO:13) and 9GL-Rev-351 5'CATTG GGGACCTAAATACTG3' (SEQ ID NO:14); but wild type ASFV-G DNA is not detected by these primer sets. Assays were run in parallel.

Samples from vaccinated animals were analyzed for differentiation and confirmation using the set of primers by means of Sybr Green real time-PCR. Samples (n=5) from vaccinated animals tested positive only to ASFV-GΔMGF and negative for wild type ASFV-G. After challenge, samples (n=5) from vaccinated pigs tested positive to ASFV-G by real time-PCR. Non vaccinated control pigs (n=5) tested positive to ASFV-G by real time-PCR but tested negative for ASFV-GΔMGF.

TABLE 3

Swine survival and fever response in ASFV-G ΔMGF- infected animals challenged with parental ASFV-G viruses.*

| | | | Fever | | |
|---|---|---|---|---|---|
| Virus | No. of Survivors/ Total | Mean Time to death (Days ± SD) | No. of Days to onset (Days ± SD) | Duration No. of Days (Days ± SD) | Maximum Daily Temp (F. ° ± SD) |
| ASFV-G ΔMGF $10^2$ HAD$_{50}$ | 5/5 | — | — | — | 103.54 (1.42) |
| ASFV-G ΔMGF $10^4$HAD$_{50}$ | 5/5 | — | — | — | 103.42 (0.99) |
| Mock infected | 0/5 | 8.4 (0.55) | 4.6 (1.14) | 3.8 (1.1) | 106.4 (0.56) |

*The animals IM-infected with $10^2$ or $10^4$ HAD$_{50}$ of ASFV-G ΔMGF were IM-challenged 28 days later with $10^3$ HAD$_{50}$ of ASFV-G virus.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A recombinant African Swine Fever Virus—Georgia 2007 isolate (ASFV-G) mutant virus, ASFV-G ΔMGF, wherein the ASFV-G ΔAMGF mutant virus genome comprises SEQ ID NO: 2.

2. A vaccine composition against ASFV-G comprising the recombinant SFV-G ΔMGF virus according to claim 1.

3. A method for the protection of swine against African Swine Fever Virus—Georgia 2007 isolate (ASFV-G), comprising administering to swine a live attenuated ASFV-G ΔMGF vaccine comprising a recombinant mutant ASFV-G ΔMGF virus according to claim 1 in an amount effective to protect said swine from clinical ASF-G.

4. The method of claim 3 wherein the amount effective to protect said swine from clinical ASF-G is a vaccine comprising $10^2$-$10^4$ $HAD_{50}$ of ASFV-G ΔMGF virus.

* * * * *

SEQUENCE LISTING

```
<160> NUMBER OF SEQ ID NOS: 14

<210> SEQ ID NO 1
<211> LENGTH: 189346
<212> TYPE: DNA
<213> ORGANISM: African swine fever virus

<400> SEQUENCE: 1
gaatatacca tattattgct attgccatca atgagaatgc cacgtaggca taggtcatcc      60
tatggccgga ccaatccatg gctgcactta aaatatcaa aaaagtttaa gttttgggcc     120
ggcgttaaaa tttaaacctt ttctggttga tctttagcca tgtatagctg cgatgtttgg     180
tgccttatct acatgctatt ggcattcctg atattcgcac taaagtgcta tgttacaacc     240
gtcttatgcg tgatttttat ccaccttatt ggccgaaggg ccgccttgta tttcctgtta     300
ggtggtttgg ccgtattcta ctggtggcaa gcagctatca ataaaattta atggctctca     360
cttaagatcc ttgctgtaag cgggcgttta catactttga tcaagaaaaa aattattttt     420
ggaccccccc ccatgtttta tacaaaaatc atataataaa gtggcgacaa tcaacatatt     480
aatcaaccac agcattttat gatgtgttaa tcaacatata ccatattaat caaccacagc     540
attttatgat gcgtcaatca acatattatt acggagagcg tcaatcaata taatattgag     600
aacagcgact tgataccgtg tatggtggtg gcggcggcat gttgtttgta acagcatttt     660
tcatcattcg aagcttacaa aagatatgta taagatagca tattaatgtt attaacagta     720
atatcaataa ggcgtagcta tagatcttca ctttggtaga ccaataatcc atggttgcgc     780
ttaaaaatac caaaaaaaac attaagtttt ggagggtaag attggttttt caccattggt     840
aaagattatt attctaaatg tttaccccat agatgtgaaa caatgattct tcatatatta     900 acatatttt tgacttatac ttttcttcat ctagtaaggc gttaattttt tccggatctg     960
tcgtttttat tgataaaaga gaagagtctg gactgtaatt tttaaataat aagatattta    1020
ttaatatcca attattcgtt tggctcgcta tttccatgct ctcttcgaaa gcatcagctc    1080
ctaaatctat acaaaggaat aagttacctt cacaaaaatt cattaccgag gtaatcattg    1140
cccgattaat gtcagccccc aacataaaac aataatatat agttgtataa ttacaatcat    1200
acatacaggc caactgcatc atttcatcaa tgtctatatt tgtcttctct ttgttataaa    1260
tttcatgaag gtcaaagacg ttgttataag caacccccaca tattaaccgc caatctttaa    1320
aatgactata tcgttgataa aaatattgga tggcttcagt aagcttatat agtatcgcca    1380
tactatacca atacctagtt agcatttcgt tgaatgaaat attatccaat gtaaagttaa    1440
ttgataatgt atctagttca ccaaaaattc ttaatttcag ttgagcatta tttaggaaaa    1500
ggggattatc agataataat tcatggcata gaataatatt actgctagtt ttaacatact    1560
gtacattata aaatatttct aaaatttat tttcactcaa agctttcctc gcacctaact    1620
tttggcatag gtcctggtgc actccatatt gacagtaacc aacccaaagc tgatgtctgc    1680 acccccattcg gtaaacagct ctattaaacc atgattgttt tcctgtacag ccttcattaa    1740
tgcaacattt aatgttaaac catgtttaaa acttgctgtt tttattaata tttgttcatc    1800
tatacaagta tgataaatcg taattggggc ttcatgccac cacaaaccac aacgctctaa    1860
```

```
aatacaataa tcatctttta acacaggctg tgtagctagt acttttttag taagtgcttg    1920
taaagtagat ggcatcttct atctgcaaaa taattatttc cgaaaaaaaa atcaaattaa    1980
aatactaaat tctattttt tttttaataa agcctgtaaa ttatataata aatctcgccc    2040
accgtattat ttccggacac aactttttat acctcattat attttagat ctatagtttt    2100 ttaacaaggc attaattttt tctggatctg tcgttttaa agataaaaga gagacgtttg    2160
aactataata atctttaaat gataatattt ctactaatat atcatgattc ttttgttttg    2220
ctaattctaa gctctcttcg aaagcattag ctcctaaatc tatacaaaag aacaagttat    2280
tcatataaaa gttttttacc gaggtaacca ttgcccgatt gatgtcagcc cccaatacaa    2340
aacaatagta aatggttaaa aaattgctat ctctcataca ggccagatat atcatttcat    2400
caatattcat atcaaccttt tttatatgat acatttcatg aagatcagac acgttattaa    2460
aagaaagccc acatattagc cgccaatctt taaaatgact atatcgttga taaaaatatt    2520
ggatggcttc agtaagctta catagtatcg ctatactata ccaatatcta gttagcattt    2580
cgttgaatgt tatttcattc aatataaagt tgatcgatat cttctctaga aacaacaaa    2640 ttattacttt taattcctct atattctgga aaaggggatt attagataac aatttatggc    2700
ataaaataat attactacta gttttaatac gatgtatttt ataaaatatt tgtacaatat    2760
ccatttcatt caaattttt gcgcctaact cccggcagaa attccaagta tgctccgtat    2820
tgacagtgac taagctagag ttgatgtctg caccccattc agtaaacaac tctattagat    2880
catagttgtt ttcctgcaca gttttcatta atgcgagatt taactctaaa ccatctttaa    2940
aaattgctga ttttatcatc aattgattat cctcattagt agaaagcata attggagctc    3000
catgccacca caaccacaa tatttcaaaa taaagtagtg ttctttagat atgtgctgtg    3060
tggccagtat ttttttagca agagcctgca gagaaattgg agtagacata ttttttttg    3120 caaaatggtt taagttttc aagaatacag attggataaa ttaggttgtt gacttagtta    3180
caggaggtat taaatattat gtagacataa aaatgagatc ctccaaaaaa ataaacaaca    3240
aaaaaaatat gtttaatatt aaaatgacaa tttctacatt gcttattgct cttattatac    3300
tacttattat tattttagta gtgtttttat actataagaa acaacaacca ccgaaaaagg    3360
tctgtaaagt agataaagat tgtggtagtg gagagcattg tgttcgtgga tcatgtagct    3420
cattgagctg cttagatgcc gtaaaaatgg acaaacgaaa tattaagata gattctaaga    3480
tttcctcatg cgaattcact cccaattttt accgttttac ggatactgct gctgatgagc    3540
agcaagaatt tggaaaaaca cggcatccta taaaaataac tccatctcca agtgaatccc    3600 atagcccca agaggtgtgt gaaaaatatt gttcatgggg aaccgatgac tgtacaggtt    3660
gggaatatgt tggtgatgaa aaggagggaa catgttatgt atataataat ccacatcacc    3720
cggttcttaa atatggtaag gatcacatca tagccttacc tagaaatcat aaacatgcat    3780
aaataaatac attaggctca tcgtatcttt ttaaaatcca taaatattcg tttgatatat    3840
gctgaaattt ttataaaaaa aataactatt tcctataaat catctagaaa tagtcctcgt    3900
tttgatcggt ttatatctta taatattgtg catcgatgca caactgcttt ttttggtcct    3960
tctggaacat cattatattt tctttcatta atataccatt cagatgtaaa cgttaataa    4020 tttttatggc aacaatctac cattgaatta tatttagtaa catctaatac atcgtttgtt    4080
ttatcaggct cagctctata atcttgataa ttttgttat cagcttctaa agctccatca    4140
ttatttttca aagaagtatc cataattatg tttggtaaaa atactttaag ttttaatgtg    4200
```

-continued

```
atatttaaaa tggttgttat ataaatttac cgcttacagg taatctttat tcagtgtcat    4260
aaactatact tttgatgatt cagtattttg tgaatcagta catttattat cattaatatt    4320
tttaggctgt ttttccaatg ttttattgtt gcaatgagcc tgctcctcct ttgacgagga    4380
agtgtctgtt ggagtcatct gtttaggaag agtatcatcc atatctatta tgaagaaaat    4440
atataaatat tgatatacaa tcaaaaatat ttttgatcac gtctttgtta tctatcgata    4500
ttgttgataa cgtcttgaat aacctacatc atttttttac ataaaaaaat agatataatt    4560
tttattatat ctcaattatt ttaaagataa ttatcaatac agcaaatatc ataagctaac    4620 atattttcg aataatagtt ttttagtaaa gtattaatct tttcaggatt ggtttctttt     4680
gataataaga taggattcgc tttataaatt tttaaagata atatattcac aatgatagaa    4740
taaccgtata tatctgctaa tgtcttactg tgttcaataa cattagcccc taaatccata    4800
caaaagaaca tattttcaat acaaaagttt tttaccgaga ttaacattgc tcgattagcg    4860
ttggctccca atgcaaaaca gtagtaaatg gtcaaaaaat tattatcgcg catacaggcc    4920
agctccatca ttttattaat actcatatga attttcgttg tgttacatat ttcatgaagg    4980
tcaaacacat tgttgaaaga aagtgcacaa attaatcgcc attcatcaaa atgcctgtat    5040
tcttgacaaa aatattgaat agcttcttta agattatatt ttaccgctat gccataccaa    5100
tatttggtta gcatctcact aaatgagatc tcatttaaca tagaatttgt tgttaaatcc    5160
ttcaactccc aataaatgat catccttaaa tccaccatgt ttacatttg taaaaaaggg     5220 ttattagaaa ataattcatg acacaaaatg acattactac ttgttatttt cactttgtt    5280 tcaaagaaaa atcgtaaaat ttcacttgtc tcaagctctt ctttagctcc caattttcgg    5340
cataggtttc gagtatgctc gttattaata aaagtaacc cataattaat atttgcaccc     5400
cattcagtaa acaacatgat tagatcatca ttgttttcct taactgccaa taccaatgca    5460
gtattaagcc ttatacccct ctttaaagcat aatgtcctta tcattatttg attatcatca   5520
tctatataca ttgagatagg agcttcatgc caccataaac cataacgctc taaaatataa    5580
taatcatctt tagatacgtg ttgcgtggcc aatgcccttt tagcaagtgc ttgtaaagtc    5640
gatggctgca tgtttattct gttaaaaaaa atcaaattat cgggtaaaca taaggatcaa    5700
cccgtagtta atatttgcag tagtatttt taacaatgaa ttataataaa aaataattc     5760 attactatct attataaaac ccatcttaa ctttaaagaa gaactagatc atcttttttt     5820
tgttgtgtca gaacttcttc aatttattac ccacatttta tctaaaaaaa taaaaactac    5880
atcatatctt gtttcttcat caaattatca taccatttat agggtgtagg ttgggaacat    5940
tccatcatgt ggtaatcagg gtatttatat attttttgat agtaacatct atttggcaga    6000
tgtattgtcc aacaatcatg tctaataaaa tcattttcac ctatggggga atcatcttaa    6060
aaaccttatt cctacagatt ccattttgac agtcccagca aaagtcacaa tattttccat    6120
gagtacacca atgttcaagc tctctttcgg gaggaatgct gccaatttta tgttttttag    6180
cttctaactc tctgtacaac atcagttggg aaagcagaaa gaagattacc aggagaacca    6240
ttaaatatat aatagtctgc aaactacgtt tgcgaatgta atttgcaact aaaacacaac    6300
ccacaaggta aaatccataa gttaataact tttgccattt tcgtatgaca gcctcgtgcc    6360
attcatggtt gtgttgtggg cattctgttc ggtaaacttc atgaggcttt atagaagtta    6420
catagtaggt acagaattca ttgtgacgaa aaacactgca gttagctatg tagtcatttt    6480
caagaatggg agaatggttt tcaaagacct tattcttaca gatgccatct tgacagtccc    6540
aacagaacct acaatgattt gcataggtgc accagtattc aagctccttt tcaggagggg    6600
```

```
ttcttgttag atccaggagc tctagctcat atgtataaag aagagttgga atggatagta    6660
aagtaaatat ttgcagacca agcatggcta cttgtgaaca agtggctgct cgtcaacaaa    6720
tagctgttta tcagcaaata gctgtttatc agcaacaact aattatcagc aaatgctgct    6780
tgtgggtaag ccaataaata ggccataccc ttgaaaggag aattcagttt gataaaaaaa    6840
ataacgagtt ttctaataac ccggtcaagc atttaataaa tgaatagcat cacacgtctg    6900
catcgtgcat tctgcctgga aaatgggccc atctctaata tatttacact gacggtgaat    6960
catacagtgt tccatgggat agctatgctc ctgtacagga ggcatatctt ttagaacttt    7020
attcttacaa agaccatctt gacaagccca gcaaaaccga caattttca catattgaca     7080
ccagtatcta agctcctctt ccaggggatt gtcggtcgaa aacccctgta gactagctag    7140
gccagctagc agcaagccga ggtaactaaa gaacctcatt gtagtgttat attacgaaaa    7200
aacatgttaa aatttggaaa aaaagcccct ttttatagat ctggaaaaaa attttcacaa    7260
atctaattaa aagccttaca gatcatcctt ttcataaatt ttcattaaca attggtgggg    7320
gcggttgtga ggtactggat cagaacaatc cataacatgg taatgtccat ttccttcacc    7380
atatgtacac tggttatacc agcgagaaac ctcacaagat gtcaaataac tgttctcaac    7440
aatcaatggc atgctcttat tcaccttgtt cttgcaaatt ccatgtgcac attcccagca    7500
aaacttgcag ttttccatgt aagtacacca gtatccaagt tcttcttgtg gaggattatc    7560
cgttgaacga agatgccctc ctgcctgagt aggtagtcct aagacctgat tggccagcag    7620
gccaagaatt tccaagaaga tcaccaacat tgctacggct ggctgaacag ctggcagata    7680
gctagctaat tagcaaacca agtgactcgc cctctctact cttaatatga gaatttaaga    7740
ttcggtccgg cttttttccc atgttttaca gggaaaaggt attttagcc tatgaatgta    7800
catggttccg cacattaaaa aaaataaaag aaattattta atattggctg ttattttctt    7860
tcaactagca acaagccagg taactaaaga acttcattgt agttttatat tacggaaaag    7920
gttaaatttt ggacaaaaaa atcatatcta attaaaaatc ctcacagatc tttcttttca    7980
taaattttca ttaacaattg gtaggggcgg ttgtgaggta ctggatcaga acaatccata    8040
acatggtaat gcccatttcc ttcaccatat gtacactggt tataccagcg agaaacctca    8100
catgttgtca agtagctgtt ttcaataatc aatggcatgc tattattcac cttgttcttg    8160
caaattccat gtgcacattc ccagcaaaac ttgcaccttt ccatgtaagt gcaccagtat    8220
ccaagttctt cttgtggagg attatccgtt gaacgaagat gccctcctgc ctgagtaggt    8280
agtcctacga cctgattggc cagcaggcca agaattccca agaagactac caacattgct    8340
acggctggct gaacagctgg cagatagcta gctaattagc aaaccaagtg actcaccctc    8400
tctactctta atatgagaat ttaagatccg gtccgacatt tttccgatat tttacaagaa    8460
aaagatattt ttagctacaa atacacttca tatatcccta aaaaacaaa aatttattta    8520
attttaacta ttatttttctt tccactctct ctttaagatt ttgtaaggat tccagggctt    8580
tggttcagaa caggccatta catggtgaat ccctgtcct agatcataca tacatttatt    8640
tagccagcgg gaaactatac atgattgcac atactcattt tcaagaattg ttgtattctc    8700
caatttgccc tcacaaaggc cattttgaca attccagcaa aacttgcagt tttctgtata    8760
agtgcaccag tattcaagtt cttcttgtgg aggattatcc gttggatgaa gttgtccagc    8820
tggttgatta ggtagcccta agacctggtt gcaattcatg gtatggtaga taccctatc    8880
taaatcatac atacatttat ccagccaacg ggaaaccaga catgatttca catactcatt    8940
```

```
cttgtaaatt actgacccat ctattttgtt tatacaagtg ccgtcttggc agtcccagca   9000
aaattggcaa cttttccatgt aggcacacca gtattcgagt tcttcctctg gaggctcctc   9060
tgttggacga agttgtccaa cgagctgact tgaaacctgg ctggccagaa ggccaagaat   9120
tcccaagaag atcaccaaca ttgctacggc tggctgaaca gctgactgaa tagctagcca   9180
attagcaatc cactgtactt ttcataagat catttaagat tcggtcggca ttttttcaat   9240
agtttgctag gaaaaaattt ttaattttat agattcacac tacttcattc tcatgcttag   9300
gaaaaaaaca aactaaatct tacaatgtat ctggatctaa tgagaagcta gaattcatct   9360
tttttcaaat cctttctggg atgttcattc ttttttccact ccttccttgc aattttataa   9420
ggattccagg gctttgggtc agaacagttc atgctatggt aaatgtgctc ctccacatca   9480
tatctacata ggtcaccccca gcgggaaacc tcacaatatt ttacatagtc attctcaata   9540
atacttgtgg agttgtttcc ccaaaccctg ctggtacaaa tcccatcttc acaatcccag   9600
cagaaccgac agctttccac ataagtgcac cagtatccaa gttcattctc tggggttca   9660
aatgttagag gaagatgtcc acctacccga gtagaagtgg aggatgaaac caggttgcta   9720
ctggccagca ggccaataat tcccaggata atcaccagca ttgtgctcaa ccagcaacgg   9780
ctagcaacga ctagcaactg actagcaata gctagaaatg gctagcaatc agtagtagct   9840
aacgctctac tctttataag aaaatttaaa attcgatcag attttttag aattgagaat   9900
gagtaaaacg cttatattct ttttctagct agaaaaaata agctagttta agataggatt   9960
tcccttacta acggtttaat ttttagcaaa ggtataggta aaatacactt gtacttagct  10020
gcaaaaaaat aagcttatgg cgtataagcc gccataagtt tatttaatta aaatgttaaa  10080
ctctgtgata agactggaat cttaggcagg tttgatgtgg agaacagcat gaaatacaag  10140
agtgcctgtt acacgaataa gttctctcaa accggggatg gtcatactca catctatgaa  10200
atcctggtct aggagattca tttgatgcat gatggccgca cccacactta tgagacactg  10260
aagaactaaa gggtttaatt ttgatctgaa tggtactata taggatgatg gcaatccata  10320
tcaagattag agcaatcaaa atcacctcct caagaagcat gatgtagcct taaatcttag  10380
actgctttaa accttaggcc ctcactatct ttaatgaagg agtttaaatt ttgatcccctt  10440
tttcaagacc catttagaag aaaaaataaa gtttatatca atctaattca taagtcatct  10500
ctttcataaa tcttcatgta ttctctatgt ggataagtat gggatgttgg atttgcgcag  10560
tccatttgat gatctgtatg gttttttgggt ccttcataat aactacatat accattccag  10620
cgggaaaccg tgcaatttat aatccagtca ttttgatgaa taactggcca atctgtttga  10680
atcctgtttc ggcagatacc gtggacgcat tcccagcaaa agtcacattg gtttgcgtaa  10740
gtgcaccaat aaactagctc atgttcagga ggataacggg ttggtagtaa atcttctaat  10800
ttacgtatag gagcggcttg aaggacaacc acccccagta gtactagaat cagtaccttt  10860
atagtggcca ccctcacacta gacctctaag ttgaagacaa agaactaaaa tttagagccg  10920
tttaattact actaataatt atatttttta ttgtctacaa taggattcta ttaaaaaata  10980
atgattttta ccaagaaata tttttataaa aaattaatat attttgtaat aaactttatt  11040
tccaatgact gttaaaataa ggaaactatc cttagttagt cgaggaagat ggttaggtta  11100
tttcgcaatc cgataaaatg tttattttat cgtaggtctc gtaaaatcca ggaaaaaaaa  11160
ttacggaaga gtttaaaaaa gctaaatttt taccaccctc cagaagattg ttgtcaaata  11220
tatcgtttgc tagaaaatgt tcctggagga acttacttta ttacagaaaa tatgacgaat  11280
gatttaatta tggtcgtaaa ggattcggtg gataaaaaaa ttaaaagcat taaattatat  11340
```

```
cttcatggaa gttatattaa gattcatcag cactattata ttaatattta tatgtatctt    11400
atgagatata cccaaattta taaatatccc ttaatttgtt ttaacaaata ttataacatc    11460
taagtaaata ttcttggaat ggattttctt atagaatggt tacaggatat gtcagcgaca    11520
ggcttaataa caaatttgtt aatatttttt tgttaaataa atgaacaggc caccatttaa    11580
tattacccgt tgcaaaataa gaaaaaaaaa caaacttata gttacaaatc atcttgatta    11640
atcacatgtc gttttaactc aatgaaccat tctaaatctt tgggttgtga acaattcatg    11700
ttatgttgat agtgtatcct aaagtgagct tcatacatac accggtcatg ccaccgggaa    11760
actgtacaat taacaatata atcattttgc gtaataatag ggtggtcact aaacacttta    11820
tttttacaca ttccatcttt acaggtccag cagaagtcac agtgttttgc ataggtgcac    11880
cagaacttga gatcccttc aggaggccta cgcatttgca tcggattatc tgtgaaaga     11940 ggtaggttca ttattatgtt cgtcatcaaa attcctaaaa gaacatagaa gccaagaaag    12000
ataagcagtc ttgtagcggc ttgcattcgc attcgtgagt attgtttgcg aacatagctt    12060
atgagagcaa tggtagctat catacaaaga caagtatgtt tgatattctc agtgtcaatg    12120
accctatcct cctttatttg cattaactca tcaaaccaat cataatatgt gggatttgta    12180
cagctcatga tgtgaaagcg gcgtatccta gagtctgtaa agtagctaca tctttcatta    12240
tagcgagaaa ccctacatat ttgtatgtaa tcatttttttt tgatgagagg gtgttttttca   12300 aaaaccttat ttttacaaac cccgtgtcga caattccagc agaagtcaca cgattttgca    12360
taggtgcacc aatactcaag ctctctcttt ggaggtctcc gggtcattgg taactctcct    12420
gttcctggaa aagattggct tgaatgacc ggctgcatga ccgccagtac caaaaggaac     12480
acaatcacct tcatggctgc aacttataag ttgcaactta tggttgcaa tactgcaacg     12540 tataggttgc accttataga tcgcgactca aaaggtatga aaaccttacc ctcaatacag    12600
aatttaagtt ttaatcctga taatgtatct gtttatgaaa aaaaatttttt tttactcatg   12660 tatgaattct tatacgaatc ataatatgta ggctgagaat aataattcat atacggtgtt    12720
gcgggctcaa taaaaatttt gttaccacaa aaaataaatg ctggattttt aagatatata    12780
tctattaatg actaaaccct ttatacgctg taggctgaaa acaatccata taatgaatat    12840
acggtgattt gggtttaata aaatacatac aacggtcaaa atagcgggca atactacatt    12900
gactaatata atcattttgt ttaataagag gcatatcatc ccacacttta tttttacaaa    12960
taccgttcct acattcccag cagaaatcac agtgttttcc atacgtgcac cagtattcaa    13020
gctctcttat aggaggcgta taagtccttg gtaaattttg tttcatataa aagatggaaa    13080
ggggtcgatt taaacccggc tgagatagcc aaatcaaaat acataaaaga gcaagtagtt    13140
tcatagtggt atttagatgt aaattttttat agtatgcaaa tacaatgtaa cctacaaata    13200
caatactaaa tacaaggtaa aaacaacaat gtcttataat gattggccaa taatcacccc    13260
cccccccccc atttttccat gaatatttca tttcctgtat agggtctagg atgtgaacac    13320
tccatgttat gatgattagg catttaact gatatttcat aaaaacaccc ccaggaattg     13380
cgattaacta tacagtttac aatcgaattc atcgaattag actcatttgt tatcttattt    13440
ttacaaatgc cattttgaca atcccagcag aagtcacaat tctttacata cgtacaccaa    13500
tatggaagct cctccttagg aggatgctgg gttcttggta attctggtaa ttcatgtgca    13560
agaatgagga ctgagtagcc caacaaaagt cctagaacct tcatgttgtg tccaaatggc    13620
acctgtcatt ttaaaaaaga tttaaatttt gctaccgcaa aaaaaatcca gtatgtattt    13680
```

```
ttttaataca tataattatt gaagtcttat aagataaagc cgagaacact atattttgta  13740
tagatgatgt atccggtatt caaactctct tataagtaca tgtaggaaat ggtcaattat  13800
tcaagattgg ctgagataac aacaaaacca aaatactcaa aagcataagt aatttcatgg  13860
ttgtactcag tcgtagattt ttgcagatcg caaatgcaac gcaaccagca aatacaaagc  13920
taaatacaag gtaaaaacaa taataccttt taatgattgg ccaattctta tccctccatt  13980
tttccatgaa catttcatgt tcataaagtc taggatacga acaacatttc atgctatgat  14040
gattaggtat tttaagtgat atttcataaa aacaccacgg ggttgttggt gattgatagg  14100
taagaataag gatggttgaa taacctagta aaagtcctag aaaaaccttc atattgcgtt  14160
cataccacag atgttatttta aaaaaaatat aaattttaca gtatgtgata tacacatacc  14220
acaaaaatgt tcttatatta actaaaatat gtgggcagag agcaattcat ataatgaata  14280
tatggtattt taggctcaat aaagtacata caacgatcaa taaaacgggt aatactacat  14340
ttactgatgt aatcattttg aacaataaga ggcatatcat ccaaaacctt attttttacaa  14400
ataccattct tacaatccca gcagaaatca cagtgttttc catacgtaca ccaatattca  14460
agttctctca taggaggcgt ataggtcctt ggtaaaattt gtttcgtata aaagatggaa  14520
aggggtcgat ttaaaactgg ctgtgctaac caaaccaaaa tactcaaaag aacgaaaagt  14580
ttcatggttg tactcagacg cagattctta caaagcgcac atacaaagca gcctgtatat  14640
gcaataccaa tgatgaaata gagacagtat tgctttatag ataattgttg atggtcaccc  14700
cccccccccc cccatgtttg catgaatatt tcatttcctg tatagggtct aggatgtaaa  14760
cattccatgc taaagtgatt aggcatttta gatgaaattt catataaaca ggattgagtc  14820
ttggaatcac ggaaaactct acagtttaca atagaatgat tggagtcaat gaaacgagat  14880
tccgttatct tattttttgca aatgccatct tgacagtccc aacagaaatc gcattgtggt  14940
acatacgtac accaatatga aagctcactc ttgggaggat gctgggttct tggtaagtct  15000
ggtaattcat gtgcgagaat gaggactgag tagcccaaca aaagtcccag aagaaccttc  15060
atgttgcgtc taaatgacac ctgcacttac aaaaaaaaat ttaaattttg aatataacac  15120
aaaaaaacca ccttaaaatt tcttatatta tttcttggat ctgccccgac gtcatacaat  15180
gtattaaaat tatagaccaa tcatcttttt gtatataggc taatcatctt tatatataga  15240
ttttagatgt ttgcttgttg tatcaactta actgctagcg aagaaaatgg ataaaaactt  15300
tctgtatttt tataggttga aatcatttta tgcacatcgc taggatctaa tattttatt  15360
tgaagaaccg aatgtgggct taaaatttt ttccttagaaa aaagtagaat cataatattg  15420
ctatgttttt gtttaatgat ttcttgtatc ttttttgtat acgggttggc acccaaacct  15480
atacaaaaat atacattact caaataacta ccttctatac ataatctttt ttccccacgt  15540
atttcctat ttatttccct atttatggaa ttaaggata tcaatctctc taaggcacgg  15600
tcaaggtctg cgcctaaggc aaaacaataa tatataccta atttattccc agggcgtgca  15660
caggcaagaa acatcatgac gtttagccct aaacgtatat tttcctgaaa atacgcatga  15720
tgaacttcat caatattacc taagtatatg gccgtttgta aacgccaaag atctaaatga  15780
ggaaattttt tactaagata atgaataggt tttgtgagat taaaatctat ggcgaactta  15840
taccaaaatt ttaatacaag tgtatttctc gtcatttctt cttctttttc atctaaatat  15900
aagataaaac gattgtaaac aaagtctatc aataggtgaa aatcattgct attaaagctg  15960
tcgagaatca aaatattgtc ataataaatt tcgatcgcca gtaaaacctt ttttcgtttg  16020
acgagataaa caaacatatt atacaaccct acatctaaaa attctggatt ggctcctagt  16080
```

```
tggatacaca ggtctttagt ctgcttcgtt ttggcacaca tgatgccaaa attaatatca   16140
gcaccccata aaacaaataa cttgattaga tcagtctggt tttccttcac agcttttact   16200
aaggctctgt caagctcata gctgtcgaca tcagagcatg acatagagcc accggttacc   16260
attttacatt gcttacaaaa acctatgggt ccgttttccc accatagtcc aagctgttgt   16320
agaataaaaa tatcatcctc atgataattt gaaaagcct  tggtttctat caagactttt   16380
tttgtaagaa cctgtaaaga gttcatcgta ttattatgaa taacaggagt aaacgtaatc   16440
aattataaaa gtgatttttt cgaaaaaaac tttagatggt tgaaaatgat aatgtacatg   16500
ttcatacaaa aaatagatgc agtgatgtct aaaatcaaaa tttaattttc tatgtaaaaa   16560
gtacagactt acttatttgg gttaaattgt ttattttaaa ctttaattaa ccgtttgagt   16620
tagcgatgtt tgatttatct tccatactca tccggggggg ggggggtcctt atagctctga   16680 cattattgtg gattattgaa tataatgaat acttcataga tgctaaacat tttaatagta   16740
gttctgaggc ttaattgtac tctataaatt tataaaaact ttttgatcaa aatttaatttt  16800 cttataaaaa gagtacagac gtcgcttgtt taagcttcat catgtttcat tcattacttt   16860
ctacaattac gggggggggg agtcccctca tagctttagt attgctatgg tttactaatt   16920
attatgtaga atttatagaa gcatatgtac ctgaaagtat acctactcta taaaattaaa   16980
taatttcagt atattttttt tatgaataga acggaaatga tataaaaata atttaatatt   17040
gcaaaaaaaa ttcataatgt tggtatgtat tataaacata atagcatgtg taatttataa   17100
actgactcct ctatataatt attagatgag gtaccaacct acttatgata tgccgatgat   17160
agatattgta tactataaaa caaaattatt ttaaatgtat tcatggatac attataacat   17220
ttttaccgca aattgtctct cagcgaagaa aatgaatgaa acgtttctgt atattcatag   17280
gttgaaatta ttttacgcac ttcactaggt tctaatattt tcttatgaag tattgaatgg   17340
gggcttaaaa gtccttttctt aaaaagaagt ttcatcataa cattcttttc ttgtctaaga   17400
agagtttctt gtattttttt tgtataagga ttggcaccca aacttataca aaaatgtaca   17460
ttactccaaa taccataatt tgaaagaaa  gttatttccc tatttacttc atgattaatg   17520
aaacctatca acgtctctaa ggccgtattg atatttgcgc ctaaggcaaa acaatagtat   17580
atacccaatt tattttgagg gtacatacaa gcaagcgaca tcatgtcatt tggatctaaa   17640
cgtatatttt cctgaaaata tgcatgatgg atttcatcaa cattacctaa gtatacagcc   17700 gttttttaaac gccaataatc taggtgagga aatttcttac taagaaaacg aataggtttt   17760
ataagattaa actctatggc gatcttaaac caaaatttta atacatatgt atttttttatc   17820 attttttctt tttcatctaa atttaagata aaacgattgt aaataaagtc tatcaacacg   17880
taaaaatcat ggctatcaaa actgtcgaga atcgaaatat tgtcataata aatatctata   17940
gctaataaga ccttttgttg tttaattaga tcaacaaaca tattatacaa ccctacatct   18000
aaaaattttg gatcagctcc tagttgaata cacagaactt tcgtcctttc cgtcttggca   18060
catatgatgc cataattaat gttggcaccc cataaaacaa ataacttgat tagatcagtc   18120 tggttttttct tcacagccct caccaaggct ctgtcaagct catagctgtc aacatcagaa   18180
catgacatag agccactggt taccatttta cattgtttac aaaaacctat gggtccgttt   18240
tcccaccata atccaagctg ctgtaaaata aaaatatcat cctcatgata atttgaaaaa   18300
gccttgtttt ctatcaagac tttttttgta agaacctgta aagaattcat cgtattatca   18360
tgaatgaaag cagtaaatgt aatcaattat aaaattgact tattgaagag aaatgttaaa   18420
```

-continued

```
tgagtgaaat cggtgtttat gatgatgtac atgatcatac gaagaaacac gttcactggt    18480
gtccatgatc aaaatttaat gttttacgta aaaagtacag atgttaactg tttagtttaa    18540
acataaattt aacctttagt ttaaacccta gttaatgatg tttaatattt cttctatact    18600
cattcaggga agtgtaatga ttctaatact gttgttatgg attattaatg aaaactttac    18660
agatgctgga gggaataatt ttaatcatac tgttttaatg tagctatata agctttcatc    18720
aaaatttaat ttttttata aaaatacacg aattaaacta aagtctaaac tttagtttga    18780
ctatttgagt taatgatgct taacttatct tccatgctta tcaaggggg gtcctaatag    18840 ttttgatact attgttgtgg attgttgaat ataataaata ctttatagat gctgaaatgt    18900
ttgaaaataa tagtacatca atgttgtaag tttgatcaaa atttaatttc tcataaaaaa    18960
ggtacacatc aacattgctc atttaagttt catgatgttt gattcattac ttcctacaat    19020
tactgggggg gggggggggt ctttaatagc tttagcattg ttatggtttg ctgactatta    19080
tgtagaattc atagaagcac gtttagatag taatatcact gcagtgtaga ttatgaaata    19140
catactaaac taatttcagt atattttttt tgttcatata agttaaggta caaaaatgat    19200
taaacattgc aaaaaagaa atcacaatg ctattataca tagtgatcat agtggcttgt    19260
atcatttcta aactagttcc aaatgaatat tgggcaatac atctattttt tatcattatg    19320 attttatgg tatatatgta tgaaaagtta gatatacatc aaaaatctca gttctggaat    19380
tataccatgt caggcttatc tggacataac gtacaggtaa catgtaagtg ttactaaata    19440
ctatgaagta tctattttt ttgttgtaaa aaaagaact tgatagtatt ttttaaaaaa    19500
taaaataatt aattgtacgt caacttcctt attttattct ttaaaaataa ctcgtaagta    19560
ttatttatct attttttgaa aaaatagatg taatcggttt catcatttag gtgtgtattt    19620 cttttagca tctatcaaga attcattgtt tagtgatatg aaaacaatga atgatcatta    19680 tcttctatt aacaaccacc taaataaatg aacgtctttt tcatcttaac tgattaccaa    19740
aagttatttt gcgaaaaggc atacatatga tcaatatcag acctacaatg aatatttcca    19800
taatatccct ttattgtaat aattctattt ttgcattccg atatctcatc atctgtgcta    19860
ttatatgttt ccataactgt ttcatcatca aacataaatc ctgttaaata ggcaaaagac    19920
tttaatcccg gatagatttt taccatttc ctgagagccg tgtatagctt gtaataaatg    19980
gccaaaaata tgcaataaag cgtagaaaga gagtaatttt tggcataaaa gattttgaag    20040
gtttgatgaa tggctaaatc gcatataata taagatacga ttttaaagcg caccctgttca    20100 cgcagatttg ttgaaaaatt cgtggaaaga tttaacaaat aaaaggttat taatagttgc    20160
tcatcattcc ccttatacga catcgtcaga cgctctaata ttttactact aggcacatct    20220
gccacatgtt gaacatttaa agcctgttct tcttctgtgt tacggcaaaa gagccgtgcg    20280
tattcaggtg aagctcccca ggataacaac gtccttgcta cggctaaatt ttttttgacg    20340
atgactttta tcagaaataa gtctttattt ttgcattgat cactatgcga atttgtatag    20400
ttgacgccgt tgcattgagt acattgatat aatgttttac aattccagcg tagccctaaa    20460
tggtataaaa gaactgtatt ttcgacataa gcatgctgat taacgatgtt tttgagacaa    20520
cacgtcgtta aggacaccat attgtctcca atttgttaga taaagtctt tactaaaaaa    20580 atagatttt agttttaaca atcgagattt tattatttgg atgcatcatc aaaaagattt    20640
ataagtataa gaggttgtat aagaaaaaaa tgatgttata ctatttatgt taaaatttaa    20700
tttatcatat aaaagtaca gatttaatca gttggtaaa ctatttagtt aattaaacta    20760
aatagtttaa ccatttagtc agactacttg gttagcaatg tttgagcttt cttccattct    20820
```

```
tatccggggg gggggtcct aatcgttcta atactattgt ggatagttga atataatgaa  20880
gactttatag atgctataat gatgaattct agtatgcctg tataaaataa ttaacctttt  20940
tgatcaaaat ttaattttt tataaaaagc tacagagtag tgttttatta aacgtggctt   21000
atttaaaagt tacacaatgt taaaatctct acttacttta attctttgtg ggttttatt   21060
aactttatcc atattatggc ttactactta ccatgtagaa cttatagagg caatagatga  21120
tttctacgac tgaaatatag aatagtccat tttctatttg taaaataatg atttatattc  21180
tttcctaaaa atgatacttt atatggtttg aaaacaaata ttaacaactt gattttttt   21240
tctataaata aactataaat gaaaatagta aaactcatag agtcttataa gtgaacatct  21300
tcataatgtt actcaaacgt tggactatta aaaatattc cgtgtgcatt attgctttta   21360
atcagtatga ttactttata cgaagccgct attaaaacgc ttcacaca ccgaaaacaa    21420
attttaaaac accccgatag ccgtgaaatt ttactagctt tggggttgta ctgggataaa  21480
actcatattc ttgttaaatg tcgtgaatgt gggaatatga gtcttaccgg aaaacacagt  21540
acaaaatgta ttaacattaa ttgtctactt attcttgcca taaaaaaag aataagcgta   21600
ttgttgatac cttgatagga atgggcgcgg atgtaacata tatacatctt ttaaagaata  21660
agataaaact gtcatacaac cagctgtcta tgcttaaaag caactcgcag atttcattga  21720
aggagcttca tgctatatgc tatcttttat atggtcggct tcccaaaaaa attaaacaag  21780
ggatgcgact gtgtaaaaca atggcgggac tatgtggtga acttttatgt gcatttttag  21840
ctccgtaaat gataatatgt atttaaaaca aacagatatt accaaaatat attctatgta  21900
cataatatct gggaaattat tttttttct catacccttaa aatataaaaa tattgggttt  21960
cttcactaaa ctttagaggt aaaaattttt ctttgttttg caccatcatg tatgggttta  22020
ggctgtccca gggattgttt atttgaatat ttcctaaata ggaacacaac gccatgatca  22080
tatatctttc attctggtaa gcttttgat acatcttcaa agatgccgta cctccgagtg   22140
tgtaacagca aacaaacgtc cgtactttc catgggtcgc agcccattcc attccgtagc   22200
tcagcatctt ttgctgtatt tttttattcg ctttataaaa aagttttttc atccattcca  22260
cgttctcata aaaacaggca cttaaaaaga gcactagggg tagtgtagtc ttattataga  22320
atgtaggaat gtatgtttta gttatttttt tcaacgcgtg ttccatacta tgttttaccg  22380
ccataaaaat acaaaaccaa taccaacttt ttctataaaa ggttttgctg tacacatata  22440
aacgagcaaa atatatttca aactctatat tcttttata aaaaactcg agacagtcgt    22500
ttatgttacg acttttcta aataccctcaa aaacagtaat taattcactg tcgctgtgga  22560
aatgttcgta agctaactgt ttaatgtctt taggggtcaa ttcttttttt gggagcagtg  22620
gtttgagatt cggcaaaggt cgtctaaagt agtgagcgaa cttttcattc gctccccaac  22680
acaaaagccg ataagccagc atgtagttat cacgttttac cgcgtaaata agcaaatagt  22740
ttatattgat acatgtacca tgttgctgcc cgtttggaca tatgttgccg cattctgaac  22800
acttatgaat gagatcatag ttcttacaac ataaccccaa acgggttagt acttctttgt  22860
cacgttttaa aaactcgaca tgattcttta atgttaatgc tttgagcgca atgttaaata  22920
aactctgcat tttattaaaa tgaggttagt atcatgtttt agtataaaat ttagcggctg  22980
tttacataat gctaaataaa cttaacgttc ctactaaacc aaaaaaaatc aaattgacta  23040
agtcatagag aatttgacga tgttggtagg taatttttta acatggtata tattttttta  23100
gggtcggtta tattaggtaa taaaagagga cgtgccgtta aagtattttg cttaagatcc  23160
```

```
tttagatcct tacaaaaata tagattgttc gtctgatgat gccactgtgt tgcagtgatg   23220
gcttgatcaa tatcacctcc caagacaaaa cagtagtata tcgttaaaaa gttgtaatct   23280
ttcatacaag ccaactgcat cattttatcg atgtccatat gaacgatctt ttgctcgtat   23340
atttcatgaa ggtcaaatac attgttgaag taaatggcgc acatgagtcg ccacatacta   23400
aggtgcccat atgtttgata gaaaaggag atagctcttt taagcttata ttttactgct    23460
atggcatagc agtatttaac gaatacgttc atgggtacat tatctaagat ataaaatatg   23520
aaaaacttta actctcgatg aatctcttcc cccatttcct gtacatttag agcttccaac   23580
ataggatttt tatcaaatat ttcatgacat aaaataatgt tattgctcgt tttatgacgc   23640
attaaaccgg tgaaaatttc cttattattt aaactatctt tagctcctaa ctttcgacac   23700
agctcctgag tttgttccgt cctagcacag gtcagcccat aataaatgtt tgctccccac   23760
tcggtgaaca gccttattac gtcatagtta ttttctttta tggccatgat taatgccaca   23820
tcaagatgaa gaagttcccc cttaaagggg gttgagctta aaataacgta attacagtag   23880
tgacataagc taatgggctt gttttgccac ataagccac aatatttaa aatataatga    23940 tactcctcag gcacgctctg tttggccaca gccttttttgg ccagggtttg caaggagagc   24000
atgataactt cttgaaaaaa aaactcaaat taagttccta ctttttttaaa atattagtat   24060 ggacagatct accatcatat gaaggaattc tttcatcgtt aaacactgaa gagataatac   24120
tttcatcgta tagagaatat catgtcaatc catatattga atgttatata tcattaaacc   24180
catcattaat atagtgttta tgtgctatgg acaggttttt tgaatgataa tcttttaaca   24240
tacgttttat aacttcggga tcagtttctt ttaaagataa agaatcattc atgttataac   24300
aatttaatga taacatgctg gcaatgaacg agttgtcttt ttgatgcgct agagtctttc   24360
cctcctcaaa ggcattggcg cctaagtcta tacaaaagaa tatgtttccg atattataga   24420
actgaataga atgaaacatg gcctgattga tatcagcccc taagacgacg caacagtaat   24480
aaatcgttaa atagttatag ttcttgcgac aggcccactt tagcatttca ttcatgtcta   24540
tgcgaatcct ctcctttcg tacacttcgt gaagttcaaa cacattattg taaaaagggg    24600
cgcacataag ccgccaccga tgtagatgag catatctctg ataaaaatag caaatcgcct   24660
ccttaaggtt acattctatt gccatcgcgt accaatattt agtaaacatc tcgcttaata   24720
tatcggtttc taccattaat ccctccagtt gttcataaat cattccctt acttcaaaac    24780 gatttatggt atctaaaatg ggattattag aaaatacctc atggcagaaa atgatgttac   24840
tgctagttag atcacgtttc aatgtgtaaa aaaatcgtaa aatttcctgg tcatttaact   24900
gttctttggc acctagctgc ctgcacaggt ctcgggtgtg ctccgtgttg acagaaagca   24960
aaccgtagtt gatgtttgca ccccactcgg tgaacaattc tattagatcg tgattgtttt   25020
cctccacagc tttcaccaag gccgcgttaa gatttgtgcc gttcttaaaa tacggcgtcc   25080
atattttctt ttgatgatac atgatagggc cattatgcca ccatagaccg cagcacttca   25140
aaaaatgagg atggcatttg gccggatact ggctggccag caccttttttg gtgagagtct   25200 gcagagagag gaccatattt cttttttttg aaaaaatcaa attaaaaaaa tcatgcttgt   25260
ttagcataca tgtaatattg ttataattac gttataatta cgttataatt acgttataac   25320
tatattataa caatggtata acaatggtat aacaatgtta taacaatgtt ataacgatgt   25380
atcattgatg tcatcattca actaggccaa catactttt aatttatagt tttttaatag    25440
atgatatatt ttgttaggat ctgcttcttt taacgttaat agcgaggagt ctgcactata   25500
aatgtctaat gataaatgat gagatatcaa atagtaattc cgttgctctg ctagggcctt   25560
```

```
tgcctcttca aaggcgtcgg ctcccagatc tatacaaaag aacaagttat ccatattata   25620
aaatcgtacg caggcaagca tagctgaatt aatattagct cctaagagaa aacaataata   25680
tatggttaaa aaattgttat cttttgtgca ggccatccgc atcatttcat ccacgtccat   25740
gcggatcttt tccttttcat acaaattatg taggtcaaac agcttattaa acaaagagc    25800 acagattaac caccacgtat ttagatactt aaaatgttgg taaacataag aaatggcctc   25860
cctaagatta tcctgcaatg ccactataaa acagtatatc gttaacatat caccatccga   25920
catattactt aatatgtcgg tgtcttctac taacctttc aacttccaat atatggatga    25980
ccttatttcc cttataatga cataggctgg aaagggatta tcattaaaaa gtttaagaca   26040
taagataata ttactgctag tagtgccagg gtgtattaat ttaaagaaca tgtgcataat   26100
cttcttttta tccacgcggt acttggctcc taattcccag caaaattctc gaacaggcgg   26160
cgtattggcg caaattaacc catagttgat gtctgcgccc cattctgtaa acagttttat   26220
taactgatag ttgttttcct ttgtagccaa cattagtgcc gtattaaggt ccaagccgtc   26280
tgcaaagctt ggcagcttta tcagcatatg tttgcaatca agggaaattg gggccttata   26340
ccaccatagt ccgcagcgtt ctaagataac atggtactca atagatactt gctgtctggc   26400
tagtaccttt ttggcgaagg attgtaagga aggaaacatc ctgtttcttt ttttttaaaa   26460
atcaattatc tttgttcata atcaagaaaa atccccatat ttattgagtg ataattttt    26520 aacatgcaat ttatttttc agggtccgta acgatcgaca acagagaaat aaccggattg    26580
taatgcttta atgataaggc atgggctatc agataatttt cctttgttc tgccaaagct    26640 ttgccctcct caaaggcatc ggcacccagg tctatacaaa agaacaggtt tccaagatta   26700
tagttttgta tggaaacaag catggcttga ttgatgttgg ctcccatgat aaaacagtag   26760
taaatggccg aatagctata atcttggatg caggctatgt gcatcatttc atcaatatcc   26820
atgcggaccc tttctatttc gtacagctcg tgaaggtcga acacgttgtt gtaaaaaagg   26880
gcgcacatga gccgccacct atgtagacgc gggtatttct ggtaaagta gcggatagca    26940 tctttgaggt catagtccac cgctatcgcg taccagtatt tggttaaaac agtgctaaag   27000
ctatcatcat ggtccagcat gaaggttatc tccatgagcc ctcttaactc ccacatgatt   27060
tcccccctca gatccagatt atctataatc cttaaattgg ggttattgga aaacacctcg   27120
tggcaaaaga taatattgct actggtttta tcgcgcgttg tatcaaagaa aattttaaa    27180 atatactctc tttctaaata ttctttggct cccagctctt tgcacagatc acgggtattt   27240
tccgtgagag cacaaatcat tccatagtta atatctgcac cccattcagt aaacagcttt   27300
atcaagtcat gattattctc cttcacggct ttcatcagtc ctatgtttaa ctcgatacct   27360
tgactaaaac aggttgacct tataaataat ttattgcgtc gaatatgaag cataatgggg   27420
ccattatgcc accacaggcc acaacacttc aggacatgat attgatctac cggtatacac   27480
tgcccggcca gtactttctt cgtgagggat tgcaggaag gcaacatgcc tttccatcct    27540
ttgacggaaa tcaaattatc tactaataac tatcagtgtt tatattaagt atttagatat   27600
tatcccgggc tggatacgta gtatcgctat tcacatgtac ttccaactct agccggagcc   27660
tgcagggtca tttattttta atattgattc tttttttgtat ttaatcattt agagaaggtc   27720
atcataggag ccagatgttc tctctccaga acttatgtcg aaaaacatta cctaaccgta   27780
aacttcctga attttttgac gaatatatat tacaactgct gggattatac tgggaaaacc   27840
atggaactat tcaacgagca ggaaacaact gtgtgcttat acagcaacat accctcattc   27900
```

```
ccgtaaatga agccctgaga acagcagcat ctgaagaaaa ttatgagatc gtgagccttt    27960
tattagcgtg ggaggggaac ctttactatg ctattatagg ggctctagag ggcaaccgcc    28020
acgacttaat tcgtaaatat gatgaccaaa tcaaggacca tcatgaaatt ctgccattca    28080
ttgacgatcc agtcatattt cacaaatgcc atatcatgcg gcaatgcttt tttgattgta    28140
ttttatatca agctgtaaaa tatagtaagt ttcgcgttct tctttacttt aaacatagat    28200
tagaggatga tttgcccttc actcatttac ttattgaaaa ggcatgtaaa gatcataatt    28260
atgaagttat taaatggata tatgaaaacc tacatatcta caatatgata gatacctttg    28320
aatgtgctat tgcccataag gatctacatc tatattgttt ggggtataga tttatatata    28380
acagaatcgt acccgataag tatcatcatt tagatattcg catgctttca agcctacaac    28440
tcctacataa ggtggcagcc aaaggatact tagattttat cctagaaacc ttaaagtatg    28500
atcataataa agataatata aatattattc taacacaagc tgcaacctat aaccatagaa    28560
aaattttaat ctatttcatt cctcaatcaa cccacgcaca gatagaacaa tgtttactag    28620
tggcgataaa agcaaaatct tccaggaaaa ccttgaactt actactgtct cacctaaacc    28680
tttccatcaa cctcatcaaa aaaataagcc attatgttgc cacttacaat tcaacaaata    28740
taataggcat tctgagtatg cggcggaaaa agaaagtata tttagatatc atattgacaa    28800
aatttgtaaa aaaagctatt tttaataagt ttgtcgttcg atgtatggat acattttcta    28860
taaacccgga agaatccttt aaaatagccg cgcgaataaa taggatgatg ttagtgaaaa    28920
aaatatctga acatgtttgg aaaaatcatg cggttagact taaataccttt aaacatgcgg    28980
tacacacgat gaagcataaa gatgggaaaa atagactcat gaactttatc tatgatcgct    29040
gttattacca tatgcaaggg gaagaaatct ttagcctcgc aagattttat gcaatccatc    29100
atgcaccaaa gttgtttgac gtttttatg attgttgtat cctagatacg atacgattca    29160
aaagccttct tttagattgt tcacatatca taggtaaaaa cgctcatgat gctaccaata    29220
tcaacatcgt gaacaagtat atcggcaacc tgtttgttat gggagttctt agcaaaaaag    29280
aaatcttaca ggactatcca tccatttatt ctaaacaata catgccttag tttatttttt    29340
ttgcggccga acattattc ttaccctaga aaacgcttat agtcatctta aatcataggt    29400
aaggaagatc atcatatttt ttgaaacgta attttttaac gcatgatcta tgatttcagg    29460
gtccgtgctt ttaggcaacg gggtggtggc cggactataa atctttaggg ataaaatgtt    29520
ctttataagc tcatacccct cccctaaagc tgtagtaccc tcttcgaaaa catcagcccc    29580
cagatctata caaaagaaca tgttttctat attatagtac tgtattgagc taagcatggc    29640
ttgattgatg ttggcgccca ggacatagca gtagtacatg gttgaaaggt tgtggtcttt    29700
gatgcaggcg atccgcatca tctcttctat gtccatatgg atcttgtcct tttcatacgc    29760
ctcatgaagg tcaaacacat tattaaaaca aagagcacat gttaaccgcc acgtattcag    29820
gtgtgtatat ttttggtaaa aatactgtat ggcctctttc aggttatagc gtatggctat    29880
agcgtaccag tatttgagta gtaatgtact gagcgaaaac tcattattta gcagatcggt    29940
ttttactatt aactccctta actcccagaa aatttctatc ctcatttta tattatttac    30000
tttttgtaat atcggattgt tggaaaacac ctcatggcat aaaataatgt tactactagt    30060
tttatgaaac tttagatcta taaaaatttg taaaatttct tcttcattca aggtttcctt    30120
ggcacctagc tctcgacaga ggtcccaggt gtgctccgtg ttgacagata ccagcccgta    30180
gttgatgtcc gccccccact ctgcaaacag ttttataagg ttgtagttgt tttcccttac    30240
agccttcact aacgccgtat ttaggtttaa gccctcttta ataccctgctg attttatgag    30300
```

```
ccttaggtta tgatcaaacg tgatcggagc atcatgccac cataggtcat aacactttaa    30360
aagataatgt tggttcgtgg gcacgcattg tccagccaac accttttgg  tcagagattg    30420 cagggaaggc aacatgtctc ttcatctttt aaaaaaaaat caaattaatt agccgaataa    30480
atttttcttt cgagggcttt ttaaaagagc tctttaagag ctcttaaga  gcttttaag     30540 agattaaaaa attattcttg ctggcattct gccaagtatg cggcattcct atcatctata    30600
gtatattatg agaatattcc caaatgatgg ataagttttt tgatttataa tcttttaata    30660
aactgcttat ttcttcgggg tcctttaagt ttagtggcaa ggaagcatct gagctgtaaa    30720
tatccaaagc caaactatgg ctcagaaaat tataaccttt ttgttccgct atggcacgac    30780
cctcttcaaa ggcattacca cccaaatcta tacagaaaaa tatattaccg atgttataat    30840
attgtactga agtaagcata gcttggttga tgttgccccc cagcgcgtaa cagtaatata    30900
ttgttaatgg attgttatcc ttggtagaag ccagacatat catgtcatgg acgtctattt    30960
ggatgttttc cttgtggtac atctcatgaa gctcatatat tttgttataa tacaggagac    31020 atttttaatcg ccattcatta agatccgtat atttctcatc tagaaaacaa atggcgtcct    31080
tacaatcgta ttgtactgct ttggcgtacc aatacttcac tagtaaacca tttaactcgt    31140
ccgtttcttt tatttctatg agcccccata gtctttttata aattaagccc cttaattgta    31200
taacaaattt gttttctaaa ataggattat tcataaaaat ttcatggcac aaaataatac    31260
tgccgctggt tttattgtgc attatcctgg taaaaatacg gaaatatcg  ttgtcctcta    31320 gagtttcttt ggcgcctagc tgtctacaca actctcggat gtgcttcgta ttgatagaaa    31380
gcaaaccata gttgatattt gcgccccact ctgtaaagag ctttatcaga ctatagttgt    31440
tttccttaac agctattatt aatgccacac gaaggtctat atcttctcct aaaaatcctg    31500
attttatttg tattcggcca cgatccatac aaagcttgag aggagcatca tgccaccata    31560
ggccacaata tttcaaaatg cagtgttcat ctattgacaa acactggctg gctatcgtct    31620
ttttgacgag ggtctgcaga gagagcggca acgacatgtt tcttttcac  caaaaaaaat    31680 caaatgttct cgtctttaaa ggttaattca tgttcttaaa atgttcattt catgatagtg    31740
attaataata tggtttaata acgctagaag gcttgtttat aagacagtca taagcagtct    31800
ataagacagt ctataagcag tctataaagc agtctatgac ttagtctata actataattt    31860
ctggatgggc tgtaagatac tcttcggctc gtttcagatt ttttgaagta tatgtcttta    31920
gcatatcata tatttcctgg ggttcggtta catctaatac caaggtcaca tcacggctga    31980
aaagctgctt tactaagaaa atgttgctca agttatacat ataagctttg tgcgcaatga    32040
gttgtgccct atcaaaatcg gcagccccca aatcaataca gaaaacatg  tttaaagtat    32100 tattgttata gatagaaaga ttcatgccat aatcgagact agcccccaac ctatgacagt    32160
aataaatggc cgcgtaattt ttttcccgca agcaagcaaa tttcatcatc agattagggc    32220
tgatgcaaat ctcttttttca cgacacaact cgtgtatgtc aaaaatgtta ttaaaataaa    32280
ggctacaagc tacccgccaa tagaggtgat ttttatgcct tttatagaaa tagtgaatag    32340
cctttgtaaa attatgtcgt aatgccaggg caaaccaaaa ctttgttaat aggtggtgcg    32400
ccgtatcccc cgtcaacgga atgtttgaac aggtgtacgt aactgtgtct aaagtggttc    32460
tagttacggt ttccaagagt ggattatgac aaaacatgtc ataacccagc agaactcctg    32520
cacaggattt tagcctggcc acttctttta aaatttccag aagacggggt tcggatacag    32580
gcgttaagcc tcccagttcc gcacacagcc gctttagata cacggcagga acacgtataa    32640
```

```
gcccatattc aggatttgcg ccccaatcca caaataaacg tataagttca agattatcgc    32700
tcttcacggc ctttactagc gccgcttcga gacaaagatc atcctcagaa aaacactgta    32760
aatgtttata cgaaaaaact tgcttacaat tgttacatag gtgaatagga cctaaatccc    32820
accacaaacc aaaacgctgc aacgtataat catagtcact tgaaagataa ttgcatgcca    32880 caacttttt ggccaacgtt tgtaaagaca acatactaag tttaaaacat cttaaatcta    32940
agctagctaa cttcaagaa aaccctctat ccctaagaat atatcttata actagactta    33000
tagcagtaaa aatcaacttt ggttattctt tttaatataa aacgtctaat tacttgcaaa    33060
ggactataaa gcccattttc ctcagctaga attttatt tttaatgaag taggggata    33120 tgttttccct tcaagacctt tgccgaaagc atcttttat tcttcccgat gttttggcg    33180 agcatgtact acaacgatta ggactgtatt ggagatgtca cggctccctt caacgcatag    33240
gagacgacca catactcata cgacgggatc tcatcctttc caccaacgag gccttaagaa    33300
tggcgggaga ggaaggaaac aatgaagtag taaagctctt gttactgtgg aagggaaatc    33360
ttcattacgc cgtcatagga gccttgcagg gtgatcaata tgacctgatc cataagtatg    33420
aaaaccaaat cggcgacttt cattttatct taccattgat tcaagacgcg aatacgtttg    33480
aaaaatgcca cgctttagaa cgttttttgtg gtgtttcatg tctgctaaaa catgctacaa    33540
aatacaacat gctccctatt ctccaaaaat accaagaaga gctgtctatg agagcgtatc    33600
ttcacgaaac cctatttgaa ctagcatgcc tatggcagag gtatgatgtc cttaaatgga    33660
tagagcaaac catacatgtt tacgacctaa agattatgtt taatattgcc atctccaaga    33720
gggatctgac tatgtactcc ttaggatata ttttcctttt tgatagaggg aacaccgaag    33780
ctacgttgct aacgcaacat ctcaagaaga cagcggccaa agggctcctc cactttgtgc    33840
tagaaacgtt aaaatacggc ggcaacatag ataccgtcct gacccaagcc gtaaagtaca    33900
atcatagaaa acttttagat tattttctgc gtcaactacc tcgtaaacat attgaaaaac    33960
ttttgttgct ggccgtgcag gaaaaggctt ctaaaaaaac attgaactta ctgttgtcac    34020
atttaaacta ctccgtgaaa cgcatcaaaa aactaccgcg ctatgtgata gagtacgagt    34080
ccaccttggt gataaagatt ttattaaaaa aagagtgaa cctgatagat gccatgttgg    34140
aaaagatggt aagatatttt tctgcgacga aagtgaggac gatcatggat gagctttcga    34200
ttagtccgga aagagtcatt aagatggcta tacagaaaat gagaacggat atcgtaatcc    34260
atacttctta tgtttgggag gatgatctag aacgtcttac tcgtcttaaa aatatggtat    34320
acaccataaa gtacgaacat gggaaaaaaa tgttaattaa agtcatgcac ggcatataca    34380
aaaacttatt atacggcgaa agggaaaaag tcatgtttta tttagccaag ctctatgttg    34440
ctcaaaacgc ggccacccaa ttcagagaca tttgtaagga ctgttacaaa ctggatgtgg    34500
cacggtttaa accgcggttt aagcaactaa tattagactg tttagaaatt attactaaaa    34560
aatcttgcta tagtatcctg gaaatcttag aaaaacatat tatttccctg tttactatga    34620
aagttatgac tgaagaagaa aaaaacctat gtttagaaat attatataaa gtaattcatt    34680
ataaaacaat acaatgttaa aattcaatag atatccatca ttaatattga ttatattttc    34740
gaatattatc ttctatggtg caagataatc atctagcgcg tgaaacatgt cctcttctct    34800
tcaggaactt tgtcgaaaaa agctgcctga ctgcatactt ccagagtttt ttgacgacta    34860
tgtattgcaa ctgttaggac tgcactggca agatcatggt tcccttcagc gtatcgagaa    34920
gaaccagata cttgttcaac aggaacccat ccatatcaat gaagcactca agtagcagc    34980 atcggaaggg aactatgaaa tcgtagagct gttgttgtca tgggaggcag atccccgcta    35040
```

```
cgccgtcgta ggagccctag aaagcaaata ctatgacctg gtttacaaat actatgacca    35100
agttaaagac tgccatgata tcttgccgct gattcaaaat ccggaaacat tcgaaagatg    35160
tcatgagtta aacagcacct gttcactgaa atgcttattc aagcatgctg tgataaatga    35220
catgctgccg attcttcaaa aatatacaga ctatctggat aggtgggagt attgcagcca    35280
gatgctgttc gaactggcat gtagtaaaaa aaaatatgag atggttgtgt ggatagaggg    35340
agttctaggc gtcggcaaag ttacatctct tttcaccatt gcgattagca acagagacct    35400
acagctgtat tctctgggct actcaattat ccttgagaat ttgtactcct gtggacagga    35460
ccccaagttt ttactaaatc atttcctgcg agacgtttca ataaaagggc ttctacccct    35520
tgtaatcaaa accatagaat atggtggaag caaggagata gccataactc tggctaaaaa    35580
atatcagcat aaacatattt tgaaatactt cgaaacctgg gaaagctagg ttcagtatgg    35640
tgtactcact attgtagtga atcgtatcct gtaaattttg taaaaaagct taaacttttg    35700
accacatcat attgttttag aaatctcaaa ccagtgaaca acagtcttat catacattaa    35760
aattccagta aaatttatat ttttttttggt aaacaaatgt tttctcttca agacatctgt    35820
cggaaacatc tttttcaact tcctgacgct tttgatgaat atatattaca agcgctagga    35880
ctatactggg aaaaacacgg atctcttcaa cgaataagaa aggacgctgt gtttgtacag    35940
cgaaacatcg tccttttctac caatgaggcc ctgagaatcg cagcctcaga gggaaacgaa    36000
agggtaataa aacttctgtt atcatgggag ggaaattttc attatgtgat cataggagct    36060
ctagagggtg accaatatga cctaattcat aagtatgata gtcaaattaa agactaccac    36120
atgattttat cattgatcca aaatgcaaat acctttgaaa agtgtcatca gttatccaat    36180
agtaatatgt ggtgtcttat acagaatgct ataaaatata atatgctccc tattctccaa    36240
aaacacagaa atattctgac acatgaggga gagaatcagg aattgtttga gatggcatgt    36300
gaggaacaga aatatgacat agttttatgg ataggacaaa ccctaatgtt aaatgagccg    36360
gagtttattt ttgatatcgc cttcgaacgg atagattttt ctttattaac aatgggttat    36420
agccttcttt ttgataacaa gatgagtagt atagacattc atgatgaaga agatcttact    36480
tcattaccaa cagaacacct cgaaaaagca gccactaagg gatgtttctt ctttatgcta    36540
gaaactttaa aacatggtgg aaatgtaaat atggcagtct tatctaaagc tgttgagtat    36600
aatcatagaa aaattttaga ccatttatt cggcggcaaa aatgtttatc acgtgaagag    36660
attgaaaacc tattattaac cgccataacc aattgtgcat ccataaaaac gttaaactta    36720
ctcttgtctt acctaaacta ttccgtaaaa aatatcattg gaaaaatagt acaacatgtc    36780
ataaaagatg gtgattatac catcatatta cttttaaaaa aaagaaaat aaacctagtg    36840 gaacctgttt taacaggttt tatagattat tactatagct attgtttat aaaacatttt    36900 atccaagagt ttgctattcg tccggaaaaa ctgattaaaa tggccgcgcg aaaaggtaaa    36960 ctaaatgatga ttatcgaatt ccttaacgaa aaatatgttc ataaagatga tcttggaact    37020
atatttaaat atctcaaaac cctagtatgt accatgaaac ataaaaaagg aaaagagaca    37080
ttaattgttc ttattcataa aatatatcaa gatattcatc tggagactaa agaaaaattt    37140
aaattattaa gattttatgt catgcatgat gcaactatcc aatttctatc tatgtgcaaa    37200
gactgtttta atttagccgg ttttaaacca tttgttttag aatgtttgga tattgctatt    37260
aaaaaaaatt accctgatat gatacaatat ataagaattc tatcgaaatc tgagtaaaat    37320
ttattttttt gatcagagta agaaaatgtt ctccctccag gagatctgtc gaagaacat     37380
```

```
ctactttcta cctgactggc tcggtgagca tgtgattcag cgactaggtc tgtactggga    37440
aaaacatggt tctcttcagc gaatcggaga caactatgta cttatacaac aggacctcat    37500
catccccatc aatgaagccc taagaatggc aggggaggag gggaatgatg aggtggtaca    37560
actcctatta ctatgggagg gaaacattca ttatgccatc ataggagctt tggagagtga    37620
ccattatagc ctaatacgta agctctatga ccaaatcgaa gactgtcacg acatccttcc    37680
cttgattcaa gacccaaaac tctttgaaaa atgccatgaa ttagataaat cttgtaacat    37740
tttatgtctc gtattacacg ccgtaaaaaa cgatatgctt tgcattcttc aagagtataa    37800
aatgcatcta agtggagagg atattcaagt ggtgtttgaa acagcatgcc gttcacaaaa    37860
aaacgatatt gtgtcatgga tgggacaaaa tattgcaata tacaaccccg aagttatttt    37920
tgatattgcc tttgataaga tgaatgtgtc cttattatct ataggtata cgcttctttt    37980 caatcatcat ataaataata cgaacgaaaa tattaattct ttattgacac aacatcttga    38040
atgggctgcc ggcatgggcc ttcttcattt tatgctggaa actttaaagt atggcgggga    38100
tgtaacgata atagtcttgt ctgaggccgt aaaatatgac cacagaaaga ttttagatta    38160
ttttctccgt cgaaaaaact tgtaccaaga agatcttgaa gaactattat tgttggcgat    38220
acgtgcagat tgttctaaaa agaccttaaa cttgttatta tcttacttaa actattccat    38280
aaacaatatc cgtaaaaaaa tattacaatg tgtaaaagaa tatgaaacga ccgttattat    38340
aaaaatttta cggaaaagaa agataaatct gatagagccc attttggcag actttatagg    38400
atatcatagc tatacctata tggtagattt tatgcgtgag ttttccatcc atccggaaaa    38460
aatgatcaaa atggctgcac gagaatcgag ggaggacttg atcataaaat tttccaaaaa    38520
agtttgcaaa gagcctaaag atagacttca ctatctcaaa agcttagtgt atactatgcg    38580
acataaagaa ggcaaacaac tgttaattta tacaatccat aacttataca agcttgtca    38640 tctagagagt aaagaaatgt ttaatttggc acgatttat gcacggcata atgcagtgat    38700
ccagttcaaa tcgatttgcc acgatctctc caagctcaat attaatatca aaaacttgtt    38760
gttagaatgt ttaggtattg ctattaaaaa aaattacttt caacttatca aaacaataga    38820
aacggatatg cgttatgagt aacatttta gatgagggaa gattctacca aactaactaa    38880
gacctttcgc tagaatgtat cttattgtta atatagatga gatatgtcat tgtgaaaaaa    38940
tagattaggt aggttgtgaa aaacagatta aacttaaaat tatgtgtatt atgtaaaatt    39000
ttagaaataa aaatttattt ttttattga gggtacggaa aatgttctcc ctacaggacc    39060
tctgtcggaa gaacatttc ttccttccaa atgattttag caagcatacc ctacaatggc    39120
tgggattata ttggaaagag catggatccg tccatcgagc agaaaaagac agcataatga    39180
tacagaatga attggttctt tctatcaatg atgctttaca gcttgcagga gaggaggggg    39240
acacagatgt agtacagctc ttgttattat gggagggaaa tctgcattat gccatcatag    39300
gagccttgaa gactgaaaaa tataacctaa tatgtgagta tcatagccaa attcaggact    39360
ggcatattct cctacccatg attcaagatc cagaaacatt cgaaaatgt catgatttaa    39420 gccttggatg tgactttatt tgccttctcc aacatgctgt aaaatacaac atgctttcta    39480
ttcttgtcaa atataaggag gatctactaa atgcaaggat taggcatcgt atccaatccc    39540
tgtttgtttt ggcatgcgaa aatcggagaa ttgaaattat tgattggata ggccaaaatc    39600
tgccaattcc tgaacctgat gccattttta gcattgctgt tgctacaaga gatttagaac    39660
tgttttcctt agggtacaag attatttttg attacatgca aagacaggga atcattcaat    39720
taaccaatgg agttcgcatg gttgtgctaa atcgtcacat tagcatggca atagataatg    39780
```

```
gtcttttacc ttttgttctg gaaactttaa aacatggtgg gaatatacat agagccttat   39840
cttatgcagt aacacacaat agaagaaaaa ttctggatta tcttattcgc cagaaaaata   39900
tagcccctaa tacaattgaa agactttat atctggccgt gaaaaatcaa tcttccagga    39960
aaactttgaa cttgttgcta tcttacataa attacaaggt gaaaaatgtt aaaaagctgg   40020
tagagcatgt agtaaatgag aaatccactc ttgtgttaaa aatttatta gaaaaaagg     40080
aaaatctagt ggatgctgtt ttaacaagac ttgtaaaaca ttctacatat ttccaggtga   40140
gagaatttat ccaggagttt tccatcagcc cagaaaaatt cattaaaata gctgtgcggg   40200
aaaagaaaaa tgtgttaatc gaggctattt ctgaagatat tgggaaaat cccacagaaa    40260
gaattactta tctcaaacag atagtgcaca ccataaaata tgaaagtgga aggcgatttt   40320
tggtagacat cattcacagc atttaccaaa gttactcact aaaacacgaa gatattctta   40380
aactggcaac attttatgtc aaacacaatg caatcaccca ttttaaagac ctctgcaaat   40440
atctttggct gaacagagga acagaaagta agaaactgtt tttagagtgt ttagaaattg   40500
ctgatgagaa ggagtttcct gatattaaaa gtattgtgag tgaatatatt aactacttgt   40560
ttactgcagg agctattacc aaggaagaaa tcatgcaagc ctatgatgct ttagagtagc   40620
catgtattaa cattctgaaa gtagaataaa atatactata tactaaaaac caaattagcc   40680
atttttaact atcttcttct taaaaactct ggataaaaat ttatttttt taatttgggt     40740
agggaaaatg ttctcccttc aggacctctg tcggaagaac accttcttcc ttccaagtga   40800
ttttagcaag cataccctgc atttgctggg gttatactgg aagggcatg gatctatcca    40860
aaggataaag aatgatggtg tgcttataga gcatgatctt actctttcca tcaatgaagc   40920
cttaattctt gcaggagaag agggaaacaa tgaagtagta aagctcttgt tactatggga   40980
aggaaatctt cattatgcca tcataggagc tttgaggact gagaactata acctagtatg   41040
tgagtaccat agtcaaattc aggactggca tgttctcctc cctttgattc aagatccaga   41100
aacattcgaa aaatgtcatg atttaagcct tgaatgtgat ctttcatgcc ttctccaaca   41160
tgctgtaaaa tataacatgc tttcgattct tgttaaatat aaagaggatc tactaaatgt   41220
actatttagg caacaaattc aaggactatt tattttagca tgtgaaaatc ggaagcttga   41280
gattcttacg tggatgggtc aaaatctgcc aattcctgat cctgagccta tttttagcat   41340
tgctgttgtc acaaaagatt tagaaatgtt ttccttaggg tacaagattg ttttttgaata   41400
catggaaaac caaggacttc atttaaccca ggtagttcgt atggttatgc taaatcatca   41460
ctttggcatg gtaataaata aaggactttt acccttgtg ctggaaattt taaattatgg    41520
tgggaatgta aatagagcct tatcttatgc tgtcacacaa aataaaagaa agattttaga   41580
ccatgttgtt cgccaaaaga atatacccca taaaaccatt gaaagaatgt tgcatctggc   41640
tgtaaaaaag catgctccca ggaaaactct gaacttgtta ctatcttaca taaattacaa   41700
ggtgaaaaat gttaaaagt tgttagaaca tgtagtgaaa tacaactcta ctcttgtgat    41760
aagactcttg ttagaaaaaa agaaaaacct gctggatgct actttgacaa gatatgtcaa   41820
agattctaca tactttcagg tgaaagaatt tatgcaagac ttctccatca gcccagaaaa   41880
attcattaaa atagctgtgc gggaaaagag aaatgtgttg atcaagggta tttctgaaga   41940
tatttgggaa aatcccgcgg aaagaatcag gaatcttaag cagatagtgt gtaccataaa   42000
atatgaaagt ggaagacaat tcctgataaa tatcattcac accatttacc agagttattc   42060
tttgaaacct gaagaaattc ttaaattggc aacatttat gtcaaacaca atgcaaccac    42120
```

```
ccattttaaa gatctctgca aatatctttg gctgaacaga agaacagaaa gtaagaaact   42180
gtttttagag tgcttggaaa ttgctgataa gaaggagttt cctgatatta aaagtattgt   42240
gagtgaatac attaactatt tgtttactgc aggagctatt accaaggaag aaatcatgca   42300
agcctatgct ttggagtatg ccatgtatta aatttctgaa tcagtaagca atagatagat   42360
tttagaatat gctgtattaa gttagtttct gaataagtaa ttaatagata gattttagtt   42420
tatgtaaaaa tgttaacatt tgttcataag ttttagatac cattttagag ttacttttt   42480 agatattact attttagcca ttattatctt aaataatcac tattttagat aggtccccgt   42540
attaaaaacc aaattaacca ttatctatgt ttttaataat acttttaaa aaccctccat    42600 aaaaatttat tttttttcat aaaagtagag aaaatgttct ccctacagga tctctgtcgg   42660
aagaaccttt ttcttccact tgagcccttagggcaagcatg tggttcaacg gctgggatta   42720
tactgggaag gccatggttc agttaaacga gtgggtgatt gctttatatg tgtagaccag   42780
atttggatgc tatcaatcca taaggctata caaattgcag cctcggaagg aaatgagaac   42840
attgtcaagc ttttcttact atggaagggg agtctacaat atgccatcat aggagcctta   42900
gagggcaggc aatatgatct gattcaaaaa tattacaacc aaattgggga ctgccatcag   42960
attctaccac tgattcaaga tccagaaatt tacgaaagat gtcatgaatt aaatgttaca   43020
tgtacctttc aatgcttatt tcaacatgct ataagagata acatgctgcc cattttccaa   43080
aaatatggag aagatctgaa tggaaacagg agaatggttc aacttctgta tgagatggca   43140
tgccgattac aaaattatga tatcatcaaa tggataggat ctaacctgca tgtttataac   43200
ttggaagcca ttttagcat tgcttttgtt agaaaggatt taactttgta ttctttaggc    43260
tacatgcttc ttctgggtag aatgagtact gaagatagaa actttatctc aatcataaca   43320
cgccatcttg aatacgcatc aaaaaaggga ctttttgact ttgtactaga atctttgaaa   43380
tatggaggtc aagtggatac agtgttgttt caggctgtaa aatacaacca taggaaaatt   43440
ttggcccatt ttattcatga aattccccgt gaaacggttg aaaagctgat actccatgct   43500
gtggagtcac gggcctccag aaaaacattc aacctgcttt tatcttccat aaactactgt   43560
gtgaaccctt ttgtcaaaaa actactgcac gctgtggtga acacaagta catgcttatc    43620 ataaagcttt tgctcgagcg gcccaaaaag aagataaacc tggtagatgc tgctctattc   43680
aaacttgtaa aatactctac ttatacgaaa atagtaaaat acatgggtga gttttctgtg   43740
gacccaaaaa gggtggtcaa aatggcagca cgactcatga gagtggacct gattaaaaag   43800
atttctaatg atgcatggga agataaaacta gagagaatca agcaccttaa acagatggta   43860
aataccatga accacagaaa tggaaaaaat ctattgatgt acaatattca caatattact   43920
ggatatacct atctgaacac caagaagca tttaacttaa caagattta tgctgtccac    43980 aatgcaacat gtttgtttaa agaaatgtgt aaaagctgtt ttgtacatga taaaatacag   44040
ctcagagaat tgcttgaaga ttgtttacat attgctaata ggcatgatta tatccagatt   44100
gcagaaaccg cagatgaatg tatcaaatat atagatctta ttacatttaa gtaaaccatg   44160
tatatatcaa gtaaatccag attaaatcag gctaattgta aatagttgta gataccatat   44220
aatgaatgtt ttattaggat agtagttcag ttaagatagt agtttagtta agatagtagt   44280
ttagttaaga tagtagttat gttaagatag tagttctgtt aagataatag tttagttaaa   44340
actagttcat gttaagttaa tagttttgtt aagacaatag ttcatttaag tcaatagttc   44400
agttaagtca atagttttgt taagtcaata gtttagttaa gtcaatagtt tagttaagtc   44460
aatagtttag ttaagtcaat agttatatta agacattagt tctgctaata cattagtttt   44520
```

```
gttaagataa taaaaattta ttttttttca tcagggtaga gaaaatgttc tccctacagg   44580
agctctgccg gaagaacatt tacattcttc cttacccctt ggctaagcat gtacttcaac   44640
aactagggct gtactggaag ggacatggat ctcttcaacg aatcggagat gaccatgtac   44700
tcttacagca ggacctgatc tttccatca acgaggcctt aagaatggca ggagaggaag   44760
gaaacaatga agtagtaaag ctcttgttac tatgggaggg aaaccttcat tatgccatca   44820
taggagcttt agagggcgac cgatatgacc ttatccataa atattatgat caaattgggg   44880
actgccacaa gattcttcct ttaatccaag acccgcaaat ctttgaaaaa tgccatgaat   44940
tgagtaactc ctgtaatatt cgatgccttt tagaacatgc agtaaaacac gacatgcttt   45000
ctattcttca aaaacacaag gagcaaataa gattacacat ggcattaacc caaatactat   45060
ttgaattggc gtgtcatgaa cgtaaaaatg acatcattag atggatcggt tattccctgc   45120
acatacacca tctagagact attttgatg ttgcattcgc ccataaaaat ttatccttat   45180 acgtttagg gtatgaactt ctcatgcaca aagtaaatac agaggctgca tatatagaat   45240
tacccaattt gctatcatat caccttcgaa ctgcggcggc aggaggtctt cttaacttta   45300
tgttagaaac aataaagcat ggtggatatc tggataaaac ggttttatcc gcggctatca   45360
ggtacaagca taggaaaatt gtggctcatt ttattcatca ggttccccgt aaaaccgtta   45420
aaaaactgtt actctatgct gtgcaggctc gggcccccaa aaaaacactg aacctacttt   45480
tatcttcctt aaactactcc gtgcacacca tcaccaaaca actcgtacac aatgtcgtca   45540
tctacagttc cacgcttatc gtaaagcttt tactcatgcg gcgaaaaaac aagttaaacc   45600
tagtagatgc cgttttagcc agacttgtaa aatattccac ctatacagac attgtacaat   45660
tcatgggtga gttttctgtg agcccagaaa gggtgatcaa aatggctgca cgggaatcca   45720
ggacctttct gattgaaatg atctccaaag ctgcttgggg aaatcaccca cagacgttga   45780
ttcatcatct caaacaacta accaatacca tgaagcctca atctggaaaa gaccacatca   45840
tatataccat ccactatatt tatctaaact ctaatatgct ggtagcggag gaggaaaaaa   45900
atatttttaa attagcaaaa ttttatgcga atcataatgc ggtaaacagg tttaaacaaa   45960
tttgtgaaga ctattatata ttagatgcac gatttaaaac acttatttta gaatgttttg   46020
aaattgccgt ccagaaaaac tatcctagaa ttgcaaatat tgtggatgac tatattcgat   46080
tcctttttta caggggaaat ataaccgagg aagaaattcg tgaagcctat tctttaaaag   46140
atgctgaggt ttatgtagat ttaaaatggt tacaacaagg agaaatggtt taaaccaaat   46200
ccggtttaaa ctaaatccaa tttaaactac atttggttta tcattagtca ttgaaaccat   46260
cgaaaaaaaa gctatttgtt tatccccata aactcatctt tttttgtct caaagtttga   46320 cactaaaatt cagtgtttta tagtgtttat aattaagtgt tttgcatgca ttgcagaaat   46380
tttcatcttt tttaattggt tcaataccac atgtcataca atatgttgtt tgattatcaa   46440
gattaacttt atgaaaggaa agtaagtgag ccgcaaattt aaaagtaaaa tatctttcat   46500
ttaaaatgat cttatgaatg tattttcgat aaggaggaat gaaagcattt gccaaaataa   46560
atcgcataaa aggcttggaa aaacccatat cttctaatct tttgtgggta taaaccctat   46620
tttggtgttt tacaaaaact tcattgttat aatagtcgtt atagctatca atcatttttt   46680
taagtcctat aatgcccaag gttgcacgca taaagccaca gtttctgctc caaaaagcat   46740
gcacctgtaa agggtgcttt tcatataacc aattacaaaa tttcattccg caacagtagc   46800
atgttatttc agtgggggat gtatagaata atccggcatt cgaaaatttt tcataatttt   46860
```

```
ttatgtcatg gattgcgaag ctttgatttc gtgcatctat ggagctatag cctacatatt   46920
taggttttac ttcaaataat cgcaaagaga tgtatggatc tatcgtattt attttaggaa   46980
acatttcata atttaaatt cttatatata ataaaaaaa aattacaaac atttgtaatg      47040
atcatcctca attgaaggct gagttgtagg ctttattttt ctaattatac gaagaaggta   47100
ggttctcata aagccttcaa gatgactatt gatgtttcca atacattttc tcaatgagtt   47160
cataaaccca gacattttgc taatggcttg gcaaagtgcc aacaagttgt ccacaaagta   47220
ctggtagatt gccactagct atagctagct atagtgagcc aacctctctg tatgtatttt   47280
atatatttca tttttaata gatttaatat tttataaaa aatatttagt tttttataca     47340
agaatgtcga caaaaaaaa gcccacaatt accaagcaag agctttactc cttagtagcg    47400
gcagataccc agttaaataa agcattgatt gaaagaatct ttacaagtca gcaaaaaata   47460
atacaaaatg ctttaaagca caatcaagaa gttattatac cacccggaat caagttcacc   47520
gtcgttacgg tgaaagctaa acctgctcgc cagggccata atcccgccac aggagagcct   47580
attcaaatta aagctaaacc tgaacataaa gccgtaaaga tacgagcatt gaaacctgtc   47640
catgatatgt taaactaaac tataaagtca tattcttctt tatcgttatt atcttcaata   47700
tatttttgcc aatcgaaatc gaataaattc agatcctgga catttaaata cttatcatcg   47760
tacattttaa tataatttaa acatgagttg ttgtcaaaaa cttttagcgt ttttgttaaa   47820
attatcatat gaataatttc cttattaaga gttgccggaa taatacaaaa cctatttta    47880 ggtacatcat ccatgataat agtaaaatta gtaaaaattg tttcttgttt ttcttttgtt   47940
tcaaataaac gttgtaaggt taaggtttc tcgttcaatg gtttctttga agataaaaag    48000
aatgtataat ctggtttaaa ggtatttttg gtttcaatcg tgattccatc tgcttgagca   48060
tatactaaac cagaccaaat ataacggtcc actattacaa tataatttag cttaagtagc   48120
actgcaattt ctgcgataaa ttcactacga tgttttgtaa ataatttatg taattgttcc   48180
gatgacattt ctatggtttt atttaacacc tgcaatataa gatcaccggt ggtcgtgtct   48240
ggattaggaa aatgtataca tatagcatta taatccatgc attccaatgt ttctttaat    48300 ttcattgcct gtgtgctttt tcccacacca ttgattccct cgatggcaat gagtattcca   48360
cgcatgatta ataaaaggaa aaaagaatt cagttttaa catttcttac aaatctttt     48420 ttatacaaca ttgtacaaca ctgcattagc ggtatatgat gttatagctt cattaaatat   48480
ttgcttttat ataatcttta ccaacctata tttggtagat cactgcagat ggtcataaat   48540
aggccataac taagataaaa attatttcag acgctactac ggtagtatta ttaaaatcat   48600
gtgtggcaat gtatgacgtc ttaatagata aaacatttaa ggaaaacaaa tttgaataaa   48660 aaataattg ttatgatggc gttgttacac aaagaaaagc ttatagagtg catctatcat    48720
gagctagaaa atggcgggac aatattgctt ctaacaaaaa atattgttgt gtcagaaatt   48780
tcatacattg gcaatactta taaatatttt acctttaatg acaatcatga tctgataagc   48840
aaagaagatc ttaaaggagc aacatccaaa aacattgcta aatgattta taattggatt    48900 ataaaaaatc ctcaaaataa taagatttgg agtggtgagc cgcgtactca aatttatttt   48960
gaaaatgatt tatatcatac aaattacaat cataaatgta taaagatttt ttggaatgtt   49020
tcaacttcag tcggtcctca tatctttaat gatcgtagca tttggtgtac taaatgcaca   49080
tccttttacc catttaccaa cattatgtcg cccaatatat tccaataaat tagatatctt   49140
tgctattaaa atagttaaaa accttatagg ataattagg acttattac gataaattat      49200 gatattttat aattagttac tttattataa ttaatctctt tattaatgaa ttatcataag    49260
```

```
ataactaatt attttttcc atatatcaga taataaatct gatatgggct aaaagtatgt   49320
ttcaaactat ttacaataga atttctgtta agaaaacata cataatttga ataaaatttt   49380
tttaaatatc accgaaacaa tcaacatggt gttaatagag ttttttaacag gtttcttcta   49440 tttatatgga aagagactgt tttccattag taaagtcatg gacatgatat gtctagacta   49500
ttataccatt attcctgctc ctctggcgat gatgttagcg gcaagactaa aaaactatga   49560
cctcatgaaa cgactgcacg aatgggaaat ctctattgac tacgctctac ttgtagtaga   49620
tgatgtgccg tctattgact attgcttaag tcttggcgct agatccccga ctagagcaca   49680
aaaaagagaa ctgctgaggg acaacacgtt taatcccgtg tataagtatc ttatgaactg   49740
ttccggcttc ccaacaaaga gagaaaaaaa cattccttgt gatgttcaat gcgaaagact   49800
gcaaaaaaac attataaaag aactggtatt taactgctct gtactgcttg aaatggtact   49860
gcacacagaa agagaatatg catacgccct acactgtgct gcaaaacata accaattgcc   49920
catcctcatg tattgttggc aacaatccac agacgcggaa tctattttgt tgaaaacctg   49980
ctgttctgat aagaacatca attgttttaa ctattgtatt ctatatggcg gcgcccaaaa   50040 tttgatgct gcaatggtgg aagcggcaaa gcacgatgcc cggatgctga taaactactg   50100
tgtcatgctt ggtggaagat ccttaaacga agcaaaagaa acggctgcca tgtttggaca   50160
cattgaatgc gcacaacact gttttaaact gcagtcttac gtcgtggaca catcgaatac   50220
agacgacact gattaaagcg acaatcttac gtcatgaacg actgtctttt gagtatctat   50280
acttacatta tattttttta tgaaaaaaat ataaggttg tatacaaacc tttgtataca   50340
agaaatttgg atcattaaac aataattaat ttggacacag gaaacgatct agatcgatca   50400
aaaagctatt ttttttgcac acagaacatt tagataattg agagattact ttccatactt   50460
gttaagcttt tttacacaca ggaactttgg attctgttca ggaagttttt catagacatt   50520
atgtttacag ccagtaataa taattttggg ctttttctta aaccaccggt ggaaaacatc   50580
cagcttgtaa agagggaaat gcatgtagag aggttttggt agtcatggtt aagagatttg   50640
actaactcca tgtttcctgt aaagactgcc cagtcccaag cagtaaaacc tctatgatag   50700 tcttttttgag tcggatctgc tccaaatttt atgagagaaa gcatatttaa agaacggccc   50760
cgtattgcgg ccttcatcac aggagtcatc ccattaaaat tcggtaaaca aattctggtc   50820
ccattttttc cgaaatagcc caacacccct tccaggatta aatgattttt tttctcagct   50880
aaataatgta aagcagagtt tccatctta tccctcctat gagggttaat tatttctcca   50940
ggataagatt cttgttcaaa aagaaatttt aaaaagtcta tacgtccgta gatgcatatc   51000
cacatgaata ccgaggatcc attttatcg catctattga caatccacgg atctgtttta   51060
aaaaattcct caaatagtgt aagattccca tttctaatat gtttttaat ccatttaaca   51120 aacaagtttt ctatctccct ttctggaaac atgtgttcca ttttgaatgt cgcccctact   51180
ccactatatg attttactcc tttaattttt aatgtccttt ttttcggac ttctttggat   51240 aagctgttta ttaccatctt taaatgcctt atagcgggga ggagccaggc ccttttccca   51300
tatgtgcggt aattcttggt gtttatgctt gcctttggca taaccaggcc agtattttc   51360 gatatattca gggtttgttt ttacgtattc ttttaaaggtc cgataggctt cttgaataca   51420
ggtaggctca ccggtataat ttccatgttc atcttccttt aaaaagccat taaccctgtc   51480
ctttctccac ttaagattgt gctttccaaa aatgcgatca agatcttgcg cctgctgggg   51540
tggaatcata aatccctttt taggtcgaag cttttattt tttccatagc ttcggccatc   51600
```

```
gcgttgcgaa acagtggtta ggacgcctga tagtctttcc atgggcgtcg catctaatcc   51660
tatccatcca ccctgatgaa tatcaatggc aacaagctct cctttatttt gggcaagcca   51720
agtttccaag aatgccatgc tttcttccca gggataaggc ccgccaacac cacgggttgt   51780
ccaatcttgc aaggactcca ggtccgacac ctggtaaggc tctaaagaag acggttcctt   51840
gtttttgtac tgcaaataag atttaatgac ccatttatac catgtgtcga accgcagcgt   51900
ggcgcctcca aagtgaaagc cgtcgttgat tttaggatat ctgcaacata tttcaaccgt   51960
acgtttgagt tctgcaaaag cggccttcca aggaagtctt tcgctgcggg taagacggtc   52020
tattttgccc tgcgtgccat agcgtatggc atgtcgtgcc aattgcaaca attctgacac   52080
cgatccgtgg gccccgatcc agtttatcgg ataggcaacc tccgaagggt ttaaaagatg   52140
ctcgtaaaag cgtggatctt cagatgccaa ggcgtctgca aagggataa tgctagaaaa   52200 cctgtctaga catacgtttt ctgtgtttac ttctaaaggt agaaaatgg ttgcgtgagg   52260 cttttgaacc tgcttgttca gcggtctgca tatgctttga ataatgtctc taggactatg   52320
tcgcggcgct gcaaaaaata ccgcgtttag ttctggaacc tctacgccct cttgaaagag   52380
tcgacagttt aataaaataa cgggttcctt tgaggaacaa aattctgtaa atgttttgag   52440
gataacctgt cgcggcaggg ttgagtgagc tatcagggca tagacccctt ggtctaccaa   52500
cgccgcgtat agctccttgg cctgtttaat atcacgggta ataccagca ttttaggagc   52560 cggtatattg gttttaaat aggctaaggc cattataatt tgcttacta tgatctgttt   52620 cgtggtctcc tctttggtac tcggttggtg ggccaattta ggcgcggcta ccatctgcaa   52680
ttcaaaatca tttacatagc cggcctctat gccttctcgc agatagtagc gaaaggcaac   52740
gccgccaaaa agttcacgat ttttcatgga aagcggggtg tcgtacctgg gcgttgccgt   52800
taaaaaaagt cggtgccctt ttttaaagtt gagcaacacg tgggtaaagg gccgtgtctc   52860
ccattcgccg caaatccggt gacattcatc gctaataata agatcgaaat catccaccag   52920
tagcgtggag gattggtagg tggcaatcac aagaagagaa ggggcctccc gtatccgttt   52980
tgcaataaag acaggattgg tggtcatttc tatattgtcg tgatttagca caatgcgggt   53040
ctggtcagac cccacaagca aaacgttctt caaagaaatt ccatactgat agagttttc   53100 cagagtctgc cgtagtaggg acaggcccgg caccaggtac aaaactttc cttgaagata   53160 attggagagg ataagatagg cgacgcgagt tttgccgcat cggcaggcca tctgcagaat   53220
ggccctccca cttcgccgca gctcctgata gcccatattg gccgcctcct tctgataaag   53280
tcgatcctcg attgcagtcc gtgtctcatc tgtagaaaaa aataatacgt catctgcgaa   53340
atgttcatct tccacaggag ttatcaccag gtgtctcagt ttctccttgc ttatcagcgg   53400
atcagagggc aaagatggct caaccactat cgtggaatca ttcatctcat aggcgggaga   53460
atcacacaaa gtatagctta tgtccagaca gtttgcaaca tcctcagcca attgttttat   53520
tttttcgggt aaaagacata cgagttcttt gtttttgacg cgaaaaaact gtgcacaata   53580 taacaccct gcttcaattt tttgcgcatc cttctttgta gatgtttcca atgtgaaaca   53640
atacttccat tcatccgtaa aacaggttgt ataagatcca tcatgaagcc tagcggccaa   53700
gtttcctgtg tgcccaactt tatgtaagga ttgggcctcc agccagggat gaaccgccac   53760
gtaaaatcct gcgcacatgc tatatcaaat tgcagtttct taataactgt acacaggatc   53820
tgaaaaacat gtgattacaa aatttagata agaaatattt aatattaaaa atcacagaat   53880
acatgtcact gtgtagagag aaagccaaaa actcctcttg accgccgtgg gaaatcatcc   53940
agggtagtag gttgtgtttc ataaagttgt atgccgtagt gatcaccgtg gactccagat   54000
```

```
ggttattggc atctttgcaa tactttgcca tcttggcaga aaagacgata aatccacaaa   54060
ttctacccca gttgataaga tccttaaaca gctcagtcac aaccccagta aactgggttt   54120
taatttcttg aacactcgta agagaaaagg taattgtaac ctgtttgttc aaacactcat   54180
cataataggt taaaattttt tttatttgtt gttgatatgg gctaagctca tgctctgaaa   54240
tatcattaat gtaatattta atatatccca ctagtatttc attaatgata ttatgatata   54300
ttaactcttc tccctccata gcggcaccct atattttttt atttaggttt caatgttatc   54360
acaattgcga tacaattgtg atacaattgt gacacaactg tgttgtatac aacaaatgtt   54420
aggccacgta tagcaaccta tatgttaaga aatattttta tcccaacatt agttggaaac   54480
gagcagccgc aaagaagtca tttaaaataa gccatttaaa gatttagaat ttatatgtat   54540
acaactgtac aatggaagca gttcttacca aactcgacca ggaggaaaaa aaggctctcc   54600
aaaattttca tcgttgtgct tgggaagaaa ctaaaaatat tataaacgat tttcttgaaa   54660
tccctgagga acgatgcacc tataaattca actcatacac aaaaaaaatg gagcttttat   54720
ttacccctga attccacacc gcctggcatg aagttcctga gtgcagagag ttcatattaa   54780
acttttfgag actcatttcg ggacatcgag tggtattaaa aggccctaca tttgttttta   54840
caaaagagat caagaatctg ggcattccta gtaccatcaa tgttgacttt caggccaaca   54900
ttgaaaatat ggatgatcta cagaagggaa atctcatcgg caagatgaat atcaaagaag   54960
gctaaataaa acaactaaca tcaaaaaaca ttaaaggcta tgttgtggac gatgcctttg   55020
tctcaatagt ttcgaggtca tccaataact catgtaacgt aaaaaagttg gtccattttt   55080
ttgaaaacat taaaagacgt tcgtcttcat aaataaaaaa gtcattcgaa ggaaaaatga   55140
tatactcaat accatagtct tgtaatattt ttttaggtc tctcagggtc cagggattta   55200
ccaggcttct acgcgaagtg agcatcataa aaatatctaa tatttttgc gccataagcc   55260
agcgcggatt ctcattggcc cacaaatcaa caataattct cttatcaacc gtgagcattc   55320
ctacttgatt cgaagaaatg attagatgcc cagcagtcca ccccatgagt agataacgca   55380
gcgttgtaga aatgtcacat atggaaggca ttcctccaca acatgaaccc aaattaggat   55440
gcgtgtgaaa cacaaacata gcaggcttgt tggccaccct gctataaata tcagcaggca   55500
tcatagcctc gctgccaaaa taaatgttct ctcctgccct ataggggctt ggaatgattt   55560
ccactatctc gggtacaccg tttatcatat taatgcggcc gcaccattca cggtcatcgt   55620
ccaaaaattt tttgatggca ccccgaacat tgtcccagtt aagcaacaga gtattcacaa   55680
tctcattacg ctccgcccag tattccttaa aacttctttt agacttgctg agctgttccc   55740
aggattcgaa ctcagtccaa tgtttttttt cttttgggga agacttccct tttgaaacat   55800
tttttgcggc tccaccatct acactatgat tttccaaaat aatctccttc atcgtttgag   55860
ttatatgggc attgctaagc accttagtgg taacctgttt acctatgtga tttagcagaa   55920
aaccaagttt gtccatttgt gtctcaacca tttattctta acaaaacaaa aaaaattaaa   55980
aatcatcgtc gtttaaaaag agtttgaagg caaacgcatc atccttaaca cagttctgat   56040
actgcgtagg tcttaactcg aaaaagttgg tttttcctac ttcattaaga aagaatttag   56100
tcatctgagg aaaagggttt cccacccttat aaatgcttt gcactgcatc atgaagcaca   56160
aattatctgt aaagtagcgt atatattgaa atagcatttc ttttgaaaaa ccgggaactc   56220
ttcctcttgc cttgtcaaag gcatagttaa taaactcatc caccaactcc acagcctcct   56280
tcaaaatttt gtgaatgatc ttttcctcgg gaatgttata cacgtaattt gagataagaa   56340
```

| | | | | | |
|---|---|---|---|---|---|
| aacacgcaaa | actacagtgc | atcccttcat | cacgtgagat | aaactcatta | tagcttacaa | 56400 |
| gccccggcat | aatattctgt | tccttaagaa | actggatcgc | cacaaagtgg | ttttgaaata | 56460 |
| aaatgccttc | tacggcggcg | aagcccacca | gccgctcacc | tagagtgttc | ctgtcgggt | 56520 |
| ccatccactg | ccgcacccac | tgcgccattt | ttttatgat | agggtgtttt | tcaatgccgc | 56580 |
| taaagatgcg | ctgttgttcc | ttctcatccg | ggatcagcgt | ttttacctgt | attgagtagg | 56640 |
| cttcgctatg | aacgcactct | tgggcagcct | gcattgtata | aaagtataac | acttccttta | 56700 |
| ctttaatttc | gcgcataaaa | ttggttaaaa | ggttttcgat | aacaatttcg | tcggcaacaa | 56760 |
| caaagaaggc | taaaatttgt | ttataaaatt | cgcgctgtgg | ctttggcatg | gcttcccaat | 56820 |
| catcaatgtc | cttacacatg | tccacctcct | gcgccgtcca | cgtcaaactt | tctaattttt | 56880 |
| tataccagtt | ccaacattcg | gggtgctgaa | taggaaaaat | agtgaaacgt | tgggaatttt | 56940 |
| caattagtaa | ttcctccata | tttgaaataa | atattaacat | cttcaaattt | attggctgcc | 57000 |
| atggagacgt | ttttattga | gacgttggca | tctgatgtgt | atggaaaggc | gttaaatgtt | 57060 |
| gatttagata | gactatcgca | ggcgcaggtt | aaatataccc | ttcaagagct | tatttcctac | 57120 |
| tgcagcgctc | taaccatttt | acattatgac | tattcaaccc | ttgcggcgcg | tctttcggtg | 57180 |
| taccagctgc | accagtcaac | ggcctcctcc | ttctcaaagg | cggtgaggct | gcaggccgca | 57240 |
| caatcctgct | cacgcctgtc | cccccagttt | gtggacgtcg | tttacaagta | caaagccatt | 57300 |
| tttgacagct | acattgacta | tagcagagat | tacaagctgt | ccctcctggg | gatagaaacc | 57360 |
| atgaaaaatt | cttatttgtt | aaaaaataaa | gatggggtca | tcatggaacg | cccgcaggat | 57420 |
| gcttatatgc | gggttgccat | catgatctat | gggatgggaa | gagtggtcaa | tatgaaaatg | 57480 |
| attctgctaa | cctatgacct | gctttcccag | cacgtcatca | cacacgcgtc | gcccaccatg | 57540 |
| ttcaatgcag | gcaccaaaaa | gccacaactc | tccagctgtt | tcctgctaaa | tgtaaatgat | 57600 |
| aatttagaaa | atttatatga | tatggtcaaa | acggccggca | tcatttcagg | cggcggcggt | 57660 |
| ggaatagggc | tgtgcttgtc | aggaatacgg | gcaaagaata | gttttatttc | tggtagtggt | 57720 |
| cttaaaagta | acggcataca | gaattatatt | gtgctgcaaa | atgcttcaca | atgctacgcg | 57780 |
| aaccagggag | gcctacgtcc | cggagcctac | gccgtctact | tagagctgtg | gcaccaagac | 57840 |
| atctttacat | ttttacaaat | gcctcgccta | aaaggacaaa | tggctgaaca | acggcttaat | 57900 |
| gccctaatc | tcaagtacgg | cctatgggtc | cccgacctat | tcatggaaat | acttgaagac | 57960 |
| caaatacaca | acagaggcga | cggcaaatgg | tacctctttt | cgccggatca | ggcccccaat | 58020 |
| ctacataagg | tctttgattt | ggaacggtcg | cagcacgaaa | acgcacaccg | cgaatttaaa | 58080 |
| aagctttact | atcagtatgt | tgctgaaaaa | aggtacaccg | gcgtcacaac | ggccaaagag | 58140 |
| attatcaaag | agtggttcaa | aacagttgtt | caagtaggga | atccctatat | cgggtttaaa | 58200 |
| gatgccataa | atcgtaaaag | taatctttca | catgtaggca | ctatcacgaa | ctccaatctt | 58260 |
| tgtattgaag | tcacaatccc | ctgctgggag | ggtgataagg | ctgaacaagg | tgtttgtaat | 58320 |
| ctggccgcag | taaatctagc | cgcctttata | cgtgaaaatg | gctacgacta | ccgtgggctc | 58380 |
| atagaagcat | caggcaatgt | cacagaaaat | ttagataata | ttatagataa | tggctactac | 58440 |
| cccacagaag | ccacgcggag | aagcaatatg | cgtcaccgac | ctattggcat | cggggtcttt | 58500 |
| ggcctagccg | acgtgtttgc | gtcttaaaa | atgaaatttg | gttcacccga | ggccattgcc | 58560 |
| atggatgagg | ccatccatgc | ggccctatac | tacggggcca | tgcgacgatc | catagaactt | 58620 |
| gcaaagaaa | aaggaagtca | tcccagcttt | ccggggtctg | cggcctcaaa | gggtctactg | 58680 |
| cagcccgacc | tatgggttcg | ctgtggtgat | ttagtttcct | cctgggaaga | acgcgtggca | 58740 |

```
cagacgacgc agggtgtgtt gacgccgaaa aggtggtcgc agctacgcct ggcggctatg   58800
cagggacttc gaaatggata tgtcacagct cttatgccca ccgcaacctc ctcaaattct   58860
acaggaaaaa acgaatgttt tgagcccttt acatccaatc tatatacacg tagaacgtta   58920
agcggggagt ttattgtttt aaataagtat ttaatagacg atttaaaaga aattaatctt   58980
tggacagaag ccattcaaca gcagctacta aatgcgggag gtagcattca gcacattttg   59040
gatataccgg ccgagatccg cgatcggtat aaaacctcca gggaaatgaa tcaaaaaatt   59100
ttaacaaaac acgcggccgc acgaaacccc tttgtatccc aaagtatgtc cttgaactat   59160
tacttttatg aacctgaact aagccaggta cttacagtgc tcgtcctagg ctggaaaaaa   59220
ggtttaacta ccggttccta ttactgtcat tttagccctg gagcgggtac ccaaaaaaag   59280
attataagaa actctgagaa agcgtgtaat gcggactgcg aggcgtgtct tctgtaggtg   59340
tctcgcggta aaagagcagc ggggaccata tggtaaaccc caacaagagg ataatgaata   59400
aaaaaagtaa acaggcatcc attagttcca tattaaattt tttttcttc tatataatgg    59460 aatattttgt tgcggtagac aatgaaacct ccttgggggt ttttacttct atagagcaat   59520
gtgaagaaac gatgaaacaa tacccccggcc tccattatgt cgttttttaag tatatgtgtc  59580 cggcggatgc agaaaataca gatgttgtat atttaatacc ctcgttaacc ttgcataccc   59640
ccatgtttgt agaccactgt ccaaatcgta ccaaacaagc acgacacgta ttgaaaaaaa   59700
taaacttagt gttcgaggaa gagtctattg aaaattggaa ggtttcagta aatactgtgt   59760
tcccccatgt tcacaacaga ttatctgcgc cgaaactttc catcgacgag gctaatgaag   59820
ccgtagaaaa gttttttgata caagcaggac gactcatgtc tctgtaaatg tctcttcctt   59880
tatgggtgac gtctcttcct tgccgagga agtctctgtt atgggcaaga ggtttgaaac    59940
aacgcaagga ctctgcttaa tctgctgtct cacaaaggga atcaaactac ctgctttcgt   60000 attttttaatg tagtaattac ccttgttgtg atgaatttta agaccatagc gtagtcccag  60060
tactttatta atgaatttta aaattgtttg agggtccgtt ttattgggct ttttaagctt   60120
aaactcaaag ctgatcgcgc ttaaatcata ctgaacaaat tcatcaacga gtttcgtcat   60180
taattgttca ttggtcaata tattagggtc ctgaacgcat ttaaagccgc acttagttaa   60240
tagcataata gcgtacatat gagattgaaa actataatta aattgtagat catgatgctc   60300
tgcgtgttgc atggcccatt gatgaaagtt taattcctga gtttgtaaca tagtgagcga   60360
ctcgtatact gtctttccgc ggcttatttg gacacggcca gtatagttct gttttgtcat   60420
aaaactattg tattgttcaa caaatttggg agtaatttta tgaccgtgcc atgcataaaa   60480
ttcgagtagt ttatactttt catacgcaaa taggtcttgc tggtctactg tgatgccttc   60540
ctttaagttt tgtttaattt gtaaagcttt attggcatca atggtttcag ccgaggcaat   60600
gtttacatag tcctggtgtt taatttccat tttaatgctt gtatattgtt tgactgtctc   60660
cagcttttca cccgtcagta taaacacctt agcgccggtg tcggcgatct ggttaataaa   60720
tcgggttata aagtgatttt ttgatagatg ttgtatccgc attgtttcga gccatagatg   60780
gtagtatgga gttttataat atatcggcct acctgtttcc ttactatacg tgaaggaaag   60840
ctggtgattg cttatggtct gaaaaagggt gtcacgtttt tgtaacgtaa acatttcaat   60900
gtcttcgatg gtttctggat agtaattttg tttccctgt aagcagattt tataacactt    60960 acttttaat tcacgcacgc ggcccaacat ttggcaacat gtttctacgt cacacgacat    61020
attgttaaaa aagccgtata aaacatcaaa tctcttatct tcgtatgaaa cacccgctga   61080
```

```
aatcgtgggc gtatagataa ggatatcaac gagcccccaa taatacgata cattattaaa   61140
atgggattcc cgttcatgag cagtgctttt agaactataa acccaatttt ttttttccgg   61200 aaacttttt tggataaatg attgcaacag ccgggcctcc attaatgaat tgtagggat    61260 aacaattttt ttgtcttcta gcaaatcctt taaaaggtta tttaaccaag tttctcgtga   61320
agaggtaaaa taatacgtgt catgctgggc ccttttatat tgattccagt gaaagaagat   61380
agggacatcc ccgcgaaaac gctgtagaat attatacgtt cgatttccta ggtttgcgtc   61440
caagcatata acataatttg ccgtttcgag catccacatg aaaatggcaa aagagggagc   61500
aaagtatttg tgcaggccgc tattgaattg attaaaaatc gattctacct catccaaaat   61560
aagtaggtct acaggctcgg ctgtggaggt tagccggaaa agtgattcta cctgaatgat   61620
gactctttcg tagctgtcca aatctccagt tacttcgctg tacaatgtga aattcggtag   61680
ccgggattgt atatttttg agaagatctg tcgaaacgtc acaaaccgta tggtttgttg   61740
ttttgaaata gaattattgc cgtagtattt ttgcaaatag ttgcgcagtt ggacggtttt   61800
acctattttc atttgagcct ttacaacaag cgtagggact cgttcatatt ctcgcatact   61860
actttcatca tagatgtgtt tttgagtatc aggcagttct tcaaagagaa tggactcatg   61920
aacctctatg ctctttgtca tcacttggtc cacatatgtt tccacaaaat tatttgtgcc   61980
ggaaaggctg cccatgagaa ggctatgttt attgtcatgg cgacagtgtt gatacacttt   62040
gtttcccgtg actcttaaaa ttagggtatt gtccttatca tgcatacgct tacatatttc   62100
gcagtaactt ggacttgtac gtttaaacaa tactaaattt ttatgaacac ggaggaagca   62160
atgattttta catagtgttc ctgcaaattt taatacctct tcaagttcac tttgttggat   62220
agtatcgcag gaactcggtg ttgtttcttt tacatttgtg aagatacaag gtaaacacgt   62280
cgtttcaaag ggggttgcta aagggtatc actcttttc gtggttgtac tggtctcaaa    62340
cacctctgca agctcctcat taaacatttt aacacgcatg ctaccttttt tatgagaccc   62400
tatgatgcga aaattttgaa acttttgtt gacctggggg tcaacaaaag gataaacgtg    62460
tttgggaaga ttttctaaca ctttggatgt aaagactttg gcctcattat tgtttaatac   62520
tgagtatgta taaagtatga tatgaaagga gtatttaagt tctcgctttt tatttaatcc   62580
gatagaatct gttagcaaaa tttgttcacg cgttagattg atgttataag gtaaagaata   62640
tgtctcgtaa aatacatcca tgatgacgtt aattatcatg tcaaggatgt catagacatt   62700
gtcttcgaca ttatcattgt catcaacatt gtcatcagag tatgacttat ttaccggaaa   62760
gtcgatgtca aattttaagc gctgaggcaa aaacccaaat accacttcgt ggaaacactt   62820
ctgctcaaag ggctgagccg cctcccactc ccaaaagtca tcacgacttg aaaaaactct   62880
aaaaagatta ttatattcat ctcgcaccac gaagtgattc tttaaggttt cgagagaata   62940
tttatcctct acggcttctc cttgggagtt acagcgaaga aacttgaatg tttcttgcat   63000
tttgatattt aaaattaaat caattatgat gcggccgcta atgcggcggt tgacgcggcc   63060
gcgccgctga cgcagccatc atacataaag cggcatggcc gttttataac gactagtcgg   63120
ccgttatatg acgaactata taaaaatgaa ttcttttaat tagagttaag tattgttgat   63180
tgtataatcc atcatggttg agccacgcga acagtttttt caagatctgc tttcagcagt   63240
ggatcaacaa atggacactg taaaaaatga cataaaagac attatgaaag aaaaaacgtc   63300
ttttatggta tcattcgaaa actttataga acgttacgat accatggaaa aaatattca    63360 agaccttcag aataagtacg aagaaatggc ggccaacctt atgaccgtca tgacggatac   63420
aaaaattcag cttggagcca ttatcgccca acttgagatt ctaatgataa atggcactcc   63480
```

```
acttccggca aaaaagacaa caattaagga ggctatgccc ttaccttcat caaacacgaa    63540
taatgaacaa acgagtcctc ccgcctcagg caaaacaagt gaaacaccta aaaaaaatcc    63600
cacgaatgcg atgttcttca cgcgtagcga atgggcatcc tcgaatactt ttcgagaaaa    63660
gtttttaaca ccagaaattc aagccatatt ggatgagcag tttgcaaaca agaccggdat    63720
cgaaagattg catgccgagg gtctttacat gtggagaacc caattctctg acgaacagaa    63780
gaaaatggtc aaagagatga tgaagaagta atattttttgg taaaaatatt tttatcaaaa    63840
ttttttacca aataataaaa atattttttac tttttttcttt cataatatac atagaatgcc    63900
tacaaaagct ggcacaaaaa gtaccgcaaa taaaaaaaca acgaagggct cctccaaatc    63960
tggttcttcc agaggccaca ccggcaaaac ccatgcttct tcgtccatgc attccgggat    64020
gctctataaa gatatggtaa atattgctag atctagaggc attccgattt accagaatgg    64080
atcgcgtctt actaaaagtg aattggagaa aaaaattaaa cggtcaaaat gaatataatc    64140
aggaaactta agcctggaac aattagcctt gtgctgggac ccatgtttgc cggcaaaact    64200
acgtttctta ttcattgcat ttacatgctc gaacgtttgg aaaaaaaagt agtcttcata    64260
aaatctacca aaaacacccg agacaaaact attaaaacac actccggtat acagctacga    64320
cccaaacaat gtaaaatcat agaaagcaca cagttatctg acgtgggttc tctcaccgat    64380
atccatgcag ttgtcgtaga tgaagcgcat tttttttgacg atttaatcac atgccgcact    64440
tgggcagagg aagaaaaaat tattattctt gcgggactca atgcttcctt cgagcagaaa    64500
atgtttccgc ccatcgttcg tattttttcct tactgcagct gggttaagta tattggccgc    64560
acctgtatga aatgtaacca acataatgca tgctttaatg tgcgtaagaa cgcagacaag    64620
acgcttatcc ttgcgggagg aagtgaactg tacgtaacat gttgtaacaa ctgtctaaaa    64680
aatacattta ttaagcagtt gcaacctatt aaatattaaa aatcttatac aataatggat    64740
cattatctta aaaaattaca agatatttat acgaagctcg agggtcatcc ctttcttttt    64800
agcccgtcga aaaccaatga aaaagagttt attactctgc taaaccaggc cttggcctca    64860
acgcagcttt accgcagcat acaacagctg ttttttaacga tgtataagct agatcccatt    64920
gggtttatta actatattaa aacgagtaaa caagagtatt tatgcctgtt aattaatcct    64980
aaactcgtta ctaagttttt aaaaataacg agctttaaaa tttacattaa tttcaggctg    65040 aaaactttttt atataagtcc taataagtat aataattttt acaccgctcc ctctgaagaa    65100
aagactaacc atcttctaaa agaagaaaaa acttgggcaa agattgttga agaaggagga    65160
gaagaatcct aagtcgctta catttttttt tgctatttt atagaatgta cacgcatgtt    65220
gatgttgtcg gaatagctga agcctcagcg gccctctacg tgcaaaaaga tagggatcgc    65280
tacttagacg tgctaacaac cattgaaaac tttatttacc aacacaaatg catcataaca    65340
ggggaaagcg cccacctact ctttttaaaa aaaatattt atctttacga attttactcc    65400
aacaatgtgg cggagcacag caaggctttg gcgaccctgc tttataaact tgatccggaa    65460
tacctcactc gttacacagt actcattacc aaaattccca accattggta tgtgattaac    65520
gtagatcagc gagaatttgt gcgcctatat gccatcccgg cagttaaaca acacttaccg    65580
attcccattt taccettcta ttgcaccagc gcactcaccc agcaagaatt gttttgttta    65640
ggacctgaac tgcagttaat acaaatatat tccaagctct gtaaccccaa ctttgtcgag    65700
gaatggccta cgttgctcga ctacgaaaaa agcatgcgga tgttattttt agaacagttt    65760
ccgcaaagat tggaaatgac gggcgggaag aaggaggaga aggaaaagca tgaaagtatc    65820
```

```
attaaaaaaa taatactaga aatggtctct acccgtcagc gaatcgttgt tgggggttac    65880
atacaaaaaa acctgtacaa ccatgtactc aagaatagaa atcgtttaca gcttattacg    65940
agcttaaata tttatgaaga aaaagatatc atccagcaat tttgtgattc aaatggactg    66000
aagatcaaaa tacgtatcaa caatccgctc ttgcctacaa atccggaatt acggcgtttg    66060
actatttatt ttaatcataa taatgatgat gatcagtcat atctaatagt agatatgtac    66120
aacacgggaa gctatgagct agtgcctaca aatcagataa acacgcttga tggcagcttt    66180
ttaataggaa caccettcgt gcaagcgcga ttttgttgg tagagatctg ggtgcttatg    66240
cttattgcgc agcaaactaa aaaggacacc aaaaaaataa tacaattttt tataaatcaa    66300
tatgaaatgc ttatgaatag tccttggccc agtatggagg cccttttcc ctcaagcagt    66360 aaaagatatt taggcaacta tgtagaccct aacgcgctca taagtgggc acaactcaaa    66420 ttaaaaagaa taccgccttt ttatcctgga aagccggatg aagaatcatg ttaagccgat    66480
taaaaaatca tgttaagctg gttgaaaaat catgttaagc tggttgaaaa actcttggtg    66540
aaagcacgga tgtaatatta acattggccg ctcgcatttc gtgttgaaat acgatggaag    66600
agcgacggct atctaccatg ccgatatcgg cctggacatc acagttcatg cacttgtaga    66660
tgggatgact cgcgttatag atggcaggct cgccacagtt tctacagatg taggagatgc    66720
agccatccga gtcgtcgtgc gattttttcta tgatggtttg catggcgccc tgcgccgtaa    66780
gcacccaatg ctccatttct cccagacgaa gacctccgtg cgatcgtttg ccgtccaacg    66840
gctggcctgt gagggcatcc gtgggcccat agcttgcaac ggcgtatcgg tcatccagca    66900 caaattttg caggcgctgg tgataggtcg gtcctatgaa gatggccgca tcaaagtact    66960
cgccggtctg gccgttgaac attttttggc atccattgaa gcgtagacct tcttgcgcca    67020
gtctttctga aagaagctgc acattaatag gcaggaatgc ggtgccgtct gttaccaccc    67080
cctgtagggc atttgctaga ccaaccgtgg tttctatcat ttgaccgttg gtcattcggg    67140
agggatgtga gtgggggttt acaatgaggt cgggctgcaa tccgtcctct gtgaagggca    67200
tgtctgaagt gggcagggcc agcgccgcaa tgcccttgtt cccgctgcga gaactcattt    67260
tgtcgcctat attgagattt ctttcatagc gcaggcgcat gaggccaaag atctcgtcat    67320
taggcccatg gggacgcatc acagcatcca cgacggccgg ctcatcgaag ccgtacatga    67380
cagaccggtc gatgtatttg ttgagttcgt ctttttcgcc ccgtattttg gccacttttc    67440
ctataatgat gtcgcccttt ttgaccaccg ttcctacggg cacgaatcca tctacaagct    67500
tttcgtaatt agcaccaggc ttaagatttt tggtgattaa agggtcgggc ttcccaaacg    67560
actctatatc gctttctaat tctacttttt cttctcggta gaaggtgccg gcaaagccgc    67620
ccctgtcaat aaaggactgc gacacgatca cagagtcctc ctgattgtag ccgccgtaga    67680
tcatataagc cacaatggta ttaagcccgt tgggtatgac atagttatgt gctatggtct    67740
ttacaagcgg catttcattg taaaactgga agaagcggtt catgtcgaca cgatatggcc    67800
agctaaagca ataccagccc cccgtttgcc ggccttggtt tgtttcatag gtaacacgcg    67860
caggttgggt acagtttgcg taggggaca ctagggcggc aaggcccaaa atagcttggg    67920
gcacgtccac gtgtgtgaaa cgacgcgtta catcatgttt atgtttgcgt agctcgatga    67980
tggagaaggc aacaagacag ttttccgcct cctcggggt aatgaactca cagatgccct    68040
gtgctacgag atcttcaagt gtaagcgttc cggctaaaat gtcttttgcc atttgaggcg    68100
taaatcgcgt atttgaatg aaagggattt tatgttttc ccagtcttta tcgccttttt    68160
ttctggcctc tgcggccttg tagcaggctt gattgtattt ttcaatatta ttatctacaa    68220
```

```
tgagtagggg gcgggtcagc ctaccgacgt ccaaccaaaa ttctacttcg tctaccatgc    68280
tatcccagta gatggtggta tggggatgca caaccttgcc ctcacggcga agcattctat    68340
accgctgagc aagctcaaag gcattggtgc agcagccgat ccattctccg ttgataaata    68400
cgcgcgctag gcccttccgt acaatgtcct tgttggaaac atcggctaac tgttgaatgg    68460
ccggatctga tagaaggcgt tgttttaacg aaagtacttc tccggcggtg cagacattgg    68520
cagtgatggc taactgttta gacatgccta cttttccacc agtatcggct gactgggcta    68580
cgcagatgta tccaggatag gatgcgtgca cgcgacgcat catgtcagcc ctttctgttt    68640
gtttggatgc gttggtggtg ttatgagtat ttaccgtacg caatgctgaa atggtattta    68700
ataaattttt tctttccaaa ctttgagtag atactctgtt tacaatgggg cgctgtcgca    68760
ccatgatggt tttatttcct gaaatgatag actgttccat actgcgatta agatcggagg    68820
cggtattttt tgataaagcg gcagaaaatg cctcgataat gtttcgctga gtaagctcct    68880
caaaggctgt tgtttaaga agttctttga acccattgat gatgggtgct atcacggaag    68940
tattaaaaat agccttaaag gccttggcga gtgagacccc tgagccgtgc acccgcttgg    69000
tgcggtagct atcacggtcc gtgggtggaa acacattcat aatgacaaga agtattttat    69060
gaataagcag gcctaaaaag cgcagctttc gtacacgtgt atctgcggtt tggcccatgt    69120
gtggcagcaa tattttgtct aaaatagtaa gttgtctttc atttaagtat tgtaccgcat    69180
tttcatcgct tttgtaagca gatgggtttg agacaaattt ggaaaccttc tcggataaaa    69240
actggataat ttttctcgg ttcagctcgt gttggaccgg ttgaaatatg gggtctaaaa    69300
catgaatgga ttttccaga atttctatca tgaaggtatt cacaagggag ttggattcta    69360
gatcaaatac cacttgctca atgatgctgt catcgcctgt cattccaaac atgcgaaaga    69420
tgagatacca aggtatgcga agttttgaga acttggtgct attgatttca atggtaatgg    69480
cgccggtggt catgtagcgt ataataattt gagagctatt ttcgaaggca cctcccggtt    69540
gggagataaa ctcgccgcga atgatttcat tattcccttg ttgcatggta tggtaatgga    69600
tgtgaagcgt gttaaagcgg atgttttcta agaggtctac gacccattcc ccgcctcggg    69660
ctataaagta gccgccgggt tcattagggt cttctcctat ttcttttttt gcggttttg    69720 ataggtgatg agtgtggcag cggttgctgc cccgcatgat gggaaatgta gatacctgaa    69780
aaggaggaat acttgctcgt tttacctcct gccgaccatt gctgtagtgc gccgttaaaa    69840
taacctcggc ggctagatta accgggcccg aataggaaag gccacacagg cgtgccttat    69900
tgggtagtaa atttatcttg tttccctgtg aatagtttcg atgttgcggg cgttcaatgt    69960
tcacatctgt aaagttaaat tggatctgaa ctgattcccg aagcttatct atttcagtat    70020
ggtcgcgttg gtcttatataa gtaatatcca cgttaaacat ttgttttaca atttgcggaa    70080
ttccattgtc cataagatcg tcgaagcttt tgatgttata ccctatcaat cctgtagagt    70140
ttactgcagc ggagataaag ctcagcatat cagcctctgt aagctcctca ttatccacgg    70200
tttcaatggg gccgtaggtt atttgcggcc gcaagggttc catgattatg aagtactaca    70260
ttaatattca gttattcttt aaaataaatc tttatttata aatcttattt ataatataag    70320
aatgccttat gcaagagaca tcacaaagtt tattacggca acggaaccag aggtgggtct    70380 tccctgttg gcgctgcagc gctccaaatc catcataggg gttattcttc ttgtaataag    70440
tttgttattt attttcattg gcattattat attatcagtg agtagtggtc ataccacagc    70500
agcctctata tttatcgtat tgagtcttat cctaggtggc ggtggttttt ttcttatta    70560
```

```
taaagataat tcttaaccca cataaaattt gaaaaaatat agagtaagaa aatgtccaat   70620
tactattatt actatggcgg ggggagatat gattggttaa aaacagtaga acccactaat   70680
tttttaaaaa tcgggttgcc ttaccaggca cacccattac atcttcaaca tcaggcaact   70740
actcccccat ctatcttaga aaaatttaaa cgagcagaca ttcttcttaa tgaggtgaag   70800
gccgaaatgg acccactcat gttacaacca gaaaccgaaa aaaaactatt ccagatattg   70860
agtagtattg atatgttcaa aggtctgcga aaaaaagtag aattcacgta caatgctcaa   70920
attgttacga atgcttggct taaaatgtat gagctgctaa ataccatgaa ttttaataat   70980
acatctcagg cattttgcaa ttgtgagctt ccaggagggt ttataagtgc aattaaccat   71040
tttaattata caatgatgca ttaccctact tttaactggg tagcttcctc cctttacccc   71100
agttcggaaa cagatgccct ggaagatcac tatggtcttt atcagtgcaa tccggataac   71160
tggttgatgc aatctccttt actgaaaaaa aatatagatt ataataacgg ggacgtaacc   71220
atcgctagca atgtaaaaaa cctagcgctt agagccacac aaaggctgac gcccatccat   71280
ctatatacgg ctgatggggg tattaatgta ggacatgact acaataaaca ggaagaatta   71340
aatcttaagc ttcactttgg tcaagcccct acgggtttgt tgagtcttag caaaggcgga   71400
aacatgatac tcaaacacta taccttaaat catgcattta ctctttcttt aatatgtgta   71460
ttttctcact tttttgagga actatacatt accaaaccta cctcctctcg gcccacaaac   71520
tctgaaacct atattgtggg taaaaacaga ttacgcttat ttaccccccaa ggaagaacaa   71580 gtccttctaa aacggctaga atttttttaat gatacgcccc tcgtagacct aagtctttac   71640
caaaatttac ttgaaagcgt ttactttgcc gtagaaacaa tacatctaaa acaacaaata   71700
gaatttctaa acttcggaat gaaatgttat cgacattttt ataacaagat taaactactt   71760
aacgattatt tagctccgaa aaaaaagatt tttcaggata ggtggcgtgt gcttaataag   71820
ctttatgttc ttgaaaaaaa gcataaactt aagctttgtg cctcctaggg atctgttgct   71880
taatttaaca gatgcaatct taacagatgt aaactaaaaa gtgtgttcat acaaggattg   71940
tatttatgaa tatttattaa catataaggt tgtgatgtaa cactgtataa cctatataac   72000
tacactatga agcacggcgt ataataattt atattgaaca cgatgttgac tcatttattt   72060
gcaaacaaat atttgtttgc aagacgtttg catgcattta ctaatatgtt gttgactagt   72120
ttatttgcaa actagatgtt tgattgcaaa ctagatgttt gcacgtattt atttgaacta   72180
atatacactc cttgttttat ttgttatata cacagcatac ataagtgtat attgtttaca   72240
cttatgttta taactcgacg taataacatt ttacacgctt ttttttttgca aatcttaata   72300 atattgtatg ataaatcaaa caatgtctta tatatgtggt ttattatttt aggcgccgca   72360
agatgtactc cattctcatt gcatgcttgg tgttattact ctgtctagtt atatatgtcg   72420
gtcatcgtgc cgatcatgca cgaaaatatt tagaaggaat gtggcatgga gatccggttt   72480
ttctaaaaca gtcggggcta caatccttt atctctacat acaacctgac catacatgtt   72540
tttttagcat tgtgaataaa aatggtgaaa agctgatgga aaccaaaata ccttgtacga   72600
taacaaataa aatatatatg tttttttaaac ctattttttga atttcatgtt gtgatggaag   72660
acatacatag ctacttccct aagcagttta actttctgtt agatagtaca gaaggtaaac   72720
ttattttaga aaacaatcac gttatttatg ctgtattgta taaggataat ttcgccaccg   72780
cactaggaaa aacggttgaa aaatatataa cacaaaatta atcatgtttt ctaacaaaaa   72840
gtacatcggt cttatcaata agaaggaggg tttgaaaaaa aaaatagatg attatagtat   72900
attaataatt ggaatattaa ttggaactaa catcttaagc cttattataa atataatagg   72960
```

```
agagattaat aaaccaatat gttaccaaaa tgatgataag atattttatt gccctaaaga   73020
ttgggttgga tataataatg tttgttatta ttttggcaat gaagaaaaaa attataataa   73080
tgcaagtaat tattgtaagc aattaaatag tacgcttact aataataata ctattttagt   73140
aaatcttact aaaacattaa atcttactaa aacatatatt cacgaatcta attattgggt   73200
taattattct ttaattaaaa atgagtcagt actattacgt gatagtggat attacaaaaa   73260
acaaaaacat gtaagtttat tatatatttg tagtaaataa tattttttaat tacttaaaat   73320 ttttatatat aagttttga tactatatta taaaacatat gttcataaaa tgataatact    73380 tatttttta atatttctca acatagtttt aagtattgat tattgggtta gttttaataa    73440
aacaataatt ttagatagta atattactaa tgataataat gatataaatg gagtatcatg   73500
gaattttttt aataattctt ttaatacact agctacatgg ggaaaagcag gtaacttttg   73560
tgaatgttct aattatagta catcaatata taatataaca aataattgta gcttaactat   73620
ttttcctcat aatgatgtat ttgatacaac atatcaagta gtatggaatc aaataattaa   73680
ttatacaata aaattattaa cacctgctac tcccccaaat atcacatata attgtactaa   73740 tttttaata acatgtaaaa aaaataatgg aacaaacact aatatatatt taaatataaa    73800
tgatactttt gttaaatata ctaatgaaag tatacttgaa tataactgga ataatagtaa   73860
cattaacaat tttacagcta catgtataat taataataca attagtacat ctaatgaaac   73920
aacacttata aattgtactt atttaacatt gtcatctaac tatttttata ctttttttaa    73980
attatattat attccattaa gcatcataat tgggataaca ataagtattc ttcttatatc   74040
catcataact tttttatctt tacgaaaaag aaaaaaacat gttgaagaaa tagaaagtcc   74100
accacctgaa tctaatgaag aagaacaatg tcagcatgat gacaccactt ccatacatga   74160
accatctccc agagaaccat tacttcctaa gccttacagt cgttatcagt ataatacacc   74220
tatttactac atgcgtccct caacacaacc actcaaccca tttcccttac ctaaaccgtg   74280
tcctccaccc aaaccatgtc cgccacccaa accatgtcct ccacctaaac catgtccttc   74340
agctgaatcc tattctccac ccaaaccact acctagtatc ccgctactac ccaatatccc   74400
gccattatct acccaaaata tttcgcttat tcacgtagat agaattattt aatatgtact   74460
atatattaat tatttaacct ttcaagctgg tcttcattta aatttaaaat ccactaataa   74520 aatgtattt ctagtagcag atcatcgaga acatcatgtg attccttttc ttaaaaccga   74580
tttccatcac atgcatcaaa atcctataca aaaaaatcaa gctctcctag aaatcaaaca   74640 gcttttact ggagattatc tcatctgcaa aagccccttct accattctgg cctgtattga   74700
acgaaaaacc tacaaagact ttgcggcttc tttgaaagat ggacgttata aaaatcgcca   74760
aaaaatgctg tcgctgcgag aacaaaccaa ctgtcaactt tatttttttg tagaaggccc   74820
ggcatttcct aaccctcaaa aaaaaattaa tcacgttgcc tatgcaagca ttattactgc   74880
tatgacgcat cttatggtta gagatcatat ttttgtcatt caaacgaaaa atgaggccca   74940
cagttcccaa aagcttgtgc agcttttttta tgccttttct aaggaaatgg tgtgcgtcgt   75000
tcccacctcc ctcaccccca cggatgaaga gctatgcatc aagctatggt cttctctttc   75060
tggtatttca ggcgtgatag gtaaaatctt ggcaaacact tgttccgtag ctcatttggt   75120
tcatggaaag ctttcatcgc agaatattga tcagttaaaa actccctcca accgaccatt   75180
ccccaaaaaa gtaaaacgta tgcttataag cattagcaaa ggaaataagg agttagaaat   75240
aaaattgctc tcgggggttc ccaatatcgg gaaaaaatta gctgccgaaa ttttaaaaga   75300
```

```
tcatgcgctt ctttttttc taaatcagcc cgtagaatgc ttggcaaata tacaaatcgt    75360
tcaaaaaacc cgtacgatta agttgggaat gaagcgagcc gaagcgattc attattttt    75420 aaactggtgt ggctctgccc atgtaaccga tgatagccaa atatcacag aggcgtcgcg    75480 gtccacaatg caggtcgcga cgcagtccgc cgcaatacag cccgctgcaa cgcagccatt    75540
gcacgaagta tcagatgatg catcatcaga tgcttcatca cccgtagggt atcaaacatt    75600
atctaaagaa atgttattga acacagcctg atgttaataa ttcactacat ctaaagaaat    75660
gttaacctcg atactaaaaa gtcattgaac acaactactg gggcgctaag ttgtccaaca    75720
catctaaaga aatgtcaaca tcctcgatgc taaagggtc atcgagccgg tcaataatgt    75780 cttcccaaa aagtccggga gaactgtagg ccgagatgtc gtccatggag ctatcttccc    75840
cagagcacac aaagtcctct ccaaaaatca taaagttaaa tgcaccgggc ttacttaaca    75900
gcttttcgct ttgaataata gtgttgagtt ctgtcagcgc aaactctctc acaatattca    75960
caacccagga gggctcttta atttcataca gcgttaagaa acttatacat aaaaattcta    76020
tagagtaaag caaggcgctg gcaggatctg ttacccgtag gtgtttaaat gtagtgtgat    76080
attcattcac aacgttaggc agcaccttt ccaaatcctc cttttcctcg tacgacaggt    76140
gctttacaag ccttttcaaca tgtataggag gcttgttaaa tgtactaacg tgccgcaaac    76200
agttataatt atataagaaa atacgtacgg cagagtcgac cgccatgagc cttggatcat    76260
ccattgaggt aggtggtggc ggggcaccct ggccttccct gatgtctgcg taggagcgcc    76320
cctccatggc ccctatggcc tctatcacag caggactgat atccaaaatc ttggccgtct    76380
tgattatttt tccgtaatcg aaagtccatg gctcctgtgg aggcttgggt tgtgtttcgg    76440
tggagggcgt ggtcatatct ttctttattt gaatagaacg gatcgacatc ttttccttat    76500
cgtactggtc tttataatta ttataatagt catgaactaa ttcgggttga aaagatgat    76560 cgtatataat ataggtaaaa agtccgcact tgacacattt tttatcctgg aagtcgtgta    76620
atcctccctt ggggcagcgt gactcgtaga aggcataaaa ggtgttaaat tctaagctcg    76680
cctttagggc tgtttggacc ttttttatgt ttaattgccc cacctcatgt tgtagcacgt    76740
ggcatacaga acagcgtaga tcggcaagtg cataatggtt gtcaattttt tttatgacgt    76800
ctttgcgtgt tacttcaatc tcggcgggtt tctgcgaact gtctacggcc ttgtaaacgt    76860
aaatggtcca cttatgagga agccccctt catcgtatag ggttgaaatg ggaagccttt    76920
tatactcaaa cagccgagtc cgttggtcgg ctcttcctgt gttaggatca aatatgttat    76980
aaaatccttg ctgagcaagc agggccttt gctcgccata agcattttcg tacgttttga    77040
attctgcaag ttcggagtta aaattaggtg catttgtaa atacttaaga ataattcat    77100 aggctctaag gtaaatgaga gttgaggttt tttcctcatc ccgtcctccc caccacaccc    77160
gcaggctttc ttcttgaaaa tagatgtcat tcagacgcgt caactgcgta aaatcaggcc    77220
gatatttaga ggtataaatt ttatcataaa attcttttg cgataatagc tcggccgggg    77280
tacgtcctat cacggtttta aactcatatt cagcctcctt gggagtccgt ggtttgtgca    77340
tagggatgct gccgtcaata cgggccactg tggcagcata atcatacatg gggtccagca    77400
gaatctctgt caaagtacc ttggtgtcgt cctgcacgct aagcccttgt agcccatttt    77460
ggtggataat tttttgaaa gcctcccgaa aattattagc aatccactga tccgtaatct    77520
cagatagctg attattata ccgctatatt gctgcatcat ttctccaaa agaaaggtca    77580 cgtatgcatt caaagagcta tccgccttca ttccatgaat ggtaatcgta agaaattctt    77640
tatttttttg cgagctataa atgagattca aaatataggc atagatgtag atcacagcat    77700
```

```
acagctgcgt taaaggatcg taatcctctt ccttttttaat attttcgatg ctatacacga   77760
gcggcaggca gacatttacg gctatattgg caaactgttt cacgtctaca agctttccaa   77820
agtggataaa cgtgcaggcc ttcatggttt cctgccaaat aaaaacacgg agcttactat   77880
taagatcgcc gatgatgccc acatctgccg tacgatcctc ttgaataaaa tgggccagct   77940
cttcgccaca aattttgcaa aagtaggagt aaataagccc ctggttgttt tctttctcct   78000
tgtttattcc tgaaaatttc attagcttgg ttcgcatggt gtcgtaggac gcttctgccg   78060
cttgaagctg tataagcatg tccacatggg gacaaagcag cttaaacccg caggctttgc   78120
atagattcca attggtggta ttgttttttt ccttgtagag tacacgaata ctttctaata   78180
cttttaataa ctccgcgtat tgaagacccg aacgcaactg ttttaccagc ttgagatgag   78240
cacatgcatt ttttcttgg agttcccact gttttttaat gtttaggtat tctgttgtaa    78300
taagttctgc ctcctgtttc ccacaggctt taatgacttc ttgaaggatg ctgttagggt   78360
catccacttt accctccatt gtaagaattt cacgtatagc atccgactgc accctaccta   78420
ttttttcttc cataaatttta aaatactgtc tcgcctgggt aatgacctct gtgagcttca   78480
tgtccacctg ctgcagaatc atttgctcct tttcacgctg ttcagcatgt tgtaaaaact   78540
tttgttctac agggttccaa agcacctcca aatagcctgc tctatatagg tcataaagca   78600
agggcatgta tcccgatgta aaaccgggg acaccgagta catcgtagac aactctttta    78660 aaaaaatat cacgcgctta atgttctcct ccggttcaat ctcctcggtt tcaacgatat    78720
tagatatatg actgccctga tcctcacggt ctagctttcg gtgtaccatc tcctctgcta   78780
gccgattaat gagccagcta tgcccgccgc tccgcaaaaa cttataaagt tcgatatact   78840
ggtgcgtaaa ctggatgatg ttttccttgg tggttacgac aacccttct ccgtttttt    78900 tccaggtttc ttgatccacg catttcataa atactcgaat aaaattggtc aaattggctc   78960
ctgaggcgac gtagcccaag gtttcaggcg agaaggagcc tatctcagcc atacgcataa   79020
aacactgcgg ggaaaaagtt tttagccgca acttaagtcc atagatttca atgggggctt   79080
ctgcgggaac ggccaggtgc gtcccattaa ttaaaaaaat ttctttgcgt gtgctagggc   79140
gaacacgtaa ttcctttttt ttttcactca cgatggggac cacatcgggg tctaccagca   79200
gttgacgtat gtaggcctct atgggcatgg atagatcggg cagctttgac tgctcggcgc   79260
gaacatggtt cacaaaatct tttagagtga aagaaagtc tattaaacgt atgtttttta    79320
tatcattaga ccctttaagg gtagagtaga tttcatccac tagtgcctcg atttcctcat   79380
tattgagcga taagatatct gtgccacggt ggactatttg cgcgatcgta attacttcct   79440
ccattagata gaaactgaat attatattta aaataaatac aaaatgtcaa atgaaagttt   79500
tcccgaaacg ttggaaaact tactttcaat gttacgacc aaacagcaaa acgcaattca    79560
gtcagaggtg attgaatggc tgcacagctt ttgtgaaacc tttcacttaa aaatacactg   79620
ccataaacag tttattccta gcggggaaaa aaaacgagct aaaatacccg ctcaagaaac   79680
acagggaaac acgcagccct cccaccatgt gtaccgggtt gttctctcca gagcacagcc   79740
agtcaaagca caggaatctc tgctaacaac catgtgcaac ggactggtgc tagatgcaaa   79800
cacatggaca tgcctagcca ttcctccgcc tgcgcctttt caacaggcga cccgccaggt   79860
ccaacacttt taccgtaaca atttctacga agtggttccc atccaggatg gcacccttct   79920
cacaatctac cactgggatg accctgaata tggcccctcc tggtgcctag caagtaccca   79980
cggatatgat gtgagtaact actgttggat aggcgacaaa accttcgccg agcttgtata   80040
```

```
cgaattgctg cagcagcact ctacctgcga cgtcaccctg gaaaaaaata aaacgcgggg    80100
aacgcgtctt ttctttgata acttaaatcc cgattactgc tatacgattg gaatccggca    80160
ccataattta cagccgctca tctatgaccc tcaaaatatt tgggcgattc aatctacaaa    80220
cctaaaaacg cttaaaacgg tatatccaga atactacggc tatataggca ttccaggaat    80280
tcagagtcaa gttcctgagc ttccccagta tgatttacct tatctaatac gatcttataa    80340
aactgctatg aatcaagcca aaaatgctat aaaaaatggc aaaaaagaca agggatactt    80400
taattatggc tatttactca tttcgcgagc gcctgccatt actaaaagta cttctaatgt    80460
tttgttaaaa tcgcctctgc tggtattttt acaaaaaagt gtgtaccaga aaaacacaa    80520 tatctctaac agccagcgac tagaatttat tatactgcaa aactacttga tgcagcattt    80580
tcgagatcat ttcattgctc tatttccgca gtacatatcc tattatacga ataccaaaa    80640 catgttgaat atgattatcc atagtattgc aactaaagat aaagatcatc cctttgcagg    80700
agccgtggta aaaaagtgt tggaagatat tgaaaacgcc gaaaacatta ttgatcatac    80760
aaccattcaa aactatgccc atcaaagcaa gtacgccatg ctttacttgt caattatttc    80820
ccatttttaa tctaatacgg ccaaagccgc gggttttta ataaactaac atttaaaaaa    80880
actgttttat taaaaattat aatacttta ttatatatgg aacatccatc tacaaactat    80940
actcccgaac agcaacacga aaattaaaa cattatgttt taatcccctaa acacctttgg    81000 tcttatatta aatacggaac gcatgtccgg tactacacca cacaaaatgt tttccgagtc    81060
ggtggctttg tgcttcaaaa tccctacgaa gccgttataa aaatgaggt aaaaacagca    81120 ataagactgc aaaatagttt taacacaaaa gcgaagggc atgtaacgtg ggccgtccca    81180
tatgataata ttagcaagct atatgccaaa ccagatgcaa ttatgcttac catacaagaa    81240
aatgttgaaa aagctcttca tgctttaaac caaaacgtac tgacgctcgc atcaaaaata    81300
cgttaaatat aattttttgta gaggataaaa agctatttta gctaaaaaat aattcatata    81360
cgtttatgca gaggaagaac ggtggctttc aaattcagat tgcatccacg tagaccgtag    81420
cgtttttttt gcttctggtt tatatcgtaa accgtaataa acatcatcat ttgtatccgt    81480
tggatctttt tcccactccg gataaaaaat cggttttctt tttttggtc gtttttgca    81540 gtaagctgta aattaaggga atatagctta tcgaaaagtt gttcctgatc catataaata    81600
gcagcatata ttaaaaaaaa taaaaaaaga cgcttcaacg agtcagtacc actgcttgcc    81660
aacgatttac gttggttggt gcattatggt gatatagtaa tgagtgcctg cacaagtgct    81720
tgcacaagtg cctgcacaag tgcttgcaca agtgcttgca caagtgctta cacaagtgct    81780
tgcacaagtg cctgtacaca ttactgcatc gccaaagcac ctgcaatgcc tacttcctca    81840
acagagtacg ataactaaat gcttttaagc accgcttgcg tcgatgtgtc cttcgggca    81900 atcgggttca attggatcca atattattag tcataattac ctaatactta ttcaatttta    81960
tcttttttac cttgtaagat ttaaacagcg ttttagcttg tttaaagcaa cgtttaaaac    82020
aagctaaaat gctgtttaaa acaacgtttt aaacaagtta aaacaaataa gcttataaat    82080
ataccatgac aaaattagcc caatggatgt ttgagcagta tgtcaaagat ttaaacctaa    82140
aaaatcgagg gtccccctcg ttccgcaaat ggctcacatt gcaaccctca ctgctgcgct    82200
attcgggtgt gatgcgtgct aacgcctttg acatcctaaa atatggctat cctatgcagc    82260
agtcaggtta tacggttgct acgcttgaaa tccactttaa aaatattagg tcttcctttg    82320
ccaacattta ctggaaccgt gatagcgagg agcctgagta cgtctgctgt tgtgccacct    82380
atcaatcgca cgatggcgaa taccggtatc gatttgtttg gtaccaaccc ttcatagagg    82440
```

```
cttataatgc catagaggcg gccctggatc ccctggaaac cattatcctg aacctcattg   82500
cggcacgaga tctagacttc gttgttcaca tatttcctta taataagggc catgaagact   82560
atttggcctc cacgcaactt attctcaaaa tctttattgc gacgctttta atggacattt   82620
taagaattaa agacaacacg ttggacgttc acttaaattc cgactatatt attgtgatgg   82680
agcggctttg gcctcacata aaggatgcca tagaacactt ttttgaagcc cataaggact   82740
tactagggta cttaattgcc tttcgcaatg gggggaactt tgcaggaagt cttagaccct   82800
cctgtgggca aaagattgtt cccctaacga ttcgagaggt cctacaaatg aatgatatta   82860
atttagccgt atggcgggag gtgtttatta tgcaggaatg ttccgactta gtcatcaatg   82920
ggatagcgcc ctgtttcccc atttttaaca cgtggacgta tttgcaaggt attaaccaga   82980
ttttttttga aaacacgtct ttgcaggaga aatttaaaaa agattttatt gcccgagagc   83040
tttccaaaga aattatcaag ggccaaaaaa cgttgaatga caaggagttt aaaaagttaa   83100
gcctacatca aatccagtac atggaatcct ttctacttat gtcggatgtt gccattatga   83160
ttaccacaga gtatgttggc tatacccttc aatccctgcc gggtattatt cgcgatcca   83220 gctatttatc ccccatcgtg aaaaacattt tgatggacga agactctttt atgtccctac   83280
tatttgacct atgctatggc gcctacgtgt tgcataaaaa agaaaatgtg attcacgcgg   83340
atttgcacct gaataacatg acctactacc atttcaaccc aaccagtttt acagatcgca   83400
acaaaccagg aaaatacacc ttaaaggtca agaatcctgt gattgccttt ataaccgggc   83460
ccaaagtcga aaccgaaacg tacgtgttca agcacataga tgggttcggc tgcatcattg   83520
actttagcag agccattatg gggccaaacc atgcaatcaa gcttgagcgg cagtacggcc   83580
tcgcttttgt aaaaaccctt taccgcaatc aaagtgagca tattttaaag gtattacggt   83640
actattttcc tgaaatgcta accaatcgcg aaaacgaaat cagggggtg attttatcaa   83700 actttaattt cttttttcaat agcattactg ccattgattt ttacgccatt gctagaaacc   83760
tacgtagtat gctttctttg gactatttac acacctctga ggtgaaacga aacgtagaaa   83820
tttcgcaaac attttttggat acatgtcaat ttttggagga aaaggccgtg gaatttttgt   83880
ttaaaaatct tcatactgtc ttatctggca agccggtcga aaaaacggcc ggggatgtgc   83940
tttttaccat cgtatttaaa aaattttat acccaaatat tcctaaaaat atattacggt   84000
cttttaccgt aatagatgta tacaattata ataatataaa gcgttattct gggaaagcta   84060
tacaaacgtt tccaccctgg gctcaaacca aagaaatctt gacgcacgcc gagggtcgta   84120
catttgaaga tattttttcct agaggagaat tagtttttaa aaaggcttac gcagaaaaca   84180
accatttgga caaaattta cagcgtattc gtgagcagct tgctaatgaa atttgtaag   84240 gcttgcagtt cttgtatggt cagaacctat gtcgatggaa acattatttt tcgctgcagc   84300
tgcggcgaaa gcgttcaagg ggatagtcag aacttgctcg tctctagcaa ggtgtaccac   84360
accggggaaa tggaagataa gtacaagatt tttattaaaa atgcacccctt tgaccccacg   84420 aattgccaaa taaaaaagga ttgcccaaat tgtcatttag actatttgac acaaatctgt   84480
attggaagcc aaaaaatcat tatattggtg tgccgctgtg gctatatgag caacagagga   84540
taaaccatat catcccaccg aattatgaca ttcctttaaa accgtccgcc taaatagttt   84600
tcacaccttt ggtggcagac tatttttataa aaagtaatgt tggttcatga agataaagtg   84660
tgccaaagaa acttttataa acaaatgatt aatgtaggtg ctagtcgtgt gtacttaaac   84720
agggtattct atagccaagt attttctata gccaagtatt ttctatagcc agtattagtc   84780
```

```
aagtatttag atgtcagggt attttttatag ccagtatttt tctatatgta caaactattc  84840
cagtaaacat atgtgtgttc tttattgagc agcatcatgg cattaacaag tttattaaac  84900
tgctctaatg ggcattaaat gacaactcgg tgcttagcaa aagtgcctat acctttaac   84960 aattagggcc gggaggcatt cccagctttt ttctataatc agccatacag taccctgag   85020 cctcatacac gggaataagg tccttccatt ccttgttggg atcggcgggc cagctctcaa  85080
atgaggtgtg aatgtaaggg tcctgttctt tttccttaat gaagcgttta atctccattt  85140
gatgttgttt acttttttgt tgcggcgga gcgtgttccg caccaatacg taaaaaatac   85200
caagaatcac acataaaaga attattaaaa aaaatatcat catcgcgggg tttaaaaaac  85260
gatcccatgc aacaggaatc gttcttaaaa ccttgtctgg cagggctgta aacatgaagt  85320
ctcctcctat aatcgggtg ggactgtagc ctaacagttc aaggtcctgt cgttctagat   85380
acttattggc gaactgccca cccttttgccc ccgttttttt attaatcaag cagcgctgca 85440
ttttccacca ttctaaatct tcaggagaaa gctcaatgcc atatatcaac tttaacgtta  85500
ttgcatcttt ttcaatatcc ttatcaattt ggctgagctt ttgagcttta agcgggtcta  85560
gtgtgtactt ccatttaaac ttagtgtcct gtagtttggc tacatgaaat acggaacatt  85620
tcggcggggc ctttgtgacg cccttacact gcggaagttt atcattagga caggcgcata  85680
gatgagactg cgccacagca tcgcgaacta catcgcagac ggagtacatt ttcctcctat  85740
gttaaacaat aaattttttt catagctgaa atttgtgggc ctatcttttc ccttgcccgg  85800
ataataatta taagggagtg ttgaaacatc tgggagagaa ttgcttaaaa aatgggtttt  85860 tgggagggt aactgcgact gttgtacgtc gttggccagg gagattctat atgccgggct   85920
aaaggtgcaa cgttcctgtg aacaacttag tacgcgcgtt gttaatacaa atggactggt  85980
attagcaaac ctcgtaaact cttccggact tgtttgtttt tgtatgatgt ttagcaggga  86040
gtctgccttt tcgagaatcc aaagcgtcgc attgtagtaa aataaaaata gcgacttatc  86100
ggcaggcgtt gcaaaagcgc cgtatagaaa ataaagcagt aagtactggg gagacaccac  86160
aataaggtta tcttgaatga tagatatcgc tagctctta aacatagtgc taaaaaaatg   86220
tatgtcgttc gtcttgaata tagggggact atagtccatg tagggctcac atatctcagt  86280
caggtgaagg cccatttctt ttatgacttc ttccggggttg tacgtcgcta acaccagcgc  86340
gggataggct ttgggcatat ccacggtaag tgttatgttt ttatcattct tatggtagga  86400
gtaagatggt tgtggaaatt ctgttttcca ctccgggact ttgcaggtaa ttctcagctc  86460
atttagagtc tggtacagga gggcgtatgc cgcaaagccg tgtatggcca cttgtttaaa  86520
gggaattgaa aacgttttac tttcgtatgt cgacttcaca ggaacaacgg gaatggggta  86580
atatttttct atgaggttat accgctgcaa atcctttta aacctgctaa aaacatcttc   86640
ccttggtggg ttatcaaaag gaaagcaaaa tgctaggtgt agcccggccc gctggtaatc  86700
ggggtgaatg attttaaggt ttttatacgt taatgtgggt atggtgttaa agatattggg  86760
gggcatatat gaaagatcag caacccacac aaagtccgtg cgcacccgca tggtctgcac  86820
atggatggcg cgcaccgtgc ccacctgctt gaagcccttt tcatacaaaa tgtcagcaag  86880
ttcgtaggcg tcctcaacgt ggttggggga aaacatatca aagtcgggtc tttctccctc   86940
gggataaatt gagctgcctt taagatgcag ggcataatca atggcaatcc ccccgtacaa  87000
aataagcttt ttcttatga taaattcgcg gaccacctcc aaagccgcct caatctccac   87060
ggcatttgcc tcacgttttt gagcaatgag ccggtactta gaaacattaa atcagtctt   87120 tagtaaagac gtcataaata gtgtttaata tatattaaag gtttgaataa aatactaaat  87180
```

```
agtaaaaatg gatgccctat taaaggaaat agaaaagtta tcgcagccat ccttgcagaa   87240
agaaaacaat gatgtatgcg atctctgttt tatgcaaatg aaaaaaattt ctaactatca   87300
gcttttatgc gaagagtgcg gtcagctgaa ggactggttt gaacctgaat ataatgaaaa   87360
attcacggta tattctcgtc taaagatcgt gggtgccaat agttcctatc accagcgcga   87420
tttggacaag gccaactcaa gtgactatag ctccttgcaa tttcatcaca ttttagagga   87480
gctcaaatcc ctaaatgtta agtatatgga tgcggggcaa aagcccttc ctattcaggt    87540 gttaaaagaa actgctcaca gttataacca agtacaacaa catcgggtca tacgcagcat   87600
tacaaagctt cagatcttag ccagtattct acgtagcatt tgtttaaaat taaacattgc   87660
ttgtacggtg gcagacgccg cgaggtttac tcaacttaat accaagggga tctcaagggg   87720
catggatctt ctgcgctccc tatttgtaga caataaaatt actttaaacg ttgatttaaa   87780
ccctatagac agctttatta atagtaccta cagtgcctta caaattaaac aaatccacca   87840
agaactgcag gaggaaaatg tttataattt aaaagaaatt gttaagagct ttatattata   87900
cgcggatgag aagaacatcg gcgtcgatct taacaggaga accgttgtga ttgctacgat   87960
gtataatgtt ttacgccgtg cctactaccc catagaaatt gatacggtgg tgtatcaatg   88020
taaaatacga aaaaatacaa ttacacgtgc tcttaaaatg tatgaggatt actactccca   88080
ctttaagtct ctttatgagc agtatcattt aaacgcggca aaaaaattaa tttaaactaa   88140
acgtttaaac taaatgttta aactaaacgt taaaactaaa catttcgact aaagtttaaa   88200
acctagtcta acagcgggat gcccatttcc ctggggttcc atatttcaac aatttttga    88260 ccttcgggtg ttaccttgat gcagcgcatg acgagcagtg gaattttcct attaaagagt   88320
tcttgcttag ctatatcaat aggactgcta tatttttttt taagcattgt agatccatta   88380
attgccaatt gttgcgctct aacggcgacc aaccttgtgg cctcaaaggt ggttaaaacg   88440
ttggaggtaa tgcgctcgtt atcgggtata atgaccaatg tttgcgacga ggcctgcaca   88500
aagccctcgc agatggacgg agactccacg atctcgtcct tgtcctcgga ctcctcctca   88560
ctgtcgacga ggttctcctc ttccgttttcc acatattcct ccacgaggtc atccatgata   88620
agatcctcgt tgtcattatc agccatatta cactgttatc aaatgtactg tttaatacgc   88680
aaatggattt actacgtttt aattgtatgt cttcatgtgc aggctctagt ggaaagtaat   88740
tttctcacaa ttttttggcac cgttacactt gtgcccacaa aaacccgcga tttttttatt   88800
ttatattact tttggaagta cgagtttaac cagtcgcttt caaaccttat gcgtctatct   88860
cgccaaaaaa cgctcacagc ggtgttggat attaccttta aaaaaataac attaattttt   88920
accacagagg gcgtattgcg tatggattct acgaataagc caggcgtgcc actcgatata   88980
gacccccagt tcattgacct tgatagtatt ttaatgaac tggatcatta ggacctctcc    89040
cgcccattta aattttagt ttctacaata ataaatgcg cgaggaatca tgggaagacc     89100
acgataccat tcagctcacc gctcagcgca aatacctcgc cgaggtgcaa gctctagaga   89160 ccctttttgac tcgagagctt tcagtctttc tcacagagcc aggcagcaaa aaacaaata    89220 ttattaatag aatcacagga aaaacctacg cacttcccag cacagagcta ctaagactct   89280
acgagcatct cgagcaatgt cgcaagcaag gcgcccctcat gtattttttg gaaagacagg   89340
ggacctactc gggtctcatg ttggactatg accttaaact caatacaaat gctgttcccc   89400
cgctggaacc ccccgcgcta tcacggcttt gccatcgaat atttgtgcat ataaaaaaca   89460
gcagtgtgct gcctgagggc agccataaaa tccacttctt ttttacatta aaacctgaag   89520
```

```
tggttcaggg caaatatggg ttccatgtgc tcattcctgg tctcaagctg gcggcttcta    89580
ccaaaaaaag cattatagga tccctacagc acgatgccac cgtacaaaaa attctacacg    89640
agcagggcgt tacaaatcct gagtcctgtc tggaccccca ctccgcctcc gttccctcgc    89700
tcctctacgg ctcctccaaa ctaaaccaca agccctacca actgaaaacc ggctttgagt    89760
tagtctttga tagctctgat cccgactaca ttcccattca tcaaataaaa aatttagaat    89820
cttataattt agtttctgag ttgagcctta cgaatgaaca gggaagcctt gtaagacctg    89880
tctattgcgc ggcagacatt gccgctgaga aggaggaaga gatcccgacc gaggatcact    89940
cgctctccat attaatgcta catgatcccg aagcccggta tttacataaa attttaaatc    90000
tgcttcctcc ggagtattat gtagagtacc ccctatggag caacgtcgta ttcgctttgg    90060
ccaatacatc cgctaactat cggcccctcg ccgaatggtt ttcgcaaaaa tgccctgaaa    90120
aatggaatac gggaggaaaa gagaaactag aaaaactttg gaatgatgcc tcgcaccaca    90180
ctgaaaagaa aatcaccaag cggtccatta tgtactgggc ccacaaacat gcccccagc     90240 aatacaaaga aattgtagaa caaggctact tttccattct cgctgaatat gtgtatagct    90300
ataacggcat gcttgagcac tacatgatcg ccaaagtcat ctatgctatg atgggcaaca    90360
agtttgtagt ggacgtggat tcaaacggga agtacgtttg gttcgaattt gtgctaccgg    90420
gccagccaat gaatcaggga gaaatatgga agtggcgcaa ggaggtaaac ccggatgagc    90480
tgcacatcta tatttccgaa aacttttcaa gggtgatgga ccgaatcacg gagcacatca    90540
aataccacct cagtcaaccc catgaaagca atatttttaaa ttattataaa aaactattaa    90600
aagcctttga acgctctaaa agtaaaatct ttaatgacag ctttaaaaag ggagttatca    90660
ggcaagctga gtttttattt cgccaaagaa gctttattca aactctggat accaatcccc    90720
acctactggg ggttggcaac ggggttctct ccattgagac catcccggct aagctcatta    90780
atcattttca cgagcatccc attcatcagt acacacacat atgttatgtg ccctttaatc    90840
ccgaaaaccc ctgaacaaaa ctattattga atgcactcca agacatcatc ccagaacttg    90900
atgctaggct gtggatcatg ttctacctaa gcacggccat atttcgcggc ctgaaggagg    90960
ctctgatgct tttgtggctt ggaggcggct gcaatggaaa aacttttcta atgcgacttg    91020
tggccatggt attgggcgat cactatgcct ccaagctcaa catcagcctt cttacaagct    91080
gcagagaaac cgcggaaaaa cccaacagtg cctttatgcg gcttaagggg cggggatatg    91140
ggtactttga ggaaaccaac aaaagcgagg ttctaaatac gtcgcggctg aaggaaatgg    91200
taaatccggg cgatgtcacc gctcgagagc ttaatcaaaa acaggaaagc tttcagatga    91260
cggccaccat ggtcgccgcg tccaactata acttcatcat tgacacgacg gaccacggca    91320
catggagaag actgcggcat tatcggtcaa aggtgaaatt ctgccataac cccgacccca    91380
gtaaccccta cgagaaaaag gaagatcctc gctttattca cgagtacatc atggatccag    91440
actgccaaaa cgcattcttc agcatactcg tctattttgg ggagaagcta cagaaggaat    91500
acaacgggca gattaaaaaa gtgttttgtc ccaccattga gagcgaaacg gaggcgtaca    91560
gaaagtcaca agatacgcta cataggttta tcacagaaag agtcgtggag tcgccctccg    91620
cagaaactgt gtacaaccta tccgaggtcg tgacggccta cgcggaatgg tacaacacca    91680
acattaacgt aaagcgccat attgccctcg agctatccca ggagttagaa aactctgtgc    91740
tagaaaaata ccttcagtgg tctcccaaca aaacgcgaat tctaaagggt tgccgtattt    91800
tgcataaatt tgaaacgctg cagcccgcg aatcctacat tggggtgtcc acggccggca    91860
cactcctaaa cacacccata tgcgagccaa aaaataaatg gtgggaatgg tcccctaatc    91920
```

```
cctctgcccc tcctgagaaa gaagcgtctg caccaactcc ttagggaata tccttagaag   91980
catgtctttc ggcagagcca ttaccggtag caaaaaagca acattgagta tattatatgc   92040
cttagcctgc tcataagcgt ccttttttt catggtattt tatgttttta aatatttta   92100 attatttttt aaatacgatg aacagttcgt gctccgaagg ctgtttacta aaaatcggtg   92160
tgaatccgca ttctttaaat atggtttccc attcggggat ggtatggaaa tccatgtctc   92220
tacgaatagt atggtgccca agtgcgtcct gcaggctgtg aagccagaag gcctcctgac   92280
cttgatgaag gtcgtacatg ataagaaaac catcaggttt caacagatgg taaagcttgt   92340
taaaatcgtt tatcgtaaga tgatgcgccg ccataggtaa ccctatgagc tccacagagt   92400
tttcatgctg gacatcgtcc atatcggtat aaaacgtttc acagtaaatg agacgcttaa   92460
acgagtatcg atgacaaaca tttatttcca agtaggtttg cactacgttt ttaggtatat   92520
cgggaatcat gttgattaag gttgtttcgg gaaacttaat catctgacta ggcttcattt   92580
tcaactcttt aaaggatttc ccggagaagt gaaaatgggt cttacgtat ttatgtaaaa   92640 atacctgaat gggcagaggg ggctcctcct cttcgttctc gacgcctccc aaaatatttg   92700
gaatttcctg acgtggcaaa agaaagttta tgtccacgtt tacgaatcca tcgaggacgg   92760
acacaaagct tggctctaat ctccattcca tatactgttt agaaacggga gatagcataa   92820
tcctaggcgt cacaatgcac gaaggggtttt taatcaccgc atcgtggtaa gaaaagtgta   92880
ttccatttct tccagtataa agaagcctat gttcgtcgta gcagaaacaa ttaaggcggt   92940
atgcctcata catacactgt ttcaaagtac aaacacgttt taaaaggtt tctgcattgg   93000 cggaggccaa gcggttttgc cattggtgga aggggttcaa tcctacaatg gccagctcgt   93060
ttaaaatatc ttcgcggcgc gctaaaatct gcaccataga agaatacttt agcattttt   93120 tttcgcacca ttcgcgaaga tgtttagcta cattattaac cttattattg ataaagtata   93180
cgatggcatg ttggaagcct tcaaaaataa agagcccctc caaaagatca tctgccaata   93240
gaagatggat gttggtgtaa gcattgtcaa tattttgtag aaacggcgga atgcctgcca   93300
aaaccgcttc agcaagcata gctccgttcc gttgtttact gtccaataga ttcgtaagtt   93360
ttttgtccgc aacagacacg acggctagga tggttgcaat gtcagaaatg gcggcttgcc   93420
agaaataacc cgaaaagcac atgcgcgctt cttctataga taaaaacgaa aagcgagagg   93480
caatgtctcc gagctgcgtg agttgaagac ctttttctcc tctggttaaa aggcctgcca   93540
caatggcccg ctcaatggct gatgccagcg catccgtggg gggaggatcc agcatatcaa   93600
tctcctctgc cttaaaacg ccttcctat ttttttaat cgtttctacg acaatgctaa   93660
gaaaaatggc cccagggcct tccgtaatga tttcaggata ctgctgcact ggtatttgct   93720
caaagacgtg ttttgtgtaa agcgggtaaa agtgcccagg aaatactctc cctacacgcc   93780
cctttctttg ctcgatacgg ctttgagccg cggggcgcgt aataagccct cccgcccatt   93840
cgggatagta ggtttcaatg cttctgttcc accccggatc tatgacgtac ttcagcgttt   93900
caatggtaag gcccgtttcc gcaacaaccg tggaaacaat gacccttctt aaaggttttt   93960
ccactttagc ggttaaggga ttttttcaccc acagattctt aatttccgct ttcaggccaa   94020
ggtaggcctc attttcctgc gcaatcgcct cactatcgat cggcaaaatc aacattaacg   94080
gcagcttttc tttggcaagg tccatatttg cattattcag caacatcgaa aggaagcgta   94140
tttcagccat accgggcatg aaaattaaaa tatctgcttc cgtgggacga tcatgaatgt   94200
tttctttatg aatagtgaga gccgtttcgc aggcggtctt aatgtagttg ttggtgttat   94260
```

```
acagcggcca gtgggtttcc acaccgtact gtcgtccttc caccaaaata atgttttctt    94320
ttccgatacc aaaataggtt gagtatttat gggtatcaat ggtggcggag gttaaaatta    94380
caaagggaat acgcagcgcc cctatgcttc ctctttgcaa catgcgctga agcatacttt    94440
taatatacat gagcataagg tcgatgccta gggctcgctc atgggcctca tctataatca    94500
taaaggcata gcgggaagct atctcatcat ccgtcattgt atgtagctgc gccaacagaa    94560
cccccgcggt tgcataaata aggccccgat tgggttttc cgtcagaggc ttcgtttggt     94620
agcccactgt ttggcctaat atcatgtcgg ggtagtgggt tgaggcgccg atgtctttgg    94680
cgagggtcac cgcggttagg actcttggct gggtacaaat aaccgagcgt cccaagtatt    94740 tttgaaaga atgcgtgttt tcatttctca gaattctgaa cacgtgtacg ggtaaggccg     94800 tggatttttcc ggaaccagtg cgtgacttta taatgagcac ccggtctgcg agggaggttg   94860
gaatggcccc tccaaactcc gggagacgtt gtttttatcca agtgatgatg taatgaatag   94920
gaacatcatt cttgtgctca gcgggcacgt tatagagatg accaggctcc aataaagtcg    94980
gttttcccat attctattgt tttaaggatt gattgttcat aaatatttt atactctgac     95040 caagaaatta tttttttatt aagccggtta tttacgttgt tatggaacgc gaaggtccag    95100
tactgaaagt cctccgagtt gtttaatgtc aagggatttt ttgtaagata cgaaaaggcg    95160
tggtgctggc acctggtgca tggcagagac tcgataaagt tcagtatcca ttggatggct    95220
tcatattttt ctttccagct aggagcgtct gaaaaaaga tagcatatag atgcaaggat     95280
cgccagtatt taggtcccca atgcaacatt tataacctt tgaaaaatct cattccatat     95340
agaggtaaat atttttttc catggagaat tttttgcac tcttgaaggg attgcgccac      95400
atcgtcaaat gttttttgtt ttccatgtat tttggcgtaa ttccagccag tatctgtgtc    95460
atggtcctta atgtcatccg ctaactgaaa ggcatgtcca aaacaatggg cagcccttc     95520 aatcatccca atgtcttcaa cggatccagt tcctaaaacc cagcccataa taaacgcgat    95580
cttaaaaaag ggaatggttt tttctggagt gtctactaac tgaccggaac ccgcgctgtt   95640
tagagagtgg cttacaaagg tacacagcag cgctcccagt tggttgggat ccggaaacct   95700
tggacagtgt tccttaatcc agtcgatttg ccggcaaata ttttgaaatc cttgcatggt   95760
tagcgccaga gcgctcatct gcgccttggc tacgccaaag cgggcccaca ctgtatcttt   95820
atttcgccgc ttcacatcgt tgtcaaagga gggcatatca tcgataatca aagaagctac   95880
gtgaaagtac tccgctgcta gggcggcctc tgccggataa ataggcgccc caaaggaatg   95940
ttgcaactga caggcccgaa caatttccat caggataatg ggacggatat acttcccacc   96000
tcttagagcg taagagcaag gctctgttag ttgtccctta aagtccccat cttcaatagc   96060
attatttaag atggtctcaa actcttcact aaaggtttta aattttttag gattcagtgg   96120
atgtattcca tgaaaaagcg cgacactacg cggtgctgtg attctaaaat acttaggttt   96180
gcgcgtatag gatattaaaa taataataag aactacaatg atggagatat agatgagatg   96240
caacatgctg agttgtctcc ccgcagggaa tggtccttttt ccgcgcttgt taacggtacc   96300
gaggaggcgt tgaaatcttt aggaaaggtg ctgtctagtt tggaatctcc aattcctccc    96360
gtatatttag gtatataatt attgtgtcta gaaattgttt gctttgaggt atcaaaatat   96420
tcagcctgac cgctatttct tttagaataa ttcggtatag ggcttgagta gttggcaata   96480
ctcttaaacc ggggcaccaa ggtaacaata ttttccatat aatgggtttg atacgctttg   96540
tttaaaaatg ggcttaccgg ctttatgctt gttagttgtg cattgagtac cggtatgtct   96600
tctaggattt gtggctttat agaatgatta gcaaacacag aatgtagtat attagatact   96660
```

```
tgtagcatat gtctatttgc ggaaaattcc tggtattctc tgccgtgttg cgaatctttg    96720
ggcggaaggg gaccaagcat cggcacgtcc gtgtaggtac tggtggattt tatgagttcc    96780
tgctctatgt tcggtttgac atgtggattt cctaaaggaa tacctctacc tgcaatccct    96840
ttttctaccg acgcaggtag attgtgcgct aaacacaaaa tattgtacac gtctttgtgc    96900
ggaatatatc cgttatagtg ctggcccggc atctgatcgc caaggtgctg ctcatgctta    96960
atggtaccct ttgttctgag tttaggaaga tcctcgtacg aaaaaattt tgtgtgctcg     97020 ctgaacctcg tagaaggaac cgaactattt tttgggtttt ttaaggaagg caatgaggaa    97080
ggctgggtca gacaattttt ctgtgtgccc tttaagctag ccacctgcgg aaatgttttt    97140
ttttccgtac gaacaacatt gcgcctaatt aggttttccg tatgggttga aaaagcagga    97200
cgatgatttt taaaatgatt aaaaagttta tttttggaa tggagctgta cggctccaga     97260
tcttgcgcat cgccgtaacc aatgtttttg tgctgagggt tcagcataaa agaaagtta    97320 cgtagatcac tgagttgcaa tccctttca gccttttcag gactattagt gtattcattg     97380
tatacaggcg cggctccatt tttgttgccg cagtaccggg aatttagtat attatcagaa    97440
taccggttat gacgcggcaa atcgcttttcc caaagaggtg gatctgacct ataatcggct   97500
aacagctttg aagcataatc atgatacatt gtatataaaa gttaattatt atattgagaa    97560
ggcataatta cttcttgtag gggtacaaga ggctttgaat caggcaaact gacgggtttt    97620
gaatcggccg gctttggacc ggcaggtatc ttttaggtt gatcttcttc tagctcatta     97680 gacacgatg ggggagaaat aggaggaata atttcatctc cgcccttata tttgtcatgg     97740
atagaagaaa caattacatc catgtttgat ttattataaa tgtcgtttaa ctggtgattt    97800
aaaacataat aatgcaaaaa taatagggct acaatgcata tatatacgta aatagccgtc    97860 ttcgttttc gttttttatc caccggcgga ttacaaattg caaaaaatac aactaatacc     97920
accgctgtaa tgattaaggc cacaatgaaa ggattttgaa aggatgtttt gaacggttcg    97980
cacgtataaa ttttttctcc taaattattg atacccgcaa taaaatctac attcattta     98040 tatatttata aattatgaaa aattagagt tacatctccg ccggaccaat cattgctaaa     98100
atttgaagat tcttcaaaaa ggcccgactg gttgaatgtc ttctgctcag gtttccaaaa    98160
attttccaag aatggatttt gaacaatagg ctcatcttga ttttcttctt caaggatatt    98220
ttctttgata tcaagaacag cttcttttaaa ctcaggtgta tcttgattaa actcaggttt    98280
atcctgatca atcgcaaaaa tattatcttc ttcagatata tcctgtttaa tcgcaagaat    98340
agtttcttcc tcaggtttat cctgatcaat cgcaagaata ttttcttctt caggtttatc    98400
ctgaccaaac tcaacaatat cttttctcgct aaatccgttt ttagtgtgaa gctcttggtt    98460
ttgaagagaa ttatcaaaat ctattttagt tgttgtccta gaccgtggca cgggatagtt    98520
atctaatggt ttacttacta tagtcctcga atgtggcacg ggataattgt ttggtgactt    98580
gctggttagc tcttggcttg ttaatagttc ttgtttctc aataattcca tctctactac     98640 ttcttttga tccgctggtg tctcttttg gtattcttca ttagaaaaat gttcagaggg      98700
taatgtttca ataaactttg tgagtggata gctgctcttt gatgtagaag agcgttgaat    98760
ttgctgataa aggagttgaa caagtcgccg gtattcactc tgtctttttt catatttttt    98820
acgtagcgtg gagagatctg ctaagagcga cttgttttca gatgttaatt cttcaatttg    98880
atgaagaagg ctgcgattgt atgaactaag tcttgcatac gtttcttcta attctgtctc    98940
cggctccaca taggcctgtt ttcgcagaaa tttattgtat agttccattc ttttttttgag   99000
```

```
cagaaaggta agactataat cttgcatttc tttcgtaact ttatggtagt tttctttccg    99060
gtttttgata taaagggca gcatttttc tgttgtgata aggtgccca gattgctaat      99120 gtagtcgcac agtagcaatt ccaagataga ttctttcttt tcaaggctta tagattggct   99180
gtattcttta ggtatgaaag aatcaacaat cgttgttacg aagtttgaaa agtttaatgt   99240
tttgctgtta atttgggtaa tgttacaaaa atatttgtaa aaactatcta gcattttttc   99300
ataaagtttt ttattttgtt taaccccctaa aatatagccc tttacttgat actgatattc  99360
cgtaacaatg gaatgttttt tgtatagtgc attttttgtat aaaaagttat aaaaaatgtt  99420
gataaaatac gcaccaaggg tttcaaaaat acttataacg tgggattctt cctgatccat   99480
tatatcatat gtaatattat tttaataaaa aattactgac gaataacatg caaaaaaaat   99540
atgtttaaac ttattttaag ctagcactta tttaaaagtg ttttaaacac gttttaaatt   99600
gtatgttaat acacttaaaa attaagccga aatttgctcc aataaggatt acttttatca   99660
atgaccacct ctttactata aacggcttta cataatttta ataatgcttt agagccaaag   99720
ctgaaggcag tgggaagcgg cactgtacta tggtaaaaat gttgccgatg ttcatcctcg   99780
cggatgtaca caagtttcct atatccttta aacacaatat ggctaatttc ttccacatac   99840
tccttatcct gtttggaata gcggttgctt tgacgggaaa aattcgacat acaaatagag   99900
gcatttgtaa aaatgaaac aaatgcgttt ttacgaagat tggcgggtaa atcggtatca    99960
tcttggcagc aaataatcat cgaaataaaa cagtgacgat tttggtaaaa aaactttta   100020 aaaatttctt ttgtaaataa tgggtgcagt tcggccgcgc agtcgtctaa tattaaaagt  100080
aaacgaggat taagattgat atagtttaac gtaaactttt catcctctgt aaggcataag  100140
tttttataca tatgaatgtt ctgtataata attttttta aaagttgctg ataaagcgat    100200
gtaatctttt cttctttttt ttggtccgtt tgttcagcct ttaagcactc cacttttgca   100260 atattttgt tttccttttg ctgtatatcg atcggaagtt tatgatacaa tgtttttagc    100320
atatcgatgt tgtttactcg actgtagatg gaggacatca tagtttgccg ctgccagatg   100380
gcctccaaaa agcgttcagc gcccttgttg tcattttttt tttgcttatc ggcgagccac   100440
aagcggtagt gtattagagt tggatgtaca aaaccctcat atgaacgatt tgagggttcc   100500 gaggggggcaa ccactaaaat ttgttcaata tggggttgca ggattttcat aatatgttta  100560
acgtacacgg ttttgcctgt ttttgagggg ccatatagca cagttgtttt atctataaaa   100620
tgatgtgctt tgaactgtag ttcaggaatt agcttccctg aatgggtcgt tagggccatc   100680
tctatattat tacaattctg cttttgtata taaaatttct ttttcgagtt tattattatt   100740
gttgacccac atatctaccc gtatcgtatc atcaggcaca ttgagcattt caagcgcatt   100800
atctaactgt tttttttgttt ttatcagctc gctttcttca tcgggggtta aattttctt   100860 actaagcagt tgcttaattt tttcttcgca gtcgtctata aaatcatact ctcgagcttt   100920
tttgatattt ccagatgctt tttctaggtt ttttagctcc ttaaaggaaa gcagtccctt   100980
aatcccgcta tccgtgtgaa aggttgaatt atagatggag agccccggag catccgggcc  101040
agtttcttgt atatttttg ctttttttgtg gtaaatagta tttcgtaaaa tctctttttcc  101100 tatctttagg tcttcctcat gacggtccaa aatccgtttt attatttcat tatttttgatt  101160 aaaataattg tagcgctctc tgttggcctt aaagcttccc aggagtgtcc agttgcctaa   101220
ttgaatggat gaaacctctg agaaaatctg gtctttatat ttataataaa attcatcaac   101280
cttttgttgg ttgctgctat ccaccacatc ataaataatg aaggcaaact ctaggtcggg   101340
tttttctggg tagatgcttt ccgtagcggc ccgcaactct tcgtaattat cctcaatgta   101400
```

```
ataattccac ttataaaaag tatcctgagg tggaatatgc tgcgaaagat atctagtaat    101460
ttttgtgtta aagagaatgg gtttaaacgc cctcggattt tcaagcatat gtttaatgct    101520
ttggtgaagt tctatatttt gtaatatgtg ggctgctgcc ctatagccct gtggggtttg    101580
ggtgattgca tcaatatcgg cctgaagctc attaggcaca tttaatgttt tttgcatgat    101640
gtgtaaaggg atgcgctcag gatctgctaa atcggtgtat tctgtgcttg tacaagtgct    101700
tgcacaggta tctacattgg tatctgcaca catgcttgca caggtgtcta cattggtatc    101760
tgcacacatg cttgcacaag tgtctacatt ggtatctgca caagtatacg cactttgagc    101820
atgaagatta ggatcaaaca caaaatgttc tcgtaaaaag ctatcgatcg ttgttttagc    101880
ttccttgctt ttctgcgtct gggttttgca gctatctgct atagataaaa ttgtatttac    101940
taccgattca gagggaacat cattagtttc ctgtttcaaa gtatcaacta acgttattag    102000
ctcactgaga agagttttgg tcgtgtgggt aggttttgaa taggaaggca tccattcctg    102060
cagagctttg aagacatatc caataaagct agtcattata agacgtcgaa tatactgctc    102120
ccgcaaattt gtaaaagagc aaaaggccac cctgctatca tttttgaact gtttgtaagg    102180
gttcgtcctt tggtaaagct gtttaagcgt ttcttcggat atttcagtag agggatcctc    102240
caatacgttt ttgagaagct catcaatatt aaattctgcc atatcttaga gtttattata    102300
tacatattaa agctttaata taaggggggt ataacaatgg acgaaatcat caataaatac    102360
caagctgttg aaaaactttt taaggaaatt cagcaaggat tggccgcgta tgatcaatac    102420
aagaccttaa ttagtgaaat gatgcactat aataatcata tcaagcagga gtattttaac    102480
tttttaatga ttatttcacc ttatcttatt agggcgcata gcggagaaac gctgcgaaac    102540
aaagtaaata atgaaattaa acgtcttatt ttggttgaaa atatcaatac caaaatatct    102600
aaaacgctgg taagtgttaa ttttttacta cagaaaaaac tttcaacgga cggggtgaaa    102660
acgaaaaaca tgtggtgcac caataatccc atgctgcagg taaaaacagc ccacaacctt    102720
tttaagcaac tatgcgacac acagtccaaa actcaatggg tacaaacttt aaaatataag    102780
gaatgcaagt attgtcatac cgacatggtg tttaacacca cgcagtttgg gctgcaatgt    102840
cctaactgcg gttgtattca agaattgatg ggaaccattt ttgatgaaac acattttttac    102900 aaccatgatg ggcagaaagc aaagtcaggt atctttaacc ctaaccgtca ctatcggttt    102960
tggatagaac atattcttgg tagaaatcca gaacaagagt tggggaccaa acaagatccc    103020
tgcggaacca aggtgttgca acaactaaaa aaaattatta agcgcgataa taaatgcatc    103080
gcgcttttga cggtcgaaaa tattcgaaaa atgttaaaag ataaaaccg cacagactta    103140 aataattgtg tttctcttat attgcgtaaa cttaccggag tagggccgcc tcaaatatca    103200
gagtcgattt tactacgagg cgaatacata tttacagagg caattaagat acggaaaaa    103260 gtgtgtaaaa aagggcgtat taataggaat tattatccgt attatatata taaaattttt    103320
gacgccattt tgcctccaaa tgataccacg aatcgacgca ttttacaata tattcatttg    103380
caaggaaatg atacgctagc taataatgat agtgagtggg aatctatctg tatggagctc    103440
cctgaaataa aatggaagcc cacagatcga acccattgtg ttcatttttt ttaaagatga    103500
agatttttta gatgattttt tttagttttt taaaagacga aaaattttt taaagatga    103560 atattcttaa accccgcaaa ttactttttt ttaggtactg taacgcagca cagctgaacc    103620
gttctgaaga agaagaaagt taatagcaga tgccgatacc acaagatcag ccgtagtgat    103680
agaccccacg taatccgtgt cccaactaat ataaaattct cttgctctgg atacgttaat    103740
```

```
atgaccactg ggttggtatt cctcccgtgg cttcaaagca aaggtaatca tcatcgcacc    103800
cggatcatcg ggggttttaa tcgcattgcc tccgtagtgg aagggtatgt aagagctgca    103860
gaactttgat ggaaatttat cgataagatt gataccatga gcagttacgg aaatgttttt    103920
aataataggt aatgtgatcg gatacgtaac ggggctaata tcagatatag atgaacatgc    103980
gtctggaaga gctgtatctc tatcctgaaa gcttatctct gcgtggtgag tgggctgcat    104040
aatggcgtta acaacatgtc cgaacttgtg ccaatctcgg tgttgatgag gattttgatc    104100
ggagatgttc caggtaggtt ttaatcctat aaacatatat tcaatgggcc atttaagagc    104160
agacattagt ttttcatcgt ggtggttatt gttggtgtgg gtcacctgcg ttttatggac    104220
acgtatcagc gaaaagcgaa cgcgttttac aaaaaggttg tgtatttcag gggttacaaa    104280
caggttattg atgtaaagtt cattattcgt gagcgagatt tcattaatga ctcctgggat    104340
aaaccatggt ttaaagcgta tattgcgtct actggggcgt ccagctataa aacgtgactg    104400
gcgtacaaaa agtccaggaa attcattcac caaatccttt tgcgatgcaa gctttatggt    104460
gataaagcgc tcgccgaagg gaatggatac tgagggaata gcaaggttca cgttctcatt    104520
aaaccaaaag cgcaacttaa tccagagcgc aagaggggc tgatagtatt taggggtttg    104580
aggtccatta cagctgtaat gaacattacg tcttatgtcc agatacgttg cgtccgtgat    104640
aggagtaata tcttgtttac ctgctgtttg gatattgtga gagttctcgg gaaaatgctg    104700
tgaaagaaat ttcgggttgg tatggctaca cgttcgctgc gtatcatttt catcggtaag    104760
aataggtttg ctttggtgcg gcttgtgcaa atcatgaatg ttgcatagga gagggccact    104820
ggttccctcc accgatacct cctggccaac caagtgctta tatccagtca ttttatcccc    104880
tgggatgcaa aatttgcgca caagcgttgt gacatccgaa ctatattcgt ctagggaatt    104940
tccatttaca tcgaatctta cgttttcata aagtcgttct ccggggtatt cgcagtagta    105000
aaccaagttt cggtacgcat tctttgtgcc gggtacaatg ggtcttccaa aaggatctac    105060
aagcgtgtaa acgcgcccct ctaagggtgt ttggttgtcc cagtcatatc cgttgcgagg    105120
aaacgtttga agctgcccat gggccccat ctgggacgtg ccctgaatcg gagcatcctg    105180
ccaggatgaa tgacatgcac ccaatatatg atggcccacc atatcatgga aaaagtctcc    105240
gtactgggga ataccaaagg taagcttgtt tcccaaggtg ggggtacccg tatgcgggcg    105300
tactttattg tattcaaacc ctactggaac ataaggctta aaatgcgcat taaaatgcac    105360
caaatgtgtt tcttcgattt gactcaaagt gggttcggga tcgggtttcc cataacttt    105420
gttcacattt ttaatgttag agatcctgct attcagcaag tcttgggcca atataatctt    105480
gtcggccttc ccatcgttag caataagaca aaaagctcct cctgatgcca tatataatgt    105540
tataaaaata atttattgtt tttattaaat atggcggttt atgcgaagga tcttgataat    105600
aacaaagagt taaaccaaaa attaattaac gatcagctta aaattattga cacgctcttg    105660
ctggcagaaa aaaaaaactt tttggtgtat gaactacctg ccccttttga cttttcctcc    105720
ggcgacccctt tggccagtca gcgcgacata tactatgcca tcataaaaag cctcgaggag    105780
cgcgggttta ctgtcaaaat atgtatgaaa ggggatcgtg ccctccttt catcacctgg    105840
aaaaaaatac aatccattga gataaacaaa aagaagaat atctgcgcat gcacttcata    105900
caagacgaag agaaagcatt ttattgtaaa ttttagagt ctagatgagc ttttacgcaa    105960
tgttgtacag tgttgtatat atgtcttgta agcatttgtt gtagagtaat aagtaaaaga    106020
taaataaaaa tgactattaa aataaagccc aaaccattaa aaatatttt atctgttaga    106080
tttaatttaa taaatggctc atggaatgtg tggtgcgccg ctgcatgagg tgtggccgca    106140
```

```
tgggatgtgg tcgcataaga tgtagctaca tgggatgtgg catttgcttg catgtaagga   106200
tcatgatgtg ttgggtcttc atcccagcaa taatcgccat ctttatctag ctgaattgta   106260
taccccatta tatatcactt attatttttt tttaatgttt catgaatttc attataggcg   106320
gtgaaagggt cctcaggccc cttctgtaaa agattataga gatcttcgga cgctttatgt   106380
ttcgtgcgaa ttaaggcggg atataacaaa agagagggcc ccagttccaa acaaatttta   106440
cttagcgggc tcatattttg caccaagttt cccactactt gcgatgtttc ataacgcatt   106500
ttaaagagct ttatcataaa agtgttatgc aggccggtgt agtctggcct atagttaagg   106560
aagggatttc tctggtacc gtcaaacacg atctcaagtc ctctagcaag cccgatcaaa   106620
atttcttcag caatggatga gtatctaatt cctacattac gaagcgtaag catttctata   106680
acatcatcta tttcctgcat agaggaatct attgtaggaa ttttaatatc atctgtgctg   106740
atttgttcat tcccaagata ggtaagcagc atattaattt tttctagctt tactagctta   106800
gtcttacgct cataatcatg atctttttta taaaagagt tgggatcacc gttggaccgt   106860
agatgattaa taaggcggtc tacttgcttt gtactaggtt taatactttt ttcactatac   106920 tcgcttttcag catagtggtt tttacgatct cttttagaaa tagctgtttt ttgagatgcc   106980
tcagactctg catattttt tctatgcgta gaaagagaat aaccgcggtc attacgtgaa   107040
ctactgttgc atgcaaggcc tcggcgcgtc ttaccgctgc gcacactgcc attgcgtata   107100
ctgccatcgc gcacactgcc gctgcgtata ctgccattgc gtatactgcc gctgcgtatg   107160
ctgccgctgc gtatgctgcc gctacataca ctatcactac atatgctgtc agtacatacg   107220
ctatcgcggc gtatgccgcc gtgtacctta tcgccgcccc tacccgaggg tttttttagat   107280 ataatactgt gtgggagtc aagcgaaaat tcagggtcat taaagttaat gcccaatgac   107340
tttgccaatc cattaagctc ttcatcaaaa tgatcggtag gaaaactttg ttgcttgccc   107400
atgacctgtt tttcaagttc ctccaaattg gcttgctcat ttatatggag attattcata   107460
agcgtcgtaa ttccagcaag atttgctcct tctaaaaatg tggtgtcctc catcggatat   107520
actatactat ttaaaagctt ttaaataaaa atgtgtttgg aagaaatgct ctcttcaagc   107580
gtgtgtagct cagatataaa tgcctcctca gaaagctttc caccatactc ctttctcatc   107640
gtataggagg gcgccggttt aatgtaggaa atccactggg aggtaaaaaa ccggtacaac   107700
atatttagca gctcgcgggc ctcccacctt ttgggctccg tatagtgcac atcaacataa   107760
gaggcggcgc atgaaaagct gcaaagttg ccgagaacgc ccatctcaat ctctcctcgc   107820
tcattttcac gcatataggt gggcacgaat tttgggacag tcttgaaata gagatgcact   107880
gtccagcatt taaagctaga atgggtaacc catttggaaa cagtggtgaa tacggagggt   107940 agctttttt cgacctcggc ttcatcgtca ttcgtattta acgtatcggt ggcagttttt   108000
ttggattgca agcattcttc aatggtaatc ccggataagt ataaatatt aggacaatta   108060 gtttccataa ttttgatagt tatttttata caacatggat ttaattaaag ataaatggag   108120
gacgaaacgg aactgtgttt tcggtcaaac aaggtgacga ggcttgaaat gtttgtctgc   108180
acatacgggg gaaaaattac cagccttgca tgttcgcata tggagttaat taaaatgttg   108240
caaattgctg agccggtgaa ggcattgaac tgcaactttg gccaccagtg cctaccgggc   108300
tacgaatctt taataaagac tccgaaaaaa actaaaaaca tgttgcgccg tccgcgcaaa   108360
acagaaggcg atgggacttg cttcaatagt gccattgaag cctccatttt gtttaaggac   108420
aagatgtata aattaaaatg ttttcctagt accggggaaa ttcaggtccc gggcgtcatt   108480
```

```
tttccggatt ttgaagacgg aaaaaacatt atacagcagt gggtagactt cttgcaacat 108540
caacccattg aaaaaaaaat ccagattatt gaatttaaaa cgattatgat taattttaag 108600
tttcaaataa acccagtgtc tccccgcgtc atcattcatt taaaaaaatt tgcagctttg 108660
ttggaacaca tccctactcc atatcccata cgtgaaataa agcctccatt agaagactca 108720
aaagtatccg caaaatttat ggtcagtccg ggaaaaaaag tacgcattaa tgttttttctt 108780 aaaggtaaga taaatatttt aggctgcaac acaaaggaat ccgcggagac catttatacg 108840
tttttgaaag atcttatcag cgtacattgg caagaaattt tgtgcgtgtt accggtaccc 108900
gattaaagaa tgttttcatt aataaggtaa tcgactatgc taaaaagaat aacaagaaaa 108960
ataccttgaa gaactatacc aaagtaggta ggttttctgc atgtcacggc atggttaaaa 109020
ttgctaataa tgtagtccac aaaagcattg ctcaatacga ctaaaaatag taaaaaaagg 109080
ataagtgctc tttttatatc catatacttt aaaacttatt ttttacacta ataatttcct 109140
gcggccgcaa tataaactgt aggtcatcta taacgcccag acctgttaaa agtagagtac 109200
tatgttttaa gggatttaaa atatccgccg caagaatgtg aatataattt tcaaagtggt 109260
ttacaggaat gcgtaagcgt ttttttttgc actgcggttg gtttagggtc gaatactggc 109320
aggaggtata tatattaata agaccgcggt cgatggtttc aatatcttca tagaattcaa 109380
tgcgcggcgt caaaagtttt ttaagatgtt gacataactc atcatacgtg taggactgga 109440
ggggggaaag aagggtgtag tcaaagttaa aaatgttttt ttgaagaacc tttaaagcat 109500
gttccgcgtc cgtggtttcc aaaatatgtt ttatggtatg aatgtcattt aaatctacaa 109560
agtctgacag ctttgtgtag aactcggtga cggaggttat tttctggaaa tcggtttttt 109620
gaaaaagatt ttcaatgtgt ttgcgggttg agttgctttg cagtccatac aagacatcaa 109680
aaaattcaat cagcaaaaac ttatacaaat ggttaatata aaaagctttg ttggccttat 109740
tctgctgagg atatggttcc tctaggggat atagaatggc ttggtctata tccctaggat 109800
caatagtcaa tgttgcgatg ggaagctttt ccagcgtagc gggaagagtt tgggttggag 109860
cgtagtaaaa gtatagcccg gttttttccct ctgaaagaaa gcccacaaat tcttttttta 109920
tattttgcag caccgctgag ggtacgattt cgtactgttt atactgtttg ttgaaaaggg 109980
taataaattt ccaggtttct tcaaagcttg caatctgggt gggccgcaga tcaaagtcga 110040
tgggaatgtc gtcatgaatg taggatgata gtcttatagg aaaataaata gggcgatcgg 110100
tgtctgaatc gataagtaaa gcataacaaa agttatgcct gttgataagt ttttttaccaa 110160 ccgtgtagcc gggaatgttt ttcacgtcat ggatatccca ccagttatcc ttgcacataa 110220
actcgctcat agactggatg acctccatca cagggtcatc ttcggtaaaa atatactggg 110280
cctcactgtt tttcagaaat cttttttttgct gggtgatggc cattgggtag atcccttcgt 110340
ccgtgtcaaa gataatggct atcttcttcg atgggctaag aatttttttgt attgtgctgg 110400 gggacacctc aaacccgatg tcgccctgtt tatctttaaa aaagacacag tgaaggtcgt 110460
agcatatggc aacaaggtcc agaaagatgt cctgccatgt ggtgtcccat tgaagcagtt 110520 ggttttttttg ttcaacaaag gtttgtaaga taaggtttgc cagctccgcg ccgctggaaa 110580
acatgttgcc ggccccattc cccaaaatat agtactgcgg tgtgttggcc gcctttgcaa 110640
tttcaatggc aagggccttg ggggcaagat ccaaaattcg agcaagggaa taaaaaagcc 110700
cggcattgct aattccaagc atggtttgct ccaccccccac aatgcaaaaa atgtcgggct 110760
cttttatcgt atttaaaaac agttcatctg ctatctggtg gggtagaaag gcaatccggt 110820
tcaccggtat tttttttttcca taggacaagg tatgacgcga tgtttgtgta ttaagatcct 110880
```

```
ccaggtcttg ttctacaaac gtgtgcttgg tgaggcaggt attgttaata tagaaccgct 110940
ttgtgcccag cagggccttc gtcttttggc agcacggcag acagtaattt aggggtggc  111000 ggccttctag taggcttaga tgagggtagt caggatgcgg gcagctatag taggcaggta 111060 cccctccgt  gaaattccaa tactttacta gctccttgcg cttggctggc ggcatggact 111120
tcacctcggc ctctgagtaa atgacgggtg gccgtgggtg ctggcatagg acggagtaaa 111180
ccgttgcctg cgtgtcgtac ttgcgcaggt catacaggtc ggggtcctgt tcttgaagcg 111240
cacgtagctg agaggctccc tttccttgtt gtttatcgtg cagttgagag agtttattaa 111300
ccaaaatttt gtcaggcccg gtgatcaagt tatctaaaaa cacaaatagg taaacccaaa 111360
gatagttaaa ctcttcctgg gtaatgttaa acatttctat tttgatatct gtaaccctat 111420
ggtagatgcg aatgttgcgg ccgccgtaga ttgtttccca ccgggccgca acatttgtgt 111480
caaagaggta cgcatacgtg ttttggagca acgcaacatt gatgtccatt ttgcgccccg 111540
gaccggagga ataatgatc atccgttcga tttcgtgggg atcatacgaa taaatcccct 111600
ttttaaataa aaaattgtag accccggttt gctggaggcc ccgcacggaa ataatccctg 111660
cttgctcgta ttcccgccaa cgacttttga gctcggtaaa tcccttgcta gaaagcgtat 111720
agggccaaaa ggtggacacc gacatggagc tgatagaaat ttggatgtcc tcgttggagg 111780
gaaggggcag actccctcca cgaggaaacg cggcaggccc catatcatta attgtatgaa 111840
taataggatt tatgaaatta tttagggtgg acaccacgga gttaaagtcg tggcgctcgt 111900
tttctgacca attgctttcg ataaagtagt gcccattatt ttgtatggta agaataaagg 111960
cctttttatt gataaagcgt attaaaataa tagtgggtac acggaatgtt ttattgctga 112020
atttttcagg ctccgtggaa gttatgtggt gtttggaaac cacggtggga cctgttttac 112080
tataaaagaa caccaccagc tgaggaatat cgggagtagc tggaaatagg tcgaaaacat 112140
tgcgcacatt aatttgaata tttacgaggg gtgaaatttt aatcattgcc gaggtgacgg 112200
ccaacgtgcc gcgtgttagt ctattcccct cgtacttggc aatgacttgt tgtgctctgg 112260
catacgtaaa gtttattagt ttttgctcta ggagaagcct ctttttaaga ctggtcaagg 112320
atggagaaag agcaggatac tgtttttcca tttgtaaggg agattgtacc aatagtttaa 112380
aggcatcggg ggaaagaaga ggccaatact tcataataag gccgtaatag agtaagtcaa 112440
attggtaatt atcctctatg gcaatggaga tttggcgccg catgggggcc actagcgtgt 112500
tgaggtctgc tacaaagatg tgatgaatgt ttttatgag ctggaagctg tcgagcgctt 112560
ccacatagag ctcatctttt tgactttcca tagatgcgtc gatgttcacc ccacccacct 112620
gttgaaactc cttttgtag tcgcgaatgt ctaacgccac cccgctaccg cttaacaata 112680
ggcgatacgt tacctgaagc gcattgtttt gaaaaagaa aatgtgttgt ctataagggg 112740
ggatccctgt ggcaacgtaa atttttctc gaatgtcttt aaagtgtct tcagggaaaa 112800 tactatactc gctatacatc gtctcaattt ctggcatcat cacgtttgtc tcctcgccac 112860
gatcctccac aaaaagtttt tcaaactcat ctaaatcatc gctatctcca cccaccacgt 112920
attgggaaag ctttttctcc caatcctcgc cgtaaaaatt ttgtaaaatt tctttgtcct 112980
taggggttcg ctgcaggtct ttgcggcagg cctgtaacac gtttgcagga acggatccca 113040 aaaaataaa  cgtcttcgtg tactcatttt ccacaggatt ataagagta  actcgtagag 113100 gatttgttaa aaagtcattt tggaaatcca ttatacccgg tatagaaaat aaaatttaaa 113160
ataaaaacgg atgatatcta tcatggaccg ttctgagatt gttgcacggg agaacccggt 113220
```

```
gattacccaa cgagttacaa atctcctaca aaccaatgct cctctactat tcatgcccat   113280
tgatatccat gaagtacgat atggagccta cacactttc atgtatggtt ccctcgaaaa    113340
cggttacaaa gcagaagtaa ggattgaaaa catcccagtt ttctttgacg tacagattga   113400
gttcaatgat acaaaccagc ttttttaaa gtcgctactg acggctgaaa atattgtgta    113460
tgaacggctg gagacgctca cccagcgtcc tgtaatgggg taccgcgaga aggaaaaga    113520 gtttgcacca tacattcgaa tatttttaa aagcctgtat gagcgacgaa aagccattac    113580
ttacttaaat aatatgggct acaacacggc cgcggacgac acaacctgtt attaccgaat   113640
ggtttcccga gaattaaaac tacctcttac aagttggata cagcttcagc actattccta   113700
cgagcctcgc ggcttggtac acaggttttc cgtaaccccc gaggatcttg tttcctatca   113760
gaatgatggc cccacagacc acagcatcgt tatggcctac gatatagaga cctatagccc   113820
tgttaaggga accgttccgg acccaaatca ggcaaacgac gtggtgttca tgatatgcat   113880
gcgcattttt tggattcact ccacagagcc tctagcgagc acgtgcatca ccatggcacc   113940
ctgcaaaaag tcctcagagt ggaccaccat tctatgctcc tctgaaaaaa atttgttgtt   114000
aagctttgct gaacagttta gccgctgggc tcctgatata tgcacagggt tcaatgattc   114060
tcggtacgac tggcccttta tcgttgaaaa atctatgcag cacggtattc tagaagaaat   114120 cttaacaaa atgagccttt tctggcacca aaagctggat accattctaa aatgctatta    114180 cgtaaggaa aagagagtca aaatctcggc cgaaaaatcg atcatttcct ccttttgca    114240 tacccctgga tgcctaccca ttgatgtccg caacatgtgt atgcagcttt accctaaagc   114300
cgaaaaaaca agcttgaaag cgttttaga aaattgtggg ttagattcga aggtagacct   114360
gccgtaccat ctcatgtgga agtattatga aacacgagac agcgaaaaaa tagccgacgt   114420
ggcctattac tgcattatag atgcccagcg ctgtcaggac cttctggtgc gccacaatgt   114480
tatccccgat cgcagagagg taggaattct gtcatacacc tcgctgtatg actgtatcta   114540
ctacgcggga ggacacaagg tatgcaatat gctcattgcc tatgccatcc atgatgaata   114600
cggccgtatt gcttgcagta ccattgcccg aggtaagcgg gaacacggaa aatatcccgg   114660
cgcctttgtg atagaccccg ttaaagggct tgaacaggat aaacccacca caggtctcga   114720
ctttgcgtcg ctgtaccct cactcatcat ggcctacaac ttttcgccag aaaaatttgt    114780
agcctctcgg gatgaggcaa atagcctcat ggccaagggt gaatctcttc actacgtctc   114840
ctttcacttt aacaatcgtc tcgtggaagg atggttgtg cggcataata acgttcctga    114900
taaaatggga ttgtacccaa aagtactcat cgatctactt aacaaacgga ccgccctaa    114960 acaagagctt aaaaaactag gtgagaaaaa agaatgtatc catgaatccc atcctgggtt   115020
taaggaacta cagtttcgcc atgccatggt agacgcgaag caaaaggcgt tgaaaattt    115080 catgaacacg ttttacggcg aggcaggtaa caatttgtcg ccccttcttc tgcttcctct   115140
agccggagga gtcaccagtt cgggtcaata taatcttaaa cttgtctata actttgttat   115200
caataaaggt tacggcatca agtacggtga caccgactca ttatacatta catgcccaga   115260
tagtctttat acagaggtaa cagacgcata tttaaacagc caaaaaacga taaaacatta   115320
tgagcaactc tgccacgaaa aagtgcttct gtctatgaaa gccatgtcta cactatgcgc   115380
cgaggtgaat gaatacctgc gacaagataa tggcaccagt tacctacgta tggcctacga   115440
ggaagtactc tttcctgtgt gctttacagg caagaaaag tattatggta ttgctcatgt    115500
aaacacaccc aattttaata caaaagaatt attcatccgc ggaatagata tcattaagca   115560
gggtcaaaca aaactcacca aaacgatagg aacgcgaatt atggaagaat ccatgaaact   115620
```

```
acgccgccct gaggaccatc gccccctct tattgaaatc gttaaaacgg ttttgaagga    115680
tgctgtggtt aacatgaagc agtggaattt tgaagacttc atccaaacag atgcgtggag    115740
accggacaaa gacaacaaag cagtccaaat ctttatgtct cgcatgcacg ctcggcgtga    115800
gcaactaaaa aaacacggcg ctgcagcatc gcaatttgct gagcccgagc cgggagaacg    115860
cttctcctac gttatcgtgg aaaaacaggt acagtttgat atccagggcc accgcacaga    115920
ttcctccaga aaggggggaca agatggaata cgtctctgaa gcaaaggcta aaatcttcc    115980 tattgatata ttgttttata tcaacaacta tgttctaggc ttgtgcgcga gattcattaa    116040
tgaaaatgaa gaatttcaac ccctgacaa cgtcagcaat aaggatgaat acgctcagcg    116100
ccgagctaaa tcctacctac aaaaattcgt gcaatccatt caccctaaag acaagtctgt    116160
cattaagcaa ggcaatgttc atcgacagtg ctacaaatac attcaccaag aaattaaaaa    116220
aaaaataggc atctttgccg acctttataa ggaattttt aacaacacca caaaccccat    116280
cgaaagcttt attcaaagca ctcagtttat gatacaatac tttgatggag aacaaaagt    116340 aaaccattct atgaaaaaaa tggttgaaca gcatgctacg gctagtaatc gagctggtaa    116400
gcccgctggt aatccagccg gcaatgcgct gatgcgggct atatttacgc agctgattac    116460
ggaagaaaaa aaaattgtac aagccttata caataagggg gatgcaatac acgatcttct    116520
cacctatatc attaacaata taattacaa aattgccacg tttcagacga acagatgtt    116580 gacgttcgag ttttccagta ctcatgtaga actgctatta aagctgaata aacgtggct    116640 tattttggct ggaattcatg tggcaaaaaa acatctgcaa gctttttgg attcatataa    116700 caatgaatcg ccgtctagaa cattcattca gcaggctata gaggaagaat gtggcagtat    116760
taaaccatct tgctacgact ttatttccta atacttctta agaaactctt taaacaagga    116820
cttcgcatgg tcaaaggttc taaacccatg gcccttatga ttcgccaaaa aagcggtttc    116880
atcaagattt tctaaccctt tcacggatga agaaataagg tgttcggcct cgtttgccca    116940
ttttctatga ttttttttca cctcgggttc tagatctgtt ttctccatat actcattgtg    117000
gtcatatttt ttttgggag gaggcgtggg tggaggaatg ggtggaggaa gtacacccga    117060 cttcccgct tcaaccgttt tataaaaaaa tagaagcata atacaaagaa taaggactat    117120
cgcaaatatg ataaccagtg tcccagtcga gggcattttg ttatataagt aacgttttt    117180 ttattttta taattcgaat gaagaaccat gttgaatagt cttctactca aagacatttt    117240
gttatacggt aaatgagaat ttataaaatc cgaatatcac tatcatactg tttatctgag    117300
aaggtctcac tgggtcctgt gatggagaac ccatactctg taatgctggg gtttataatg    117360
tggtcaggac tgacaagcac atttctgaac tgcgagagtt ctaggtttag acgcagtcgt    117420
aatagtcgct gtatatttgt aataaatatt agattgcgta tgaggcgagt gtcaaagcga    117480 tccttttccaa tttgtactaa ggtgggcttt tgtattccaa ctcccacttg tttaacgatg    117540
gaccagggtc cttcttcccg attttgttcc gtgatatagg tcagcacact attttctgta    117600
tatgaggtat gatgtcgcat attaataacct ggtgccattc caactggcgg ttgtgcaatt    117660
cgggctgtac cggacccaa ccatcgtgga gttttataaa catatcgttc tagcgtattt    117720
aaaaattcct taaggttatt tacgagtagc atgaagggtg ctattaaaac aggtggatgg    117780
tttataacca ttgtcataaa ccattgcatt gcttcaatat cattttgtaa tgcttgacgg    117840
ggaggcgggg caggtaatcc acgtatgttg aataaagcgg ttaattgtgc accggctgtt    117900
tggggcgtaa tattttgtat taaatttatc atcgaattgg cttgcccggc atttcctata    117960
```

```
agatcgatta aattggttat ttgacctcga tattgttgta cccagttttg aatggcagcg    118020
atgatctcag gggttggatt gttttgaatt tcaggtgttt gtattagatt attcacttct    118080
cttcgtgtat cttcaagctg agtcctaaat gcatttaact cgcctataat ttggtttcta    118140
tcaataacat ttcttaaacc tcgaactgtt tcagccaatc gtatagtacg cacaatttca    118200
tgtaaggcct ggtttatgta tattgacatg ggatggcccc accgctcacg tccacgttga    118260
atacctgcgg ccaaactagg acctgcctcg tcataatcaa attgtgtagg ataaaggctt    118320
ccaaatagca ctttattgaa aatttggtca gaaagaaatt tagggcggcc catatttagc    118380
gcgttgtccc ctctaaagat gcgtgacatg tatccggcgt tgcctttgga tagtaactca    118440
ttcccatatt gagtaataga gaccgagaca taggggttta taagaagttt tagcataaat    118500
tctcgagtat ttatgggggg acgattcgga atgtttaata cctctgcaac atctggttga    118560
ggagccgtgg tgtccagaga tcgtactttt tcagccgaaa tgccgtacat aagacaagca    118620
atttcttcaa aactatagtc atagttgtaa atattggcaa gtggtataga tcgcatcagc    118680
gcatttacat tgataggtat aatattcata tcaaacaagt taaatatgcg ctcgcgctct    118740
ctattagagc caagagtgcg tgtttgacct ttcggcgaca ctattttgtg aatatgattg    118800
atttgctcct cttggtaaga gctttccacg aaggaaatta cgtcttgcaa tgttttacga    118860
agcgaataca ctgcattcat ccctattccc gctgttataa tgggtttatc gtctctgttc    118920
tcgctaataa gattaactcc accaaaagta ttttcattgt acatcatcac tgttttaaaa    118980
ctacggatat ttatgataaa tcggagagcc tgaatggcgt gggtataaaa gtgttcaaat    119040
cgcgtgggag taatttgttc gcgagcaact accgtttcat tatagttttt catgataagc    119100
tgtactccgg gcatatctga gagctgtacc ggatcatttc ccagtaattt tcttgtgccg    119160
tatagtagtt taaactcggg ggagccgctt tcaaggttcg ggtaagaag aggatcatat     119220 acctcattat tttctattct taggtcatgt aaataataga gcgaaagtga aaatggcata    119280
agaggctcct tattgtaccg ggacatatag ttttgaatga agtgttcttc tgtttcaaga    119340
tagatgggat gatcggtaag ctcgtgcagg acctccatgg cagaatctgc cagagtgtga    119400
gagcctctaa tgatcccgtc gatcactgcg accagtcgct ttcgcacaac atcgctcgta    119460
ttattttgtg cgtctcctag gggcataagc gtaacattgg gacgaaatac gccgccaatt    119520
ccccgcaggg ccgcctgacc gacggatagt cctgtcgcag gaacattgtt attattataa    119580
taaataacgg aatcattatt ggctcccaag agtgccgtca gattagggcg agctagttgg    119640
acatttgtgt attgtataaa ttgttttaga agctctccct ggctaataag aatattaaac    119700
attttgttaa atagtggaag attggctcta taattttctt taaggtaaat gggaatttct    119760
gttaaagtag aaataagatg ctgactcagg ccctggcgat tggtatcctt aataagccgc    119820
tgaagtataa gtcccaaaga cagaagaagc accgactgct ctgtggggtc gcctctatga    119880
ccaaagacgt tgttattgcg tgctaagtca gggtgagcat atcccatctc catcactgct    119940
tggctaaagt tcccattagc gaatgcatta ataagattta gatatatttt tccgctggga    120000
gcatcataaa atcgggtaat atatgaagct atgagctggt taaacaccat catcatacta    120060
cgattatttt gaataccata gtctgatccg tataggcgat aacgtcgaag gttgtttgcg    120120
gcatcattga cattggcata ggttctgagc gctatgttgt cccagtagct aagagtattt    120180
tcctcctggg cgttgttggt acgaataaga ttggagagtc taaagtctcc tagtgccacc    120240
tgctctacac gaagtccaga gttattctcc aaagcatcg aaaatacgag tctactgaat     120300
actcttccgt attgttcaaa gcgttcagag gattggggat tgttatttat ttgaatatta    120360
```

```
gccgcgtccc ttctttgcgc cccacctcga agttgcagta cattataagg ctttgtaagc   120420
aaggtgtagg ttttattaat gatttggtta acccctcca ggcccaattc accgccagga    120480
agcggccttc ctccggcatc ggtaggtggt ttaataagtt tgtcaattaa atgttcttcc   120540
aaccagtaaa atgagccagg attagatcta ttttcatagt attgaataat gtttttatca   120600
atatgcgggc gtagaagatc aagaaaatac ttcgtgtcgg ccatcaaaga atcaattaag   120660
gaaataagac ctgtaaaatc taaatgcact tgagcggtgc tggtttcagg gaagcgaact   120720
tgaaccattt tgttaaaact ggaggtcatt tcgaagatat tggtcaacag gagctgcatg   120780
attcgctgat tatctactaa ataccttgcg gccaactctt gctccggacg aactcctcca   120840
ccagcaggaa tacccacata tggtacaatc aagcaaaaa gagtttctgt ggttaaattt    120900
cggtcttggg ctgctgcagc cgcttcggta gtgggatcag ggtacaccat agaaagccgc   120960
atattgattt ctttaatgac taatcctgga tttctaatct cagagatggc cccgtgtttt   121020
cttccgagcc agtcaataag attggcgcgg ttcacgttgg cagcttgtgt ctctcgtaac   121080
cattcgataa tgcttttttg aatcgtatct aggtctaaac ctttaatgtt attacgaaag   121140
ttattaagaa gtacgtaaat agcactcaat aagttaagac ctgtaataac ggtttcatga   121200
aacagaaata ttttgttaac atctgtatct gccagtgact cagagccttg aataagtttt   121260
gaaacgattt gaattttatc ggtatgctcc tttttgagtt cattgatagc ctggcgaatg   121320
agttcttggt aggaaatttt gcccaattct tgttgcagac tgggatcttc aaacatctca   121380
ctaagctgtt tcctaaattt ttgtaccaaa tcccactggg agttgggctg cagcattcct   121440
gtttggacat ccacagagtc tatattgtat agtgccgggc gccacttggg ggtaggctgg   121500
gttgaaggac taataaacct atcggaggga agtaattgtg aggattgtgt atagccatcc   121560
tcatcaggaa gaatggagta gttggtttga ttcatcattc caaaatcatt catagttcgc   121620
gcttcctgaa caatgcgttg aaattttttcc cattcggtgc gtgtaatgac accgaatctg   121680
cggtttattt catttacaaa atggataagc gcttttttgg ttgcttcttg ttcaccatac   121740
tctaagttaa agtgttggta aatgacgttt atttctttga taagctgacg aatttcggtt   121800
tctgagtagt caccaatgtt aataagctca ataggacgca taaagataat gcgaataagt   121860
cctgagaaga ttccttccag ctcaggaagc atcgagatct gtacattttc atctctaaag   121920
gaaaacaact tttgataaaa ttcggcgagg cggggaaggc ggaagtaaag ctctgctgcc   121980
tcgggaatta cctcgggctc tagctcatcg gcaccccca atatcatacg cgtgggtata   122040
agtttgtaca cgggctcagg ccgttcaaac atgtcgtaaa tccctaatac aataaaaatc   122100
ttggcggcca tacttttcag catgaaggtg aagaagacgt cctcggtttc ccagcgggtt   122160 gataggcgt cgttaactct cacagtagag aggtagaccc gctgagccgc ttcctcggca    122220
gtctgtgcaa gcgccatcct ttgtcctcca atttctgatt gatttagatt tttaagtccc   122280
acggaaagcg cagaatgttg aagatattca agcaaggttt tatagatttg caggggcgac   122340
atgggcacca tttgccgcag ctcctctccc ccaagcatgt ccccaatccg ggcaaaggca   122400
ttgatgatat ttttaagcgc ctgaaagtta gaaagagagc gcccgataag gtcgcgaatg   122460
tttttagcct ggcttgctct gacgggacgg agggtaccaa cgcttcggcc ttgttggatt   122520
tcagccgcaa ctttttcgta gtagtggccc gcaggagcat tatccgtaaa gacgttggag   122580
tcgttgcctg tggaggtggg aaaactttca aagacttgtg caagcgtgtc ccctgttgtc   122640
tcggtgaacc atcgtcctat aatgcgcacg ccatccagca tctgttggac tgtttgaata   122700
```

```
gaatctatgt tgtttacaaa cgttttggta atgttttaa gataaagatc tagcccttcc   122760
agagctcgat agaatcggcg ttttacatca tactccagct cgatggcgct tacggttgcc   122820
ttccagtcta cttcctgggc acctccagga tttgggccca cgtgtcctct ggcaagatct   122880
acagccggag aattaatgcg cgcatttttt tccgtatcca actgcatgag gcgtcccgca   122940
atagcatctc cgagaatagt ggcatagttt tcctcgtagg attgaaactc ctgtttgtta   123000
tgcgttaaat tggagtaaat ctgggccaca taatagtaat acataaaggt gttaattgcc   123060
tggttgaggt caacctgcga tcgcgcggcc ttgctgagcc caagctcttc aactgttagg   123120
gcagcaccgc ctaccttgt acactcgcag tcctcctcgc ctccatactt ttttgcaca    123180
atatcggtat aaaaatcaat aatctgtagc aagcgagagc aggagtcata aagatttta    123240
aaattagggt cggttttaga tatctcctcc aaaacatttt taacaagcgt aagctgtgtt   123300
aagaaggttt cgcgttcttc tcgtgcggcc gcattggtgt aaaagccgat aagacttaga   123360
tcaagtgcga tggtgcccat atcattaatg cgcgaaagag catctcgaag cctcgttatg   123420
ttcggcgtca aggcaatttc tttaacaagt ttgatgccta tttttttcac attttccaaa   123480
aagtcgttat aggcttgtgt gcttttattc aaaaattcca tgaggatgtg ctttctatcc   123540
agtctttgcg cttcaatcct cctatctagt ggcgttttct cctcatcgcc cccttttg    123600
gcacaactgt tctcaaggat tttgtggcgt tcattaaagg tctgtcgcaa caggttcacg   123660
gcttttcaa actcagcaat gttttctgcg gagacaagac cactaaacct tttgaggtca    123720
agctccttgt caaactccgc ccagtttttg ctttgaaggt actgttcaac cttgagtcct   123780
actttctgga gagccttatt aattttattc gcaacagacg cagcaatacc tagattacaa   123840
agtgtgtacg aaagtacttt tccaaaattt ttggttccca agacactatt tgtatcattt   123900
aaaagtttaa taatatccac ctcatccgtc tgcagtttat caagttcctt ttgggtggga   123960
gttaaaatat tgtcaataaa attcgttaaa atgttgattt gcaggttttg ttcatttaaa   124020
agtcgacgat atactgcttc aatcatggtg actgcattaa tgacttcctc attggggct    124080
gctttggtta cctccgtcac catgcgctcg tgaagttgct taatggcgtc gtttaacagc   124140
ttgatattt caagtgtatt ttctatactg ccgtgtacat caagatactc tgcgcgcagt    124200
ccatgagtta gggagttaat gtacagaact atttgtcgac atatactggc ggcccttcg    124260
gtggtatcta taagcttatc ctgacctaaa tcaataaatt cctggttaat ggcgtctgca   124320
atcattttac agacggtctc ctgttttcc gcatttttta caaaggtgga accggctcga   124380
ggatcgggca gttgttttt gatatcttta agaatatctt cgatgggctg ctttgtgtct    124440
actttgaacc ctattttggc aatcgccctg ataattcctt ctataatccg cagctttgct   124500
ttactcgata cggagtctat gtgataatct ttaatgtgtt gtacaggatt tttgtccccc   124560
ccgccattaa aatatcctcc ccctgaaaaa ggacgagttt gtctttgtat atgatcctgt   124620
aacttcgcat atatatttgc ttctgatgaa ggcagtggtc tactagaggt tgaagatcca   124680
cggttaccca ttataataaa aaaaataaag atttaaaact acaaatattt tgctgtttat   124740
aaacccaatc atataagact aactaaaaca ttaaatgtag gtgagataaa agcttatttt   124800
ttttaaaagt ttaataacca tgagtcttac cacctctttt tcttcttcct ttagagggggt  124860
tccataaatg gtttgaataa aattatgtgc tctaataacc ttgttaaaat caggtgcctt   124920
tccatattgt tcaatatgtt gcacagtctt ttgtgcaagc atatacagct tggagtcttt   124980
aggtacctcc gatgagggct cttgctcaaa caacgtttca aaggaggatg tgcattcatt   125040
ggtttcatta tcattttttt catgaatgtt ctccgaagat gctgaggatt ccgtctcctc   125100
```

```
ttcaaacagc acatgcagaa tcatattcca ttcttcttga gcctgatgtt cagtataccc   125160
ttgccctgca tatatacgag cagatttcac aatatcatac ttaacagtac taagcaatgt   125220
ttttatagcg gtcgtaacaa ttctaccgct attgataatc tcaacagaaa accaattata   125280
caggctaccc gcatgaaaca caacttgtga agatgatctt aaatccgttt tgaagatgac   125340
ctccattttc atggatatat ttaaaataaa atccattcaa ttttaaaatt ataaaataat   125400
aagaagatgc cctctaatat gaaacagttt tgcaagattt ctgtatggct acagcagcac   125460
gatccagatt tattagaaat tatcaacaac ttatgtatgc ttggcaattt atccgcggca   125520
aagtacaaac acggagttac cttcatttac cccaaacagg caaagatccg cgatgaaata   125580
aaaaaacatg cctactccaa tgacccttca caagccataa agaccttaga atcactcatc   125640
cttccatttt acattcccac tccagcggag ttcaccgggg aaatcggctc ctacaccgga   125700
gtgaaattag aggttgaaaa aacggaggcg aataaagtta ttttaaaaaa tggagaagcg   125760
gtcctagtac cggcggccga ttttaagccc tttcctgatc gccgactagc ggtctggatc   125820
atggagtcag gctctatgcc cctggagggt ccccccctata agcggaaaaa ggagggtggg   125880
gggaatgacc cgccggttcc taagcatatc tcgccgtata ctccgcgcac gcgtattgcc   125940
attgaggtgg aaaaggcctt tgatgactgt atgcgtcaaa actggtgtag tgtcaataat   126000
ccctatcttg ccaagtcggt ctccttgctg tctttcttgt cgctcaacca tcccaccgag   126060
tttattaagg tactgccgct tatagacttt gaccccttgg tgaccttta tctacttctt   126120 gagccctata aaacgcatgg ggatgacttt ttaattccgg aaaccatttt attcggccct   126180
accggatgga atggtacaga tctgtatcaa agtgccatgc tggagtttaa aaagtttttt   126240
acccagatta ctcgccaaac ctttatggac atagccgatt cggctactaa ggaggtagat   126300
gttcccatat gttactcgga tcccgaaacc gtacattcct atgccaatca cgtgcgtact   126360
gaaattttgc atcacaatgc cgtcaataag gttacaacac ctaacctcgt cgtgcaggcc   126420
tataatgagc tcgagcaaac caataccata cgacattacg gccctatttt cccggaaagt   126480
accatcaacg cactgcgttt ttggaaaaag ctgtggcagg atgaacagcg atttgttatc   126540
cacggcctgc accgcacgtt gatggatcaa cccacctatg aaacctctga gtttgcagag   126600
atcgttagaa atttacggtt ttcgcgtccc ggcaataact atataaacga gcttaatatt   126660
acaagtcccg ctatgtacgg cgacaagcat accaccggag atattgcgcc caatgataga   126720
tttgccatgt tggtggcctt tatcaacagt actgactttt tatacaccgc gattcccgag   126780
gaaaaggtag gggggaatga aacccaaacc agtagcctta cagacctagt tccaacacgg   126840
ctacactctt ttttaaatca taatctaagc aaacttaaaa tcttaaaccg cgcgcagcaa   126900
acggttagaa atattctttc aaatgattgt cttaatcaac tgaaacatta tgttaaacac   126960
acgggaaaaa atgaaatact aaagttactt caagaataag tatgttgata cctgtggtgt   127020
gttttacctg tgggtttcct attggaacct acgcggcaat ttttgacaag gctcgtaccg   127080
agtatattaa aaccaaaatg ggcggaacat tgccgcaaaa tatcccatta gatgcttctc   127140
tccagattga gttaaaagac ctcattacag ctctgggaat cccaatgcgg gtgtgttgtc   127200
gcactcattt aattactacg ttggattatc gtaaatatta ttaatatcta aaattgaaaa   127260
aatattttta atgttactag taaaaatgac tacacacatc tttcacgcag atgatctcct   127320
acaagcattg caacaagcaa aagcagaaaa aaattttttca tctgtatttt ctttagattg   127380 ggataaaatta cgcacagcga agcgtaatac aacggttaaa tatgttacgg tcaatgtcat   127440
```

```
agtaaaaggc aaaaaagctc cgctaatgtt taactttcaa aatgaaaaac atgtaggaac   127500
cattcctccc agtaccgatg aagaggttat acggatgaat gctgaaaatc caaagttttt   127560
ggtgaaaaaa cgtgacaggg atccctgttt gcagttcaac aaatacaaaa tctcgccgcc   127620
attggaagat gatggtctca ctgttaaaaa gaatgagcag ggtgaagaaa tacccccgg    127680 cgacgaagaa aaatctaagt tgtttcaaat tattgaactg ttagaagaag cctttgaaga   127740
cgctgtgcaa aaaggtcctg aagccatgaa acgaaacat gttataaaat taattcaaag    127800
aaaaatttct aatagcgcgg ttaaaaacgc agacaaacct ttgccgaatc ctatcgcacg   127860
cattcgtatt aaaatcaatc ccgctacaag tatactaaca ccaatattgc ttgataaaaa   127920
taagcccatt actttacaga atggtaaaac aagctttgaa gagttaaaag atgaagacgg   127980
cgttaaggcc aatccggata atattcataa gcttatagaa tcgcattcta tacatgatgg   128040
catcattaat gctagatcta tttgcatcag caatatgggc atttcatttc cgctttgctt   128100
ggaaatggga gttgtaaaag ttttgaaaa aataatggg attgatgtga actccattta     128160
tggctcagac gatatttcaa ctcttgttaa tcagattgct attgcttaaa caatttgctc   128220
aaaacaagct tataaacgtt tcttaggtat gcgatacgta aatcctaatt ctttaataag   128280 ttcttttca gtagtgattt ttagaggtac taaagtttga ttttaaata atccatactg      128340 atttagctta taattctttt tttttaacgc agctcgaatt cttattaaat aagaaacggg    128400
acccgtaaaa tgaagtactg cgtatggctt ttcctcggct aaggccgtaa aaagatcaag    128460
ttgatatgtg ttttttttcc attcaataaa agtacacac tttcgttctc cgcagacttt     128520
tacagaaaaa gaaagatcct ttatgcgaat gttgggcagg acgtgtttta aaagttttt     128580 ttctggaaca ataataagaa gatccacgtc attaagcatt ttctcttcgc gtcttaagct    128640
accaacagca acgatgtttt ttgataaaat ttttataagt tgtccattat attcaaacgc    128700
aagtcgggag cgtaagtcat ttacaatttt ttttccttga ataagcgtta acattttata   128760
tttaatatta aaatcttttc attttatata ttatatacgc aaaatggcac ttgatggttc    128820
aagtggtgga ggctctaatg tagaaacatt acttatagta gcaatcattg tggttattat    128880
ggcaatcatg ctttactatt tttggtggat gccccgccag caaaaaaaat gtagcaaggc    128940
tgaagaatgc acatgtaata acggaagctg ttccctaaaa acaagttaaa acatgcaatt   129000
atatgcatgc atataaacgc atgcatataa acgcatacat ataaaatgcg taaatactat   129060
ataaaaaact ataacatatc aatcaaggaa tcaacacttt tataatttc cgtaatatat    129120 ttttcatcca taatgatgtc agagtacatg gtccctatgc gaggaacaga gcccataagg    129180
gtaggcgcgg caataccgta aatgggattc acggcggagt caaccgcagc atctgtcaag   129240
acctggactg gagacgacaa ggccattcgc aacaacacgt tggaaggctc tcttgcatta   129300
agccctgcct tttctagaga ggtaacctgt cccgttcttg tcatgagatc tgcgtacatg    129360
agtaaatgac gatggttggg acccttgtcc cccataaccg ttctaatttc actaataatt    129420
ttttgccgtg ccgcttctat gccgtaaagc tccatggtgt ctcctataga ggacgatacg    129480
atggtgtatg ggtcgatgtt atcatcaagc attgcgccaa aaatattagt cccgtttgtt    129540
ttgatggcgt agatattgtc tagtcttacc agtttcccct gggcatccac acggtggcgc    129600
ataagcttaa caacattcgc attttgatg cctggtattc ctctaatcgt gctatttaat     129660
agtttatcca ccacatttac ggcaattttt tcatccgtag ccattcgggt attggtactg    129720
cgtctaaagg cgctttcccg taggtatatg cgaataatga tgggaatccc tgaggccgtg   129780
ttttccacag aatgcatgat gtaggtgttg gggtgtttag ctcttagact attaataata    129840
```

```
ctttctagac taatgctttt taatatcatg gttgttttgt ttaattccaa gcggatacac   129900
cagtttgcaa tatcctctgg gggctgtagt agaggatggt tttccagaaa atccgtcatc   129960
cattccacat cacttgcaaa atcggggtac atcacatttt tttttgtgct tgaatacgtt   130020
tcgtacaata ggtgccactg caatatcaac cgttcgaacg ttataagctc tatgctgtta   130080
gcaatttctt gcgcatatgt tttatttgtt tccacttccg ggttctttag acgtaaaagc   130140
atttcagagg attgttcagc ctctacgggc ttcgcgctaa agatctcctg gggccgcaca   130200
attcccgact tgttggttcc cccggccacg gaccggtggt gggagtccag catatattgt   130260
gtcaagggct ctgatacgga ctgcgccgcc aggattccca ctgcctcacc gtagttaata   130320
agactttgag tatattgtag ccttatgagg tccaggatgg cactcatctg ctcgcaggta   130380
atgtttaatg ttttaacggt tgccagttcg atgcgaataa gcatgcgcat cagagaggca   130440
gcccgtttaa gataaacggg tatgggcgtt tgtagtcgtt cctgaatgtt gttaataaac   130500
acgtatggaa gattttgca aaacgttttg accatcgcgt attttgtag aatacttttt     130560
tcgtcgaagg gaagcacgcc actggtggag ctcagtagaa tgttttttac gatgctggcc   130620
acgtttaccg gcacctgtct aacatctgta agcagctgac tgaaattaaa attttcgacg   130680
tttaggaaga tctgtcgata tttatctcta tccttttaa ggcgtgaaaa ttcttcttca    130740
aacaagggcg attgtatccc ggtgtacttg aatttgtctt caagttcctg gtccgacagc   130800
atgatggttt caaaccgtac ggtttcaagc tggcgcgcat caaggccgtc ctctccgtac   130860
aactgctgca caagacgcgt atcgatgaaa cccgtcggt aataatccac aatacaggat    130920
tgaaggccaa agatggcttt acggttggca tagcctgtgg atgatgtcga taatgctttg   130980
ttgatcaagt cgaatcttcc attcatttcc ccaaagataa attcagggga ggtaaggccc   131040
gcaatatagc tgttgcagat gaacccgtag gcctgcgcct ccagggcaaa cctggggtag   131100
tacaccaggg tcctaccgaa ggaaaactgg ggttgaatgc gttgtgtatt aatttcaatt   131160
tggccgatgc ccgccatgat gtgaatcata ttggggtttg agcccttggc gccagtggcc   131220
accatctgaa aaagcccatt ggtttccgga ttaatggaat tcataatcgg ctttaaaatt   131280
ctatcgggaa atttaagcgc attcagctgc aattttcgt agaagtcatg cgttgtcagg    131340
cctataggcg gcatgatgtc tccatgaagc agccggttgt ttatttcctc cgactcaagc   131400
agcagttcat tgataatttc ttggacctcc tgatgtgcct ccggggttag gagcatgtcg   131460
gccgtggaca ctgtgaatcc ggcgttgcgc acgtagttta gggcgagctg ctgggtcgca   131520
aatatcattt tcaaggcctg ctgcggccca tacctacgcg aaataaggtg atagattcca   131580
ccggaggaac ccgctccgac ggcctttttg tcaaggacgc cttcaatgag ttcgccgttg   131640
cgtatttgtg tagagatgtc ctgcttgtta taatgcatgt agggtgcata cacttctgag   131700
taccatgtgg gggctcgttg ataattgatg ggggtctgcc tcagtagcat agatacaacc   131760
gatttgccat ccagcaggtc agttggggag tagttggcaa acaaggtgg gtcggtttgg    131820
gttgtttgaa acaaccccat ggcgtgcagc ttgttcatca catttttccc catggggtg    131880
ttcgtgcgtg taagcaaaaa gcttcccacc gtggagtcct gcacctgccc attaacggga   131940
cccgagctct ttgtggaaat gaaccagttt cgcacagaac aaagtagttc ggcctcaacg   132000
cggctcatga cgctccaggg aacccagaga ttcatctgat ccccgtcaaa gtccgcatta   132060
taccaggcac atgcgctgac attcatttga aacgtagaaa ttttgggtt ttcaagaacg    132120
acaatccggt gaaccctat gctgcttcgt tcgagagaag gctggcgatt aaaaaacgcg    132180
```

```
acgtcgccag tgacgacgtc acggtaaagg atgtctccta cctccagcct aaagtcttgt  132240
ttgagaccct caatgtcgtg aacggattgt gttatttgct tatacactct tgaacaacca  132300
gggtactggc gctttccatt taaaaaatag ggcattaatc tattaatatt ataatgttgc  132360
actgtttccg caacttgcag cgttcgtgca aaggaaatgg gatagccaac ctcgtccagg  132420
tgaaggtctg agttcccgca gatggtggac cggctgatcg accatacctg gctgcccagt  132480
agggatttac gaattcttcc ctccttgcga ggaagtcttc gcatgatgga gggagcaggg  132540
cgtgccccca tgacgatccc acgctttccc gtgcctccct gggttgcggt ggtggaaacg  132600
gaatccaaca aaaagttata gtaaagttgc tgtatggttt gcaaattgcg gtcaatattt  132660
aaaggtattt tttggccgcg cacgatttgt aggtccttcg ggatcagcag attctttcga  132720
accagatact gaatcacgtt gttaatgtcg tgaaagcttt ggggggcctga cccgattccc  132780
aatctgatgc caggtcgtat gctgatgggg gggatctgaa tggccttaag cacaagtttt  132840
tcgggatggg agttttttact tcgccccagt tttacaacgg tgtcgtaggt tacgcgcgaa  132900
aaaatctctc tgatgatctg cgggtacagt ttgtcaatct tgccctgctg atccgcccaa  132960
aaggtaaaat aatcttccga gtccttaaca attttgggggt gtactgcctt acagacgtag  133020
cactgctttc cttcggtttg gcttgaagcc gcttcaataa gacgcttagg cctaataagg  133080
tgctcgtacc tctttaggtc aacgatggga gccccgcagt tgagacatat aacccttaac  133140
catcgtcgta tttcggcgat gaagagcggc tgaagcaccg gagcatgcat ctgcagtatc  133200
ccagggtgtc ccatacattg cttgcgctgg tgtgagcaag tgatgcattt ataatggtga  133260
tcggtggttc ccattcgcgc atcatagata ccccccttcgg cgggaagggt gccctcaaat  133320
aaattagaaa tggtaaccct cataacgcct tgcctcttat gatcattgtc accggcaata  133380
ttgaactgaa cggcggctat ttcggcatat ccagcctcca tatttttgct aaatacataa  133440
taaaacttca aatgttaaaa aaaataacat cggttggcat attttttttgt taaaaccaag  133500
tgttaaatga tttctaaaac atttatcggt tcacgaaaac ctaccgcacg ggcctgaaga  133560
ggaatgccag ttttggggga aagctcggca tattccacgg taagctcttt tccataaaga  133620
tgtttttttaa ataaggcggg cgtgagtttt tgaaaaagag cataacgatc cgcgtacgtc  133680
aaatgcttag gagtgactac aaaccgcttt ttgtttggca attcgcaaac ccataaaatg  133740
gcgcctaagt cctttccctt ttttcccctga gtatagtcca ctaaaataaa ttcagcgtct  133800
agcagcggtt tcagcttggc aagatgcgct gagtggtagt tgttgtatcc cggctcatag  133860
ggcccattgg cattgcgtac gatggctccc tcgtagccct ccttaataaa ctgcgcctta  133920
agcctaaggg cctcatccac attcttcacg ctaaaatttt caacttggtg gataaaggta  133980
agatcttcct tctgtttaaa aatatttgtt aatagctgtt gtctcttgtt ggaaggcatt  134040
tgaagctgat cactccaaaa acagtcaaac acgtaaaagt gcagctcgga ggaatctgtc  134100
ttcgcattcg cctgccccgc gatccattgc agaggtttgc ggtgtaaata aagctcacca  134160
tccaaatata ctctcacgtc tataaataaa taaagctgtt tgagctcttt tttaatattg  134220
tcaagaccta aaaattcctt tttcgtgcgc gaatacaaga gaatgctacc atcgccctgc  134280
tggcaggcca cagctcgaac gccattacgc ttgcgctgca cgatgggatc tgtttcttct  134340
tcaaaaaatg tcttaggaat tatattaaaa tattttacca gcataggggg gataattcct  134400
ctatttgtgt gggctccccg cttttgtctg gcatggcgat tatatttact aagggcgtcc  134460
ttgaatgcct gatggactac cgttgtggca tttttttttac ccaagttttt tccctcggta  134520
acacgtgtca ttttttgatat ccgcaccgcc ccttcttcca caaaaaattt tgtgaaaatt  134580
```

```
tcagcaacgg cgtcttttac atctgtggaa aacatctcat ctgtgatggg aatgatcgtg 134640
ttgtgctgca ccacttgcac acaaataatc catgaggcct tttttccgct tttcgtttca 134700
gactcaatcg gaggaaaaca aaaaatgttg tttgaatatt gcccaggaaa ttgatttagc 134760
atggttttaa caataaaata agcctatcaa ttttttttata atttgaatag ttattccaaa 134820
ttcaatatgg cttctttaga taatttagtg gcacgatatc agaggtgctt taatgaccag 134880
tctcttaaaa atagtactat tgaacttgaa atacgttttc aacagataaa ttttttatta 134940
ttcaaaaccg tatatgaggc acttgtggca caagagatcc ctagcaccat ctcccacagc 135000
atccgctgca tcaaaaaagt tcaccatgaa aaccactgcc gggaaaaaat tttgccgtcg 135060
gaaaatcttt acttcaaaaa acagcctctc atgttttta agttttcaga gcctgcatct 135120
ctgggctgta aggtctcgct ggccatcgag cagcccattc gtaaatttat cttggactcc 135180
tccattctcg ttcggctcaa aaatcgtacg acctttcggg tatctgaact ttggaaaata 135240
gagcttacca ttgtaaagca gctgatggga agcgaggtct ctgcaaaact tgccgctttc 135300
aaaacgcttc tgtttgacac cccagagcaa caaacgacaa aaaatatgat gacgttaata 135360
aacccagatg acgaatatct ttacgaaata gaaatagagt atacaggaaa gcccgaatcc 135420
ctaacggcgg cagatgttat aaaaattaaa aacacggtgt tgacacttat ttctccaaac 135480
catttaatgc taacagccta ccaccaggcc attgaattca ttgcctccca tatactgtcc 135540
tcagaaatcc ttcttgctcg tattaagagc gggaagtggg ggcttaaacg cctcctcccc 135600
caggtgaaat ccatgaccaa agcggattac atgaaatttt atccgcccgt tggctactat 135660
gtaacggaca aagcagatgg aattagaggc atcgccgtca ttcaggacac gcaaatttat 135720
gtggttgcag accagttata cagcctaggt accaccggca ttgaacccct taaaccaacc 135780
attttggacg gtgaatttat gcctgaaaaa aaagaatttt atgggtttga cgtcatcatg 135840
tatgagggca atctattgac gcaacagggg tttgaaacaa gaattgagtc tttaagcaag 135900
ggcattaaag tcttacaagc gtttaacata aaagcagaaa tgaagcccctt tatttcgcta 135960 acaagtgcag atcccaacgt gctcctcaaa aactttgaaa gcatttttaa gaaaaaaact 136020
cgcccatatt ctattgatgg catcatttta gtagaacctg gcaattctta tctaaataca 136080
aacaccttta agtggaagcc cacctgggat aacacattag actttttggt gcgaaaatgt 136140
ccggagagtt taaacgtacc agagtacgcg cccaaaaaag ggttttccct gcatctacta 136200
tttgtaggca tctccggaga gcttttttaaa aaattagcgc taaattggtg tccaggatat 136260
acgaaactat tccccgttac acagcgcaac caaaactact ttccagtaca gttccagcca 136320
tcggattttc cattggcatt tctttattac cacccagata cctcgtcatt ttctaatata 136380
gatggaaagg tccttgaaat gcgttgtctt aagagagaaa tcaatcacgt cagctgggaa 136440
attgtaaaaa tccgggagga taggcagcag gatcttaaaa ccggcgggta ttttggcaat 136500
gatttcaaaa cagccgaact cacatggctt aactatatgg atcccttttc ctttgaggag 136560
ctggcaaagg gcccttctgg aatgtacttc gccggtgcca aaaccggcat ataccgcgct 136620
caaacagcac ttatttcctt tattaaacaa gaaatcatcc aaaaaataag tcaccaatcc 136680
tgggttatcg atcttggaat aggaaaaggg caggacctag acgttacct ggacgcaggg 136740 ataaggcatc ttgttgggat cgataaggat caaaccgcgc ttgcggagct tgtttatcga 136800
aaattttcgc atgctacgac ccgacagcac aagcacgcta ccaacattta cgtgttgcat 136860
caagacctcg cagagcctgc gaaagaaatc agcgaaaagg tacaccaaat ttacgggttt 136920
```

```
cccaaggagg gagcttcttc cattgttagc aacctgttta ttcactatct tatgaaaaac    136980
acgcagcagg tggaaaacct ggccgttctg tgccataagc ttcttcagcc gggggggaatg   137040 gtgtggttta ccaccatgtt gggagaacag gtcttagaat tacttcatga aaatagaata   137100
gagctcaatg aagtatggga ggctcgtgaa aacgaagtgg tcaaatttgc tattaaacgt   137160
ctctttaaag aggatatatt acaggaaact gggcaagaaa ttggagtcct gttacccttc   137220
agcaatggcg acttctacaa tgaatatctt gtgaacacag cgttttttaat taaaatatt   137280 aaacatcacg gcttttccct agttcaaaag cagtccttta aggactggat tccagaattt   137340
caaaacttta gtaaaagttt gtataaaatt cttacagaag ccgataaaac ttggacaagc   137400 cttttttgggt ttatttgtct gcgcaaaaat taaatatttt ttcataagaa gtactaccca   137460
ggttttaaag aaatagctaa aaatatcata tggatactgc catgcagctt aaaacgtcta   137520
ttggtttaat tacatgtcgt atgaacaccc aaaataacca aatagaaact attctggttc   137580
aaaaacgtta cagccttgct ttttcagaat ttattcattg tcattactct ataaatgcta   137640
atcaaggtca tctgattaaa atgttaata acatgacaat taatgaacga ctgcttgtca   137700
aaacactgga ttttgaccgc atgtggtatc atatttggat tgaaactcca gtctacgaac   137760
tataccacaa aaaataccaa aaatttagga aaaattggct tctcccggat aatgggaaaa   137820
agcttatttc attaatcaac caagcaaagg gctcaggaac acttctatgg gaaatcccta   137880
agggtaagcc gaaggaagac gagtcggacc ttacctgtgc catacgggag tttgaagaag   137940
aaaccgggat tacccgcgaa tattaccaga ttctcccaga gtttaaaaaa tctatgtcat   138000
actttgacgg taaaacagaa tataagcata tctacttcct tgcaatgtta tgtaagtcgt   138060
tggaggaacc caatatgaat ctttctttac aatacgaaaa ccgaattgcc gaatttcta   138120 aaatttcttg gcaaaatatg gaggctgtac gttttattag caaacgccag tcattaaacc   138180
tggagcctat catcgggcct gcatttaatt ttattaaaaa ctatttacga tacaagcact   138240
aggatgccgc attaaaatgc cacataaggt aatacactag gaatgtcgca cacgcacaag   138300
aatacaacgt cgccggagat ttattatcta gtacacgttt tatgtatgta caatccgcct   138360
tcatttaata tattgagcgg atgtactatg tatttatttt aacaaaaaac attattttttt   138420 ttaatcttca tcatctgttt ttataaactc agtaatatca aaagtagctt gtggggtttc   138480
agagggttca ccttggttat cctccgtgag gataacatgt tcttcaggtt cgtcgtcact   138540
ggagaaccca tcatttaatt cctcttcact caacatctgt aaaaaatctt ccaagctttc   138600
gctatcgtta aaatcctcat catccataag aataatggta ccttcctcat cgtttcctcc   138660
ttgtttcgtg tctaaatagg cctgcatggc atttgcaaaa gtatcaaaat aggctgagtc   138720
agattgctgt tccaaaatat ggccttgcgt attaaatgtg gttgcatcgt tgttaaatgc   138780
ttgcaaatac agtaagggat ttatatccat tattattaag caaaaaaaat ttaaattatt   138840
tttcgaccga tgttaggtaa aattaaacaa ttgctatagg tgttaagcaa tgtttattga   138900
ttttaagtac tcaacaacca tgatgtaaat actatacagc acttttggat ttttaatcaa   138960
atccagatta atactaactt cttttgtgat acagttcgta ataatagtat cctgctcatc   139020
gttttgtaag atttcttttta atatatttt ttttaccggg atactaagca attgattatt   139080
ttcttttaaa aactccttt gatattcaat cgtcttattc attgaatatt tgtatataac   139140
tataattaca aatgttcaat gaattgttat tcatgtcggg agatggctat ttaaaaatca   139200
tgtcctattt ttctttgctc aataagcatc caaatatttt catggcgttt tattaattgt   139260
tcattattga acgtatcaca aagatcattt ataaattgca gatagtttat tatttctttc   139320
```

```
aagagagtaa caaacattac ttcagcagaa catataatag gtaattcagt ggcgttaaaa  139380
gaattttgat cttgttgata cgccaatggc gaggacttaa ggagatttgg gggtcttgcc  139440 caaaaccta  ggctgctgtt cttgttttt  agggcgtcat aaagaaatga aagcacattg  139500
caaggcttaa gccgcgacat ctccttcccc ttgggccctt tccatatttt tagatctaag  139560
atctcatccg agcttataga gtaggtatag taaagttttt caaaaaagca tatctgcttg  139620
aagtcttttt tagaacgact ttcaagaagc atttctataa tgttaacaag ttttgttagg  139680
tttaaggcct gttcctgtgt aagctcctct tgcacgtgat agactgaaaa agtgtgctta  139740
ggaatgaaaa tactccccgt ggcactggcc tgttgtctgc caggtatata gtacacgctg  139800
ctgttagcaa gctgtaccgg cacaatttgc cccacttctg caacattatt ttgcgattcg  139860
gacgagggta tgacaatagt tacgggttca gtcaataggc tttcgccgag aataatatta  139920
ctgtcatttt taataatttt aacggccgct attaaatcaa aggcatttaa gtaagaaaca  139980
acagcagaaa atcttacatg catatatcct cttccgctat tattcgtacg cataataaaa  140040
caaggggagc gttgtataac gccagtaata ttaagaataa aactgttttt gaaacactta  140100
cccacataaa tgttttcaag ctccttcaaa agatgagcct ccacatttgt acaaaaattg  140160
gtaggatcat caatattcaa cgttgtctca aaaatttttt ggtcgatcat atctataata  140220
tattctgtct atttcaattt aaataatata cgaataaata acgagattat tttattaaat  140280
aagcaatggt gtatacactt tgtatttact ttgagatata ctttgtgtat cacaacgtgc  140340
cctaagatgt gtgcacaagt gacggcattt tgtcgttaaa aaggtaaaac cagcggattc  140400
catcctgcat tccatttggt tgattacgag cctccatttc tttttgcaaa aggttattgc  140460
gaatgagtaa gcagagcttg atggcactaa tctttgtaag gtttaaactt atgcccaatt  140520
ggtcagcaat ttttgttgc  tcctcccgtc cgcgtgtttc gcatacggct ccccggttta  140580
gcatgcgaat atcagtaatc tcattctttt ttaaaacctg gataggtggg cggattttaa  140640
atttaagggc ctttcccttg ctttccatat agcctatgac gatgtcgttt tcttttcgtt  140700
taacattaat attaagcata taaagcggaa tttcatgcca ggttttatct tctcgcgagg  140760
taataagtcg cacggagtcc tccgtggcat agcccactag agtgttgtca tccccaggca  140820
cgtggcttat aatttaaaa atgtccggaa atggctgaat atctttttt  gaaaaagcga  140880 tgaaaaactt tttataaacc tcgacaaggg cccccatacc tgcaagatta tctataataa  140940
gtgcttctag catcgtatag tgaaatgaag cggggtagtg gatgagtacc tgctccattg  141000
gctcatcctg aaaatccttc tgaaacttt  catacaaatc ttgaaagggt tctttggtct  141060
gcgagtgttc gaggtatttg gtaatacgga tgctgtgcat cgcgggaggc tgaaaatccc  141120
gaatatatgt ttcaatatct aataccggtt ccttttatg  gttaagcacc gcagcgacgt  141180
acaaatgctc aggctttgcc ggcacatgca taatggtgca aagacgattc tgtatccata  141240
attccttgca ctggtttttt gagtagcata gagaaatgag cgccagcgcg aagttgtcct  141300
ctgagaagag tttattatcg atggtaattc cctgtatgag cttgggagtg gaaacagcct  141360
tccatagctc ggagtacgtc cacacggggc gtgccataaa caaagatata ataatattag  141420
aaattgtttt tacctcttgc tccccgtatc cataggcctc aaaggtattg aggacggtgg  141480
ctccgacgtt tgccggcgtg atggatggac taagggcag  actttccaac ataggcttat  141540
caatcttaat ctggttggtg aacccatcaa tggcgtgctt tcgcagcgcc ttatccccct  141600
cctgtattaa aatgtattct tttaattttt gtgcgtactt agcgagctct ggccctccat  141660
```

```
cgggtgttgt cgatacgtac aaataaattg tcacgttgcg ctcactgggg gggagctcca    141720
tgtgtgaatt ttttcgcacc accctcccaa atacctgaat aagccgggga atatcaaggg    141780
gcaatgacat aatcatctcg taccgcacgg cctgaaagtt caaaccctcc acaatcacct    141840
tggacccgat gagaatacgc agctggtggc cttccaggtt ggacgaggcg ttaaaaagag    141900
ccaggcttcg ttcgcgtaca gcgggctcta tttcgctgtg cagaatggtg aaccgtactg    141960
gaataaactg atggtcgcta tgtgtgtgct catcgcgaat cgcggcgcag atggagcagc    142020
gggtcgttcc cacaggggac gaaacttcat ttaaaatgcc attactttgt aaaatttctt    142080
gcaagataag aaccccgac atgcggaccc gattgtggta aattaaaatt ttcccccggc     142140
cttgccgaat aatggaaaga atgtctttca tcatttgagt gtattttccg ctataaaagg    142200
ccaatcccga gatgtgcgtt ggtggctgca gcgacaaaaa gctgccactc acattaaagg    142260
gggctctacg cgaaggctca ataatctgta ccccgttttc cagaagccag tctgtgcttg    142320
ccatagaaag ggcggtgggg gtttccgtcg agttaaacag gccgtaagcc ttgggttccg    142380
tttgttttga aaattttggg ttgggaaaca ccatgtcata aatgctgtac gcattactcg    142440 agatttttagg gtcagggccc agctgtttaa gcgtttcaag ctgatactca gacatggggc    142500
attcgatgaa atgtaagtac ggcaatgttt cgtctttata ggacaacatc tttccggcaa    142560
atattctttc ggggtaaaaa ttggtgttgg tatccaacaa aaaagatacc cttccggtgc    142620
tcagtctttc cacaagagct agggcgtcct ttttccattt aacggaatgc ccactgctgt    142680
caaacagttg ctggcgctgg aggggctggc cgttgggcag ctcatgccgc ggaaccaaaa    142740
ggtttaacag gtcgacgtat tccatgacac tcccggttac gggcgttgcc gacatgaaga    142800
cggccctggg ggcctggtga ggtggaaagg catccaggac atactgtaaa gcgatgccat    142860
aattatttcg ttcctggata ttgtacacgt tgtgtatttc atccgcaatg agcagtcctc    142920
ccctaagttg ctccatgatt ttttgattca cccggatgag gccgtttgtc tcggcctcgc    142980 taatttttg cacgaactga gatatatcgt tctcattcaa tgtatcttct gcttcgtcag     143040
aacgatgaaa cagagaaagc acatcaaagt ttttctcttc acccttactc gtaatattga    143100
aaagcttgga tgcaaattcc ttatagccgt aaaactgaaa aaagcctccg cggtttctat    143160
cggttaaacg gcgctttaac gtactaacga acccatttag atgccgtgat tcgaccgacg    143220
tggtgctgcc agactgcttt gcaatgtgaa gaagccggtg tagctcagcg acctccttgt    143280
aagaaacaaa tcccagctca ggacgtctta gcatttctgt ttgaatgatg gcgcgtgtaa    143340
agcctaccac aaaaatccag ggcgcatttt caataaaatt catgtagtgg ttcataaatt    143400
gacgcgcgat ggcaatcgcg gcaatgcttt ttcccgtccc ggtctgccag tttaataaaa    143460
gacgcgagta gggcgtgttg ggattttgaa agttttggac gaaaagctgg gcattatgca    143520
attggagacc cttgatggaa ggaaagggcg acgcgtaggg gtcacacgga aaaacgctc     143580 gcccccctt ctcgcagcca ggcccaccga tctggacaaa atgagcccgc agatcacgaa     143640
tgagctcttt ttggtcgaca ggaggggaaa tcaacgattt aaactccttt cttcgcgcca    143700
actgctgcaa aaagtctgcg gcatccaatt cgggatacgc catattatca taaaaaaata    143760
aaccttttta tgaaactttt tatgtgattc tgtattgcaa ttgttttta tgaatactgt     143820 aaataagcgt atcaacttgt ttttctaacg aagaggcgtt attcttttt tctggatata     143880 aaataataat aagtataata attaagacta aacagcaggc aatcactatc aaactcatat    143940
tatacttact ttttataaaa aagtattata tcttatgaat gcgcaagttc agctaattgt    144000
tcgtcgcttg gaatgtggga ctgcagggag gtggagtttt tccttttct aaagaatacc     144060
```

```
gggaaatggt ggtgaggctc aggttgttgt acatagtagc taggaggagg tttaggtatg    144120
ctcgacttgc agtcaatagt ccggttatag taaacgatgg caacgatgat aagaataata    144180
atgagcaaaa tcaaaatgcc caggagaatc gcagttgttc cgggatattt ggcgattgta    144240
tgggctaaaa ggccttgggt gctttgttta attccctcgc gggttgacag gttatgagaa    144300
agcagtggag acgtttcagt gtccatttat tacaattgaa cagttatatt aatctcaaat    144360
aaaatataac acaaaattaa ttatggccat gcaaaagtta tttacgtata tttacgagtt    144420
tattgaatat cgtaagatgg tgctgttgga agaaaaggta ccatatgata agtttgttca    144480
aatggtactt aatacaggat tttttcgtat taacgcggag acgctgaatc acggaatcgt    144540
atccgtgttt atctttggag caaatggcaa gtacgttcac cacggaggcg acatgagaac    144600
gcttttaacg aatacgctta atgaaaaaaa acattatgaa gaattaattt taatcgttga    144660
taagcccgtt ttaagcaaaa aaaatatttt agatataatc gtcgagcagc gcgctgcaaa    144720
tcccacgatt gtaataaaca tatatcccta ccacctgttc tgcattaaca ttcccaaggt    144780
gagtgccatt cctaaacata aactaattac tcaggaggag gcgcaggagt ttttaggtcg    144840
cgaatatctg caaccgcagg acctcatgca aattagcgcg tcagaccccc cggtggtctg    144900
gctgggagga agaccgggag actttgtgca aattgagcgg ccctcagaga cagctatgca    144960
cgctgttgtt atccgcttta tcaccaagtc caaaatttga gtcccgtgtt taaagatgac    145020
agacagctaa gtaagcatat ctgtaaaatt gtcgatgtcc tctgtggata gagcgctttc    145080
ctctgagcag caaattttttt catacatctc catgggggat ggcgaggctt taatagtatg    145140
taggtcacgt aagaactgtt gtatgatggg atatttgtct tttaaaaact ggggatgttt    145200
cataactgga attatttgaa agataaagac cttccatcca aagtagccaa ccacatttgg    145260
catttcggga cacgcggttt cataaggcat agaatagtga atagtgtact gatctttttg    145320
atacagcgtt tcaagtagtt ggcgaaatgt ttccgcgtcg agcgtgccaa aatcttgagg    145380
agcctcggtg tgctcctgtg tagagcagat cgtgatgatt ccccaggcaa gcgggagcat    145440
ggactctgga gggtggatat ccgtattggt ctcattattc gatcccagct gatgaatgcc    145500
gcacacgcga aacatggcct cgacgtagat gcccatagag ataggcggcg aaagggcaag    145560
accggattgt atttgcggca tatagtagga gggcaccgag ttttttattt ttcggttgaa    145620
tggggacttt atttctacca gcacggggat gcgtttcgtg gcctcatagc gtacgttgtt    145680
aaaaattgtt ttgatttccc aggactgttg agtgtatccc agcgttaggt gacaaaaccc    145740
atcggggcta ttactatgtc cggggtatcc caaataggtc ccatcaatat gaatattgtc    145800
acctatgacg gtggtttggc agaacaactc aagcagatct ttactaacac gctcaaaaag    145860
ggttccccag ctacaagcag cgcggttcaa attcttctta aaaagatttg cttttttccgc    145920 caaggttata taatagcttt tgtaagggtt taaacctaaa acgctggcaa ggtcagagcc    145980
acccacctga gtgcgacgaa tagcatgcca ggcatcggag cgctgctgag gagagtcttt    146040
aaacaggcgt acaaaggttt ccattatact tgttttaaca ggaattcaat ataaaaagtc    146100
aacacagttt gcaattttc caatctcaag atatagccat acatttttttt ttccaattgg    146160 cgaatatgtt taagctcatg tgtttcaata ttagcatccg gaaatttaaa tgcataaaga    146220
tgttcaaagg cctgatttat acacgtatca aaggatctgt ggtatgttat tagcttcagc    146280
atgtgtgcca gatcttcaag atggtctaaa tttatacggt tttccacgtg gtggatcatg    146340
tctgccacat cttgagcccc catccagggg atcacaaggt actccccctt aaagatgatt    146400
```

```
cgtcgttttt ttaaaaaatc atgaaaacgt tttaaagctt caagaaaggg gcagttgggc   146460
tttgacccca aaatgctgac gacgatatcc tcgggcatga tgtattcgca gtgaggatag   146520
tagtttacgg actctaattc agcggcccgc cgttttattt cgtatcttgc ccagttattc   146580
agagagtact ccacgcctcc gaccacaaca gacatcctat ctattaaaaa ataacaataa   146640
aaaccttatg aaatctatgt atagtggccg ctaaaatgtc tatattagaa aaaattacgt   146700
caagtccctc tgaatgcgca gagcatctta caaacaaaga tagctgttta agtaaaaaaa   146760
tacaaaaaga gctcacctct tttttggaaa aaaagagac actcggttgc gattcggagt     146820
cctgcgtaat tacccacccc gccgtgaagg cctatgcgca acaaaaggga ctggacctct   146880
ccaaagaact ggagactcgg tttaaagcgc caggacccag aaacaacacg ggtcttctta   146940
caaacttcaa tattgatgaa acgctgcaga ggtgggccat aaaatacacc aagttttca   147000 actgtccttt ttccatgatg gactttgaga gggtccatta taaatttaat caagtggata   147060
tggtaaaggt atataaggga gaagagctac aatatgtaga aggcaaagtg gtcaagcgtc   147120
cttgtaacac cttcggatgc gttttaaaca cggacttttc aacgggcact ggaaaacact   147180
gggtagccat ctttgtggat atgcggggcg actgctggag catcgaatat tttaattcga   147240
cgggaaattc tcctccaggt cccgttattc gttggatgga acgggtcaaa cagcagctat   147300
taaaaataca ccacaccgtg aaaacgcttg cagttaccaa cattcgtcac caacggtcgc   147360
agaccgagtg cggcccctac agcctgtttt acatcagggc acgcctcgac aacgtgtcat   147420
acgcccattt tatatccgct aggattaccg acgaagacat gtataagttt agaacccatc   147480
tgtttcgcat cgcataaact aataaagttt gaattcttta taggaataaa aatggaagcg   147540
tttgaaatca gcgatttcaa agagcatgcg aagaaaaaaa gcatgtgggc tggcgccctc   147600
aacaaagtca ctatttcggg tcttatgggg gtctttaccg aagatgagga ccttatggcg   147660
ttacccattc acagagacca ctgccccgct ttgttaaaaa ttttgacga gatcatcgta     147720 aatgccacgg atcatgaaag agcttgccat aacaaaacaa aaaaggtaac ttacattaaa   147780
atttcgtttg ataaaggtgt gttttcttgc gaaaacgatg gcccgggaat ccccattgca   147840
aagcatgagc aagccagtct tatcgccaag cgcgatgtgt atgttcccga ggtggcttca   147900
tgtcactttt tagccggaac gaacatcaat aaggccaagg actgtatcaa gggggggaacc   147960 aacggcgtcg ggctgaagct cgccatggtg cattcgcagt gggccattct taccaccgcc   148020
gacggcgcgc aaaagtatgt tcaacatatc aaccaacgcc tagatatcat tgagcctcct   148080
accattacac cctccaggga aatgtttaca cgtatcgagc tcatgcccgt ataccaggaa   148140
ctagggtacg cggagcctct gtctgaaaca gagcaggcgg atctttccgc ctggatttac   148200
cttcgcgcct gccaatgcgc ggcctacgtg ggaaaaggca ccaccattta ttacaatgat   148260
aagccttgcc gcacgggctc tgtgatggcg ctagccaaaa tgtacaccct gttgagcgcg   148320
cctaatagca cgatacatac ggcgaccatt aaggccgacg caaagcccta tagcctgcac   148380
cccctgcagg ttgcggcggt cgtgtccccc aagtttaaaa aatttgaaca cgtgtccgtt   148440
atcaacgggg taaattgcgt aaaaggagaa catgtcacct ttttgaaaaa gactattaat   148500
gaaatggtcg ttaaaaaatt tcaacaaacg attaaagata aaaaccgcaa acaacatta     148560 cgagacagct gttcaaacat ctttatcgtt atagtgggtt ccattccagg aatagaatgg   148620
accggccagc ggaaggatga acttagcatc gcggaaaatg tttttaaaac gcattactcc   148680
attccttcta gttttttaac aagtatgaca agtctatcg tggatattct tctgcaatcc     148740
atttctaaaa aagataacca taaacaggtc gacgtagaca aatatacgcg tgcccgcaat   148800
```

```
gcgggaggaa aaagggcgca ggactgcatg ctactcgcgg cggaagggga tagcgcactt   148860
tccctgctgc gcacgggact aaccctggga aagtccaacc caagcgggcc ctcctttgac   148920
ttctgcggca tgatctccct gggaggagtc atcatgaatg cctgcaaaaa ggtgacaaac   148980
attacaacgg actctggaga aaccattatg gtgcgcaacg aacagcttac caataataaa   149040
gtgttgcagg gaatcgtgca ggtattgggt ctagacttca actgccatta caaaacacag   149100
gaagagcgag caaagctgag atacggctgc attgttgcgt gcgttgatca agatctggat   149160
gggtgtggaa aaatccttgg actgctgctg gcctactttc acctgttttg gcctcagctt   149220
attatccatg gtttcgtaaa acgactgctt accccgctga tacgtgtgta tgaaaagggt   149280
aagaccatgc ccgtggaatt ttactatgaa caagagtttg atgcctgggc aaaaaagcag   149340
accagcttag ccaaccatac cgtaaaatat tacaagggat tggcggcgca tgacacccat   149400
gaagtaaaaa gcatgttcaa acattttgac aacatggtgt acacgtttac cctggatgac   149460
tcagcaaagg agttgtttca tatttatttt ggcggggagt cggagttgcg aaaaagagag   149520
ctttgcaccg gcgtggtgcc gctcaccgaa acccagacgc agtccattca tagtgtccga   149580
cgaattcctt gcagcctgca tctgcaagta gataccaagg cttacaagct ggatgccatc   149640
gagcggcaga ttcccaactt cttagacggg atgacgcggg cgcggcgcaa aattttagcc   149700 ggggggggtga aatgcttcgc ctccaacaac cgtgaacgaa aggttttttca gttcgggggc   149760 tacgttgcag atcacatgtt ttatcaccat ggcgacatgt cgttaaacac aagtattata   149820
aaagccgccc agtattaccc aggctcctcc cacctctatc cggtattcat aggcatagga   149880
agttttggct ccaggcacct gggaggaaag gatgcaggat ccccaagata catcagtgtg   149940
cagcttgcgt ctgaatttat taaaacaatg ttccccgcgg aggactcatg gcttctcccc   150000
tacgtctttg aggacggcca gcgggcggaa ccagagtact acgtgcctgt gttgccgctt   150060
gctattatgg agtacggcgc caacccatcg gagggctgga agtacaccac ttgggcccgg   150120
caactggaag acattttggc cttggtgagg gcctacgtcg acaaagacaa cccaaaacac   150180
gagctactgc actatgcaat aaaacataag attactatac tcccgctgcg gccctccaat   150240
tacaatttca agggccattt gaagcggttt ggccaatact actacagcta cggcacgtac   150300
gtcatctcag agcagcgaaa tataattact attacggagc ttcctctgcg tgttcctacg   150360
gttgcataca tcgaaagtat aaaaaaatcg agtaaccgca tgacatttat tgaagaaatc   150420
atcgactaca gtagttcaga aactattgaa attctggtga aattaaagcc aaatagtctt   150480
aaccgtatcg tggaagaatt taaggagact gaagagcaag attccataga aaattttctg   150540
cgcctgcgca attgtttaca ttcacatcta aactttgtaa aacctaaagg tggcattatc   150600
gagtttaaca cgtattatga aattttgtat gcgtggctac cttacaggcg tgagctttac   150660
caaaagcgtc ttatgcgtga gcacgcggtg cttaagctgc gcattatcat ggaaactgct   150720
attgtacgct acatcaatga gtctgcagag ctaaatcttt cccattatga ggatgaaaag   150780
gaggcaagcc gcattctaag cgagcatgga tttccccccgc tgaaccacac gctgatcatt   150840 tccccctgagt ttgcctctat agaggaactc aatcaaaaag cactgcaggg ctgttatacc   150900
tatatactat ctttgcaggc tcgagaattg cttatcgcag ccaaaactcg tcgggtgaa   150960 aaaataaaaa aaatgcaagc tcgtcttgat aaggttgagc agcttttgca agagtctccc   151020
tttcccggcg ccagcgtatg gctggaggaa attgatgcgg tggaaaaggc tattataaaa   151080
ggaagaaata ctcagtggaa atttcattaa acgctaccgg ttttatgatg tccaataggt   151140
```

-continued

```
gttaagcaat cagttcatca acatttttt caagaatttg aaaagtttgg ataatgttct   151200
gaatactttt ttctaaaaga gttatcaaat cttcttgtga ggccttatga ataattgtta   151260
ataccatttc ttgcttatgg ggaacacact gataccccac aaagctaata tcaggaatca   151320
tttcataaat atatgttttt agcagatttc cgatggtatg ggtttcatct tttatcgtga   151380
taatggcctt tgtttttcc tcatccatgg aaaacagcac aagttccggc tgcggctctt   151440
caaagttttc ataaatttt tgaatgcttt ggattcggcc aataatgatc cggcaggcgt   151500
ttttaaata cgtgcgaacg gcctggttga tatgtggcag cggcaccgct ggaaagcaaa   151560
gccccaggcg gtggtgacgc gggtctgagg tcatagagct ttgcttgtaa ccgctaagcg   151620
ccatatattc tttttatcc gttgggtact gttcaatgtc aaggtgggaa aaatgtgttt   151680
taacggcaag attaaaggcg gcatgctttc gtcctatgcc cttttttaata tagatatcct   151740
ctataatcaa cgattttccg ggttgtagga agccaatctc aaaggtagga ttaaaaatcg   151800
ggtatttaag cttagggcct gccacctgga tgagatcgcg gctatagatg gttttaacct   151860
cacagctatt gtttaaactc cgcagagcaa ataccagtgt ctcgttttc gcataaatcg   151920
gaatgaaatt aatgcggttt ctaataaatt gttccgtcat aaacaggtcc gtggaatcct   151980
cgatcttata cccaccgggc ttaatatcta gcatataatt gggaatttca tcttgcaaga   152040
cccgcgacag gccgtggacc gcggctctgc taatgccctt aaagtccata acaacattga   152100
ccgggacgag gggcaactgc tcctcgagct gaaatagttt tttggccgca ttttttaataa   152160
agaggttgga aaagtctatc aaaaacggtt tgatttccac gttttggaaa attttttcca   152220
tttgtattat aaatatatct atatatattc aaattatggt agtttatgac ttgctcgttt   152280
ctttaagtaa ggaatccata gatgtgctac ggtttgtaga ggcaaacctt gcggcgttta   152340
accagcagta tatttttc aatatccaaa gaaaaactc gatcacgaca ccccttctca   152400
ttacgccgca gcaggaaaaa atttcgcaaa ttgttgagtt tttaatggat gaatataata   152460
agaacaatag aaggccctcc gggccgccgc gtgagcagcc catgcaccca ttattgccgt   152520
atcaacaatc ctcggacgaa cagcccatga tgccgtatca acagcccccg gggaatgatg   152580
atcagccata tgagcaaata taccataaaa aacacgcgtc gcagcaagta aatactgaac   152640
tgaacgatta ttatcaacat attcttgcat taggcgatga agacaaaggt atggacagca   152700
tgttaaaact tccagaaaag gcaaaaaggg atagcgatga tgaggacgac atgttttcta   152760
taaaaaacta acgacgtaac aattaaacaa aaataaaaat cattataaaa tgaatcttga   152820
atacgtccaa gttgttcaaa aattaatca agtactccta gaacttacca aaaagtatg   152880
taccgttgtg ggcgggagca aacccaccta ttggtatcac cacattagaa gggtttgctc   152940
agaatgtcca tccatgccga tgagtatgat aggtccgtat ctgaatgtct ataaagccca   153000
aattctaaca agggacaaga atttttttat gaatttcgat cccgcgcata atgagtacac   153060
ctttatcatt caaaaactaa aagaagcagc ccgaaatatg ccggaagacg aattagaaca   153120
gtactgggta aaacttttat ttttacttaa aagctacata aaatgtaagc cctttattaa   153180
ttaaagaatt gatgcataac taataaatgg ccggtcgtgt aaaataaaa cagaaagagc   153240
tcatagactc tactgtaaaa aacaaaaatg tgatgaatct gttccatgaa attataggct   153300
caaaaggcaa tattaatttt agcgttgtct ggcccaagtt taaaaaaatc aaacagagcg   153360
tttatgacta catttccact ctttctgtgc tggaaaaagc aaacgttatg caaaactttg   153420
aagctgataa gaaactgttg gaacttttg tacaaaagct gtgggctgcc tatgaaggct   153480
atttcaaata tcccgagatt gaaaaatatg aggtggaagg ccaggtaaat ttcaatctcg   153540
```

```
tacctcagtg cgtcctcgaa aagtttagcc agttgtatag gataagaatc aattcagagc   153600
ttgtcacact catcctaaac agctgtgcct ttatgagtaa atataacgat tatattctca   153660
aaaaagatcc ctacatacta accataaccc ccggcctatg cttttccccc attcccaact   153720
tcgaggacct aaattttaaa catctttaca acagtgataa aaattctcag catgacaaag   153780
agtttatcat gtttatatta tataagcttt atacggctgc cctaggagtg tacaatgcca   153840
tctcgattcc agacatcgac gtagaagacc ttgaaaatat catcctatcc tcggtgagcc   153900
agattaaaaa acaaattccg cgctgcaaag acgccttcaa caaaattgaa tcttcggtac   153960
acctgttgcg caaaaatttt aacacatatt acagtgacta tgtgggctca ggctacaacc   154020
caaccatcat tatggaacag tacattaaag acatatcaca ggattccaag aacatatcac   154080
cacgcatttc ctaccagttt agaaccatca tcaagtatta ccgcgacatg attgccacca   154140
ggcatcaaac gatggacccc caggtattaa acctcgtaaa gcacgtcgaa agaaattag   154200 atatgcttga tagagaaaaa aattagtata tatagttatg gtgaatcttt ttcctgtttt   154260
taccttaatt gtgattatta caattttaat tacgactcga gaactatcca ccacgatgct   154320
tattgtttct cttgtaacag attatattat tattaataca cagtatacgg aacagcagca   154380
tgaaaacaat acattttca tgccgcaaaa aaattctttt aacgaatctt ataataaaga   154440
caaaaaatct aatatacata ttccctacca gtggctggcg cctgaactga aggaagctga   154500
gagcaagtac tggtggggca attatgatcc tcatagcgag cccgttctcg ctggcgcatc   154560
ttgaatatct tcatacgtgg cacgtcacca tcaaaaacat tgcccaacag cacgggcttg   154620
atataaaggt ggccattgtg gtctcaacat cgcatttaaa taatttttg ccaatttccg   154680 gggcgcttaa catcgaatgt ataaccttcc ccagttgcgg catcaaggag atagacctcc   154740
tatgggcgcg cattaaacta tttcaacatt actgcgccat cggtgcccgt cttttatggc   154800
tggtaagtgc tgacatcagg cccctgttt cagcgtggcc agccatcgcc gacagtctaa   154860
aaaagggagc agatgcggtc gttattccct accctccg atggaacaat cttataccta   154920
ccgtcatcaa agaaatagtt gtccaccaaa aaaatgcct tgtggcggtg gatgcacgcc   154980
accttgatac agatacccag attgtagggg ccgggatggg ctgcatcgtc ctaaccctaa   155040
aggcccttat ggtgcgccta agtattggca aacagcccgt taagatactg tggcccgacc   155100
ttcacggcac tgccgagggc attcctctgg aggggtgga ggttggctgg tttttaaacg   155160
cttatgcgca taattaaat atacgctgcc taggggctga tcatattgcg cagcacttaa   155220
cttaattctt tatttaaaaa gtccacgcat ccagtggcgg cctacattaa gggcctacgg   155280
acataaatat acactggcta gaagtacgcc ttcatttaaa ccattgaatt atttatataa   155340
tggctgcaaa cattattgca acaagagccg tgccaaagat ggccagcaaa aaagagcatc   155400
aatactgtct gctagactcc caggaaaagc gtcatgggca ttatccctt tcatttgaat   155460 taaagcctta tgggcaaaca ggcgcaaata tcataggagt acagggctca cttacccatg   155520
ttatcaaaat gacagtattt ccatttatga ttcctttcc tttacaaaaa actcatatag   155580
atgattttat tggtggacgc atttatttat tttttaagga actggacatg caagcagttt   155640
ctgatgtaaa tggaatgcaa taccacttcg agttcaaggt tgttcctgta agccccaacc   155700
aagtagagct tcttcctgtg aataataaat ataaatttac atatgctata ccggtagtgc   155760
aataccttac cccaatcttt tatgatcttt cgggaccgct agatttccca ttagatactc   155820
tttcggtcca tgtggatatc ctctccaatc atatacagct tcctatccaa aaccataacc   155880
```

```
taacaacggg tgatcgtgtt tttatttctg gatataaaca cctgcaaacg attgaattat   155940
gtaaaaataa caagattttt atcaaaaata taccgccgct ttcatccgaa aaaataaaac   156000
tatatatact aaaaaatcga atcagaattc cgctatactt taaatcttta aaaacgtcta   156060
agtaataaca tttttatagt ctactcctag ttccgaaata ggctgaattt cttttttaag   156120
tcctttaaac caaggatgtg atacaagact cttaaaggaa agccgcttat tttcattaat   156180
tgttaaacat tccgtgataa actgttttcc cgtctctgaa atgttctcgg gaatataatt   156240
ttcccgtttc aggatatcat ttaaataaaa attttctgca cgaaatctaa aaagattaac   156300
cgcgaccata cctatcgtcc acacggttaa aggaagctgg tagtaataac cataataata   156360
aaattctgga cacacgtatt cccatgttcc aaacatatta tattgggggac gggtttcgtc   156420 taatctaaca gcgcttccaa agtcaatgac cttaatgatc ttttgattta tgtctataat   156480
aaggttctca tccttaatat ccccatggat aaagcccttc tcataaatgt tttgtataat   156540
aagaataagc tggaatatta tttttttggc ttcggtttcc tcaagttttt taaagtaatg   156600
ataatgaagt agatcaacac tatttggaat atattctatg attagtatat gatacatagc   156660
attttcggta tattcgataa gcttaataac accgggagta tcttgcaggg cttttcaacac  156720 gatgacttca tttcctggaa tttctttttt agaaacgtac ttaaatataa tgggttgccc   156780
tacttgatga cccaaaaaga cgttatttct gccaccctca acatgggtc tcgtcgcaat   156840 gaaatacatg tgctgcgttg tggagatcct ttccacccttt gctgtaggat aaaacgcata   156900
ttgtgcctgg ggattttta acattttttt aagctgttgt tccggcctgg acatgtttta   156960
ttagctttat atataaaggg ttagaaggtt taatttcaat atatgcctta atgatgggat   157020
tatattcgta aaaggtatag cctaatccta cgtctttgtt tttttggtaa aaaaactgtt   157080
tgccctcgta ggatatgcta taggcttta cttcggcttt tacaagcggt tggcagggat   157140
tgggcaaacg taaatcgcgt tcaaagtttt catgaaaaag caaagcattt gtgggctgac   157200
acatcagaca gccgctttcg ccattgaagg cacattcaat ggccgccctt tttagtaaat   157260
cgcggaaagc agaattaaga tggctctttt caagccccct ttcgtgaaaa cgctcatcaa   157320
tcgttttttg ttcctgactg ccttcgggaa tactataaaa catttttttga ttagccaccg   157380 cgatgtacaa aaaaggctgt acggttttct cctcgggcgg tagcgcatcg tggctaccaa   157440
tgcgtataat gcgcgccttc acttgatcct ctcgggcctt atcccagtac ggctctagga   157500
tatgaacctg ccgcccgtat ttgagatcca atccctcagc tcctgtttta gagacgagta   157560
aaattttaat aacctctccg tgtatattca gcggcgaatt ccaaagctgc tggatcatgt   157620
cgcgctcttt agataaaatt ttccctgtaa taagcgtaaa tcgtgttatt ttggaggaca   157680
ggactaacgt atgggtcggc ccatcttccg caaagttttt caccataaga tctttcccat   157740
ccttatgaag gaggatggtg ttgtgccctt cttccaatac ttttagggggc tgaaggcact   157800 ggtagccctc tatttctaaa aagcgggcca cgacgtgaag gcccaattcc acaaactgtg   157860
agtaaatgag cacagggccc ggagacgttt taatatttt tagcatgcgt actatttgg    157920 gactagaatt ttctgtgaag gcctcttttgg gcagctgctg aacagcctct gataatttt    157980 catcctcctt tactgttagc atttcggacg cgaagatgct gatcatacgg gaacgcacat   158040
agtaggagga gcctgactct tgctccgatc ctggcaggca gagggcggcg gcatttattt   158100
tttcatacat tcctgagctg gcgtgctttt ccgcgttttc aacgtctcgg gccagcagat   158160
attgcctata ctgctcgggt gacatttcaa ccttttctat aataagagga agctctgtgg   158220
ggaatagctt gttgagctca ttctggtttc cagcgtagct tatcatacc actaggcggt    158280
```

```
ttagtagttt gtccgcgttt aaagggctat tcgttgtttt attgacataa gcggtgtaga   158340
atctttcata gtgaagaggt aataagattc gcccgcttag catattaaaa cagggcacca   158400
tttcaaaggg gtccttcgaa cacggggtgc ctgttaaaaa cagaatacga atattttag    158460 cttgcataat attattgtac agctggcggg catttgtttt atcattggcg ctattgataa   158520
ttcctctaaa gaggttgtgt gcctcgtcaa cgatgagcag gcatccattt agggaccctc   158580
ccgcctttat gatctgctgc cccatgttgt aagcgtctag ggacacaaac ctgaagcgcc   158640
gcgagatttt ttgtagctct ttggagtgat ccgtcgtttc cggatataaa agtttaataa   158700
gctttaacaa agactgttgg aagtttgagt gcaacgactt gggtgcgatc agaatcgggt   158760
tgtaaatatg tgaaagtgag atggcaagcg acaggctcaa aatggttttc cccatgccca   158820
tctggtgata gatgaggagg ccccgtgtgt tttcccctg gcctatccca aatttaggat     158880
ccgaaaaggc ggtgtaaatt aaaaactggt agtatttcag ggctcgtgca aagcgggcag   158940
tgagtgaggt gtctttgctt tcctgaagct ctttatattt ttcatatacc tcttttaggt   159000
atgcttctat ttggacgggg aaggaggtgt tgttgtgcac gcaagacatg actcgttata   159060
aggatcccat attaaaactt cattagaaga atagggctgc tgatagctag cgctgcactt   159120
aaaaatgggg tagcccttt tcttgtaaat ccggtgcctg tcgtagacct ggctagaaag    159180
cgggcttagt gtatctttaa tgtccacaac gatgcgtacc ttttttcat ccgatccctg     159240 ccgggtaata cgtcccaaga tttgctccat gttgtttctg cggggcgttg ccatgatgat   159300
cgatgtcata tgcttgaagg aaatgcctct acgcccgtag ccataggtca gcaagataat   159360
ggaagcgctg tgtgcctgag aaagagcggt attttgaaacc ccgccgcata ggagcgccac   159420
ctccggaacg ataatttgaa catctttgaa ttctttggaa agcgcctgat aaaaaatttc    159480
taaaagtttg cgaaattcca cgaaaatgat gatgccatac ggctcatcgg tcccccattt   159540
gtgaggctca gcggtatgca gggagtaaag ccgctttgcc tcatttacga caagttgtat    159600
acgcgaagga tcttgaagta gtttatcaat ggtggcaatg gccgatacct tttcattaat   159660
atacacaggg ctaacgaagt caggatgtcc ctgatattcg atttccctca cgtacccgga   159720
aaaggttgtg gtgggactta cagtcctctg gggctgtcct agatggtgaa taataatctt   159780
gtccatacca tcgggccggt ccaggggtgt agcggacagt cctaatatcc gactaagttg   159840
tattttccaa aaaattttgt aattctccgg cgagtgtaat tcatgtgcct catctaacac   159900
gactagacca aagggctcaa agaactgctc aggcttcttg cgcagggtat taatgattcc    159960
cacgatgacg tcgtactctt tgctcgtcat gtccttttc ttgcacgctg cattattgta     160020
agcagctaca cgtaggtggg gcaggagcaa tgttagctcg tcgatccact gtatttgaat    160080
cgccttggtg ggcacgatga ccagggtagg gtacaaaagt ttttgaataa tgctgatcgc   160140
aatacgcgtt tccccaaac cggtatttag atgtaggtaa aagcgcccat aggggacag     160200 gagcttttta tgaatcttat cgaccatttc ttgctggtag ttaaatagtg gaaattctgt    160260
ttcaacgcat gggagggccc gcagcgacac ggggcgcgtc gtgtaaacca tgttaaacat   160320
ttcaaactgc ttttgcagca atatgggaaa ataaatgtat tcccctgca gcgtgaaggc    160380 agtttcctgt cttatggcta tgtgctttgg ctgcccgggt aatgcccgcg ccgtaacggt   160440
gagcgcctta agaacgcgcc cgaaatcatg ttgtaattta ctttgtagct tcttataatt    160500
tattcctatt ccagcaaagg atataatggc ctccattctc acgctggacg ggttatatgc    160560
agaggttcca aaattcttac cagaggcgtt acgagagggc tgtgctggca agaatcctct     160620
```

```
aagcttttat attcaacaaa ttttaaattt aatgggatgt gacggtaacg agtaccatgt   160680 tcttttacc agcagctccg aggaagcaaa tactcatatg atcatggccg ccgtgcgtcg   160740
ccatttgctg cggacgcagc aaaggcctca tgtcattatc ggagcagccg agcccctag   160800 cgtcaccgaa tgtgtgaagg cattggcgca ggaaaaacgc tgcgtataca ccatcatccc   160860 cctaaaaat tttgaaatag atcctgttgc ggtatacgat gccatacaaa gcaatacctg   160920
cttagcgtgc atttcaggca ctaatgctgt tgtcaaaacg ttcaacaaac tccaggacat   160980
cagcaacgtg ttaaaaggta ttcccctgca ctcagaagtg agtgatcttg tttatcaagg   161040
atgtattcaa caaaatccgc ccgctgatag ttttttcaata aatagtctct acggcttcct   161100
gggagtcggt gttttgggaa tgaagaaaaa ggtcatgcaa ggattggggc cgctcatttt   161160
tggaggaggg ctgagaggcg gaagccctaa tatacccgga attcatgcca tgtataaaac   161220
gctaacccag caaaggcctt ctatgaaaaa aaataaatac aatacatacg ctgttcatga   161280 aaacttaaa aaacatcagc atgtatatct acccataggg ggcgtgtctg cagaggacac   161340
gtctgcagaa aacatatcta caaaagacat gcctgttgaa ggcccgaagg gactcccggg   161400 ctatattta tttagcgttg gccgtcgcgc cgaggagcta caaaaaaaaa ttttcactaa   161460
atttaatata aaggttggcc gtgttgttga cttacaagag atactgtttc gtatcaaaat   161520
accccaaaaa tactgggaga cattattgtt catccaatta agagataatt tgaccaaaga   161580
ggacataaaa agagttatgg ttgttttgat gcatttagat accatcactc ctcgtggctc   161640
tcttcctcct ccgagccact cttcttcttt ttcttaatcg ttttgtttg ttctataata   161700 agggaaaaga actccgtggg atcttgttcc ccgtacaggt tatctgcgac cataaggatg   161760
cttagaatgg taaacaggtg agaatacata agggtttgcg ttttaagaaa accctgacgt   161820
tgaatcataa ttgaaaacac cttgcaaagc cgactcatca gttgttctgt aatggcgtta   161880
agcattttct ggaattttc ttggttttcg ggtgtgattt tatattcatg tagaaagtgt   161940
ttcacacctg aggagaagaa tctttcctcc ttcgagagcc catctttgat gatgggaagt   162000
tccttgatca gggcaaacca ttcctcctct tgggcttgcg gattctgaag atactgatgg   162060
cagatatggt ttagaatggt gcacacgtag ctaataagct ctgagctgat tctttggttg   162120
gttttcaaat gttggcgaaa gtagtttttc accgaagtgc atgtaataaa cgtcttcatt   162180
ttcttataat atacaacagt atgttgagtc tttaatttaa aattacaagg agttttctag   162240
gtctttatgc gtataggtgt ttctttgtcg taaattttca atagccgaca ttgtttgtga   162300
agcagtgttc tgagtagtga ctgtcgtgta aggctcagcc ggatgagcag gagcactcgc   162360
ggccgcaggt gcggccgccg gcccgccagt tgccatgact agtctgtccg taactgggtt   162420
gtccgtaact ggtttgtttg ttgctggtct gtttgttgcc ggtctgcccg tgactggctt   162480
gcctacactt gctgtagtcg ctccagctgg tttagaggta cctggttgtg gagtgacttc   162540
tacccactgc tgatcttgat aaggatttat aaactgtata tcttcctcct caatagcagc   162600
agcttttttc tttcttgaag agaatagata gattagaacg atgataatga tgactaagac   162660
cacgatagca atgagaatag tatacatatg tgtggagaag aagcttggtg tagtgactgg   162720
tgacaaacac tcaccataat gccgcggata accggttgaa aaaattcag aatccattta   162780 agatactatt ataaataata tataaaaatg ttgtggcgca atgaaattac agaatttatg   162840
gaccaacttt ccaagtattc tcaagaaatc ttaaaaacgt ttaagcaatt gcgtcctagt   162900
gaatataaac aatacaatga atttttaaca caagttacac cgttgctgca aaaacccct   162960 gaaaaaattc cagagttggt tgaccatata ttcaattacc tagacaacgt tgaaaaaatt   163020
```

```
tgtgagctcc tcgtgaatgc tagctcaatt attattagtt caaaaatacg agaacaagta  163080
aaacacggaa tgagcttcag ctataaagcc gacctcgact ccttggcgga cattctctct  163140
caaaaacagt acgtgcttat gcatctttca aaaatattg cggccgagta ttttaatacg  163200
tgtttaaacc aagggaaatc caagttagat ctcaaagctg cctctgtatt ttatagtagt  163260
cgttcccgaa cggcaagctc agcagaactc tatagaaaaa tgctatacgc ctatggttca  163320
ccgcaggaaa ttaattatta tactgaaaaa gcccgaaata agacgttgga tgtggaggag  163380
agcgacagca tggccatcat cgaacgaacg gcccgacaca acctttccct tatgcacccg  163440
ctagaagcca tggggcttac ctttggggca accaacacgg acgccgaccc ggaggatctg  163500
aaggacaaaa cggtgataaa tttaacgctc ccgcaggcaa cagaaagcat cacctaccat  163560
cttaaatccc taatgcagct aaaaaaagta agtacggctt caggactaaa tacaaacatt  163620
ttgaaagcat ttgataatat tatttccacc cctgtgaaaa aaaataaaat ggcctccaag  163680
ttggcgcccg ggatggatgt cgtgttcact agcgataacg gaaaaacatt ttttactaaa  163740
aacattttaa gcaaaaacat gctagcgggg cccaagagc gggtgtttgc atataataat  163800
ctcattagta atttaaataa ctcctgtttc atacaaaatc acaacgattt tttaagacag  163860
caggactctt ggcccttcta tgacgcgcac aattttacca acaagttttt aatgcagcct  163920
attttttcgg ggcagacccg tcctcggctt cagggagcca tggaggcggc gcatgtggaa  163980
acgcatctca cggcattttt acaaagtatt cagccctcta ggccacaaga tccctctgtt  164040
ttggcttccc ccaagttatc tgctctaatc ttgaactaaa aacagccttt cttggactta  164100
aatgatggtc taccagtttt tgaaataact tagagaacta tgaagatttt catgaaattt  164160
aaattagaga tttgcaaagg ttacttgcgg tcattttctg ttgaattaaa taattattcg  164220
aatagtataa tgtctgaaga tattcgtcgt ggtcctggca gaccgccaaa gaaaagggtt  164280
gttcccaact ttgagcgcaa gggcattctg gaaaaaccag ttcggccaca aagccgtctc  164340 gagtttttcct atgataaccc gctgatattt aaaaatcttt ttatttactt taaaaacctt  164400
aaaagtaaaa atattttggt gcgatgtacc cccaccgaga ttaccttttt ttcacgtgac  164460
cagtcgcagg caagctttgt tattgccacc atcgacggaa aaaacgtgaa ccattattac  164520
gccagtgatg tcttttggct aggcatcaac agagagctcg ttgaaaaaat gtttaacagc  164580
attgatcgct ctttttttaaa aattaccatc gttcaccgct atgacaagcc tgaaaccctg  164640 tttttttatct ttacggattt tgacattgac aaggagtgca cgtatcagat tacggtctcg  164700
gagcccgagc tcgatatgga ccttatcgaa atggaaaaaa gcatcagtga agaaagactc  164760
aagaactatc ctctgcgctg ggagtttacc tccaagcagc tcaagaaaac atttagcgac  164820
ttatcaaact acaccgagct cgtgaccatt gaaaaactcg gcggcgatac gccgctgcac  164880
ctgtatttcc aaaagtttaa ctccatctca taccacgaga tgtataaatc ttccaacaag  164940
atcaacctga cctcgaccat tcctaagtcg caggtgttcc agataaatgt taaaattgct  165000
cacatcaagt cgctggcctc ggctatggtc accgacaaga tccgcattct gtgcgaagaa  165060
aatgggaacc taatctttca atcggaaatg gatgccctta tgttaaatac gattaccttg  165120
aacaccacga tatagttcgg taacattaga tgttctaata tttagcatct aaataatacg  165180
ctgtagtccg gtcaggggttg cgtcacagtt ttcccatttt tttgcctcgt cggcggtggc  165240
caccgttgcc ctatcatta cgcccggtaa gacaaagcta aaggcgttca gcggggcttg  165300
gcaatgcccg cccagcgtga aggagctcgg aggattttgc gcatcccgaa atcccttagc  165360
```

```
catgttgttt aacacttcgg ttacgtcaat cgagtgaagg gatcccttgg gatccgtgaa    165420
tgtaaagacg cagtttctaa agcgcatgta tgcgatggac gattcatcgg gggttttgaa    165480
ggtaacagtg ttccccttgc tgtacttaaa gggggaccat ccggtaaaat tataccaaat    165540
gaaagcaata ataattaaaa taaccaacac aatagttata gacaacacaa agtctgtagt    165600
gccgcccatt attaaataaa aatatttag accgccggct taaaatttac ttattgctca    165660
tagcttaagt ctattttatt catagcttaa gtttattgct catggcttaa gtctattgct    165720
tatagcttaa gtctatttta ttcatagctt aagtctattg ttcatggctt aagtttgttg    165780
ctcatagctt aactccatta ctgatagctt actgatcatg acttaaataa aaatattttg    165840
cccgcttaaa aattgtttag gtttgaaaaa ataagagatg gagggggcaa cttatcgtca    165900
ttgtgtttac ccccactgga agacatcaaa cggtaaataa ttataagaat caaaatgatt    165960
aatataaggg ttaaaaaagg atgattcatc acattaatta aaaacgtatt tataacgctg    166020
ttgcagttga aattttggta taggtcggaa atattgcccg agcctccgta ttctgcaatg    166080
ttctgacata tggtgagtcc ggaggggcac tgcttgttgg tcaaaatatt tctttgctcc    166140
gttgttttat aggcattttt atttccatta cacggagcaa acgcacattc aggccatagg    166200
gtgccggagt tcacacaggc acaatactgg ctatacgcat actcatcctt tgagcacaat    166260
ccctgtttat cgcatatgct cccaataata ttgtcatcct ccgccgtttg ttgatttgta    166320
tgcgagcgta aaatagcggc ccaggccttg ggctcctttt tttgcagctc ggaaatcgaa    166380
gggcctgtac agctaaagtc gacccaaata tcattgcatt tcgtggaaac tggcatgcaa    166440
gacataattg aaataattaa taagtatata tcatggcaac aaatttttt attcaaccta     166500
tcaccgaaga agctgaagca tactacccac cttccgtgat aacgaataaa cggaaggacc    166560
tgggggtaga cgtatactgt tgctccgacc tagtgcttca acctggacta atattgttc    166620
gcctgcatat taaagtagca tgcgaacaca tgggcaaaaa atgcggtttt aaaatcatgg    166680
cgagaagcag tatgtgcacc catgaacggc tgctcatcct tgcaaacgga attggtttaa    166740
tagacccggg ttatgtgggc gagctcatgc tcaagatcat taatcttggc gacaccccgg    166800
tccaaatatg ggccaaagaa tgtttggtgc agttggtggc ccaaggtgac catgtgcctg    166860
accatatcaa catcctaaaa agaaaccaaa tatttccgct gtttgcgcct accccaagag    166920
gcgagggtag atttgggagc acgggcgagg ccgggattat gagaacttaa ttttattttt    166980
tttcttaaca taatgggagg ctctacaagc aaaaattcct ttaaaaatac gaccaacatt    167040
atcagcaatt ccattttcaa tcagatgcaa agttgtattt ccatgttgga tggcaaaaat    167100
tacataggcg tattcggtga tggaaatatt ttaaaccacg ttttccagga tttaaactta    167160
tcattaaaca caagttgcgt gcaaaagcac gtaaacgagg aaaatttcat tacaaatctt    167220
tcgaaccaaa ttactcaaaa tttaaaagac caagaagttg cgttaaccca atggatggac    167280
gcaggaactc acgatcagaa aacggatata gaagaaaata taaggtaaa cttaacaacc     167340
acacttattc aaaactgcgt ttcatccctg tcgggtatga acgtgctggt ggtgaagggg    167400
aatggcaaca ttgttgaaaa cgcaactcag aagcagtcgc agcaaatcat ctctaactgc    167460
ttgcagggga gcaagcaggc catagacacc acaaccggca tcactaacac ggtaaatcag    167520
tactcacact acacctcaaa aaactttttt gacttcattg cagacgcaat ttcggctgtt    167580
tttaaaaaca tcatggtcgc ggctgtagtt atcgttctaa tcatcgtagg gtttatagcc    167640
gtcttttact ttttgcattc acggcaccgc catgaggagg aagaagaagc tgaaccactc    167700
ataagcaaca aggtattaaa aaatgctgcc gtttcgtaat aatttaatta aagtaaaaaa    167760
```

```
aaaaggtatt gttatagtga tggcagattt taattctcca atccagtatt tgaaagaaga    167820
ttcgagggac cggacctcta taggttctct agaatacgat gaaaatgccg acacgatgat    167880
accgagcttc gcagcaggct tggaagagtt tgaacccatt cccgactatg accctaccac    167940
atcaacttcc ctgtattcac aattgaccca caacatggaa aaaatcgcag aggaagagga    168000
tagtaatttt ctacacgata ctagggagtt tacttcactg gtccccgatg aggcagacaa    168060
taaaccggaa gatgacgaag aaagcggtgc aaaacctaaa aagaaaaaac atttgtttcc    168120
aaaattaagc tcgcataaat cgaagtaaaa attgaagcga aaaaagtag aaaaaaaatg     168180 tttggagctt ttgtaagcca ccgtttgtgg tcagatagtg gttgtacgac cacctgcatc    168240
acaaacagca ttgctaatta tgtagccttc ggcgaacaaa ttggatttcc ctttaaatca    168300
gctcaggtat ttattgccgg ccctagaaag gctgtgataa atattcagga agatgataaa    168360
gttgagcttt taagatgat tgttaagcac aatctttggg ttgttgctca tggaacctac      168420
ttagatgtgc cctggtcccg taagagtgcg tttgttacac attttataca acaagaacta    168480
cttatatgca aggaagtcgg tattaaaggg ttagttttac acctaggcgc tgtggagcct    168540
gaacttatta tggaaggact aaaaaaaatt aagccggttg aggggggttgt catttacctg    168600 gaaacccgc ataacaaaca tcatacatat aaatacagta caattgagca gatcaaagaa    168660
ttgtttttac ggatacgaaa taccaggttg aaacagattg gtttatgcat tgatacggct    168720
cacatctggt cttccggtgt caacatctcc agctataatg acgcggggca atggctgcgc     168780
tcgctggaaa acattcattc cgtgatccca ccaagccaca ttatgttcca cctaaatgat    168840
gccgccacag aatgcggaag cggtatagac cgacatgcaa gtcttttga aggaatgatt     168900 tggaaatcat atagccataa aataaagcaa agcggtttat attgttttgt tgaatacgtt    168960
acgcgacacc agtgtccggc tatattggag agaaacctcg ggtcttccat gcaattacaa    169020
accgctttaa ccgcagaatt tactacatta aaatcgttat taaaataagg atgagttta     169080 gcgaatgtcc cttagttatt agtgcatgca aaaaattct acaaaagcgt attacaatag     169140
agaatgaagc acttataaat gccttaataa ccgctttagc gcagaccagc acgttgaatg    169200
atctttgttt attacctatt caaacctatt tgcttagtta taaaaatgct tttgagtgga    169260
tacacttcgt atgtattgca atcaccacta ttttggataa taagtataac tggaaggact    169320
gtacggtaga tattaattat atttttctcc atgtaaccta tatttacaat attaaaacca    169380 aggaataccct agactactgt tcttaaactt tattttttct atatttacgc caaagagaat   169440
atttaaagtt tttttgaaaa aaataatata tgtagataaa attcagttac atgatatatg     169500
tgtaaacatg tgtggtaaac aacatatggt tatgctttat aagataaatg cgcataatat    169560
atgtaaacaa aatatggtta tgtgttaaat gcatataaat gtattttaac gtatatcttg    169620
tgataatgga tatatgcatt tattaaaaga ggctgtattt attataaatc ttgctaagga    169680
tgccattgtc aacatatatc ccatgttgga caaattgcgt tgcgatccag ttcttttttt     169740
ttgattttgt ttaatgctat ccttttttgaa gggatggttg tccaccatat ttattcgatg   169800
ttcaatgaat aggtctgctt tttcgtaagg cagtgaaggt cgttccaaga ctccttgaac    169860
gatggacgtg ttttcttgga tccacttaaa aagcacgtgg cattcaaaaa caggacagtg    169920
attggatcct tggatatgct ttggacagcc aatgcttgaa gagatgtagt ccctttttctt   169980 taggacaagc ttctccacgc tggggcaaca gagatcgttc aagttctgga cggtcgcatt    170040
tggaatgttg aaacttcgta tccattcacc ctcgggtcct cccttatgaa gaaggagtat    170100
```

```
ttgctcatgg tccttagtaa tcttaaccaa atgttggaag atcatttttt tacctgcttt   170160
aaaggcctga agggtgtcag ttggcaaagc tattgaattc gggagtgggc tttcatcaag   170220
cgtgaaatgg tgaatgtgac gcgactggaa agaaaacgac cgttgattta ttttttcaaa   170280
gattgggtcg attccgccat gaaagaacag ctgcaagatt ttagaaggcg tattttttc    170340 ccaataaaaa atgaccactt ctcgtgggat taaaatcgtc tgtgtcccat tttcattata   170400
taattggccc ataaagccat caacgtcaat caacaccaaa agcatggtat agagagcttt   170460
tagaaccgga gttcgttaaa aaaatacaaa gttcgtttaa aacgtgtaat gttactaaaa   170520
aaatgtaatg tttaaatgat aatgatacca catgcattaa tgaaaaaaac ttttaaattt   170580
ttgttttaat atttgcatga aaatggaaac atttttagtc tgtttatttc acaatgcaga   170640
tggtttacat caacagattc aggaaatttt gtatttattg cggatgcata tttacgaaac   170700
aaatctttac ttaaagcagg aactatcacg gcttatatat ccaaataggc aactttcttt   170760
tgtgttactt atgccccttt cccttctaag aaactgggat gacattgaat atttaacgga   170820
cgttgtagat gataagcaga ctctacatta cgcggcaaat ttgctgacaa actacgttct   170880
acatctatcc atgtttcaaa agctgacaaa accatacttc cttttagcgg tcaagcgggt   170940
cagcgaaaaa ctcaacaaaa agcagcgaca ttcattttac gaggtattgg taacctccga   171000
aaccttgaat aattatgaaa acctatctaa aaacatttta aatacgttga tgtttgccgt   171060
gcgctacgta tttaaaccta cgccgaacta ttcagaaatt ctcgcagagt tggaaaaaaa   171120
aaataaaatt caccatatta tttttaatat ggtaattacg gattttgcgc aaatccgtga   171180
acaacaaatg gataaacatc tgtgtgaaac aaataatgag cttcgtcagg aatgtaaaga   171240 aactatttttt gatttaaagg tggtaggaaa tgtttagcca ataaactcat gcccgcattt   171300
tttacaggta caaaatatcg tggatggctc atcgagggcg cgtgtttgta cttctctgta   171360
ggtacacata cgctgcttgc agttgggaca cttataaagt tgtgacgtct tttcggcgac   171420
cttttgctgc gaacgtagag taatttctgt cttctccttt aaggcggcag aggggcaaag   171480
ctcggcgaac gtcatgctac caattgcctc cggttttagc tcgccagaaa ttagcttatt   171540
aagggcatcg ttatcctgtt gttggtgact ttttttttcg cagttaataa tatgattgat   171600
cgtcccacaa cgggttgaat attcttctaa aaaggttttt tcttgttgct ggtacgtata   171660
atgataacac gaggcctcga ttttttgcgc gtattcggtg cataaatcag tatgttcctt   171720
aaaaaacata tgttttttgaa gcgttctaaa aaacatcatt tggatgatat cacgcatttc   171780
caaaataata tagggttcta gtcttttgga atctttcata actagatcgg tggtaatatt   171840
cttagtcata caatttatta aaaatggttt aatatattgt aaatattttt taggcgtgtc   171900
agcctgtaaa aaacattctt gttcaatctt atttgtaagg atagtatttt gcaaatactt   171960
atttagcaaa aatacgatag aatcgcgggc tatatgcatt ttcatataat tttttttaa    172020 aatttaatac aaaaaaaaga agtatagact cttcttctag tccggttagt tcgttggttg   172080
cctcaacatg gagactcaga agttgatttc catggttaag gaagccttag aaaaatatca   172140 atacctctt actgctaaaa atattaaagt agtgatacaa aaagagcaca atgtcgtctt    172200
acctacagga tctataaata gcatactgta cagtaactca gaactttttg agaagattga   172260
taagacaaat accatttatc ccccgctttg gatacggaaa aactaattgt aaccagtagt   172320
acatttaagg atagtttaag cagtaaatgt agaataacac agttaagcaa taaataacaa   172380
gtatatagga atatataga atatatagaa atatatagaa atagctaagc ttaatactaa   172440
ttcagctttt ttttaacta aaacctgaat agatgcgaag tagcggacat atacatacta    172500
```

```
aaataagcca tacatttact ttcttcttga acatgaaacc ttttttctt ctgttgttgg  172560
tatataaaca ataggactgt ttgctgaggt tgtatgatct tctacaactg ctgtctcagg  172620
atgacgatgt tttttaaac taaaagtgta ggatggaatg agtggaatat agttatggct  172680
cgacttatcc tgtttcgtac aggaatattt tttacaaata gaacgcaaca agcatatgaa  172740
taaaaacaga aatgatatac aggagcataa aatagatatg aacactaagg ggtagcagct  172800
tttataacgt tccgtatttt tcttagctat caattgattt accgtaatat ttatctcggg  172860
aaactttgtt ctacaatatt ttgtttggta ttccagaaac tcatgtcctg cttattccc   172920
gcagcttaaa aaatgataca aaaatgtgtt attgttacta aaattaattc ttcttaagaa  172980
aaactgcgga agacgcttta ggtacgtctg ttcctgtttt agtaggaagt agtataaggg  173040
acaatttctt tttccacaca ttagattatt gtaatatagg taggttgggg tgttggagcg  173100
aataagtttt ctgagtatgt tataatctat gacttgtaaa tcgttatacc ttaggtccaa  173160
aaacttgagt tctttaccaa agccacctgc aatttcagaa atatttttca tcccgcagcg  173220
gataatacgg atgtcctgaa acgtctttaa aatacttgta ttgtagtgaa tacttatgtt  173280
atttttttgt aaataatcta tgtcatgaca agtgcatgaa atgccagcag cattgcttgg  173340
tatagtatta tatgcaggaa gaactatact actattgaga atagtcacat tgtacttata  173400
ccatgtatta ttttctgata taaagtattt gcaggtgacc tgtggtttaa tcctacctgt  173460
taagccactt cctaaaaaaa caaaaaatat gaaaacccctt agcatcctgt atatactatt  173520
aaaaatttat aaaattttct gtttaaattt catttagaca aaaaaataat atatatacat  173580
cagcaagaaa ttatatacag attatataat tttctgattt ttttttgcca caataagcat  173640
cattatatgc attaaaatct caatactaaa cactaaaatc taaattctaa gcattaaatt  173700
ctaagcatta aattctatgc actaaactgt aagcactaaa atctaagtaa ctaaaatcaa  173760
cactaaatgt atgcaaccta aaatgtaaag cattactcat catcctcctc ttcttcatcc  173820
tcatcatcat aggttaagat atatgtgtca tcctccattt cttcacattc atcttcataa  173880
gcatcactgg gtattggtgg aacattggat gcagcatttt taaaatattc tatgtcttct  173940
ggtgaacact catctaatga tttttgaca gtccttttaa cttccatggg atatgattcc   174000
aaatcctctt tatataagag tttacggtag ctttagctg catccacatt tgctggagaa  174060
tctggatttg gctcattgag cagtgaaatt acactaagaa gaatggtatc aatcttttga  174120
gccggagacc aagtcattcc ctgttcttca gcattgtctc cgtgtaagat agagatacat  174180
agttttccat cagagtaaat attaggatgc cacatttcag aggtgaatgt taatctgggt  174240
ggtgcatatg ggtattctgg aggaaaggcg attttttgcct tgaataagcc tccctcataa  174300
aaagtgtcag gtgggcccct taagatcaca tcccattcag tcatatcctt ctcattcacc  174360
gaaattttga aattctcaga gggattctct atcaggtgtc tgtactctgc tattaaaaac  174420
ctggaaacca tggttattta atattaatta aattccctgg tttattcctc cttaaaagta  174480
gatgaacctc ttttgttttt tattgggttc attttttacta aatttatgaa ctggaaaaaa  174540
ctttaacggc ataattatca aatgcgaagg gggatccgta taaatccta gcttgccggt   174600
aatggctatt aagttaaatt tggtaccagt aacactaata tttaaaaagc cctgatcatt  174660
aactttccac attaaaagat tattatattc gaatgtttgt ccaatatgga caactttgtc  174720
accagatgtt acatttgatt tggttgttag tggctgaagc ttggcacaat caaaaataag  174780
cccattaaca ctaagatata gaggagtggg ttgatctatt ttctcatagt ttaatattcc  174840
```

```
atctttccac gtaatagctt gataattatc cgcagcaatg agttgaaatt ttataaatag    174900
tacaggggtt ttagttgtcg ttatacattt aaagggtgtt ttataaaaat aaaaataata    174960
attgttaaaa gtatgataat aatcgccaaa ataatttcat acattttta taagaattat     175020 acatagtatg gtatttaaaa tattagctaa atttaaaaaa acttcatgat ttttaaaaca    175080
gggaaaaagg ggattaggtt gaataaaaaa ggtaagcact tgtctatata ttttttttac    175140
aatgttgcct tgagtcgcat ttttaactgg ctggggagta tcagagtgga atatcactgt    175200
agtaggtcta taaggtcttg ttaaaatatg atcggtcatt gttttcgtac tagtgtcatt    175260
tagggtcgac ctgatagctc gatataaagt tataggggat aacctatcaa atacagtctt    175320
atctgtgctg aaatgtatat cgtcttcttt atcactaata atattaggaa tggctgtcat    175380
taaataatta ctacttgttg ttgtgggtga aatagttgta ctggtattat tggaaatggc    175440
tgtcattaaa taattactac ttgttgttgt gggtgaaata gttgtactag tattattaga    175500
aatggctgtc gttaaataat tactacctat tacaagtaaa ctaatgctaa ctacattttt    175560
aacctcaata aacctaaaaa gccatactaa atacctaaac aacatcctgt tataaatga    175620 gcagaaaaaa aaataagtat aattagggaa ttattcttat tcgcttacta ttaagaataa    175680
ttcagaatct tatttagtta gaaactatca taaagtgaat aggactcatc gtcggatgaa    175740
gattccgttt cagagatagt ttcttttttct tcctcagaat aatctgttcc tacaatagaa    175800
tcggtgtcat cctcagaaag agaagtattt aaatatggac tatctatagc aatatcctct    175860
tctatctcgc aatcctcctc ctccatttcc atagtgtgta ggagaatatt tttatcatca    175920
tgctcacttc ttttttgtt gaaagatgaa ccgtcctcaa tacggttcat gttaagttcc    175980
ttcatcttat gtataatttc cgtaatccgt gatgttttg acatgtaaga tggttttaag    176040
gttatatcca cataacagg agaatctcta tcatttcat ttgataaact ttgatctttg       176100
atttcttcgt ctaaaattct tgtcttttt tgggtactag atgaaataga ggaattcata    176160
ttctgaaacg atatatcaag gggagctgga cgctttttc caattaaacc gttttcgag     176220 atactatgat tagatgaatg atctttagcc aagctgtcct tggatatact atagttagat    176280
attttacctt taaataatat tcttctatac aagttattct taggtaaaga attagtatgg    176340
attcctatat ttttatctga aggagtgtcc atatcggaga acgtcctctt acgaatattt    176400
tgaccacgag ccatttcatc cactataggc agtattttgg ctggctatgg ttctttgttg    176460
tgacaattct atgagatttg attgcaaatc aattttagt tttaaatata ttggtaccta     176520
ggacaaagaa agtatatata gccaataatt attccactaa attgatttcc agactgatgg    176580
gtatggagcc atgttgtctc tgcagacgat cgcaaaaatg gccgtagcaa caaacaccta    176640
ctccaagtat cactatccaa tactgaaggt ctttgggctg tggtggaaaa acaatacgct    176700 aaatggcccct attaaaatat gtaaccattg caacaacata atggtaggag aatatcctat    176760
gtgttacaat catggaatga gtctggatat agctttgatt cggcagtaa aggagcgtaa      176820 tatatcctta gtccagcttt tcaccgaatg ggggggaaat attgactatg gggcactttg    176880
tgctaacact ccatctatgc aaagattatg taaaagtttg ggagccaaac caccaagggg    176940
ccgaatgtat atggatgctc ttatacatct ttcagatacc ttgaatgata atgatctgat    177000 taggggggtat gagatttttg atgataatag cgtgttggat tgtgtcaatc tcatacgact    177060
caaaataatg cttaccttga aggcccgtat acctctcatg gaacaactag accaaattgc    177120
cttaaaacaa cttctgcagc gatactggta tgccatggct gtacaacaca acttaacaat    177180
cgctatccac tattttgata atcatattcc taatataaag ccatttagtc tgcgctgtgc    177240
```

```
tttgtatttt aatgatccct ttaaaatcca tgatgcttgc agaactgtaa atatggatcc 177300
taatgagatg atgaacattg cttgtcaaca ggatttaaac tttcaaagca tttactattg 177360
ttatcttttta ggggctgata ttaatcaggc tatgctaatg tctttaaagt atggtcatct 177420
ttctaatatg tggttttgca tagatttggg ggcggatgcc tttaaagagg caggggcgct 177480
tgctgagaaa aaaataaaag agtgttacaa cacatattag gtcttaatat ctttaagcga 177540
gagttgattc cccctgtaa agatcctgat ccttatcaaa tccaaattct gttaaaaaac 177600
tacattctaa aaaatgtctc aactgttttt acatattatt gccagtagcc attgtttata 177660
tcagaaaata acccatttgt ttatcttttt ttgtggggca accattaaga cccgacgcaa 177720
aaaaagatta atcttttatc agatacctaa aacgttctat aagggagtct atgagatgga 177780
tcatattttg atggtcatag taagaagcaa gcttttggc gaaaacaacg gagttaaaga 177840
atttaacccg ctcatgtttg gataggactt ttaacagcga gccaaaacag tatttaaaaa 177900
tttggcaata gttttttttgg gatgcaataa acaaacactt gatcagtgcc cgcttcactt 177960
tctgatcaga catgtttgcc gcataacagg cctttttaaa cttagtaata taattatgtt 178020
ccgcaagcac cattaacaag ggaacgatgg gaagctgctt ttcttggtga aatttacgta 178080
aatattcgat ggccaccgct tggacgactg tgtaatttac taagttagaa atgatagctt 178140
tcatggttgt aaaaatatac ataggatttt ctttttctgt atacagtttg aaaagcttat 178200
gattacgtga aatgatggcc attttttaata caagatggta tagtgtatct ttaggtaaaa 178260
atgccttgca agccgcgatg atgtcgatgt tgtctccatg aacagcgata gaaactaatg 178320
tttccaatct aaatgttttt atctgcatta atagaagaat gcagtcaatg ttattatact 178380
taataatact gtaatacacc gaatcaatga ccgtcatctg agaatcaagc tgacttatta 178440
gtaaatttaa cgttttttgg gaggcatgac ctttgatcgc ggcactaagt gcacacagta 178500
tagcaaaatt gttaaataca ttttgattta ggagaaggag taatatttc cttcggttat 178560
agtacgcagc atctgtgatg attattggcc gataaatgtt aaaatgtgtt aacagcttt 178620
taaaaaacg gaagtaattt ttttggatcg ctgtttgcat catcgaaata atgagataat 178680
cagggtatat aatgggtagg tcacatgcta cctctaacaa agaatagtcg cccaatctaa 178740
aggctgtgtt gaaaagcgta ctatcatcat acgtatcgag taccctgct gttacaaacc 178800
aagcgataag atgaatgtgc cgttccttgc aagctatcgc aaatagggag tttcctatgg 178860
aatgtcgaat aatgtactcc ctatttttt ccaaaatgtt tggaaaattg tatagcgttg 178920
cggcatacag tagacactcc attctggcgt tataatttt acttttacat atgaataggt 178980
ggaagaactc gaataattct tgagaacttg ttaaatgcat aatatggtga tattttggtg 179040
tcgttaaatg gtatgagaaa atgcattcta atacatcttt tcggttatgc tttagcgcct 179100
gagctaaggc atattcaggc tcgacccata ggactagtgt ttctataatt gagatattcg 179160
cctgctttgc cagggcatac tttaagacgc tccggttaga aaaatgttg ttatgaagat 179220
ggataaccgt atccattttt acgatgggac cattccagta tagtcctaaa tgctgtagca 179280
gatcttttgt tagttgtgaa gcgttctcgg gtgtcatata aatatgttgc agggcttttt 179340
tctgtaagga gaacatttcg tcgtaatcgt acaaaaaaaa ttaaaatttg ggcatggatg 179400
attcaaacat aacaaaatca agattttata acagtttgca ttaacctata catatatgca 179460
agtaaatgag atattatcta tcataacgaa tcaaggata tttgtatata tcaggagttt 179520
ctgaaataaa gatatgaaga ttatcatagt agtatccatc aatcacaatg caacttcctt 179580
```

```
taaggcataa tttagtaaac tcagcactcc catcttctgg atgctttaca actaacatta   179640
aaaactcctc agtcatatta tctgtaataa aataagatcc tcctggagcc atttgtagca   179700
tgtctcttat tcctacaaaa tctttttttgg gatggtaaaa actcagcagt ttcaaactct   179760 ttttttagttt tttttcctgg tatttaagcc atttgttata aaacagtttt cttatgaaaa   179820
tgcatttgaa aatattggga atgtttaacc atgcttcttc cgagcacatc tccagatact   179880
tactttcttt gtttcccatg tctaatttat tgctcactaa gttagtaatg aatctatttt   179940
aataatctac tttactaatc tatcttaata acctatctta taatctatct taataaccta   180000
attataacct atttataatt ggctaatgct gccggcattt catgcctatc taaacaactc   180060
ctactaagca atctactatt acatatatag attcacttttt tatatttgta aatcatgaga   180120
attataaaat cattactcat tttttattgta aattagtggg tatttgtaaa aatcttcaaa   180180
cgttttaaga tagtttttcta gagagaagta atctttgcca tcaatatata atgctttttcc   180240 tttaaactcc agttttgcta tgtttagtga gccgtttcta gatcttttttg ggcaataaat   180300 agattttcat tggttgcatc gtccgtaagc agaaaggtac cactaggcac gttaaaaaac   180360
atacgttcta tttcatggtc ggatttttga gaatagaaaa aatctaatttt tttaatccgc   180420 gttaactctt ttttatcaat cttttccagac tgttttatat atactttatt gcaaatctta   180480
caatcctcta tggcttcatt atactttattt tgcttatcct ctattgacat gtccgtatttt   180540 gataggtaac ttccgttaag gcggttcccc atggttttag atagattttt aattcagttg   180600 tatacttttta ttatgaggct aaaatataga agtttgatcc taaaaaaata aaaagattttt   180660 gtacatttat ttatggttta tagcggtata gaggccgata aaaggtatcc gggtagtctc   180720
ctatgatatc gtcaattttg gtataataac agttgttatg gtagtattgt ccaaaccgag   180780
tatgtatgcg ccggtgaagc gtccgcccgc taatggtaca gttccaggtt aagacaatca   180840
tatcacaccc aaaaagagag gaaacagcat aggtgcccaa aggttcatta taacatac   180900 gccgcatata ttttagttttt ttttctccat ggtaataatc acaggttttc atgtcctgct   180960
taataggatg attccccatg tatgataata tataataaat ttagtttttta gcttttttcaa   181020 aaaattgggc gctcgaaact aaattttcct tatcacagcg tttggagaaa gcgtatttaa   181080
agatatatct tcttctaaca agactgcaaa aaaaatctta ccccttattt ttataatgtt   181140
catcatagcg tttgaagata tcagaaggtg ccaggtttta taaaaatatc ctttaggatt   181200
tataacgata caagggtcta taaaatatat gcgggtataa tcttataaaa tcatcgattt   181260
tttcataata ttctccgttt atacaataaa gatcataaca gatattgatg cgtagatgca   181320
ttattcgcgt gttcgttggg cagctaaagg atatcacaac gtagttttttt ttaagaaaag   181380 acgaaactac ataagtccct aagggttcat tgaatagtaa acgccatatt tgttttaaat   181440
tttgttgttc accatagtag tattcgcact ttttcaagtc tttttttaata agcctattcc   181500 ccatgtatgc ttataaataa aaatttagaa atgtgctata ttatttgttg atgaatcatg   181560
aacacgtctt atatgttgat atgttactttt aaaacatttt gtatttttcaa cagacgcgtt   181620 ctattcttat taagaatgat gccgtctttta ttttaaacct tggtttaaaa tttaagaag   181680 tatttataaa ctataatcat gggaacttttt tcagtaactg cctctgcaaa aagtgacgat   181740
gctgtttgta agtatttaga agaaccaata gatgaaaatt acagaaacat attaagaaat   181800
gagcatgtta aaaaaaattt aaatgaggct ctgaatcgac atattactac ctataatcca   181860
gtagttgatt ggtgtaataa ctattcaaca ttttcatctc aggatttcga tgaatataaa   181920
atttatatac atagcgatct tatggatgga cgacctcgtc caaaaaaaac atggtgtgtc   181980
```

```
atcatgtaat gtttgttagt tttatataaa cgcaaaaata ttcttctagg agatgttgat   182040
atactaccta ttgaattcaa tatattaaag tacatttctg gctattccca ttacggtatt   182100
attattacta tttttaagag ctagatgtgg atttaagtaa taataacatt ctcccgttcc   182160
tcctagagac acctcatcaa attcccatcc tatgcaacct ttatgttgta aacataatga   182220
ttgacagcat tcatcttctt ttgaccaagt cgtccaaatc ctaccaagat ctatacgtgt   182280
ttttccaaat ggagattgaa gatcagcagt agtggcatta aacctataaa accaggtgc   182340 ataatcacat gaacggatcg taggatctaa tttaatatct tttatatctt gttttactgc   182400
ttctagacaa cttttatcag tacatgttcc acgtacacag tggtgtcctt tatccttaca   182460
atccgtatct gtcttacatt tttttttcgg cggtttatgt ttcagatggt aaaaacccag   182520
tattaaaata atcacaagaa taattcctat aagtacttga acaacaggat aaaacatttt   182580
aatattaaat atattttta attaaatgaa tagatttaat ccaagtagta ttaaaatttt   182640
ttagaaatag tgttctacaa ataatgaaat gaatggtcca aaaaaaataa ggtgtacaat   182700
aatgtaatat attgttaggc taagtaaatt taatatttta aagtatttgg aaaaatattt   182760
tttaacatat gatgtctagg aatattttt agacatttaa aaccatatag ttactttatt   182820
tattacactg aacttgaaaa gacttattac ctaaaatatt aatagatgaa gtaatattgt   182880
gtaattgagt ccataacatg ggtgggaaac aaaaatctcg taatatgaaa aataaacatc   182940 ctaaaagag tgcaattgtt ataagtttat gtaactttat tttaaagtaa gaatataaaa   183000
atatgagtac aagaggaata ggggccatta ctaacattgg ctccaacatc ctgttgtcta   183060 caaaaaaaa tattttttt agcaaaaaaa aatccatgga aggatattaa tacacataat   183120
tatttgacat cacattagtg tacttaccaa atagtaatat acaaccatcc taatattcac   183180
ctttatgaaa tgatcccaac ctatacggta aaatagtata ggttttaata aagaaaaaag   183240
atattctgtg gttttattt ttgtatagtg tgtaataca aaataaaatc ccaaatttta   183300
acctttcctt tttttctat acaggatgtt agaaatagta ttggcaacgc tgctaggcga   183360
cctgcagcgg ctccgggttc ttaccccctca gcagcgggca gttgccttct ttcgagccaa   183420
tactaaggag ctagaggact tcttatgctc agatgggcag tctgaggagg tactgtctgg   183480
cccccttctt aaccgtctac tagaaccctc aggccctctt gatattttaa ccggatatca   183540
cctatttcgt cagaatccca aggcaggtca gttgcgcggc cttgaggtca agatgcttga   183600
acggttatac gatgctaata tttacaatat actgtctcgg ctgcggcctg aaaaagttcg   183660
caacaaggct attgagctat actgggtttt ccgagctatc catatttgtc atgctccttt   183720
agttttagat attgtacgat atgaggaacc ggactttgct gaactggcct ttatttgtgc   183780
tgcttacttt ggtgaacctc aggtaatgta tttgctctac aaatatatgc ctctgacccg   183840
cgcagttctt acggatgcca tccggataag tcttgagagc aacaaccagg tagggatttg   183900
ctatgcttac ttgatgggag gcagcctcaa gggactagtc tccgcccac tgcgtaaacg   183960 tctgcgcgcc aaactacgct cgcagcgcaa aaagaaggac gttctttcac cccacgactt   184020
cttactgctg ctccagtagc tttttttgcc gcaggagcac cgcggatagg agctcctcca   184080
cgctcgcgat ccggcgctgg aagcggaacc gatcgaccgc cacctgctcc cagggaccct   184140
tgcgctcgat gtcgtcggct tcccacacct cgacggctgt ggcaaaatgg acatgcttcg   184200
cgtcgttcgt ccgttttttg cgccgcctcc ccattattct tcctgtaaga ttagtgttta   184260
atacctataa taacataatt ttaagattta atataccaaa acttaaacta tttttgtata   184320
```

```
gtaactatta gcatgtctac acatgattgt tctctaaaag agaaaccggt tgatatgaac   184380
gatatatctg agaaatcagt tgtcgtggat aatgcacccg agaaaccagc tggagcgaat   184440
catatacctg agaagtcggc ccgcgaaatg acatcatcag aatggattgc tgaatattgg   184500
aaaggtataa aacgtggaaa tgacgtgcca tgttgttgtc caagaaaaat gaccagtgca   184560
gacaaaaagt tttcagtatt tggtaaggga tccctaatgc gctccatcca gaagaataat   184620
taaaaaaaat attttttta gcaagttttt aaactattta aataaatgtg gtaaaaaaat   184680
tcacataata attaaagtga acgtgttaga attaatattt ttttataatc ggatataata   184740
tccattaaat caataaatga tagtgttgct accacactaa acaataacaa acagaaacgc   184800 acgataccttt tcctcatgat ttataatagc gtgttatcta aagatttttt tgaaaaaaat   184860
attaaatttt agttgattat tttttcagt tacaacattg ctttagaaaa aatacctaat   184920
tactacatag caaataaagc gagcgcattg ttacaaacaa cattttttt gcgcctggat   184980 actcctatat atgagaacta taatacggta tattaatcct attaccaaca ttgtcaataa   185040
tagtatgtag gcaatgacat actttaaata ccaaatatcc atggttattt ctaaaaatct   185100
tgaaaaaacg ttaaatttta gatcggtcac ctacgacagt aatactaatt ttaataattg   185160
atgactgaaa tcataatata atgccgtgcg aaaaataatt atttttcggt taagatacc    185220 attacataaa aaatatgcca tctactctac aagtgcttgc taaaaaggta ttggccttag   185280
gggagcataa agaaaatgaa catatatcta gagaatatta ttatcatata ttaaagtgtt   185340
gcggtttatg gtggcatgaa gctccgatta tactttgtta tgatgggagt gagcaaatga   185400
tgataaagac tccaatcttt gaagaaggca tattacttaa tactgcatta atgaaagctg   185460
tacaggagaa taattatgaa ttaataaagt tgtttactga atggggagca aacatcaatt   185520
atggattaat ttccattaat accgagcatg cccgggatct atgtcgaaaa ttaggagcta   185580
aagaaatgct tgaaggaaat gaatttatac aaattatatt caaaacatta gatgatacca   185640
ccagtagtaa tataatttta tgtcatgaat tattcaccaa caatcctctt ttagagaatg   185700
taaatatggg ggaaatgagg atgataattt attggaggat gaaaaattta acgaacctat   185760
tattaaataa tgactctatt agtgaaatat taactaaatt ctggtatggt atagcagtaa   185820
aatataatct taaggatgcg atccaatatt tttaccagag attcatggac ttcaacgagt   185880
ggcgagtaac atgtgctctt tcttttaata atgtgaatga tcttcataag atgtatataa   185940
cagagaaggt tcatatgaat aatgacgaaa tgatgaatct agcctgcagc attcaagaca   186000
gaaatttatc aaccatttac tattgttttc tattgggggg ctaacatcaa tcaagcaatg   186060
ttaacctcag tattaaatta taatattttt aacttattct tttgtataga cttagggct    186120 gatgcctttg aagagggtaa gaccctggcg aaacaaaagg ggtataatga aatagtggaa   186180
atcttatcat tagatatcat ttatagtcca aatactgact tctcatcaaa aatagaacct   186240
gaacatatta gttctttgtt aaaaaacttt tatccaaaaa atctgttcgc ttttgatcgt   186300
tgcaaccccg gttatatta ttcttagagg accgctacaa aaattatttt ttttcttgat    186360
caaagctcca aaataattat tagattaaag tcgcctatag cagcagccca ctccaaaaaa   186420
agtattttat agtacaaaaa acacgaaaaa tagtttgcgg ccggcggcaa actatttgtt   186480
gttgtctaaa acttaatgtt tttttaatat ttttaaatgc aaccatggat tgttggacta   186540
tcagggagaa gaactatagc tacatcatat tgtcaatact ggtaatacta ttaatatggt   186600
atcttatact taactattgt cgatcgaaaa aaaatgcagt tacaaacaac atgccgccac   186660
catacacggt gtcaagtagc tgttctcaat aatagggttg attgacgctc ttcgtaataa   186720
```

```
tatgttgatt gacgcatcat aaaatgctgt ggttgattaa tatgttgatt gtcgcctact   186780
ttattatata agtaatgatt tttgtataaa atacgggttt gtgagggctt tatttttct    186840 tattagaaca aagcatgcaa tttaaggcct acagcaagag taatttaaca cctacaacag   186900
taattttaag gtcagtaata atgtttaatt aaggcctgac cactaaaact taaacgattt   186960
tgtaaaaaaa aatgtctact ccactttctc tacagactct tgttaaaaaa gtgctggcca   187020
cacagcacat atctaaagaa cactacttta ttttgaaata ttgtggttta tggtggcatg   187080
aagcgccgat tacgatttgc attgatgagg atagccaaat attgataaaa tcggcaagct   187140
tcaaagaagg cttatcttta gatatcgcat taatgaaagt cgtgcaagaa aataaccatg   187200
atttaataga gttgtttacc aagtggggtg cagatatcaa ctctagctta gttactgtta   187260
atacggagta tacccggaac ctttgtcaga aattaggcgc aaaggaagct ttgaatgaaa   187320
gggatatttt acaaatattt tataaaacac gtcatcttaa aactagcagt aatattattt   187380
tatataatga attgttttct aataatctcc ttttccaaaa tatagagaga ttgagtttaa   187440
tagtttatag gggcttgaaa aacttatcaa tcaactttat attggatgat atttcattta   187500
gcgaaatgtt aactagatac tggtatagta tggcgatatt atataaccct actgaagcca   187560
tccaatattt ttatcaacga tataggcatt ttaaagattg gcggcttata tgtgggcttt   187620
cttttaacaa tttgtctgac cttcatgaag tatataactt agagaagacg gatatagaca   187680
ttgatgaaat gatgaagttg acctgtagta cgtatgatgg taattattcg actatttatt   187740
attgttttat gttgggggct gacatcaatc gggcaatgtt aacctcggta ataaactttc   187800
atattggtaa cttgttcctt tgtatagatt taggagctga tgctttcgaa gacagcatgg   187860
aactagcaaa acaaaagaat aataatatat tagtagaaat attatcattt aaaaattatt   187920
atagttcaaa tacctctctt ttatcaataa aaacgacaga tccggaaaaa attaatgcct   187980
tattagatga agaaaagtat gagtcaaaaa atatgttaat gtatgaagaa ttatctcatt   188040
gatacaaaat tatttttat aacagaactc tctgatggtg acaaatctcc gataggaata   188100
tatgacgtaa cataattatt tttttcgccc agaaaaaaat tataaatgtt attattgcca   188160
gcacttttat caactatacg tacaaaaagg tgttgaccaa aaaaataatt ttttttcttg   188220
atcaaagtat gtaaacgccc gcttacagca aggatcttaa gtgagagcca ttaaatttta   188280
ttgatagctg cttgccacca gtagaatacg gccaaaccac ctaacaggaa atacaaggcg   188340
gcccttcggc caataaggtg gataaaaatc acgcataaga cggttgtaac atagcacttt   188400
agtgcgaata tcaggaatgc caatagcatg tagataaggc accaaacatc gcagctatac   188460
atggctaaag atcaaccaga aaaggtttaa attttaacgc cggcccaaaa cttaaacttt   188520
ttttgatatt tttaagtgca gccatggatt ggtccggcca taggatgacc tatgcctacg   188580
tggcattctc attgatggca atagcaataa tatggtatat tctacttatc tattgccgat   188640
cgaaaaaaaa tgttgttaca agcggtaata cgctcgcttt agcgccaata tcgcatatgt   188700
gaaaaatgtt cgccgaaaaa aacattaaaa tttagaaccg ccgcggcatc tcaggggcgg   188760
caacattttt ttttatatgg atattgtcac acaccacctc atctatgacg caatatatta   188820
ctgctaatat caggttcccc aatagtatgt agagaaacca cacaagatag atattcatgg   188880 cgattttga cgaaaaaaca ttaagttttta gcttctttga cgcctgtgta ctaataatgt   188940
ttaacgcctg tagtataata attgataacct acagcagtaa ttgataccta cggcgataat   189000
gtctctctgg ccgcccaaa aaaaagtatt tacggtaggg tttattaccg gcggcgtaac   189060
```

```
accagttatg gtcaattttg tctggcccgc cgcccagccg caaaaaaaaa tcaattacaa    189120
ccgcaaaaaa aaatatttcc ggccgcggcg tttcaaaaaa taatctttgc gaataaattc    189180
cgcatcttgt gaaatgaacg cctacagtaa taattttaat ctttgacacc tacagcagta    189240
gtaataattt taatctttaa cgcctgcagc agtactaata ttttaatctt taacgcctac    189300
agcagtagta ataattttaa tgtttaacgc ctacagcagt agtaat                   189346

<210> SEQ ID NO 2
<211> LENGTH: 184136
<212> TYPE: DNA
<213> ORGANISM: African swine fever virus

<400> SEQUENCE: 2
gaatatacca tattattgct attgccatca atgagaatgc cacgtaggca taggtcatcc      60
tatggccgga ccaatccatg gctgcactta aaaatatcaa aaaagtttaa gttttgggcc     120
ggcgttaaaa tttaaacctt ttctggttga tctttagcca tgtatagctg cgatgtttgg     180
tgccttatct acatgctatt ggcattcctg atattcgcac taaagtgcta tgttacaacc     240
gtcttatgcg tgattttat ccaccttatt ggccgaaggg ccgccttgta tttcctgtta     300
ggtggtttgg ccgtattcta ctggtggcaa gcagctatca ataaaattta atggctctca     360
cttaagatcc ttgctgtaag cgggcgttta catactttga tcaagaaaaa aattattttt     420
ggaccccccc ccatgtttta tacaaaaatc atataataaa gtggcgacaa tcaacatatt     480
aatcaaccac agcattttat gatgtgttaa tcaacatata ccatattaat caaccacagc     540
attttatgat gcgtcaatca acatattatt acggagagcg tcaatcaata taatattgag     600
aacagcgact tgataccgtg tatggtggtg gcggcggcat gttgtttgta acagcatttt     660
tcatcattcg aagcttacaa aagatatgta taagatagca tattaatgtt attaacagta     720
atatcaataa ggcgtagcta tagatcttca ctttggtaga ccaataatcc atggttgcgc     780
ttaaaaatac caaaaaaaac attaagtttt ggagggtaag attggttttt caccattggt     840
aaagattatt attctaaatg tttaccccat agatgtgaaa caatgattct tcatatatta     900 acatatttt tgacttatac ttttcttcat ctagtaaggc gttaatttt tccggatctg     960 tcgtttttat tgataaaaga gaagagtctg gactgtaatt tttaaataat aagatattta    1020
ttaatatcca attattcgtt tggctcgcta tttccatgct ctcttcgaaa gcatcagctc    1080
ctaaatctat acaaaggaat aagttacctt cacaaaaatt cattaccgag gtaatcattg    1140
cccgattaat gtcagccccc aacataaaac aataatatat agttgtataa ttacaatcat    1200
acatacaggc caactgcatc atttcatcaa tgtctatatt tgtcttctct ttgttataaa    1260
tttcatgaag gtcaaagacg ttgttataag caaccccaca tattaaccgc caatctttaa    1320
aatgactata tcgttgataa aaatattgga tggcttcagt aagcttatat agtatcgcca    1380
tactatacca ataccctagtt agcatttcgt tgaatgaaat attatccaat gtaaagttaa    1440
ttgataatgt atctagttca ccaaaaattc ttaatttcag ttgagcatta tttaggaaaa    1500
ggggattatc agataataat tcatggcata gaataatatt actgctagtt ttaacatact    1560
gtacattata aaatatttct aaaattttat tttcactcaa agctttcctc gcacctaact    1620
tttggcatag gtcctggtgc actccatatt gacagtaacc aacccaaagc tgatgtctgc    1680
accccattcg gtaaacagct ctattaaacc atgattgttt tcctgtacag ccttcattaa    1740
tgcaacattt aatgttaaac catgtttaaa acttgctgtt tttattaata tttgttcatc    1800
tatacaagta tgataaatcg taattggggc ttcatgccac cacaaaccac aacgctctaa    1860
```

-continued

```
aatacaataa tcatctttta acacaggctg tgtagctagt acttttttag taagtgcttg    1920
taaagtagat ggcatcttct atctgcaaaa taattatttc cgaaaaaaaa atcaaattaa    1980
aatactaaat tctatttttt tttttaataa agcctgtaaa ttatataata aatctcgccc    2040
accgtattat ttccggacac aacttttat  acctcattat attttagat  ctatagtttt    2100 ttaacaaggc attaatttt  tctggatctg tcgtttttaa agataaaaga gagacgtttg    2160
aactataata atctttaaat gataatattt ctactaatat atcatgattc ttttgttttg    2220
ctaattctaa gctctcttcg aaagcattag ctcctaaatc tatacaaaag aacaagttat    2280
tcatataaaa gttttttacc gaggtaacca ttgcccgatt gatgtcagcc cccaatacaa    2340
aacaatagta aatggttaaa aaattgctat ctctcataca ggccagatat atcatttcat    2400
caatattcat atcaaccttt tttatatgat acatttcatg aagatcagac acgttattaa    2460
aagaaagccc acatattagc cgccaatctt taaaatgact atatcgttga taaaaatatt    2520
ggatggcttc agtaagctta catagtatcg ctatactata ccaatatcta gttagcattt    2580
cgttgaatgt tatttcattc aatataaagt tgatcgatat cttctctaga aaacaacaaa    2640
ttattacttt taattcctct atattctgga aaaggggatt attagataac aatttatggc    2700
ataaaataat attactacta gttttaatac gatgtatttt ataaaatatt tgtacaatat    2760
ccatttcatt caaatttttt gcgcctaact cccggcagaa attccaagta tgctccgtat    2820
tgacagtgac taagctagag ttgatgtctg cacccattc  agtaaacaac tctattagat    2880
catagttgtt ttcctgcaca gttttcatta atgcgagatt taactctaaa ccatctttaa    2940
aaattgctga ttttatcatc aattgattat cctcattagt agaaagcata attggagctc    3000
catgccacca caaccacaa  tatttcaaaa taaagtagtg ttctttagat atgtgctgtg    3060
tggccagtat tttttagca  agagcctgca gagaaattgg agtagacata ttttttttg     3120 caaaatggtt taagttttc  aagaatacag attggataaa ttaggttgtt gacttagtta    3180
caggaggtat taaatattat gtagacataa aaatgagatc ctccaaaaaa ataaacaaca    3240
aaaaaaatat gtttaatatt aaaatgacaa tttctacatt gcttattgct cttattatac    3300
tacttattat tattttagta gtgtttttat actataagaa acaacaacca ccgaaaaagg    3360
tctgtaaagt agataaagat tgtggtagtg gagagcattg tgttcgtgga tcatgtagct    3420
cattgagctg cttagatgcc gtaaaaatgg acaaacgaaa tattaagata gattctaaga    3480
tttcctcatg cgaattcact cccaattttt accgttttac ggatactgct gctgatgagc    3540
agcaagaatt tggaaaaaca cggcatccta taaaaataac tccatctcca agtgaatccc    3600
atagccccca agaggtgtgt gaaaaatatt gttcatgggg aaccgatgac tgtacaggtt    3660
gggaatatgt tggtgatgaa aaggagggaa catgttatgt atataataat ccacatcacc    3720
cggttcttaa atatggtaag gatcacatca tagccttacc tagaaatcat aaacatgcat    3780
aaataaatac attaggctca tcgtatcttt ttaaaatcca taaatattcg tttgatatat    3840
gctgaaattt ttataaaaaa ataactatt  tcctataaat catctagaaa tagtcctcgt    3900
tttgatcggt ttatatctta taatattgtg catcgatgca caactgcttt ttttggtcct    3960
tctggaacat cattatattt tctttcatta atataccatt cagatgtaaa cgttaataaa    4020
tttttatggc aacaatctac cattgaatta tatttagtaa catctaatac atcgtttgtt    4080
ttatcaggct cagctctata atcttgataa tttttgttat cagcttctaa agctccatca    4140 ttattttca  aagaagtatc cataattatg tttggtaaaa atactttaag ttttaatgtg    4200
```

```
atatttaaaa tggttgttat ataaatttac cgcttacagg taatctttat tcagtgtcat    4260
aaactatact tttgatgatt cagtattttg tgaatcagta catttattat cattaatatt    4320
tttaggctgt ttttccaatg ttttattgtt gcaatgagcc tgctcctcct ttgacgagga    4380
agtgtctgtt ggagtcatct gtttaggaag agtatcatcc atatctatta tgaagaaaat    4440
atataaatat tgatatacaa tcaaaaatat ttttgatcac gtctttgtta tctatcgata    4500
ttgttgataa cgtcttgaat aacctacatc attttttttac ataaaaaaat agatataatt    4560
tttattatat ctcaattatt ttaaagataa ttatcaatac agcaaatatc ataagctaac    4620 atattttcg aataatagtt ttttagtaaa gtattaatct tttcaggatt ggtttctttt    4680
gataataaga taggattcgc tttataaatt tttaaagata atatattcac aatgatagaa    4740
taaccgtata tatctgctaa tgtcttactg tgttcaataa cattagcccc taaatccata    4800
caaaagaaca tattttcaat acaaaagttt tttaccgaga ttaacattgc tcgattagcg    4860
ttggctccca atgcaaaaca gtagtaaatg gtcaaaaaat tattatcgcg catacaggcc    4920
agctccatca ttttattaat actcatatga attttcgttg tgttacatat ttcatgaagg    4980
tcaaacacat tgttgaaaga aagtgcacaa attaatcgcc attcatcaaa atgcctgtat    5040
tcttgacaaa aatattgaat agcttcttta agattatatt ttaccgctat gccataccaa    5100
tatttggtta gcatctcact aaatgagatc tcatttaaca tagaatttgt tgttaaatcc    5160
ttcaactccc aataaatgat catccttaaa tccaccatgt ttacatttg taaaaaaggg    5220 ttattagaaa ataattcatg acacaaaatg acattactac ttgttatttt acactttgtt    5280
tcaaagaaaa atcgtaaaat ttcacttgtc tcaagctctt ctttagctcc caattttcgg    5340
cataggtttc gagtatgctc gttattaata aaaagtaacc cataattaat atttgcaccc    5400
cattcagtaa acaacatgat tagatcatca ttgttttcct taactgccaa taccaatgca    5460
gtattaagcc ttatacccte tttaaagcat aatgtcctta tcattatttg attatcatca    5520
tctatataca ttgagatagg agcttcatgc caccataaac cataacgctc taaaatataa    5580
taatcatctt tagatacgtg ttgcgtggcc aatgcccttt tagcaagtgc ttgtaaagtc    5640
gatggctgca tgtttattct gttaaaaaaa atcaaattat cgggtaaaca taaggatcaa    5700
cccgtagtta atatttgcag tagtattttt taacaatgaa ttataataaa aaataattc    5760 attactatct attataaaac ccatctttaa ctttaaagaa gaactagatc atctttttt    5820 tgttgtgtca gaacttcttc aatttattac ccacatttta tctaaaaaaa taaaaactac    5880
atcatatctt gtttcttcat caaattatca taccatttat agggtgtagg ttgggaacat    5940
tccatcatgt ggtaatcagg gtatttatat attttttgat agtaacatct atttggcaga    6000
tgtattgtcc aacaatcatg tctaataaaa tcattttcac ctatggggga atcatcttaa    6060
aaaccttatt cctacagatt ccattttgac agtcccagca aaagtcacaa tattttccat    6120
gagtacacca atgttcaagc tctctttcgg gaggaatgct gccaattta tgttttttag    6180 cttctaactc tctgtacaac atcagttggg aaagcagaaa gaagattacc aggagaacca    6240
ttaaatatat aatagtctgc aaactacgtt tgcgaatgta atttgcaact aaaacacaac    6300
ccacaaggta aaatccataa gttaataact tttgccattt tcgtatgaca gcctcgtgcc    6360
attcatggtt gtgttgtggg cattctgttc ggtaaacttc atgaggcttt atagaagtta    6420
catagtaggt acagaattca ttgtgacgaa aaacactgca gttagctatg tagtcatttt    6480
caagaatggg agaatgggttt tcaaagacct tattcttaca gatgccatct tgacagtccc    6540
aacagaacct acaatgattt gcataggtgc accagtattc aagctccttt tcaggagggg    6600
```

```
ttcttgttag atccaggagc tctagctcat atgtataaag aagagttgga atggatagta   6660
aagtaaatat ttgcagacca agcatggcta cttgtgaaca agtggctgct cgtcaacaaa   6720
tagctgttta tcagcaaata gctgtttatc agcaacaact aattatcagc aaatgctgct   6780
tgtgggtaag ccaataaata ggccataccc ttgaaaggag aattcagttt gataaaaaaa   6840
ataacgagtt ttctaataac ccggtcaagc atttaataaa tgaatagcat cacacgtctg   6900
catcgtgcat tctgcctgga aaatgggccc atctctaata tatttacact gacggtgaat   6960
catacagtgt tccatgggat agctatgctc ctgtacagga ggcatatctt ttagaacttt   7020
attcttacaa agaccatctt gacaagccca gcaaaaccga caattttca catattgaca    7080
ccagtatcta agctcctctt ccaggggatt gtcggtcgaa acccctgta gactagctag    7140
gccagctagc agcaagccga ggtaactaaa gaacctcatt gtagtgttat attacgaaaa   7200
aacatgttaa aatttggaaa aaaagcccct ttttatagat ctggaaaaaa attttcacaa   7260
atctaattaa aagccttaca gatcatcctt ttcataaatt ttcattaaca attggtgggg   7320
gcggttgtga ggtactggat cagaacaatc cataacatgg taatgtccat ttccttcacc   7380
atatgtacac tggttatacc agcgagaaac ctcacaagat gtcaaataac tgttctcaac   7440
aatcaatggc atgctcttat tcaccttgtt cttgcaaatt ccatgtgcac attcccagca   7500
aaacttgcag ttttccatgt aagtacacca gtatccaagt tcttcttgtg gaggattatc   7560
cgttgaacga agatgccctc ctgcctgagt aggtagtcct aagacctgat tggccagcag   7620
gccaagaatt tccaagaaga tcaccaacat tgctacggct ggctgaacag ctggcagata   7680
gctagctaat tagcaaacca agtgactcgc cctctctact cttaatatga aatttaaga    7740
ttcggtccgg ctttttttccc atgttttaca gggaaaaggt attttagcc tatgaatgta   7800
catggttccg cacattaaaa aaaataaaag aaattattta atattggctg ttattttctt   7860
tcaactagca acaagccagg taactaaaga acttcattgt agttttatat tacggaaaag   7920
gttaaatttt ggacaaaaaa atcatatcta attaaaaatc ctcacagatc tttcttttca   7980
taaattttca ttaacaattg gtaggggcgg ttgtgaggta ctggatcaga acaatccata   8040
acatggtaat gcccatttcc ttcaccatat gtacactggt tataccagcg agaaacctca   8100
catgttgtca agtagctgtt ttcaataatc aatggcatgc tattattcac cttgttcttg   8160
caaattccat gtgcacattc ccagcaaaac ttgcaccttt ccatgtaagt gcaccagtat   8220
ccaagttctt cttgtggagg attatccgtt gaacgaagat gccctcctgc ctgagtaggt   8280
agtcctacga cctgattggc cagcaggcca agaattccca agaagactac caacattgct   8340
acggctggct gaacagctgg cagatagcta gctaattagc aaaccaagtg actcaccctc   8400
tctactctta atatgagaat ttaagatccg gtccgacatt tttccgatat tttacaagaa   8460
aaagatattt ttagctacaa atacacttca tatatcccta aaaaacaaa aatttattta    8520
attttaacta ttattttctt tccactctct ctttaagatt ttgtaaggat tccagggctt   8580
tggttcagaa caggccatta catggtgaat ccctgtcct agatcataca tacatttatt    8640
tagccagcgg gaaactatac atgattgcac atactcattt tcaagaattg ttgtattctc   8700
caatttgccc tcacaaaggc cattttgaca attccagcaa aacttgcagt tttctgtata   8760
agtgcaccag tattcaagtt cttcttgtgg aggattatcc gttggatgaa gttgtccagc   8820
tggttgatta ggtagcccta agacctggtt gcaattcatg gtatggtaga tacccttatc   8880
taaatcatac atacatttat ccagccaacg ggaaaccaga catgatttca catactcatt   8940
```

```
cttgtaaatt actgacccat ctattttgtt tatacaagtg ccgtcttggc agtcccagca    9000
aaattggcaa ctttccatgt aggcacacca gtattcgagt tcttcctctg gaggctcctc    9060
tgttggacga agttgtccaa cgagctgact tgaaacctgg ctggccagaa ggccaagaat    9120
tcccaagaag atcaccaaca ttgctacggc tggctgaaca gctgactgaa tagctagcca    9180
attagcaatc cactgtactt ttcataagat catttaagat tcggtcggca ttttttcaat    9240
agtttgctag gaaaaaattt ttaattttat agattcacac tacttcattc tcatgcttag    9300
gaaaaaaaca aactaaatct tacaatgtat ctggatctaa tgagaagcta gaattcatct    9360
tttttcaaat cctttctggg atgttcattc ttttttccact ccttccttgc aattttataa    9420
ggattccagg gctttgggtc agaacagttc atgctatggt aaatgtgctc ctccacatca    9480
tatctacata ggtcaccccca gcgggaaacc tcacaatatt ttacatagtc attctcaata    9540
atacttgtgg agttgtttcc ccaaaccctg ctggtacaaa tcccatcttc acaatcccag    9600
cagaaccgac agctttccac ataagtgcac cagtatccaa gttcattctc tgggggttca    9660
aatgttagag gaagatgtcc acctacccga gtagaagtgg aggatgaaac caggttgcta    9720
ctggccagca ggccaataat tcccaggata atcaccagca ttgtgctcaa ccagcaacgg    9780
ctagcaacga ctagcaactg actagcaata gctagaaatg gctagcaatc agtagtagct    9840
aacgctctac tctttataag aaaatttaaa attcgatcag attttttttag aattgagaat    9900
gagtaaaacg cttatattct ttttctagct agaaaaaata agctagttta agataggatt    9960
tcccttacta acggtttaat ttttagcaaa ggtataggta aaatacactt gtacttagct   10020
gcaaaaaaat aagcttatgg cgtataagcc gccataagtt tatttaatta aaatgttaaa   10080
ctctgtgata agactggaat cttaggcagg tttgatgtgg agaacagcat gaaatacaag   10140
agtgcctgtt acacgaataa gttctctcaa accggggatg gtcatactca catctatgaa   10200
atcctggtct aggagattca tttgatgcat gatggccgca cccacactta tgagacactg   10260
aagaactaaa gggtttaatt ttgatctgaa tggtactata taggatgatg gcaatccata   10320
tcaagattag agcaatcaaa atcacctcct caagaagcat gatgtagcct taaatcttag   10380
actgctttaa accttaggcc ctcactatct ttaatgaagg agtttaaatt ttgatcccctt   10440
tttcaagacc catttagaag aaaaaataaa gtttatatca atctaattca taagtcatct   10500
ctttcataaa tcttcatgta ttctctatgt ggataagtat gggatgttgg atttgcgcag   10560
tccatttgat gatctgtatg gttttttgggt ccttcataat aactacatat accattccag   10620
cgggaaaccg tgcaatttat aatccagtca ttttgatgaa taactggcca atctgtttga   10680
atcctgtttc ggcagatacc gtggacgcat tcccagcaaa agtcacattg gtttgcgtaa   10740
gtgcaccaat aaactagctc atgttcagga ggataacggg ttggtagtaa atcttctaat   10800
ttacgtatag gagcggcttg aaggacaacc accccccagta gtactagaat cagtaccttt   10860
atagtggcca ccctcactca gacctctaag ttgaagacaa agaactaaaa tttagagccg   10920
tttaattact actaataatt atatttttta ttgtctacaa taggattcta ttaaaaaata   10980
atgattttta ccaagaaata tttttataaa aaattaatat attttgtaat aaactttatt   11040
tccaatgact gttaaaataa ggaaactatc cttagttagt cgaggaagat ggttaggtta   11100
tttcgcaatc cgataaaatg tttattttat cgtaggtctc gtaaaatcca ggaaaaaaaa   11160
ttacggaaga gtttaaaaaa gctaaatttt taccaccctc cagaagattg ttgtcaaata   11220
tatcgtttgc tagaaaatgt tcctggagga acttactttta ttacagaaaa tatgacgaat   11280
gatttaatta tggtcgtaaa ggattcggtg gataaaaaaa ttaaaagcat taaattatat   11340
```

```
cttcatggaa gttatattaa gattcatcag cactattata ttaatattta tatgtatctt   11400
atgagatata cccaaattta taaatatccc ttaatttgtt ttaacaaata ttataacatc   11460
taagtaaata ttcttggaat ggattttctt atagaatggt tacaggatat gtcagcgaca   11520
ggcttaataa caaatttgtt aatattttt tgttaaataa atgaacaggc caccatttaa    11580
tattacccgt tgcaaaataa gaaaaaaaaa caaacttata gttacaaatc atcttgatta   11640
atcacatgtc gttttaactc aatgaaccat tctaaatctt tgggttgtga acaattcatg   11700
ttatgttgat agtgtatcct aaagtgagct tcatacatac accggtcatg ccaccgggaa   11760
actgtacaat taacaatata atcattttgc gtaataatag ggtggtcact aaacacttta   11820 ttttacaca ttccatcttt acaggtccag cagaagtcac agtgttttgc ataggtgcac    11880
cagaacttga gatcccttc aggaggccta cgcatttgca tcggattatc tgtgaaaga    11940 ggtaggttca ttattatgtt cgtcatcaaa attcctaaaa gaacatagaa gccaagaaag   12000
ataagcagtc ttgtagcggc ttgcattcgc attcgtgagt attgtttgcg aacatagctt   12060
atgagagcaa tggtagctat catacaaaga caagtatgtt tgatattctc agtgtcaatg   12120
accctatcct cctttatttg cattaactca tcaaaccaat cataatatgt gggatttgta   12180
cagctcatga tgtgaaagcg gcgtatccta gagtctgtaa agtagctaca tctttcatta   12240
tagcgagaaa ccctacatat ttgtatgtaa tcatttttt tgatgagagg gtgttttca    12300 aaaaccttat ttttacaaac cccgtgtcga caattccagc agaagtcaca cgattttgca   12360
taggtgcacc aatactcaag ctctctcttt ggaggtctcc gggtcattgg taactctcct   12420
gttcctggaa aagattggct tgaatgacc ggctgcatga ccgccagtac caaaaggaac    12480
acaatcacct tcatggctgc aacttataag ttgcaactta tgggttgcaa tactgcaacg   12540
tataggttgc accttataga tcgcgactca aaaggtatga aaaccttacc ctcaatacag   12600
aatttaagtt ttaatcctga taatgtatct gtttatgaaa aaaattttt tttactcatg    12660 tatgaattct tatacgaatc ataatatgta ggctgagaat aataattcat atacggtgtt   12720
gcgggctcaa taaaaattt gttaccacaa aaaataaatg ctggattttt aagatatata    12780
tctattaatg actaaaccct ttatacgctg taggctgaaa acaatccata taatgaatat   12840
acggtgattt gggtttaata aaatacatac aacggtcaaa atagcgggca atactacatt   12900
gactaatata atcattttgt ttaataagag gcatatcatc ccacacttta ttttacaaa    12960 taccgttcct acattcccag cagaaatcac agtgttttcc atacgtgcac cagtattcaa   13020
gctctcttat aggaggcgta taagtccttg gtaaattttg tttcatataa aagatggaaa   13080
ggggtcgatt taaacccggc tgagatagcc aaatcaaaat acataaaaga gcaagtagtt   13140
tcatagtggt atttagatgt aaatttttat agtatgcaaa tacaatgtaa cctacaaata   13200
caatactaaa tacaaggtaa aaacaacaat gtcttataat gattggccaa taatcacccc   13260
cccccccccc attttccat gaatatttca tttcctgtat agggtctagg atgtgaacac    13320
tccatgttat gatgattagg catttttaact gatatttcat aaaaacaccc ccaggaattg   13380
cgattaacta tacagtttac aatcgaattc atcgaattag actcatttgt tatcttattt   13440
ttacaaatgc cattttgaca atcccagcag aagtcacaat tctttacata cgtacaccaa   13500
tatggaagct cctccttagg aggatgctgg gttcttggta attctggtaa ttcatgtgca   13560
agaatgagga ctgagtagcc caacaaaagt cctagaacct tcatgttgtg tccaaatggc   13620
acctgtcatt ttaaaaaaga tttaaatttt gctaccgcaa aaaaaatcca gtatgtattt   13680
```

```
ttttaataca tataattatt gaagtcttat aagataaagc cgagaacact atattttgta    13740
tagatgatgt atccggtatt caaactctct tataagtaca tgtaggaaat ggtcaattat    13800
tcaagattgg ctgagataac aacaaaacca aaatactcaa aagcataagt aatttcatgg    13860
ttgtactcag tcgtagattt ttgcagatcg caaatgcaac gcaaccagca aatacaaagc    13920
taaatacaag gtaaaaacaa taataccctta taatgattgg ccaattctta tccctccatt    13980
tttccatgaa catttcatgt tcataaagtc taggatacga acaacatttc atgctatgat    14040
gattaggtat tttaagtgat atttcataaa aacaccacgg ggttgttggt gattgatagg    14100
taagaataag gatggttgaa taacctagta aaagtcctag aaaaaccttc atattgcgtt    14160
cataccacag atgttatttta aaaaaaatat aaatttttaca gtatgtgata tacacatacc    14220
acaaaaatgt tcttatatta actaaaatat gtgggcagag agcaattcat ataatgaata    14280 tatggtatttt taggctcaat aaagtacata caacgatcaa taaaacgggt aatactacat    14340
ttactgatgt aatcattttg aacaataaga ggcatatcat ccaaaaccctt attttttacaa    14400 ataccattct tacaatccca gcagaaatca cagtgttttc catacgtaca ccaatattca    14460
agttctctca taggaggcgt ataggtcctt ggtaaaattt gtttcgtata aaagatggaa    14520
aggggtcgat ttaaaactgg ctgtgctaac caaaccaaaa tactcaaaag aacgaaaagt    14580
ttcatggttg tactcagacg cagattctta caaagcgcac atacaaagca gcctgtatat    14640
gcaataccaa tgatgaaata gagacagtat tgctttatag ataattgttg atggtcaccc    14700
cccccccccc cccatgtttg catgaatatt tcatttcctg tatagggtct aggatgtaaa    14760
cattccatgc taaagtgatt aggcatttta gatgaaattt catataaaca ggattgagtc    14820
ttggaatcac ggaaaactct acagtttaca atagaatgat tggagtcaat gaaacgagat    14880
tccgttatct tattttttgca aatgccatct tgacagtccc aacagaaatc gcattgtggt    14940
acatacgtac accaatatga aagctcactc ttgggaggat gctgggttct tggtaagtct    15000
ggtaattcat gtgcgagaat gaggactgag tagcccaaca aaagtcccag aagaaccttc    15060
atgttgcgtc taaatgacac ctgcacttac aaaaaaaaat ttaaattttg aatataacac    15120
aaaaaaacca ccttaaaatt tcttatatta tttcttggat ctgccccgac gtcatacaat    15180
gtattaaaat tatagaccaa tcatcttttt gtatataggc taatcatctt tatatataga    15240
ttttagatgt ttgcttgttg tatcaactta actgctagcg aagaaaatgg ataaaaactt    15300
tctgtatttt tataggttga aatcatttta tgcacatcgc taggatctaa tattttattt    15360
tgaagaaccg aatgtgggct taaaatttt ttccttagaaa aaagtagaat cataatattg    15420
ctatgttttt gtttaatgat ttcttgtatc ttttttgtat acgggttggc acccaaacct    15480
atacaaaaat atacattact caaataacta ccttctatac ataatctttt ttccccacgt    15540
attttcctat ttatttccct atttatggaa ttaaaggata tcaatctctc taaggcacgg    15600
tcaaggtctg cgcctaaggc aaaacaataa tatataccta atttattccc agggcgtgca    15660
caggcaagaa acatcatgac gtttagccct aaacgtatat tttcctgaaa atacgcatga    15720
tgaacttcat caatattacc taagtatatg gccgtttgta aacgccaaag atctaaatga    15780
ggaaattttt tactaagata atgaataggt tttgtgagat taaaatctat ggcgaactta    15840
taccaaaatt ttaatacaag tgtatttctc gtcatttctt cttcttttttc atctaaatat    15900 aagataaaac gattgtaaac aaagtctatc aataggtgaa aatcattgct attaaagctg    15960
tcgagaatca aaatattgtc ataataaatt tcgatcgcca gtaaaacctt ttttcgtttg    16020
acgagataaa caaacatatt atacaaccct acatctaaaa attctggatt ggctcctagt    16080
```

```
tggatacaca ggtctttagt ctgcttcgtt ttggcacaca tgatgccaaa attaatatca   16140
gcaccccata aaacaaataa cttgattaga tcagtctggt tttccttcac agcttttact   16200
aaggctctgt caagctcata gctgtcgaca tcagagcatg acatagagcc accggttacc   16260
attttacatt gcttacaaaa acctatgggt ccgttttccc accatagtcc aagctgttgt   16320
agaataaaaa tatcatcctc atgataattt gaaaagcct tggtttctat caagactttt    16380
tttgtaagaa cctgtaaaga gttcatcgta ttattatgaa taacaggagt aaacgtaatc   16440
aattataaaa gtgattttt cgaaaaaaac tttagatggt tgaaaatgat aatgtacatg    16500
ttcatacaaa aaatagatgc agtgatgtct aaaatcaaaa tttaattttc tatgtaaaaa   16560
gtacagactt acttatttgg gttaaattgt ttattttaaa ctttaattaa ccgtttgagt   16620
tagcgatgtt tgatttatct tccatactca tccgggggggg ggggtccctt atagctctga  16680
cattattgtg gattattgaa tataatgaat acttcataga tgctaaacat tttaatagta   16740
gttctgaggc ttaattgtac tctataaatt tataaaaact ttttgatcaa aatttaattt   16800
cttataaaaa gagtacagac gtcgcttgtt taagcttcat catgtttcat tcattacttt   16860
ctacaattac gggggggggg agtcccctca tagctttagt attgctatgg tttactaatt   16920
attatgtaga atttatagaa gcatatgtac ctgaaagtat acctactcta taaaattaaa   16980
taatttcagt atattttttt tatgaataga acggaaatga tataaaaata atttaatatt   17040
gcaaaaaaaa ttcataatgt tggtatgtat tataaacata atagcatgtg taatttataa   17100
actgactcct ctatataatt attagatgag gtaccaacct acttatgata tgccgatgat   17160
agatattgta tactataaaa caaaattatt ttaaatgtat tcatggatac attataacat   17220
ttttaccgca aattgtctct cagcgaagaa aatgaatgaa acgtttctgt atattcatag   17280
gttgaaatta ttttacgcac ttcactaggt tctaatattt tcttatgaag tattgaatgg   17340
gggcttaaaa gtccttcctt aaaaagaagt ttcatcataa cattctttc ttgtctaaga    17400 agagtttctt gtattttttt tgtataagga ttggcaccca aacttataca aaaatgtaca   17460
ttactccaaa taccataatt tgaaagaaa gttattccc tatttacttc atgattaatg     17520
aaacctatca acgtctctaa ggccgtattg atatttgcgc ctaaggcaaa acaatagtat   17580
atacccaatt tattttgagg gtacatacaa gcaagcgaca tcatgtcatt tggatctaaa   17640
cgtatatttt cctgaaaata tgcatgatgg atttcatcaa cattacctaa gtatacagcc   17700 gttttaaac gccaataatc taggtgagga aatttcttac taagaaaacg aataggtttt    17760
ataagattaa actctatggc gatcttaaac caaaatttta atacatatgt attttttatc   17820 atttttctt tttcatctaa atttaagata aaacgattgt aaataaagtc tatcaacacg    17880
taaaaatcat ggctatcaaa actgtcgaga atcgaaatat tgtcataata aatatctata   17940
gctaataaga ccttttgttg tttaattaga tcaacaaaca tattatacaa ccctacatct   18000
aaaaattttg gatcagctcc tagttgaata cacagaactt tcgtcctttc cgtcttggca   18060
catatgatgc cataattaat gttggcaccc cataaaacaa ataacttgat tagatcagtc   18120 tggttttct tcacagccct caccaaggct ctgtcaagct catagctgtc aacatcagaa    18180
catgacatag agccactggt taccatttta cattgtttac aaaaacctat gggtccgttt   18240
tcccaccata atccaagctg ctgtaaaata aaaatatcat cctcatgata atttgaaaaa   18300
gccttgtttt ctatcaagac ttttttttgta agaacctgta agaattcat cgtattatca    18360 tgaatgaaag cagtaaatgt aatcaattat aaaattgact tattgaagag aaatgttaaa   18420
```

```
tgagtgaaat cggtgtttat gatgatgtac atgatcatac gaagaaacac gttcactggt    18480
gtccatgatc aaaatttaat gttttacgta aaaagtacag atgttaactg tttagtttaa    18540
acataaattt aacctttagt ttaaacccta gttaatgatg tttaatattt cttctatact    18600
cattcaggga agtgtaatga ttctaatact gttgttatgg attattaatg aaaactttac    18660
agatgctgga gggaataatt ttaatcatac tgttttaatg tagctatata agctttcatc    18720
aaaatttaat ttttttata aaaatacacg aattaaacta aagtctaaac tttagtttga    18780
ctatttgagt taatgatgct taacttatct tccatgctta tcaaggggggg gtcctaatag    18840 ttttgatact attgttgtgg attgttgaat ataataaata ctttatagat gctgaaatgt    18900
ttgaaaataa tagtacatca atgttgtaag tttgatcaaa atttaatttc tcataaaaaa    18960
ggtacacatc aacattgctc atttaagttt catgatgttt gattcattac ttcctacaat    19020
tactgggggg gggggggggt ctttaatagc tttagcattg ttatggtttg ctgactatta    19080
tgtagaattc atagaagcac gtttagatag taatatcact gcagtgtaga ttatgaaata    19140
catactaaac taatttcagt atattttttt tgttcatata agttaaggta caaaaatgat    19200
taaacattgc aaaaaaagaa atcacaatg ctattataca tagtgatcat agtggcttgt    19260
atcatttcta aactagttcc aaatgaatat tgggcaatac atctatttt tatcattatg    19320 attttatgg tatatatgta tgaaaagtta gatatacatc aaaaatctca gttctggaat    19380
tataccatgt caggcttatc tggacataac gtacaggtaa catgtaagtg ttactaaata    19440
ctatgaagta tctattttt ttgttgtaaa aaaagaact tgatagtatt ttttaaaaaa    19500
taaaataatt aattgtacgt caacttcctt attttattct ttaaaaataa ctcgtaagta    19560
ttatttatct attttttgaa aaaatagatg taatcggttt catcatttag gtgtgtattt    19620 cttttagca tctatcaaga attcattgtt tagtgatatg aaaacaatga atgatcatta    19680
tcttctattt aacaaccacc taaataaatg aacgtctttt tcatcttaac tgattaccaa    19740
aagttatttt gcgaaaaggc atacatatga tcaatatcag acctacaatg aatatttcca    19800
taatatccct ttattgtaat aattctattt ttgcattccg atatctcatc atctgtgcta    19860
ttatatgttt ccataactgt ttcatcatca aacataaatc ctgttaaata ggcaaaagac    19920
tttaatcccg gatagatttt taccatttc ctgagagccg tgtatagctt gtaataaatg    19980
gccaaaaata tgcaataaag cgtagaaaga gagtaatttt tggcataaaa gattttgaag    20040
gtttgatgaa tggctaaatc gcatataata taagatacga ttttaaagcg cacctgttca    20100
cgcagatttg ttgaaaaatt cgtggaaaga tttaacaaat aaaaggttat taatagttgc    20160
tcatcattcc ccttatacga catcgtcaga cgctctaata ttttactact aggcacatct    20220
gccacatgtt gaacatttaa agcctgttct tcttctgtgt tacggcaaaa gagccgtgcg    20280
tattcaggtg aagctcccca ggataacaac gtccttgcta cggctaaatt ttttttgacg    20340
atgactttta tcagaaataa gtctttattt ttgcattgat cactatgcga atttgtatag    20400
ttgacgccgt tgcattgagt acattgatat aatgttttac aattccagcg tagccctaaa    20460
tggtataaaa gaactgtatt ttcgacataa gcatgctgat taacgatgtt tttgagacaa    20520
cacgtcgtta aggacaccat attgtctcca atttgttaga taaagtctt tactaaaaaa    20580 atagattttt agttttaaca atcgagattt tattatttgg atgcatcatc aaaaagattt    20640
ataagtataa gaggttgtat aagaaaaaaa tgatgttata ctatttatgt taaaatttaa    20700
tttatcatat aaaagtaca gatttaatca gttggttaaa ctatttagtt aattaaacta    20760
aatagtttaa ccatttagtc agactacttg gttagcaatg tttgagcttt cttccattct    20820
```

```
tatccggggg gggggtcct aatcgttcta atactattgt ggatagttga atataatgaa    20880
gactttatag atgctataat gatgaattct agtatgcctg tataaaataa ttaaccttt    20940
tgatcaaaat ttaatttttt tataaaaagc tacagagtag tgttttatta aacgtggctt    21000
atttaaaagt tacacaatgt taaaatctct acttacttta attctttgtg gggttttatt    21060
aactttatcc atattatggc ttactactta ccatgtagaa cttatagagg caatagatga    21120
tttctacgac tgaaatatag aatagtccat tttctatttg taaaataatg atttatattc    21180
tttcctaaaa atgatacttt atatggtttg aaaacaaata ttaacaactt gattttttt    21240
tctataaata aactataaat gaaaatagta aaactcatag agtcttataa gtgaacatct    21300
tcataatgtt actcaaacgt tggactatta aaaatattc cgtgtgcatt attgctttta    21360
atcagtatga ttactttata cgaagccgct attaaaacgc ttcacacaca ccgaaaacaa    21420
atttaaaaac accccgatag ccgtgaaatt ttactagctt tggggttgta ctgggataaa    21480
actcatattc ttgttaaatg tcgtgaatgt gggaatatga gtcttaccgg aaaacacagt    21540
acaaaatgta ttaacattaa ttgtctactt attcttgcca taaaaaaaag aataagcgta    21600
ttgttgatac cttgatagga atgggcgcgg atgtaacata tatacatctt ttaaagaata    21660
agataaaact gtcatacaac cagctgtcta tgcttaaaag caactcgcag atttcattga    21720
aggagcttca tgctatatgc tatctttat atggtcggct tcccaaaaaaa attaaacaag    21780
ggatgcgact gtgtaaaaca atggcgggac tatgtggtga acttttatgt gcatttttag    21840
ctccgtaaat gataatatgt atttaaaaca aacagatatt accaaaatat attctatgta    21900
cataatatct gggaaattat tttttttct cataccctta aatataaaaa tattgggttt    21960
cttcactaaa ctttagaggt aaaaattttt cttttgttttg caccatcatg tatgggttta    22020
ggctgtccca gggattgttt atttgaatat ttcctaaata ggaacacaac gccatgatca    22080
tatatctttc attctggtaa gctttttgat acatcttcaa agatgccgta cctccgagtg    22140
tgtaacagca aacaaacgtc cgtacttttc catgggtcgc agcccattcc attccgtagc    22200
tcagcatctt ttgctgtatt tttttattcg ctttataaaa aaagtttttc atccattcca    22260
cgttctcata aaaacaggca cttaaaaaga gcactagggg tagtgtagtc ttattataga    22320
atgtaggaat gtatgtttta gttatttttt tcaacgcgtg ttccatacta tgttttaccg    22380
ccataaaaat acaaaaccaa taccaacttt ttctataaaa ggttttgctg tacacatata    22440
aacgagcaaa atatatttca aactctatat tcttttttata aaaaaactcg agacagtcgt    22500
ttatgttacg acttttcta aatacctcaa aaacagtaat taattcactg tcgctgtgga    22560
aatgttcgta agctaactgt ttaatgtctt taggggtcaa ttcttttttt gggagcagtg    22620
gtttgagatt cggcaaaggt cgtctaaagt agtgagcgaa cttttcattc gctccccaac    22680
acaaaagccg ataagccagc atgtagttat cacgtttac cgcgtaaata agcaaatagt    22740
ttatattgat acatgtacca tgttgctgcc cgtttggaca tatgttgccg cattctgaac    22800
acttatgaat gagatcatag ttcttacaac ataaccccaa acgggttagt acttctttgt    22860
cacgttttaa aaactcgaca tgattcttta atgttaatgc tttgagcgca atgttaaata    22920
aactctgcat tttattaaaa tgaggttagt atcatgtttt agtataaaat ttagcggctg    22980
tttacataat gctaaataaa cttaacgttc ctactaaacc aaaaaaaatc aaattgacta    23040
agtcatagag aatttgacga tgttggtagg taatttttta acatggtata tattttttta    23100
gggtcggtta tattaggtaa taaaagagga cgtgccgtta aagtatttg cttaagatcc    23160
```

```
tttagatcct tacaaaaata tagattgttc gtctgatgat gccactgtgt tgcagtgatg    23220
gcttgatcaa tatcacctcc caagacaaaa cagtagtata tcgttaaaaa gttgtaatct    23280
ttcatacaag ccaactgcat cattttatcg atgtccatat gaacgatctt ttgctcgtat    23340
atttcatgaa ggtcaaatac attgttgaag taaatggcgc acatgagtcg ccacatacta    23400
aggtgcccat atgtttgata gaaaaggag atagctcttt taagcttata ttttactgct    23460
atggcatagc agtatttaac gaatacgttc atgggtacat tatctaagat ataaaatatg    23520
aaaaacttta actctcgatg aatctcttcc cccatttcct gtacatttag agcttccaac    23580
ataggatttt tatcaaatat ttcatgacat aaaataatgt tattgctcgt tttatgacgc    23640
attaaaccgg tgaaaatttc cttattattt aaactatctt tagctcctaa ctttcgacac    23700
agctcctgag tttgttccgt cctagcacag gtcagcccat aataaatgtt tgctccccac    23760
tcggtgaaca gccttattac gtcatagtta ttttcttta tggccatgat taatgccaca    23820
tcaagatgaa gaagttcccc cttaaagggg gttgagctta aaataacgta attacagtag    23880
tgacataagc taatgggctt gttttgccac cataagccac aatattttaa aatataatga    23940
tactcctcag gcacgctctg tttggccaca gcctttttgg ccagggtttg caaggagagc    24000
atgataactt cttgaaaaaa aaactcaaat taagttccta cttttttaaa atattagtat    24060
ggacagatct accatcatat gaaggaattc tttcatcgtt aaacactgaa gagataatac    24120
tttcatcgta tagagaatat catgtcaatc catatattga atgttatata tcattaaacc    24180
catcattaat atagtgttta tgtgctatgg acaggttttt tgaatgataa tctttaaca    24240 tacgttttat aacttcggga tcagtttctt ttaaagataa agaatcattc atgttataac    24300
aatttaatga taacatgctg gcaatgaacg agttgtcttt ttgatgcgct agagtctttc    24360
cctcctcaaa ggcattggcg cctaagtcta tacaaaagaa tatgtttccg atattataga    24420
actgaataga atgaaacatg gcctgattga tatcagcccc taagacgacg caacagtaat    24480
aaatcgttaa atagttatag ttcttgcgac aggcccactt tagcatttca ttcatgtcta    24540
tgcgaatcct ctccttttcg tacacttcgt gaagttcaaa cacattattg taaaaagggg    24600
cgcacataag ccgccaccga tgtagatgag catatctctg ataaaaatag caaatcgcct    24660
ccttaaggtt acattctatt gccatcgcgt accaatattt agtaaacatc tcgcttaata    24720
tatcggtttc taccattaat ccctccagtt gttcataaat cattcccttt acttcaaaac    24780
gatttatggt atctaaaatg ggattattag aaaatacctc atggcagaaa atgatgttac    24840
tgctagttag atcacgtttc aatgtgtaaa aaaatcgtaa aatttcctgg tcatttaact    24900
gttctttggc acctagctgc ctgcacaggt ctcgggtgtg ctccgtgttg acagaaagca    24960
aaccgtagtt gatgtttgca ccccactcgg tgaacaattc tattagatcg tgattgtttt    25020
cctccacagc tttcaccaag gccgcgttaa gatttgtgcc gttcttaaaa tacggcgtcc    25080
atattttctt ttgatgatac atgatagggc cattatgcca ccatagaccg cagcacttca    25140
aaaaatgagg atggcatttg gccggatact ggctggccag cacctttttg gtgagagtct    25200
gcagagagag gaccatattt ctttttttg aaaaaatcaa attaaaaaaa tcatgcttgt    25260
ttagcataca tgtaatattg ttataattac gttataatt cgttataatt acgttataac    25320
tatattataa caatggtata acaatggtat aacaatgtta taacaatgtt ataacgatgt    25380
atcattgatg tcatcattca actaggccaa catacttttt aatttatagt tttttaatag    25440
atgatatatt ttgttaggat ctgcttcttt taacgttaat agcgaggagt ctgcactata    25500
aatgtctaat gataaatgat gagatatcaa atagtaattc cgttgctctg ctagggcctt    25560
```

```
tgcctcttca aaggcgtcgg ctcccagatc tatacaaaag aacaagttat ccatattata   25620
aaatcgtacg caggcaagca tagctgaatt aatattagct cctaagagaa aacaataata   25680
tatggttaaa aaattgttat cttttgtgca ggccatccgc atcatttcat ccacgtccat   25740
gcggatcttt tccttttcat acaaattatg taggtcaaac agcttattaa aacaaagagc   25800
acagattaac caccacgtat ttagatactt aaaatgttgg taaacataag aaatggcctc   25860
cctaagatta tcctgcaatg ccactataaa acagtatatc gttaacatat caccatccga   25920
catattactt aatatgtcgg tgtcttctac taaccttttc aacttccaat atatggatga   25980
ccttatttcc cttataatga cataggctgg aaagggatta tcattaaaaa gtttaagaca   26040
taagataata ttactgctag tagtgccagg gtgtattaat ttaaagaaca tgtgcataat   26100 cttctttta tccacgcggt acttggctcc taattcccag caaaattctc gaacaggcgg   26160
cgtattggcg caaattaacc catagttgat gtctgcgccc cattctgtaa acagttttat   26220
taactgatag ttgttttcct ttgtagccaa cattagtgcc gtattaaggt ccaagccgtc   26280
tgcaaagctt ggcagcttta tcagcatatg tttgcaatca agggaaattg gggccttata   26340
ccaccatagt ccgcagcgtt ctaagataac atggtactca atagatactt gctgtctggc   26400 tagtacctt ttggcgaagg attgtaagga aggaaacatc ctgtttcttt tttttaaaa   26460 atcaattatc tttgttcata atcaagaaaa atccccatat ttattgagtg ataatttttt   26520
aacatgcaat ttatttttc agggtccgta acgatcgaca acagagaaat aaccggattg   26580
taatgcttta atgataaggc atgggctatc agataatttt cctttgttc tgccaaagct   26640 ttgccctcct caaaggcatc ggcacccagg tctatacaaa agaacaggtt tccaagatta   26700
tagttttgta tggaaacaag catggcttga ttgatgttgg ctcccatgat aaaacagtag   26760
taaatggccg aatagctata atcttggatg caggctatgt gcatcatttc atcaatatcc   26820
atgcggaccc tttctatttc gtacagctcg tgaaggtcga acacgttgtt gtaaaaaagg   26880
gcgcacatga gccgccacct atgtagacgc gggtatttct ggtaaaagta gcggatagca   26940
tctttgaggt catagtccac cgctatcgcg taccagtatt tggttaaaac agtgctaaag   27000
ctatcatcat ggtccagcat gaaggttatc tccatgagcc ctcttaactc ccacatgatt   27060
tcccccctca gatccagatt atctataatc cttaaattgg ggttattgga aaacacctcg   27120
tggcaaaaga taatattgct actggtttta tcgcgcgttg tatcaaagaa aattttaaa   27180 atatactctc tttctaaata ttctttggct cccagctctt tgcacagatc acgggtattt   27240
tccgtgagag cacaaatcat tccatagtta atatctgcac cccattcagt aaacagcttt   27300
atcaagtcat gattattctc cttcacggct ttcatcagtc ctatgtttaa ctcgatacct   27360
tgactaaaac aggttgacct tataaataat ttattgcgtc gaatatgaag cataatgggg   27420
ccattatgcc accacaggcc acaacacttc aggacatgat attgatctac cggtatacac   27480
tgcccggcca gtactttctt cgtgagggat tgcaggaag gcaacatgcc tttccatcct   27540
ttgacggaaa tcaaattatc tactaataac tatcagtgtt tatattaagt atttagatat   27600
tatcccgggc tggatacgta gtatcgctat tcacatgtac ttccaactct agccggagcc   27660
tgcagggtca tttattttta atattgattc ttttttgtat ttaatcattt agagaaggtc   27720
atcataggag ccagatgttc tctctccaga acttatgtcg aaaaacatta cctaaccgta   27780
aacttcctga attttttgac gaatatatat tacaactgct gggattatac tgggaaaacc   27840
atggaactat tcaacgagca ggaaacaact gtgtgcttat acagcaacat accctcattc   27900
```

```
ccgtaaatga agccctgaga acagcagcag ccggagaaaa gtcaaaaggg gcaggcaatt    27960
catacaccaa aaagttttttt ttttctgcta gcaagagcgt gtcaataatt ttaagctgat    28020
cgttaattaa ttttttggttt aactctttgt tattatcaag atccttcgca taaaccgcca    28080
tatttaataa aaacaataaa ttatttttat aacattatag atccccgggt ggtcagtccc    28140
ttatgttacg tcctgtagaa accccaaccc gtgaaatcaa aaaactcgac ggcctgtggg    28200
cattcagtct ggatcgcgaa aactgtggaa ttgatcagcg ttggtgggaa agcgcgttac    28260
aagaaagccg ggcaattgct gtgccaggca gttttaacga tcagttcgcc gatgcagata    28320
ttcgtaatta tgcgggcaac gtctggtatc agcgcgaagt ctttataccg aaaggttggg    28380
caggccagcg tatcgtgctg cgtttcgatg cggtcactca ttacggcaaa gtgtgggtca    28440
ataatcagga agtgatggag catcagggcg gctatacgcc atttgaagcc gatgtcacgc    28500
cgtatgttat tgccgggaaa agtgtacgta tcaccgtttg tgtgaacaac gaactgaact    28560
ggcagactat cccgccggga atggtgatta ccgacgaaaa cggcaagaaa aagcagtctt    28620
acttccatga tttctttaac tatgccggaa tccatcgcag cgtaatgctc tacaccacgc    28680
cgaacacctg ggtggacgat atcaccgtgg tgacgcatgt cgcgcaagac tgtaaccacg    28740
cgtctgttga ctggcaggtg gtggccaatg gtgatgtcag cgttgaactg cgtgatgcgg    28800
atcaacaggt ggttgcaact ggacaaggca ctagcgggac tttgcaagtg gtgaatccgc    28860
acctctggca accgggtgaa ggttatctct atgaactgtg cgtcacagcc aaaagccaga    28920
cagagtgtga tatctacccg cttcgcgtcg gcatccggtc agtggcagtg aagggcgaac    28980
agttcctgat taaccacaaa ccgttctact ttactggctt tggtcgtcat gaagatgcgg    29040
acttgcgtgg caaaggattc gataacgtgc tgatggtgca cgaccacgca ttaatggact    29100
ggattggggc caactcctac cgtacctcgc attaccctta cgctgaagag atgctcgact    29160
gggcagatga acatggcatc gtggtgattg atgaaactgc tgctgtcggc tttaacctct    29220
ctttaggcat tggtttcgaa gcgggcaaca agccgaaaga actgtacagc gaagaggcag    29280
tcaacgggga aactcagcaa gcgcacttac aggcgattaa agagctgata gcgcgtgaca    29340
aaaaccaccc aagcgtggtg atgtggagta ttgccaacga accggatacc cgtccgcaag    29400
gtgcacggga atatttcgcg ccactggcgg aagcaacgcg taaactcgac ccgacgcgtc    29460
cgatcacctg cgtcaatgta atgttctgcg acgctcacac cgataccatc agcgatctct    29520
ttgatgtgct gtgcctgaac cgttattacg atggtatgt ccaaagcggc gatttggaaa    29580
cggcagagaa ggtactggaa aaagaacttc tggcctggca ggagaaactg catcagccga    29640
ttatcatcac cgaatacggc gtggatacgt tagccgggct gcactcaatg tacaccgaca    29700
tgtggagtga agagtatcag tgtgcatggc tggatatgta tcaccgcgtc tttgatcgcg    29760
tcagcgccgt cgtcggtgaa caggtatgga attttgccga ttttgcgacc tcgcaaggca    29820
tattgcgcgt tggcggtaac aagaaaggga tcttcactcg cgaccgcaaa ccgaagtcgg    29880
cggcttttct gctgcaaaaa cgctggactg gcatgaactt cggtgaaaaa ccgcagcagg    29940
gaggcaaaca atgaatcaac aactctcctg gcgcaccatc gtcggctaca gcctcgggaa    30000
ttgctaccga gctcgaattt ccccgatcgt tcaaacattt ggcaataaag tttcttaaga    30060
ttgaatcctg ttgccggtct tgcgatgatt atcatataat ttctgttgaa ttacgttaag    30120
catgtaataa ttaacatgta atgcatgacg ttatttatga gatgggtttt tatgattaga    30180
gtcccgcaat tatacatttta atacgcgata gaaaacaaaa tatagcgcgc aaactaggat    30240
aaattatcgc gcgcggtgtc atctatgtta ctagatcgcg agacgtttca ataaaagggc    30300
```

```
ttctacccttt tgtaatcaaa accatagaat atggtggaag caaggagata gccataactc    30360
tggctaaaaa atatcagcat aaacatattt tgaaatactt cgaaacctgg gaaagctagg    30420
ttcagtatgg tgtactcact attgtagtga atcgtatcct gtaaattttg taaaaaagct    30480
taaacttttg accacatcat attgttttag aaatctcaaa ccagtgaaca acagtcttat    30540
catacattaa aattccagta aaatttatat ttttttggt aaacaaatgt tttctcttca     30600
agacatctgt cggaaacatc ttttcaact tcctgacgct tttgatgaat atatattaca     30660
agcgctagga ctatactggg aaaaacacgg atctcttcaa cgaataagaa aggacgctgt    30720
gtttgtacag cgaaacatcg tcctttctac caatgaggcc ctgagaatcg cagcctcaga    30780
gggaaacgaa agggtaataa aacttctgtt atcatgggag ggaaattttc attatgtgat    30840
cataggagct ctagagggtg accaatatga cctaattcat aagtatgata gtcaaattaa    30900
agactaccac atgattttat cattgatcca aaatgcaaat ccctttgaaa agtgtcatca    30960
gttatccaat agtaatatgt ggtgtcttat acagaatgct ataaaatata atatgctccc    31020
tattctccaa aaacacagaa atattctgac acatgaggga gagaatcagg aattgtttga    31080
gatggcatgt gaggaacaga aatatgacat agttttatgg ataggacaaa ccctaatgtt    31140
aaatgagccg gagtttattt tgatatcgc cttcgaacgg atagattttt ctttattaac     31200
aatgggttat agccttcttt tgataacaa gatgagtagt atagacattc atgatgaaga     31260
agatcttact tcattaccaa cagaacacct cgaaaaagca gccactaagg gatgtttctt    31320
ctttatgcta gaaactttaa aacatggtgg aaatgtaaat atggcagtct tatctaaagc    31380
tgttgagtat aatcatagaa aaattttaga ccattttatt cggcggcaaa aatgtttatc    31440
acgtgaagag attgaaaacc tattattaac cgccataacc aattgtgcat ccataaaaac    31500
gttaaactta ctcttgtctt acctaaacta ttccgtaaaa aatatcattg gaaaaatagt    31560
acaacatgtc ataaaagatg gtgattatac catcatatta cttttaaaaa aaagaaaat    31620
aaacctagtg gaacctgttt taacaggttt tatagattat tactatagct attgttttat    31680
aaaacatttt atccaagagt ttgctattcg tccggaaaaa ctgattaaaa tggccgcgcg    31740
aaaaggtaaa ctaaatatga ttatcgaatt ccttaacgaa aaatatgttc ataaagatga    31800
tcttggaact atatttaaat atctcaaaac cctagtatgt accatgaaac ataaaaaagg    31860
aaaagagaca ttaattgttc ttattcataa aatatatcaa gatattcatc tggagactaa    31920
agaaaaattt aaattattaa gatttatgt catgcatgat gcaactatcc aatttctatc     31980
tatgtgcaaa gactgtttta atttagccgg ttttaaacca tttgttttag aatgtttgga    32040
tattgctatt aaaaaaaatt accctgatat gatacaatat atagaaattc tatcgaaatc    32100
tgagtaaaat ttatttttt gatcagagta agaaaatgtt ctccctccag gagatctgtc     32160
gaaagaacat ctactttcta cctgactggc tcggtgagca tgtgattcag cgactaggtc    32220
tgtactggga aaaacatggt tctcttcagc gaatcggaga caactatgta cttatacaac    32280
aggacctcat catccccatc aatgaagccc taagaatggc aggggaggag gggaatgatg    32340
aggtggtaca actcctatta ctatgggagg gaaacattca ttatgccatc ataggagctt    32400
tggagagtga ccattatagc ctaatacgta agctctatga ccaaatcgaa gactgtcacg    32460
acatccttcc cttgattcaa gacccaaaac tctttgaaaa atgccatgaa ttagataaat    32520
cttgtaacat tttatgtctc gtattacacg ccgtaaaaaa cgatatgctt tgcattcttc    32580
aagagtataa aatgcatcta agtggagagg atattcaagt ggtgtttgaa acagcatgcc    32640
```

```
gttcacaaaa aaacgatatt gtgtcatgga tgggacaaaa tattgcaata tacaaccccg   32700
aagttatttt tgatattgcc tttgataaga tgaatgtgtc cttattatct atagggtata   32760
cgcttctttt caatcatcat ataaataata cgaacgaaaa tattaattct ttattgacac   32820
aacatcttga atgggctgcc ggcatgggcc ttcttcattt tatgctggaa actttaaagt   32880
atggcgggga tgtaacgata atagtcttgt ctgaggccgt aaaatatgac cacagaaaga   32940
ttttagatta ttttctccgt cgaaaaaact tgtaccaaga agatcttgaa gaactattat   33000
tgttggcgat acgtgcagat tgttctaaaa agaccttaaa cttgttatta tcttacttaa   33060
actattccat aaacaatatc cgtaaaaaaa tattacaatg tgtaaaagaa tatgaaacga   33120
ccgttattat aaaaatttta cggaaaagaa agataaatct gatagagccc attttggcag   33180
actttatagg atatcatagc tatacctata tggtagattt tatgcgtgag ttttccatcc   33240
atccggaaaa aatgatcaaa atggctgcac gagaatcgag ggaggacttg atcataaaat   33300
tttccaaaaa agtttgcaaa gagcctaaag atagacttca ctatctcaaa agcttagtgt   33360
atactatgcg acataaagaa ggcaaacaac tgttaattta tacaatccat aacttataca   33420
aagcttgtca tctagagagt aaagaaatgt ttaatttggc acgatttat gcacggcata   33480 atgcagtgat ccagttcaaa tcgatttgcc acgatctctc caagctcaat attaatatca   33540
aaaacttgtt gttagaatgt ttaggtattg ctattaaaaa aaattacttt caacttatca   33600
aaacaataga aacggatatg cgttatgagt aacatttta tgatgagggaa gattctacca   33660 aactaactaa gaccttttcgc tagaatgtat cttattgtta atatagatga gatatgtcat   33720
tgtgaaaaaa tagattaggt aggttgtgaa aaacagatta aacttaaaat tatgtgtatt   33780
atgtaaaatt ttagaaataa aaatttattt tttttattga gggtacggaa aatgttctcc   33840
ctacaggacc tctgtcggaa gaacattttc ttccttccaa atgattttag caagcatacc   33900
ctacaatggc tgggattata ttggaaagag catggatccg tccatcgagc agaaaaagac   33960
agcataatga tacagaatga attggttctt tctatcaatg atgctttaca gcttgcagga   34020 gaggagggg acacagatgt agtacagctc ttgttattat gggagggaaa tctgcattat   34080
gccatcatag gagccttgaa gactgaaaaa tataacctaa tatgtgagta tcatagccaa   34140
attcaggact ggcatattct cctacccatg attcaagatc cagaaacatt cgaaaaatgt   34200
catgatttaa gccttggatg tgactttatt tgccttctcc aacatgctgt aaaatacaac   34260
atgctttcta ttcttgtcaa atataaggag gatctactaa atgcaaggat taggcatcgt   34320
atccaatccc tgtttgtttt ggcatgcgaa aatcggagaa ttgaaattat tgattggata   34380
ggccaaaatc tgccaattcc tgaacctgat gccatttta gcattgctgt tgctacaaga   34440
gatttagaac tgttttcctt agggtacaag attattttg attacatgca aagacaggga   34500
atcattcaat taaccaatgg agttcgcatg gttgtgctaa atcgtcacat tagcatggca   34560
atagataatg gtcttttacc ttttgttctg gaaactttaa aacatggtgg gaatatacat   34620
agagccttat cttatgcagt aacacacaat agaagaaaaa ttctggatta tcttattcgc   34680
cagaaaaata tagcccctaa tacaattgaa agactttat atctggccgt gaaaaatcaa   34740
tcttccagga aaactttgaa cttgttgcta tcttacataa attacaaggt gaaaaatgtt   34800
aaaaagctgg tagagcatgt agtaaatgag aaatccactc ttgtgttaaa aatttttatta   34860 gaaaaaaagg aaaatctagt ggatgctgtt ttaacaagac ttgtaaaaca ttctacatat   34920
ttccaggtga gagaattat ccaggagttt tccatcagcc cagaaaaatt cattaaaata   34980
gctgtgcggg aaaagaaaaa tgtgttaatc gaggctattt ctgaagatat ttgggaaaat   35040
```

```
cccacagaaa gaattactta tctcaaacag atagtgcaca ccataaaata tgaaagtgga   35100
aggcgatttt tggtagacat cattcacagc atttaccaaa gttactcact aaaacacgaa   35160
gatattctta aactggcaac attttatgtc aaacacaatg caatcaccca ttttaaagac   35220
ctctgcaaat atctttggct gaacagagga acagaaagta agaaactgtt tttagagtgt   35280
ttagaaattg ctgatgagaa ggagtttcct gatattaaaa gtattgtgag tgaatatatt   35340
aactacttgt ttactgcagg agctattacc aaggaagaaa tcatgcaagc ctatgatgct   35400
ttagagtagc catgtattaa cattctgaaa gtagaataaa atatactata tactaaaaac   35460
caaattagcc atttttaact atcttcttct taaaaactct ggataaaaat ttattttttt   35520
taatttgggt agggaaaatg ttctcccttc aggacctctg tcggaagaac accttcttcc   35580
ttccaagtga ttttagcaag catacccctgc atttgctggg gttatactgg aaggggcatg   35640
gatctatcca aaggataaag aatgatggtg tgcttataga gcatgatctt actctttcca   35700
tcaatgaagc cttaattctt gcaggagaag agggaaacaa tgaagtagta aagctcttgt   35760
tactatggga aggaaatctt cattatgcca tcataggagc tttgaggact gagaactata   35820
acctagtatg tgagtaccat agtcaaattc aggactggca tgttctcctc cctttgattc   35880
aagatccaga aacattcgaa aaatgtcatg atttaagcct tgaatgtgat ctttcatgcc   35940
ttctccaaca tgctgtaaaa tataacatgc tttcgattct tgttaaatat aaagaggatc   36000
tactaaatgt actatttagg caacaaattc aaggactatt tattttagca tgtgaaaatc   36060
ggaagcttga gattcttacg tggatgggtc aaaatctgcc aattcctgat cctgagccta   36120
tttttagcat tgctgttgtc acaaaagatt tagaaatgtt ttccttaggg tacaagattg   36180
tttttgaata catggaaaac caaggacttc atttaaccca ggtagttcgt atggttatgc   36240
taaatcatca ctttggcatg gtaataaata aaggactttt accctttgtg ctggaaattt   36300
taaattatgg tgggaatgta aatagagcct tatcttatgc tgtcacacaa aataaaagaa   36360 agatttttaga ccatgttgtt cgccaaaaga atataccccca taaaaccatt gaaagaatgt   36420
tgcatctggc tgtaaaaaag catgctccca ggaaaactct gaacttgtta ctatcttaca   36480
taaattacaa ggtgaaaaat gttaaaaagt tgttagaaca tgtagtgaaa tacaactcta   36540
ctcttgtgat aagactcttg ttagaaaaaa agaaaaacct gctggatgct actttgacaa   36600
gatatgtcaa agattctaca tactttcagg tgaaagaatt tatgcaagac ttctccatca   36660
gcccagaaaa attcattaaa atagctgtgc gggaaaagag aaatgtgttg atcaagggta   36720
tttctgaaga tatttgggaa aatcccgcgg aaagaatcag gaatcttaag cagatagtgt   36780
gtaccataaa atatgaaagt ggaagacaat tcctgataaa tatcattcac accatttacc   36840
agagttattc tttgaaacct gaagaaattc ttaaattggc aacatttttat gtcaaacaca   36900 atgcaaccac ccatttaaa gatctctgca atatctttg gctgaacaga agaacagaaa   36960
gtaagaaact gttttagag tgcttggaaa ttgctgataa gaaggagttt cctgatatta   37020
aaagtattgt gagtgaatac attaactatt tgtttactgc aggagctatt accaaggaag   37080
aaatcatgca agcctatgct ttggagtatg ccatgtatta aatttctgaa tcagtaagca   37140
atagatagat tttagaatat gctgtattaa gttagtttct gaataagtaa ttaatagata   37200
gattttagtt tatgtaaaaa tgttaacatt tgttcataag ttttagatac cattttagag   37260 ttacttttt agatattact attttagcca ttattatctt aaataatcac tattttagat   37320
aggtccccgt attaaaaacc aaattaacca ttatctatgt ttttaataat acttttttaaa  37380
```

```
aaccctccat aaaaatttat ttttttttcat aaaagtagag aaaatgttct ccctacagga    37440
tctctgtcgg aagaaccttt ttcttccact tgagcccctta ggcaagcatg tggttcaacg    37500
gctgggatta tactgggaag gccatggttc agttaaacga gtgggtgatt gctttatatg    37560
tgtagaccag atttggatgc tatcaatcca taaggctata caaattgcag cctcggaagg    37620
aaatgagaac attgtcaagc ttttcttact atggaagggg agtctacaat atgccatcat    37680
aggagcctta gagggcaggc aatatgatct gattcaaaaa tattacaacc aaattggga    37740 ctgccatcag attctaccac tgattcaaga tccagaaatt tacgaaagat gtcatgaatt    37800
aaatgttaca tgtacctttc aatgcttatt tcaacatgct ataagagata acatgctgcc    37860
cattttccaa aaatatggag aagatctgaa tggaaacagg agaatggttc aacttctgta    37920
tgagatggca tgccgattac aaaattatga tatcatcaaa tggataggat ctaacctgca    37980
tgtttataac ttggaagcca tttttagcat tgcttttgtt agaaaggatt taactttgta    38040
ttctttaggc tacatgcttc ttctgggtag aatgagtact gaagatagaa actttatctc    38100
aatcataaca cgccatcttg aatacgcatc aaaaaaggga cttttttgact ttgtactaga    38160 atctttgaaa tatggaggtc aagtggatac agtgttgttt caggctgtaa aatacaacca    38220
taggaaaatt ttggcccatt ttattcatga aattccccgt gaaacggttg aaaagctgat    38280
actccatgct gtggagtcac gggcctccag aaaaacattc aacctgcttt tatcttccat    38340
aaactactgt gtgaaccctt ttgtcaaaaa actactgcac gctgtggtga acacaagta    38400 catgcttatc ataaagcttt tgctcgagcg gcccaaaaag aagataaacc tggtagatgc    38460
tgctctattc aaacttgtaa aatactctac ttatacagaa atagtaaaat acatgggtga    38520
gttttctgtg gacccaaaaa gggtggtcaa aatggcagca cgactcatga gagtggacct    38580
gattaaaaag atttctaatg atgcatggga agataaacta gagagaatca agcaccttaa    38640
acagatggta aataccatga accacagaaa tggaaaaaat ctattgatgt acaatattca    38700
caatattact ggatataccct atctgaacac caaagaagca tttaacttaa caagattta    38760 tgctgtccac aatgcaacat gtttgtttaa agaaatgtgt aaaagctgtt ttgtacatga    38820
taaaatacag ctcagagaat tgcttgaaga ttgtttacat attgctaata ggcatgatta    38880
tatccagatt gcagaaaccg cagatgaatg tatcaaatat atagatctta ttacatttaa    38940
gtaaaccatg tatatatcaa gtaaatccag attaaatcag gctaattgta aatagttgta    39000
gataccatat aatgaatgtt ttattaggat agtagttcag ttaagatagt agtttagtta    39060
agatagtagt ttagttaaga tagtagttat gttaagatag tagttctgtt aagataaatag    39120 tttagttaaa actagttcat gttaagttaa tagttttgtt aagacaatag ttcatttaag    39180
tcaatagttc agttaagtca atagttttgt taagtcaata gtttagttaa gtcaatagtt    39240
tagttaagtc aatagtttag ttaagtcaat agttatatta agacattagt tctgctaata    39300
cattagtttt gttaagataa taaaaattta ttttttttca tcagggtaga gaaaatgttc    39360
tccctacagg agctctgccg gaagaacatt tacattcttc cttacccctt ggctaagcat    39420
gtacttcaac aactagggct gtactggaag ggacatggat ctcttcaacg aatcggagat    39480
gaccatgtac tcttacagca ggacctgatc tttttccatca acgaggcctt aagaatggca    39540
ggagaggaag gaaacaatga agtagtaaag ctcttgttac tatgggaggg aaaccttcat    39600
tatgccatca taggagcttt agagggcgac cgatatgacc ttatccataa atattatgat    39660
caaattgggg actgccacaa gattcttcct ttaatccaag acccgcaaat ctttgaaaaa    39720
tgccatgaat tgagtaactc ctgtaatatt cgatgccttt tagaacatgc agtaaaacac    39780
```

```
gacatgcttt ctattcttca aaaacacaag gagcaaataa gattacacat ggcattaacc    39840
caaatactat ttgaattggc gtgtcatgaa cgtaaaaatg acatcattag atggatcggt    39900
tattccctgc acatacacca tctagagact attttttgatg ttgcattcgc ccataaaaat    39960
ttatccttat acgttttagg gtatgaactt ctcatgcaca aagtaaatac agaggctgca    40020
tatatagaat tacccaattt gctatcatat caccttcgaa ctgcggcggc aggaggtctt    40080
cttaacttta tgttagaaac aataaagcat ggtggatatc tggataaaac ggttttatcc    40140
gcggctatca ggtacaagca taggaaaatt gtggctcatt ttattcatca ggttccccgt    40200
aaaaccgtta aaaaactgtt actctatgct gtgcaggctc gggcccccaa aaaaacactg    40260
aacctacttt tatcttcctt aaactactcc gtgcacacca tcaccaaaca actcgtacac    40320
aatgtcgtca tctacagttc cacgcttatc gtaaagcttt tactcatgcg gcgaaaaaac    40380
aagttaaacc tagtagatgc cgttttagcc agacttgtaa aatattccac ctatacagac    40440
attgtacaat tcatgggtga gttttctgtg agcccagaaa gggtgatcaa aatggctgca    40500
cgggaatcca ggacctttct gattgaaatg atctccaaag ctgcttgggg aaatcaccca    40560
cagacgttga ttcatcatct caaacaacta accaatacca tgaagcctca atctggaaaa    40620
gaccacatca tatataccat ccactatatt tatctaaact ctaatatgct ggtagcggag    40680
gaggaaaaaa atatttttaa attagcaaaa ttttatgcga atcataatgc ggtaaacagg    40740
tttaaacaaa tttgtgaaga ctattatata ttagatgcac gatttaaaac acttatttta    40800
gaatgttttg aaattgccgt ccagaaaaac tatcctagaa ttgcaaatat tgtggatgac    40860
tatattcgat tccttttttta caggggaaat ataaccgagg aagaaattcg tgaagcctat    40920
tctttaaaag atgctgaggt ttatgtagat ttaaaatggt tacaacaagg agaaatggtt    40980
taaaccaaat ccggtttaaa ctaaatccaa tttaaactac atttggttta tcattagtca    41040
ttgaaaccat cgaaaaaaaa gctatttgtt tatccccata aactcatctt tttttttgtct    41100
caaagtttga cactaaaatt cagtgtttta tagtgtttat aattaagtgt tttgcatgca    41160
ttgcagaaat tttcatctttt tttaattggt tcaataccac atgtcataca atatgttgtt    41220
tgattatcaa gattaacttt atgaaaggaa agtaagtgag ccgcaaattt aaaagtaaaa    41280
tatctttcat ttaaaatgat cttatgaatg tattttcgat aaggaggaat gaaagcattt    41340
gccaaaataa atcgcataaa aggcttggaa aaacccatat cttctaatct tttgtgggta    41400
taaaccctat tttggtgttt tacaaaaact tcattgttat aatagtcgtt atagctatca    41460
atcatttttt taagtcctat aatgcccaag gttgcacgca taaagccaca gtttctgctc    41520
caaaaagcat gcacctgtaa agggtgcttt tcatataacc aattacaaaa tttcattccg    41580
caacagtagc atgttatttc agtggggggat gtatagaata atccggcatt cgaaaatttt    41640
tcataatttt ttatgtcatg gattgcgaag ctttgatttc gtgcatctat ggagctatag    41700
cctacatatt taggttttac ttcaaataat cgcaaagaga tgtatggatc tatcgtattt    41760
attttaggaa acatttcata attttaaatt cttatatata atataaaaaa aattacaaac    41820
atttgtaatg atcatcctca attgaaggct gagttgtagg ctttatttttt ctaattatac    41880
gaagaaggta ggttctcata aagccttcaa gatgactatt gatgtttcca atacatttc    41940
tcaatgagtt cataaaccca gacattttgc taatggcttg gcaaagtgcc aacaagttgt    42000
ccacaaagta ctggtagatt gccactagct atagctagct atagtgagcc aacctctctg    42060
tatgtatttt atatatttca ttttttaata gatttaatat ttttataaaa aatatttagt    42120
```

```
tttttataca agaatgtcga caaaaaaaaa gcccacaatt accaagcaag agctttactc   42180
cttagtagcg gcagataccc agttaaataa agcattgatt gaaagaatct ttacaagtca   42240
gcaaaaaata atacaaaatg ctttaaagca caatcaagaa gttattatac cacccggaat   42300
caagttcacc gtcgttacgg tgaaagctaa acctgctcgc cagggccata atcccgccac   42360
aggagagcct attcaaatta aagctaaacc tgaacataaa gccgtaaaga tacgagcatt   42420
gaaacctgtc catgatatgt taaactaaac tataaagtca tattcttctt tatcgttatt   42480
atcttcaata tattttgcc aatcgaaatc gaataaattc agatcctgga catttaaata   42540
cttatcatcg tacattttaa tataatttaa acatgagttg ttgtcaaaaa cttttagcgt   42600
ttttgttaaa attatcatat gaataatttc cttattaaga gttgccggaa taatacaaaa   42660
cctattttta ggtacatcat ccatgataat agtaaaatta gtaaaaattg tttcttgttt   42720
ttcttttgtt tcaaataaac gttgtaaggt taaaggtttc tcgttcaatg gtttctttga   42780
agataaaaag aatgtataat ctggtttaaa ggtattttg gtttcaatcg tgattccatc   42840
tgcttgagca tatactaaac cagaccaaat ataacggtcc actattacaa tataatttag   42900
cttaagtagc actgcaattt ctgcgataaa ttcactacga tgttttgtaa ataatttatg   42960
taattgttcc gatgacattt ctatggtttt atttaacacc tgcaatataa gatcaccggt   43020
ggtcgtgtct ggattaggaa aatgtataca tatagcatta taatccatgc attccaatgt   43080
ttcttttaat ttcattgcct gtgtgctttt tcccacacca ttgattccct cgatggcaat   43140
gagtattcca cgcatgatta ataaaggaa aaaagaatt cagttttaa catttcttac   43200
aaatcttttt ttatacaaca ttgtacaaca ctgcattagc ggtatatgat gttatagctt   43260
cattaaatat ttgctttat ataatcttta ccaacctata tttggtagat cactgcagat   43320
ggtcataaat aggccataac taagataaaa attatttcag acgctactac ggtagtatta   43380
ttaaaatcat gtgtggcaat gtatgacgtc ttaatagata aaacatttaa ggaaaacaaa   43440
tttgaataaa aaaataattg ttatgatggc gttgttacac aaagaaaagc ttatagagtg   43500
catctatcat gagctagaaa atggcgggac aatattgctt ctaacaaaaa atattgttgt   43560
gtcagaaatt tcatacattg gcaatactta taaatatttt accttaatg acaatcatga   43620
tctgataagc aaagaagatc ttaaaggagc aacatccaaa aacattgcta aaatgattta   43680
taattggatt ataaaaatc ctcaaaataa taagatttgg agtggtgagc cgcgtactca   43740
aatttatttt gaaaatgatt tatatcatac aaattacaat cataaatgta taaagatt   43800
ttggaatgtt tcaacttcag tcggtcctca tatctttaat gatcgtagca tttggtgtac   43860
taaatgcaca tccttttacc catttaccaa cattatgtcg cccaatatat tccaataaat   43920
tagatatctt tgctattaaa atagttaaaa accttatagg ataattaggt actttattac   43980
gataaattat gatatttat aattagttac tttattataa ttaatctctt tattaatgaa   44040
ttatcataag ataactaatt attttttttcc atatatcaga taataaatct gatatgggct   44100
aaaagtatgt ttcaaactat ttacaataga atttctgtta agaaaacata cataatttga   44160
ataaattttt tttaaatatc accgaaacaa tcaacatggt gttaatagag ttttttaacag   44220
gtttcttcta tttatatgga aagagactgt tttccattag taaagtcatg gacatgatat   44280
gtctagacta ttataccatt attcctgctc ctctggcgat gatgttagcg gcaagactaa   44340
aaaactatga cctcatgaaa cgactgcacg aatgggaaat ctctattgac tacgctctac   44400
ttgtagtaga tgatgtgccg tctattgact attgcttaag tcttggcgct agatcccga   44460
ctagagcaca aaaaagagaa ctgctgaggg acaacacgtt taatcccgtg tataagtatc   44520
```

```
ttatgaactg ttccggcttc ccaacaaaga gagaaaaaaa cattccttgt gatgttcaat   44580
gcgaaagact gcaaaaaaac attataaaag aactggtatt taactgctct gtactgcttg   44640
aaatggtact gcacacagaa agagaatatg catacgccct acactgtgct gcaaaacata   44700
accaattgcc catcctcatg tattgttggc aacaatccac agacgcggaa tctattttgt   44760
tgaaaacctg ctgttctgat aagaacatca attgttttaa ctattgtatt ctatatggcg   44820
gcgcccaaaa tttggatgct gcaatggtgg aagcggcaaa gcacgatgcc cggatgctga   44880
taaactactg tgtcatgctt ggtggaagat ccttaaacga agcaaaagaa acggctgcca   44940
tgtttggaca cattgaatgc gcacaacact gttttaaact gcagtcttac gtcgtggaca   45000
catcgaatac agacgacact gattaaagcg acaatcttac gtcatgaacg actgtctttt   45060
gagtatctat acttacatta tatttttta tgaaaaaaat ataaaggttg tatacaaacc   45120
tttgtataca agaaatttgg atcattaaac aataattaat ttggacacag gaaacgatct   45180
agatcgatca aaaagctatt ttttttgcac acagaacatt tagataattg agagattact   45240
ttccatactt gttaagcttt tttacacaca ggaactttgg attctgttca ggaagttttt   45300
catagacatt atgtttacag ccagtaataa taattttggg ctttttctta aaccaccggt   45360
ggaaaacatc cagcttgtaa agagggaaat gcatgtagag aggttttggt agtcatggtt   45420
aagagatttg actaactcca tgtttcctgt aaagactgcc cagtcccaag cagtaaaacc   45480
tctatgatag tcttttgag tcggatctgc tccaaatttt atgagagaaa gcatatttaa   45540
agaacggccc cgtattgcgg ccttcatcac aggagtcatc ccattaaaat tcggtaaaca   45600
aattctggtc ccattttttc cgaaatagcc caacacccct tccaggatta aatgattttt   45660
tttctcagct aaataatgta aagcagagtt tccatctta tccctcctat gagggttaat   45720
tatttctcca ggataagatt cttgttcaaa aagaaatttt aaaaagtcta tacgtccgta   45780
gatgcatatc cacatgaata ccgaggatcc atttttatcg catctattga caatccacgg   45840
atctgtttta aaaaattcct caaatagtgt aagattccca tttctaatat gttttttaat   45900
ccatttaaca aacaagtttt ctatctcct ttctggaaac atgtgttcca ttttgaatgt   45960
cgcccctact ccactatatg attttactcc tttaattttt aatgtccttt tttttcggac   46020
ttctttggat aagctgttta ttaccatctt taaatgcctt atagcgggga ggagccaggc   46080 cctttttccca tatgtgcggt aattcttggt gtttatgctt gcctttggca taaccaggcc   46140 agtattttc gatatattca gggtttgttt ttacgtattc tttaaaggtc cgataggctt   46200
cttgaataca ggtaggctca ccggtataat ttccatgttc atcttccttt aaaaagccat   46260
taaccctgtc ctttctccac ttaagattgt gctttccaaa aatgcgatca agatcttgcg   46320
cctgctgggg tggaatcata aatccctttt taggtcgaag cttttattt tttccatagc   46380 ttcggccatc gcgttgcgaa acagtggtta ggacgcctga tagtcttttcc atgggcgtcg   46440 catctaatcc tatccatcca ccctgatgaa tatcaatggc aacaagctct cctttattt   46500 gggcaagcca agtttccaag aatgccatgc tttcttccca gggataaggc ccgccaacac   46560
cacgggttgt ccaatcttgc aaggactcca ggtccgacac ctggtaaggc tctaaagaag   46620
acggttcctt gttttgtac tgcaaataag atttaatgac ccatttatac catgtgtcga   46680
accgcagcgt ggcgcctcca aagtgaaagc cgtcgttgat tttaggatat ctgcaacata   46740
tttcaaccgt acgtttgagt tctgcaaaag cggccttcca aggaagtctt tcgctgcggg   46800
taagacggtc tattttgccc tgcgtgccat agcgtatggc atgtcgtgcc aattgcaaca   46860
```

```
attctgacac cgatccgtgg gccccgatcc agtttatcgg ataggcaacc tccgaagggt   46920
ttaaaagatg ctcgtaaaag cgtggatctt cagatgccaa ggcgtctgca aaggggataa   46980
tgctagaaaa cctgtctaga catacgtttt ctgtgtttac ttctaaaggt agaaaaatgg   47040
ttgcgtgagg cttttgaacc tgcttgttca gcggtctgca tatgctttga ataatgtctc   47100
taggactatg tcgcggcgct gcaaaaaata ccgcgtttag ttctggaacc tctacgccct   47160
cttgaaagag tcgacagttt aataaaataa cgggttcctt tgaggaacaa aattctgtaa   47220
atgttttgag gataacctgt cgcggcaggg ttgagtgagc tatcagggca tagacccctt   47280
ggtctaccaa cgccgcgtat agctccttgg cctgtttaat atcacgggta ataccagca   47340 ttttaggagc cggtatattg gttttttaaat aggctaaggc cattataatt tgctttacta  47400
tgatctgttt cgtggtctcc tctttggtac tcggttggtg ggccaattta ggcgcggcta   47460
ccatctgcaa ttcaaaatca tttacatagc cggcctctat gccttctcgc agatagtagc   47520
gaaaggcaac gccgccaaaa agttcacgat ttttcatgga aagcggggtg tcgtacctgg   47580
gcgttgccgt taaaaaaagt cggtgcccctt ttttaaagtt gagcaacacg tgggtaaagg   47640
gccgtgtctc ccattcgccg caaatccggt gacattcatc gctaataata agatcgaaat   47700
catccaccag tagcgtggag gattggtagg tggcaatcac aagaagagaa ggggcctccc   47760
gtatccgttt tgcaataaag acaggattgg tggtcatttc tatattgtcg tgatttagca   47820
caatgcgggt ctggtcagac cccacaagca aaacgttctt caaagaaatt ccatactgat   47880
agagtttttc cagagtctgc cgtagtaggg acaggcccgg caccaggtac aaaactttc   47940 cttgaagata attggagagg ataagatagg cgacgcgagt tttgccgcat cggcaggcca   48000
tctgcagaat ggccctccca cttcgccgca gctcctgata gcccatattg gccgcctcct   48060
tctgataaag tcgatcctcg attgcagtcc gtgtctcatc tgtagaaaaa aataatacgt   48120
catctgcgaa atgttcatct tccacaggag ttatcaccag gtgtctcagt ttctccttgc   48180
ttatcagcgg atcagagggc aaagatggct caaccactat cgtggaatca ttcatctcat   48240
aggcgggaga atcacacaaa gtatagctta tgtccagaca gtttgcaaca tcctcagcca   48300
attgttttat ttttcgggt aaaagacata cgagttcttt gttttgacg cgaaaaaact     48360 gtgcacaata taacacccct gcttcaattt tttgcgcatc cttctttgta gatgtttcca   48420
atgtgaaaca atacttccat tcatccgtaa aacaggttgt ataagatcca tcatgaagcc   48480
tagcggccaa gtttcctgtg tgcccaactt tatgtaagga ttgggcctcc agccagggat   48540
gaaccgccac gtaaaatcct gcgcacatgc tatatcaaat tgcagtttct taataactgt   48600
acacaggatc tgaaaaacat gtgattacaa aatttagata agaaatattt aatattaaaa   48660
atcacagaat acatgtcact gtgtagagag aaagccaaaa actcctcttg accgccgtgg   48720
gaaatcatcc agggtagtag gttgtgtttc ataaagttgt atgccgtagt gatcaccgtg   48780
gactccagat ggttattggc atctttgcaa tactttgcca tcttggcaga aaagacgata   48840
aatccacaaa ttctacccca gttgataaga tccttaaaca gctcagtcac aaccccagta   48900
aactgggttt taattcttg aacactcgta agagaaaagg taattgtaac ctgtttgttc    48960
aaacactcat cataataggt taaaattttt tttatttgtt gttgatatgg gctaagctca   49020
tgctctgaaa tatcattaat gtaatattta atatatccca ctagtatttc attaatgata   49080
ttatgatata ttaactcttc tccctccata gcggcaccct atattttttt atttaggttt   49140
caatgttatc acaattgcga tacaattgtg atacaattgt gacacaactg tgttgtatac   49200
aacaaatgtt aggccacgta tagcaaccta tatgttaaga aatatttta tcccaacatt    49260
```

```
agttggaaac gagcagccgc aaagaagtca tttaaaataa gccatttaaa gatttagaat   49320
ttatatgtat acaactgtac aatggaagca gttcttacca aactcgacca ggaggaaaaa   49380
aaggctctcc aaaattttca tcgttgtgct tgggaagaaa ctaaaaatat tataaacgat   49440
tttcttgaaa tccctgagga acgatgcacc tataaattca actcatacac aaaaaaaatg   49500
gagcttttat ttaccoctga attccacacc gcctggcatg aagttcctga gtgcagagag   49560
ttcatattaa acttttttgag actcatttcg ggacatcgag tggtattaaa aggccctaca   49620
tttgttttta caaagagat caagaatctg ggcattccta gtaccatcaa tgttgacttt   49680
caggccaaca ttgaaaatat ggatgatcta cagaagggaa atctcatcgg caagatgaat   49740
atcaaagaag gctaaataaa acaactaaca tcaaaaaaca ttaaaggcta tgttgtggac   49800
gatgcctttg tctcaatagt ttcgaggtca tccataact catgtaacgt aaaaagttg    49860 gtccattttt ttgaaaacat taaagacgt tcgtcttcat aaataaaaaa gtcattcgaa   49920
ggaaaaatga tatactcaat accatagtct tgtaatattt tttttaggtc tctcagggtc   49980
cagggattta ccaggcttct acgcgaagtg agcatcataa aaatatctaa tatttttgc   50040 gccataagcc agcgcggatt ctcattggcc cacaaatcaa caataattct cttatcaacc   50100
gtgagcattc ctacttgatt cgaagaaatg attagatgcc cagcagtcca ccccatgagt   50160
agataacgca gcgttgtaga aatgtcacat atggaaggca ttcctccaca acatgaaccc   50220
aaattaggat gcgtgtgaaa cacaaacata gcaggcttgt tggccaccct gctataaata   50280
tcagcaggca tcatagcctc gctgccaaaa taaatgttct ctcctgccct atagggctt    50340 ggaatgattt ccactatctc gggtacaccg tttatcatat taatgcggcc gcaccattca   50400
cggtcatcgt ccaaaaattt tttgatggca ccccgaacat tgtcccagtt aagcaacaga   50460
gtattcacaa tctcattacg ctccgcccag tattccttaa aacttctttt agacttgctg   50520
agctgttccc aggattcgaa ctcagtccaa tgtttttttt cttttgggga agacttccct   50580
tttgaaacat tttttgcggc tccaccatct acactatgat tttccaaaat aatctccttc   50640
atcgtttgag ttatatgggc attgctaagc accttagtgg taacctgttt acctatgtga   50700
tttagcagaa accaagttt gtccatttgt gtctcaacca tttattctta acaaaacaaa   50760
aaaaattaaa aatcatcgtc gtttaaaaag agtttgaagg caaacgcatc atccttaaca   50820
cagttctgat actgcgtagg tcttaactcg aaaaagttgg tttttctac ttcattaaga    50880 aagaatttag tcatctgagg aaaagggttt cccaccttat aaatgctttt gcactgcatc   50940
atgaagcaca aattatctgt aaagtagcgt atatattgaa atagcatttc ttttgaaaaa   51000
ccgggaactc ttcctcttgc cttgtcaaag gcatagttaa taaactcatc caccaactcc   51060
acagcctcct tcaaaatttt gtgaatgatc ttttcctcgg gaatgttata cacgtaattt   51120
gagataagaa acacgcaaa actacagtgc atcccttcat cacgtgagat aaactcatta    51180
tagcttacaa gccccggcat aatattctgt tccttaagaa actggatcgc acaaagtgg    51240 ttttgaaata aaatgccttc tacggcggcg aagcccacca gccgctcacc tagagtgttc   51300 ctgtcgggt ccatccactg ccgcacccac tgcgccattt tttttatgat agggtgtttt    51360
tcaatgccgc taaagatgcg ctgttgttcc ttctcatccg ggatcagcgt ttttaccgt    51420 attgagtagg cttcgctatg aacgcactct tgggcagcct gcattgtata aagtataac   51480 acttccttta ctttaatttc gcgcataaaa ttggttaaaa ggttttcgat aacaatttcg   51540
tcggcaacaa caaagaaggc taaaatttgt ttataaaatt cgcgctgtgg ctttggcatg   51600
```

```
gcttcccaat catcaatgtc cttacacatg tccacctcct gcgccgtcca cgtcaaactt    51660
tctaattttt tataccagtt ccaacattcg gggtgctgaa taggaaaaat agtgaaacgt    51720
tgggaatttt caattagtaa ttcctccata tttgaaataa atattaacat cttcaaattt    51780
attggctgcc atggagacgt tttttattga gacgttggca tctgatgtgt atggaaaggc    51840
gttaaatgtt gatttagata gactatcgca ggcgcaggtt aaatataccc ttcaagagct    51900
tatttcctac tgcagcgctc taaccatttt acattatgac tattcaaccc ttgcggcgcg    51960
tctttcggtg taccagctgc accagtcaac ggcctcctcc ttctcaaagg cggtgaggct    52020
gcaggccgca caatcctgct cacgcctgtc cccccagttt gtggacgtcg tttacaagta    52080
caaagccatt tttgacagct acattgacta tagcagagat tacaagctgt ccctcctggg    52140
gatagaaacc atgaaaaatt cttatttgtt aaaaaataaa gatggggtca tcatggaacg    52200
cccgcaggat gcttatatgc gggttgccat catgatgtctat gggatgggaa gagtggtcaa    52260
tatgaaaatg attctgctaa cctatgacct gctttcccag cacgtcatca cacacgcgtc    52320
gcccaccatg ttcaatgcag gcaccaaaaa gccacaactc tccagctgtt tcctgctaaa    52380
tgtaaatgat aatttagaaa atttatatga tatggtcaaa acggccggca tcatttcagg    52440
cggcggcggt ggaatagggc tgtgcttgtc aggaatacgg gcaaagaata gttttatttc    52500
tggtagtggt cttaaaagta acggcataca gaattatatt gtgctgcaaa atgcttcaca    52560
atgctacgcg aaccagggag gcctacgtcc cggagcctac gccgtctact tagagctgtg    52620
gcaccaagac atctttacat ttttacaaat gcctcgccta aaaggacaaa tggctgaaca    52680
acggcttaat gccctaatc tcaagtacgg cctatgggtc cccgacctat tcatggaaat    52740
acttgaagac caaatacaca acagaggcga cggcaaatgg tacctctttt cgccggatca    52800
ggcccccaat ctacataagg tctttgattt ggaacggtcg cagcacgaaa acgcacaccg    52860
cgaatttaaa aagctttact atcagtatgt tgctgaaaaa aggtacaccg gcgtcacaac    52920
ggccaaagag attatcaaag agtggttcaa aacagttgtt caagtaggga tccctatat    52980 cgggtttaaa gatgccataa atcgtaaaag taatctttca catgtaggca ctatcacgaa    53040
ctccaatctt tgtattgaag tcacaatccc ctgctgggag ggtgataagg ctgaacaagg    53100
tgtttgtaat ctggccgcag taaatctagc cgcctttata cgtgaaaatg gctacgacta    53160
ccgtgggctc atagaagcat caggcaatgt cacagaaaat ttagataata ttatagaaaa    53220
tggctactac cccacagaag ccacgcggag aagcaatatg cgtcaccgac ctattggcat    53280
cggggtcttt ggcctagccg acgtgtttgc gtctttaaaa atgaaatttg gttcacccga    53340
ggccattgcc atggatgagg ccatccatgc ggccctatac tacggggcca tgcgacgatc    53400
catagaactt gcaaagaaa aaggaagtca tcccagcttt ccggggtctg cggcctcaaa    53460
gggtctactg cagcccgacc tatgggttcg ctgtggtgat ttagtttcct cctgggaaga    53520
acgcgtggca cagacgacgc agggtgtgtt gacgccgaaa aggtggtcgc agctacgcct    53580
ggcggctatg cagggacttc gaaatggata tgtcacagct cttatgccca ccgcaacctc    53640
ctcaaattct acaggaaaaa acgaatgttt tgagcccttt acatccaatc tatatacacg    53700
tagaacgtta agcggggagt ttattgtttt aaataagtat ttaatagacg atttaaaaga    53760
aattaatctt tggacagaag ccattcaaca gcagctacta aatgcgggag gtagcattca    53820
gcacattttg gatataccgg ccgagatccg cgatcggtat aaaacctcca gggaaatgaa    53880
tcaaaaaatt ttaacaaaac acgcggccgc acgaaacccc tttgtatccc aaagtatgtc    53940
cttgaactat tacttttatg aacctgaact aagccaggta cttacagtgc tcgtcctagg    54000
```

```
ctggaaaaaa ggtttaacta ccggttccta ttactgtcat tttagccctg gagcgggtac    54060
ccaaaaaaag attataagaa actctgagaa agcgtgtaat gcggactgcg aggcgtgtct    54120
tctgtaggtg tctcgcggta aaagagcagc ggggaccata tggtaaaccc caacaagagg    54180
ataatgaata aaaaaagtaa acaggcatcc attagttcca tattaaattt ttttttcttc    54240
tatataatgg aatattttgt tgcggtagac aatgaaacct ccttgggggt tttacttct     54300 atagagcaat gtgaagaaac gatgaaacaa taccccggcc tccattatgt cgttttaag    54360 tatatgtgtc cggcggatgc agaaaataca gatgttgtat atttaatacc ctcgttaacc    54420 ttgcatacc ccatgtttgt agaccactgt ccaaatcgta ccaaacaagc acgacacgta    54480
ttgaaaaaaa taaacttagt gttcgaggaa gagtctattg aaaattggaa ggtttcagta    54540
aatactgtgt tcccccatgt tcacaacaga ttatctgcgc cgaaactttc catcgacgag    54600
gctaatgaag ccgtagaaaa gttttgata caagcaggac gactcatgtc tctgtaaatg     54660
tctcttcctt tatgggtgac gtctcttcct ttgccgagga agtctctgtt atgggcaaga    54720
ggtttgaaac aacgcaagga ctctgcttaa tctgctgtct cacaaaggga atcaaactac    54780
ctgctttcgt attttaatg tagtaattac ccttgttgtg atgaattta agaccatagc     54840 gtagtcccag tactttatta atgaattta aaattgttgg agggtccgtt ttattgggct    54900
ttttaagctt aaactcaaag ctgatcgcgc ttaaatcata ctgaacaaat tcatcaacga    54960
gtttcgtcat taattgttca ttggtcaata tattagggtc ctgaacgcat ttaaagccgc    55020
acttagttaa tagcataata gcgtacatat gagattgaaa actataatta aattgtagat    55080
catgatgctc tgcgtgttgc atggcccatt gatgaaagtt taattcctga gtttgtaaca    55140
tagtgagcga ctcgtatact gtcttccgc ggcttatttg gacacggcca gtatagttct     55200
gttttgtcat aaaactattg tattgttcaa caaatttggg agtaatttta tgaccgtgcc    55260
atgcataaaa ttcgagtagt ttatactttt catacgcaaa taggtcttgc tggtctactg    55320
tgatgccttc ctttaagttt tgtttaattt gtaaagcttt attggcatca atggtttcag    55380
ccgaggcaat gtttacatag tcctggtgtt taatttccat ttaatgctt gtatattgtt    55440 tgactgtctc cagcttttca cccgtcagta taaacacctt agcgccggtg tcggcgatct    55500
ggttaataaa tcgggttata aagtgatttt tgatagatg ttgtatccgc attgtttcga     55560
gccatagatg gtagtatgga gttttataat atatcggcct acctgtttcc ttactatacg    55620
tgaaggaaag ctggtgattg cttatggtct gaaaagggt gtcacgtttt tgtaacgtaa     55680
acatttcaat gtcttcgatg gtttctggat agtaattttg tttccctgt aagcagattt     55740 tataacactt acttttaat tcacgcacgc ggcccaacat ttggcaacat gtttctacgt    55800
cacacgacat attgttaaaa agccgtata aacatcaaa tctcttatct tcgtatgaaa    55860
cacccgctga atcgtgggc gtatagataa ggatatcaac gagcccccaa taatacgata    55920
cattattaaa atgggattcc cgttcatgag cagtgctttt agaactataa acccaatttt    55980 tttttccgg aaacttttt tggataaatg attgcaacag ccgggcctcc attaatgaat     56040
ttgtagggat aacaatttt ttgtcttcta gcaaatcctt taaaaggtta tttaaccaag    56100
tttctcgtga agaggtaaaa taatacgtgt catgctgggc ccttttatat tgattccagt    56160
gaaagaagat agggacatcc ccgcgaaaac gctgtagaat attatacgtt cgatttccta    56220
ggtttgcgtc caagcatata acataatttg ccgtttcgag catccacatg aaaatggcaa    56280
aagagggagc aaagtatttg tgcaggccgc tattgaattg attaaaaatc gattctacct    56340
```

```
catccaaaat aagtaggtct acaggctcgg ctgtggaggt tagccggaaa agtgattcta    56400
cctgaatgat gactctttcg tagctgtcca aatctccagt tacttcgctg tacaatgtga    56460
aattcggtag ccgggattgt atattttttg agaagatctg tcgaaacgtc acaaaccgta    56520
tggtttgttg ttttgaaata gaattattgc cgtagtattt ttgcaaatag ttgcgcagtt    56580
ggacggtttt acctattttc atttgagcct ttacaacaag cgtagggact cgttcatatt    56640
ctcgcatact actttcatca tagatgtgtt tttgagtatc aggcagttct tcaaagagaa    56700
tggactcatg aacctctatg ctctttgtca tcacttggtc cacatatgtt tccacaaaat    56760
tatttgtgcc ggaaaggctg cccatgagaa ggctatgttt attgtcatgg cgacagtgtt    56820
gatacacttt gtttcccgtg actcttaaaa ttagggtatt gtccttatca tgcatacgct    56880
tacatatttc gcagtaactt ggacttgtac gtttaaacaa tactaaattt ttatgaacac    56940
ggaggaagca atgattttta catagtgttc ctgcaaattt taatacctct tcaagttcac    57000
tttgttggat agtatcgcag gaactcggtg ttgtttcttt tacatttgtg aagatacaag    57060
gtaaacacgt cgtttcaaag ggggttgcta taagggtatc actcttttc gtggttgtac    57120 tggtctcaaa cacctctgca agctcctcat taaacatttt aacacgcatg ctacctttt    57180 tatgagaccc tatgatgcga aaattttgaa tacttttgtt gacctggggg tcaacaaaag    57240
gataaacgtg tttgggaaga ttttctaaca ctttggatgt aaagactttg gcctcattat    57300
tgtttaatac tgagtatgta taagtatga tatgaaagga gtatttaagt tctcgctttt    57360
tatttaatcc gatagaatct gttagcaaaa tttgttcacg cgttagattg atgttataag    57420
gtaaagaata tgtctcgtaa aatacatcca tgatgacgtt aattatcatg tcaaggatgt    57480
catagacatt gtcttcgaca ttatcattgt catcaacatt gtcatcagag tatgacttat    57540
ttaccggaaa gtcgatgtca aatttttaagc gctgaggcaa aaacccaaat accacttcgt    57600
ggaaacactt ctgctcaaag ggctgagccg cctcccactc ccaaaagtca tcacgacttg    57660
aaaaaactct aaaagatta ttatattcat ctcgcaccac gaagtgattc tttaaggtttt    57720 cgagagaata tttatcctct acggcttctc cttgggagtt acagcgaaga aacttgaatg    57780
tttcttgcat tttgatattt aaaattaaat caattatgat gcggccgcta atgcggcggt    57840
tgacgcggcc gcgccgctga cgcagccatc atacataaag cggcatggcc gttttataac    57900
gactagtcgg ccgttatatg acgaactata taaaaatgaa ttcttttaat tagagttaag    57960
tattgttgat tgtataatcc atcatggttg agccacgcga acagtttttt caagatctgc    58020
tttcagcagt ggatcaacaa atggacactg taaaaaatga cataaaagac attatgaaag    58080
aaaaaacgtc ttttatggta tcattcgaaa actttataga acgttacgat accatggaaa    58140 aaatattca agaccttcag aataagtacg aagaaatggc ggccaacctt atgaccgtca    58200
tgacggatac aaaaattcag cttggagcca ttatcgccca acttgagatt ctaatgataa    58260
atggcactcc acttccggca aaaagacaa caattaagga ggctatgccc ttaccttcat    58320
caaacacgaa taatgaacaa acgagtcctc ccgcctcagg caaaacaagt gaaacaccta    58380
aaaaaaatcc cacgaatgcg atgttcttca cgcgtagcga atgggcatcc tcgaatactt    58440
ttcgagaaaa gttttaaaca ccagaaattc aagccatatt ggatgagcag tttgcaaaca    58500
agaccgggat cgaaagattg catgccgagg gtctttacat gtggagaacc caattctctg    58560
acgaacagaa gaaaatggtc aaagagatga tgaagaagta atatttttgg taaaaatatt    58620
tttatcaaaa ttttttacca aataataaaa atatttttac ttttttttctt cataatatac    58680 atagaatgcc tacaaaagct ggcacaaaaa gtaccgcaaa taaaaaaaca acgaagggct    58740
```

```
cctccaaatc tggttcttcc agaggccaca ccggcaaaac ccatgcttct tcgtccatgc    58800
attccgggat gctctataaa gatatggtaa atattgctag atctagaggc attccgattt    58860
accagaatgg atcgcgtctt actaaaagtg aattggagaa aaaattaaa cggtcaaaat    58920 gaatataatc aggaaactta agcctggaac aattagcctt gtgctgggac ccatgtttgc    58980
cggcaaaact acgtttctta ttcattgcat ttacatgctc gaacgtttgg aaaaaaagt     59040 agtcttcata aaatctacca aaaacacccg agacaaaact attaaaacac actccggtat    59100
acagctacga cccaaacaat gtaaaatcat agaaagcaca cagttatctg acgtgggttc    59160
tctcaccgat atccatgcag ttgtcgtaga tgaagcgcat tttttgacg atttaatcac      59220 atgccgcact tgggcagagg aagaaaaaat tattattctt gcgggactca atgcttcctt    59280
cgagcagaaa atgtttccgc ccatcgttcg tattttcct tactgcagct gggttaagta     59340
tattggccgc acctgtatga aatgtaacca acataatgca tgctttaatg tgcgtaagaa    59400
cgcagacaag acgcttatcc ttgcgggagg aagtgaactg tacgtaacat gttgtaacaa    59460
ctgtctaaaa aatacattta ttaagcagtt gcaacctatt aaatattaaa atcttatac     59520 aataatggat cattatctta aaaaattaca agatatttat acgaagctcg agggtcatcc    59580
cttttctttt agcccgtcga aaccaatga aaaagagttt attactctgc taaaccaggc     59640
cttggcctca acgcagcttt accgcagcat acaacagctg tttttaacga tgtataagct    59700
agatcccatt gggtttatta actatattaa aacgagtaaa caagagtatt tatgcctgtt    59760
aattaatcct aaactcgtta ctaagttttt aaaaataacg agctttaaaa tttacattaa    59820
tttcaggctg aaaactttt atataagtcc taataagtat aataattttt acaccgctcc     59880
ctctgaagaa aagactaacc atcttctaaa agaagaaaaa acttgggcaa agattgttga    59940
agaaggagga gaagaatcct aagtcgctta catttttttt tgctattttt atagaatgta    60000
cacgcatgtt gatgttgtcg gaatagctga agcctcagcg gccctctacg tgcaaaaaga    60060
tagggatcgc tacttagacg tgctaacaac cattgaaaac tttatttacc aacacaaatg    60120
catcataaca ggggaaagcg cccacctact cttttaaaa aaaatatttt atctttacga     60180
attttactcc aacaatgtgg cggagcacag caaggctttg gcgaccctgc tttataaact    60240
tgatccggaa tacctcactc gttacacagt actcattacc aaaattccca accattggta    60300
tgtgattaac gtagatcagc gagaatttgt gcgcctatat gccatcccgg cagttaaaca    60360
acacttaccg attcccattt tacccttcta ttgcaccagc gcactcaccc agcaagaatt    60420
gttttgttta ggacctgaac tgcagttaat acaaatatat tccaagctct gtaaccccaa    60480
ctttgtcgag gaatggccta cgttgctcga ctacgaaaaa agcatgcgga tgttattttt    60540
agaacagttt ccgcaaagat tggaaatgac gggcgggaag aaggaggaga aggaaaagca    60600
tgaaagtatc attaaaaaaa taatactaga aatggtctct acccgtcagc gaatcgttgt    60660
tgggggttac atacaaaaaa acctgtacaa ccatgtactc agaatagaa atcgtttaca    60720 gcttattacg agcttaaata tttatgaaga aaaagatatc atccagcaat tttgtgattc    60780
aaatggactg aagatcaaaa tacgtatcaa caatccgctc ttgcctacaa atccggaatt    60840
acggcgtttg actatttatt ttaatcataa taatgatgat gatcagtcat atctaatagt    60900
agatatgtac aacacgggaa gctatgagct agtgcctaca aatcagataa acacgcttga    60960
tggcagcttt ttaataggaa cacccttcgt gcaagcgcga ttttttgttgg tagagatctg    61020 ggtgcttatg cttattgcgc agcaaactaa aaaggacacc aaaaaaaataa tacaattttt    61080
```

```
tataaatcaa tatgaaatgc ttatgaatag tccttggccc agtatggagg ccctttttcc   61140
ctcaagcagt aaaagatatt taggcaacta tgtagaccct aacgcgctca taaagtgggc   61200
acaactcaaa ttaaaagaa  taccgccttt ttatcctgga aagccggatg aagaatcatg   61260
ttaagccgat taaaaatca  tgttaagctg gttgaaaaat catgttaagc tggttgaaaa   61320
actcttggtg aaagcacgga tgtaatatta acattggccg ctcgcatttc gtgttgaaat   61380
acgatggaag agcgacggct atctaccatg ccgatatcgg cctggacatc acagttcatg   61440
cacttgtaga tgggatgact cgcgttatag atggcaggct cgccacagtt tctacagatg   61500
taggagatgc agccatccga gtcgtcgtgc gattttccta tgatggtttg catggcgccc   61560
tgcgccgtaa gcacccaatg ctccatttct cccagacgaa gacctccgtg cgatcgtttg   61620
ccgtccaacg gctggcctgt gagggcatcc gtgggcccat agcttgcaac ggcgtatcgg   61680
tcatccagca caaattttg  caggcgctgg tgataggtcg gtcctatgaa gatggccgca   61740
tcaaagtact cgccggtctg gccgttgaac atttttggc  atccattgaa gcgtagacct   61800
tcttgcgcca gtctttctga aagaagctgc acattaatag gcaggaatgc ggtgccgtct   61860
gttaccaccc cctgtagggc atttgctaga ccaaccgtgg tttctatcat ttgaccgttg   61920
gtcattcggg agggatgtga gtgggggttt acaatgaggc cgggctgcaa tccgtcctct   61980
gtgaagggca tgtctgaagt gggcagggcc agcgccgcaa tgcccttgtt cccgctgcga   62040
gaactcattt tgtcgcctat attgagattt ctttcatagc gcaggcgcat gaggccaaag   62100
atctcgtcat taggcccatg gggacgcatc acagcatcca cgacggccgg ctcatcgaag   62160
ccgtacatga cagaccggtc gatgtatttg ttgagttcgt ctttttcgcc ccgtatttg   62220
gccactttc  ctataatgat gtcgcccttt ttgaccaccg ttcctacggg cacgaatcca   62280
tctacaagct tttcgtaatt agcaccaggc ttaagatttt tggtgattaa agggtcgggc   62340
ttcccaaacg actctatatc gctttctaat tctacttttt cttctcggta aaggtgccg   62400
gcaaagccgc ccctgtcaat aaaggactgc gacacgatca cagagtcctc ctgattgtag   62460
ccgccgtaga tcatataagc cacaatggta ttaagcccgt tgggtatgac atagttatgt   62520
gctatggtct ttacaagcgg catttcattg taaaactgga agaagcggtt catgtcgaca   62580
cgatatggcc agctaaagca ataccagccc cccgtttgcc ggccttggtt tgtttcatag   62640
gtaacacgcg caggttgggt acagtttgcg taggggaca  ctaggcggc  aaggcccaaa   62700
atagcttggg gcacgtccac gtgtgtgaaa cgacgcgtta catcatgttt atgtttgcgt   62760
agctcgatga tggagaaggc aacaagacag ttttccgcct cctcgggggt aatgaactca   62820
cagatgccct gtgctacgag atcttcaagt gtaagcgttc cggctaaaat gtcttttgcc   62880
atttgaggcg taaatcgcgt atttttgaatg aaagggattt tatgttttc  ccagtcttta   62940
tcgcctttt  ttctggcctc tcggccttg  tagcaggctt gattgtattt ttcaatatta   63000
ttatctacaa tgagtagggg gcgggtcagc ctaccgacgt ccaaccaaaa ttctacttcg   63060
tctaccatgc tatcccagta gatggtggta tggggatgca caaccttgcc ctcacggcga   63120
agcattctat accgctgagc aagctcaaag gcattggtgc agcagccgat ccattctccg   63180
ttgataaata cgcgcgctag gccctttcgt acaatgtcct tgttggaaac atcggctaac   63240
tgttgaatgg ccggatctga tagaaggcgt tgttttaacg aaagtacttc tccggcggtg   63300
cagacattgg cagtgatggc taactgttta gacatgccta ctttttcacc agtatcggct   63360
gactgggcta cgcagatgta tccaggatag gatgcgtgca cgcgacgcat catgtcagcc   63420
cttttctgttt gtttggatgc gttggtggtg ttatgagtat ttaccgtacg caatgctgaa   63480
```

| | |
|---|---|
| atggtattta ataaattttt tctttccaaa ctttgagtag atactctgtt tacaatgggg | 63540 |
| cgctgtcgca ccatgatggt tttatttcct gaaatgatag actgttccat actgcgatta | 63600 |
| agatcggagg cggtattttt tgataaagcg gcagaaaatg cctcgataat gtttcgctga | 63660 |
| gtaagctcct caaaggctgt tgtttaaga agttctttga acccattgat gatgggtgct | 63720 |
| atcacggaag tattaaaaat agccttaaag gccttggcga gtgagacccc tgagccgtgc | 63780 |
| acccgcttgg tgcggtagct atcacggtcc gtgggtggaa acacattcat aatgacaaga | 63840 |
| agtattttat gaataagcag gcctaaaaag cgcagctttc gtacacgtgt atctgcggtt | 63900 |
| tggcccatgt gtggcagcaa tattttgtct aaaatagtaa gttgtctttc atttaagtat | 63960 |
| tgtaccgcat tttcatcgct tttgtaagca gatgggtttg agacaaattt ggaaaccttc | 64020 |
| tcggataaaa actggataat ttttttctcgg ttcagctcgt gttggaccgg ttgaaatatg | 64080 |
| gggtctaaaa catgaatgga ttttttccaga atttctatca tgaaggtatt cacaagggag | 64140 |
| ttggattcta gatcaaatac cacttgctca atgatgctgt catcgcctgt cattccaaac | 64200 |
| atgcgaaaga tgagatacca aggtatgcga agttttgaga acttggtgct attgatttca | 64260 |
| atggtaatgg cgccggtggt catgtagcgt ataataattt gagagctatt ttcgaaggca | 64320 |
| cctcccggtt gggagataaa ctcgccgcga atgatttcat tattcccttg ttgcatggta | 64380 |
| tggtaatgga tgtgaagcgt gttaaagcgg atgttttcta agaggtctac gacccattcc | 64440 |
| ccgcctcggg ctataaagta gccgccgggt tcattagggt cttctcctat ttctttttt | 64500 |
| gcggttttg ataggtgatg agtgtggcag cggttgctgc cccgcatgat gggaaatgta | 64560 |
| gatacctgaa aaggaggaat acttgctcgt tttacctcct gccgaccatt gctgtagtgc | 64620 |
| gccgttaaaa taacctcggc ggctagatta accgggcccg aataggaaag gccacacagg | 64680 |
| cgtgccttat tgggtagtaa atttatcttg tttccctgtg aatagtttcg atgttgcggg | 64740 |
| cgttcaatgt tcacatctgt aaagttaaat tggatctgaa ctgattcccg aagcttatct | 64800 |
| atttcagtat ggtcgcgttg gtcttatac gtaatatcca cgttaaacat ttgtttttaca | 64860 |
| atttgcggaa ttccattgtc cataagatcg tcgaagcttt tgatgttata ccctatcaat | 64920 |
| cctgtagagt ttactgcagc ggagataaag ctcagcatat cagcctctgt aagctcctca | 64980 |
| ttatccacgg tttcaatggg gccgtaggtt atttgcggcc gcaagggttc catgattatg | 65040 |
| aagtactaca ttaatattca gttattcttt aaaataaatc tttatttata aatcttatttt | 65100 |
| ataaataaag aatgccttat gcaagagaca tcacaaagtt tattacggca acggaaccag | 65160 |
| aggtgggtct tccccctgttg gcgctgcagc gctccaaatc catcatagg gttattcttc | 65220 |
| ttgtaataag tttgttattt attttcattg gcattattat attatcagtg agtagtggtc | 65280 |
| ataccacagc agcctctata tttatcgtat tgagtcttat cctaggtggc ggtggttttt | 65340 |
| ttcttattta taaagataat tcttaaccca cataaaattt gaaaaaatat agagtaagaa | 65400 |
| aatgtccaat tactattatt actatggcgg ggggagatat gattggttaa aaacagtaga | 65460 |
| acccactaat tttttaaaaa tcgggttgcc ttaccaggca cacccattac atcttcaaca | 65520 |
| tcaggcaact actcccccat ctatcttaga aaaatttaaa cgagcagaca ttcttcttaa | 65580 |
| tgaggtgaag gccgaaatgg acccactcat gttacaacca gaaaccgaaa aaaaactatt | 65640 |
| ccagatattg agtagtattg atatgttcaa aggtctgcga aaaaaagtag aattcacgta | 65700 |
| caatgctcaa attgttacga atgcttggct taaaatgtat gagctgctaa ataccatgaa | 65760 |
| ttttaataat acatctcagg cattttgcaa ttgtgagctt ccaggagggt ttataagtgc | 65820 |

```
aattaaccat tttaattata caatgatgca ttaccctact tttaactggg tagcttcctc   65880
cctttacccc agttcggaaa cagatgccct ggaagatcac tatggtcttt atcagtgcaa   65940
tccggataac tggttgatgc aatctccttt actgaaaaaa aatatagatt ataataacgg   66000
ggacgtaacc atcgctagca atgtaaaaaa cctagcgctt agagccacac aaaggctgac   66060
gcccatccat ctatatacgg ctgatgggg tattaatgta ggacatgact acaataaaca    66120
ggaagaatta atcttaagc ttcactttgg tcaagccctt acgggtttgt tgagtcttag     66180
caaaggcgga aacatgatac tcaaacacta taccttaaat catgcattta ctctttcttt   66240
aatatgtgta ttttctcact tttttgagga actatacatt accaaaccta cctcctctcg   66300
gcccacaaac tctgaaacct atattgtggg taaaaacaga ttacgcttat ttaccccaa    66360 ggaagaacaa gtccttctaa aacggctaga attttttaat gatacgcccc tcgtagacct   66420
aagtctttac caaaatttac ttgaaagcgt ttactttgcc gtagaaacaa tacatctaaa   66480
acaacaaata gaatttctaa acttcggaat gaaatgttat cgacattttt ataacaagat   66540
taaactactt aacgattatt tagctccgaa aaaaagatt tttcaggata ggtggcgtgt    66600
gcttaataag ctttatgttc ttgaaaaaaa gcataaactt aagctttgtg cctcctaggg   66660
atctgttgct taatttaaca gatgcaatct taacagatga aaactaaaaa gtgtgttcat   66720
acaaggattg tatttatgaa tatttattaa catataaggt tgtgatgtaa cactgtataa   66780
cctatataac tacactatga agcacggcgt ataataattt atattgaaca cgatgttgac   66840
tcatttattt gcaaacaaat atttgtttgc aagacgtttg catgcattta ctaatatgtt   66900
gttgactagt ttatttgcaa actagatgtt tgattgcaaa ctagatgttt gcacgtattt   66960
atttgaacta atatacactc cttgttttat ttgttatata cacagcatac ataagtgtat   67020
attgtttaca cttatgttta taactcgacg taataacatt ttacacgctt ttttttgca    67080 aatcttaata atattgtatg ataaatcaaa caatgtctta tatatgtggt ttattatttt   67140
aggcgccgca agatgtactc cattctcatt gcatgcttgg tgttattact ctgtctagtt   67200
atatatgtcg gtcatcgtgc cgatcatgca cgaaaatatt tagaaggaat gtggcatgga   67260
gatccggttt ttctaaaaca gtcggggcta caatcctttt atctctacat acaacctgac   67320
catacatgtt tttttagcat tgtgaataaa aatggtgaaa agctgatgga aaccaaaata   67380
ccttgtacga taacaaataa aatatatatg tttttttaaac ctattttga atttcatgtt   67440 gtgatggaag acatacatag ctacttccct aagcagttta actttctgtt agatagtaca   67500
gaaggtaaac ttattttaga aaacaatcac gttatttatg ctgtattgta taaggataat   67560
ttcgccaccg cactaggaaa aacggttgaa aaatatataa cacaaaatta atcatgtttt   67620
ctaacaaaaa gtacatcggt cttatcaata agaaggaggg tttgaaaaaa aaaatagatg   67680
attatagtat attaataatt ggaatattaa ttggaactaa catcttaagc cttattataa   67740
atataatagg agagattaat aaaccatat gttaccaaaa tgatgataag atatttatt     67800 gccctaaaga ttgggttgga tataataatg tttgttatta ttttggcaat gaagaaaaaa   67860
attataataa tgcaagtaat tattgtaagc aattaaatag tacgcttact aataataata   67920
ctattttagt aaatcttact aaaacattaa atcttactaa aacatataat cacgaatcta   67980
attattgggt taattattct ttaattaaaa atgagtcagt actattacgt gatagtggat   68040
attacaaaaa acaaaaacat gtaagtttat tatatatttg tagtaaataa tattttaat    68100 tacttaaaat tttatatat aagttttga tactatatta taaaacatat gttcataaaa      68160 tgataaatact tattttttta atattttcta acatagtttt aagtattgat tattgggtta   68220
```

```
gttttaataa aacaataatt ttagatagta atattactaa tgataataat gatataaatg   68280
gagtatcatg gaatttttt aataattctt ttaatacact agctacatgt ggaaaagcag   68340 gtaactttg tgaatgttct aattatagta catcaatata taatataaca aataattgta   68400
gcttaactat ttttcctcat aatgatgtat ttgatacaac atatcaagta gtatggaatc   68460
aaataattaa ttatacaata aaattattaa cacctgctac tcccccaaat atcacatata   68520
attgtactaa ttttttaata acatgtaaaa aaaataatgg aacaaacact aatatatatt   68580
taaatataaa tgatactttt gttaaatata ctaatgaaag tacttgaa tataactgga    68640 ataatagtaa cattaacaat tttacagcta catgtataat taataataca attagtacat   68700
ctaatgaaac aacacttata aattgtactt atttaacatt gtcatctaac tattttata    68760 cttttttaa attatattat attccattaa gcatcataat tgggataaca ataagtattc    68820
ttcttatatc catcataact tttttatctt tacgaaaaag aaaaaaacat gttgaagaaa   68880
tagaaagtcc accacctgaa tctaatgaag aagaacaatg tcagcatgat gacaccactt   68940
ccatacatga accatctccc agagaaccat tacttcctaa gccttacagt cgttatcagt   69000
ataatacacc tatttactac atgcgtccct caacacaacc actcaaccca tttcccttac   69060
ctaaaccgtg tcctccaccc aaaccatgtc cgccacccaa accatgtcct ccacctaaac   69120
catgtccttc agctgaatcc tattctccac ccaaaccact acctagtatc ccgctactac   69180
ccaatatccc gccattatct acccaaaata tttcgcttat tcacgtagat agaattattt   69240
aatatgtact atatattaat tatttaacct ttcaagctgg tcttcattta aatttaaaat   69300
ccactaataa aatgtatttt ctagtagcag atcatcgaga acatcatgtg attccttttc   69360
ttaaaaccga tttccatcac atgcatcaaa atcctataca aaaaaatcaa gctctcctag   69420
aaatcaaaca gcttttact ggagattatc tcatctgcaa aagcccttct accattctgg    69480
cctgtattga acgaaaaacc tacaaagact ttgcggcttc tttgaaagat ggacgttata   69540
aaaatcgcca aaaaatgctg tcgctgcgag aacaaaccaa ctgtcaactt tatttttttg   69600
tagaaggccc ggcatttcct aaccctcaaa aaaaaattaa tcacgttgcc tatgcaagca   69660
ttattactgc tatgacgcat cttatggtta gagatcatat ttttgtcatt caaacgaaaa   69720
atgaggccca cagttcccaa aagcttgtgc agcttttta tgccttttct aaggaaatgg    69780
tgtgcgtcgt tccacctcc ctcaccccca cggatgaaga gctatgcatc aagctatggt    69840
cttctctttc tggtatttca ggcgtgatag gtaaaatctt ggcaaacact tgttccgtag   69900
ctcatttggt tcatggaaag ctttcatcgc agaaattga tcagtaaaaa actccctcca    69960
accgaccatt ccccaaaaaa gtaaaacgta tgcttataag cattagcaaa ggaaataagg   70020
agttagaaat aaaattgctc tcgggggttc ccaatatcgg gaaaaaatta gctgccgaaa   70080
ttttaaaaga tcatgcgctt cttttttttc taaatcagcc cgtagaatgc ttggcaaata   70140
tacaaatcgt tcaaaaaacc cgtacgatta agttgggaat gaagcgagcc gaagcgattc   70200 attattttt aaactggtgt ggctctgccc atgtaaccga tgatagccaa aatatcacag    70260
aggcgtcgcg gtccacaatg caggtcgcga cgcagtccgc cgcaatacag cccgctgcaa   70320
cgcagccatt gcacgaagta tcagatgatg catcatcaga tgcttcatca cccgtagggt   70380
atcaaacatt atctaaagaa atgttattga acacagcctg atgttaataa ttcactacat   70440
ctaaagaaat gttaacctcg atactaaaaa gtcattgaac acaactactg gggcgctaag   70500
ttgtccaaca catctaaaga aatgtcaaca tcctcgatgc taaaagggtc atcgagccgg   70560
```

```
tcaataatgt cttccccaaa aagtccggga gaactgtagg ccgagatgtc gtccatggag    70620
ctatcttccc cagagcacac aaagtcctct ccaaaaatca taaagttaaa tgcaccgggc    70680
ttacttaaca gcttttcgct ttgaataata gtgttgagtt ctgtcagcgc aaactctctc    70740
acaatattca caacccagga gggctcttta atttcataca gcgttaagaa acttatacat    70800
aaaaattcta tagagtaaag caaggcgctg gcaggatctg ttacccgtag gtgtttaaat    70860
gtagtgtgat attcattcac aacgttaggc agcaccttt ccaaatcctc cttttcctcg    70920
tacgacaggt gctttacaag cctttcaaca tgtataggag gcttgttaaa tgtactaacg    70980
tgccgcaaac agttataatt atataagaaa atacgtacgg cagagtcgac cgccatgagc    71040
cttggatcat ccattgaggt aggtggtggc ggggcaccct ggccttccct gatgtctgcg    71100
taggagcgcc cctccatggc ccctatggcc tctatcacag caggactgat atccaaaatc    71160
ttggccgtct tgattatttt tccgtaatcg aaagtccatg gctcctgtgg aggcttgggt    71220
tgtgtttcgg tggagggcgt ggtcatatct ttctttattt gaatagaacg gatcgacatc    71280
ttttccttat cgtactggtc tttataatta ttataatagt catgaactaa ttcgggttga    71340
gaaagatgat cgtatataat ataggtaaaa agtccgcact tgacacattt tttatcctgg    71400
aagtcgtgta atcctccctt ggggcagcgt gactcgtaga aggcataaaa ggtgttaaat    71460
tctaagctcg cctttagggc tgtttggacc tttttatgt ttaattgccc cacctcatgt    71520
tgtagcacgt ggcatacaga acagcgtaga tcggcaagtg cataatggtt gtcaatttt    71580 tttatgacgt ctttgcgtgt tacttcaatc tcggcgggtt tctgcgaact gtctacggcc    71640
ttgtaaacgt aaatggtcca cttatgagga agccccctt catcgtatag ggttgaaatg    71700
ggaagccttt tatactcaaa cagccgagtc cgttggtcgg ctcttcctgt gttaggatca    71760
aatatgttat aaaatcctg ctgagcaagc agggcctttt gctcgccata agcattttcg    71820
tacgttttga attctgcaag ttcggagtta aaattaggtg cattttgtaa atacttaaga    71880 ataattcat aggctctaag gtaaatgaga gttgaggttt tttcctcatc ccgtcctccc    71940
caccacaccc gcaggctttc ttcttgaaaa tagatgtcat tcagacgcgt caactgcgta    72000
aaatcaggcc gatatttaga ggtataaatt ttatcataaa attctttttg cgataatagc    72060
tcggccgggg tacgtcctat cacggttta aactcatatt cagcctcctt gggagtccgt    72120
ggtttgtgca tagggatgct gccgtcaata cgggccactg tggcagcata atcatacatg    72180
gggtccagca gaatctctgt caaaagtacc ttggtgtcgt cctgcacgct aagcccttgt    72240
agcccatttt ggtggataat ttttttgaaa gcctcccgaa aattattagc aatccactga    72300
tccgtaatct cagatagctg atttattata ccgctatatt gctgcatcat tttctccaaa    72360
agaaaggtca cgtatgcatt caaagagcta tccgccttca ttccatgaat ggtaatcgta    72420
agaaattctt tatttttttg cgagctataa atgagattca aaatataggc atagatgtag    72480
atcacagcat acagctgcgt taaaggatcg taatcctctt ccttttaat attttcgatg    72540 ctatacacga gcggcaggca gacatttacg gctatattgg caaactgttt cacgtctaca    72600
agctttccaa agtggataaa cgtgcaggcc ttcatggttt cctgccaaat aaaaacacgg    72660
agcttactat taagatcgcc gatgatgccc acatctgccg tacgatcctc ttgaataaaa    72720
tgggccagct cttcgccaca aattttgcaa aagtaggagt aaataagccc ctggttgttt    72780 tcttctcct tgtttattcc tgaaaatttc attagcttgg ttcgcatggt gtcgtaggac    72840
gcttctgccg cttgaagctg tataagcatg tccacatggg gacaaagcag cttaaacccg    72900
caggctttgc atagattcca attggtggta ttgtttttt ccttgtagag tacacgaata    72960
```

```
ctttctaata cttttaataa ctccgcgtat tgaagacccg aacgcaactg ttttaccagc    73020
ttgagatgag cacatgcatt ttttttcttgg agttcccact gttttttaat gtttaggtat   73080
tctgttgtaa taagttctgc ctcctgtttc ccacaggctt taatgacttc ttgaaggatg    73140
ctgttagggt catccacttt accctccatt gtaagaattt cacgtatagc atccgactgc    73200
accctaccta ttttttcttc cataatttta aaatactgtc tcgcctgggt aatgacctct    73260
gtgagcttca tgtccacctg ctgcagaatc atttgctcct tttcacgctg ttcagcatgt    73320
tgtaaaaact tttgttctac agggttccaa agcacctcca aatagcctgc tctatatagg    73380
tcataaagca agggcatgta tcccgatgta aaaccgggg acaccgagta catcgtagac     73440
aactctttta aaaaaatat cacgcgctta atgttctcct ccggttcaat ctcctcggtt     73500
tcaacgatat tagatatatg actgccctga tcctcacggt ctagctttcg gtgtaccatc    73560
tcctctgcta gccgattaat gagccagcta tgcccgccgc tccgcaaaaa cttataaagt    73620
tcgatatact ggtgcgtaaa ctggatgatg ttttccttgg tggttacgac aacccccttct   73680
ccgttttttt tccaggtttc ttgatccacg catttcataa atactcgaat aaaattggtc    73740
aaattggctc ctgaggcgac gtagcccaag gtttcaggcg agaaggagcc tatctcagcc    73800
atacgcataa aacactgcgg ggaaaaagtt tttagccgca acttaagtcc atagatttca    73860
atggggcttt ctgcgggaac ggccaggtgc gtcccattaa ttaaaaaaat ttctttgcgt    73920
gtgctagggc gaacacgtaa ttcctttttt ttttcactca cgatggggac cacatcgggg    73980
tctaccagca gttgacgtat gtaggcctct atgggcatgg atagatcggg cagctttgac    74040
tgctcggcgc gaacatggtt cacaaaatct tttagagtga aagaaagtc tattaaacgt     74100
atgtttttta tatcattaga cccttttaagg gtagagtaga tttcatccac tagtgcctcg    74160
atttcctcat tattgagcga taagatatct gtgccacggt ggactatttg cgcgatcgta    74220
attacttcct ccattagata gaaactgaat attatattta aataaatac aaaatgtcaa     74280
atgaaagttt tcccgaaacg ttggaaaact tactttcaat gttacagacc aaacagcaaa    74340
acgcaattca gtcagaggtg attgaatggc tgcacagctt ttgtgaaacc tttcacttaa    74400
aaatacactg ccataaacag tttattccta gcggggaaaa aaaacgagct aaaatacccg    74460
ctcaagaaac acagggaaac acgcagcccct cccaccatgt gtaccgggtt gttctctcca   74520
gagcacagcc agtcaaagca caggaatctc tgctaacaac catgtgcaac ggactggtgc    74580
tagatgcaaa cacatggaca tgcctagcca ttcctccgcc tgcgcccttt caacaggcga    74640
cccgccaggt ccaacacttt taccgtaaca atttctacga agtggttccc atccaggatg    74700
gcacccttct cacaatctac cactgggatg accctgaata tggcccctcc tggtgcctag    74760
caagtaccca cggatatgat gtgagtaact actgttggat aggcgacaaa accttcgccg    74820
agcttgtata cgaattgctg cagcagcact ctacctgcga cgtcaccctg gaaaaaaata    74880
aaacgcgggg aacgcgtctt ttcttttgata acttaaatcc cgattactgc tatacgattg    74940
gaatccggca ccataatttta cagccgctca tctatgaccc tcaaaatatt tgggcgattc    75000
aatctacaaa cctaaaaacg cttaaaaacgg tatatccaga atactacggc tatataggca    75060
ttccaggaat tcagagtcaa gttcctgagc ttccccagta tgatttacct tatctaatac    75120
gatcttataa aactgctatg aatcaagcca aaaatgctat aaaaaatggc aaaaaagaca    75180
agggatactt taattatggc tatttactca tttcgcgagc gcctgccatt actaaaagta    75240
cttctaatgt tttgttaaaa tcgcctctgc tggtattttt acaaaaaagt gtgtaccaga    75300
```

```
aaaaacacaa tatctctaac agccagcgac tagaatttat tatactgcaa aactacttga   75360
tgcagcattt tcgagatcat ttcattgctc tatttccgca gtacatatcc tattatacga   75420
aataccaaaa catgttgaat atgattatcc atagtattgc aactaaagat aaagatcatc   75480
cctttgcagg agccgtggta aaaaagtgt tggaagatat tgaaacgcc gaaaacatta    75540 ttgatcatac aaccattcaa aactatgccc atcaaagcaa gtacgccatg ctttacttgt   75600
caattatttc ccattttaa tctaatacgg ccaaagccgc gggttttta ataaactaac     75660 atttaaaaaa actgttttat taaaaattat aatacttta ttatatatgg aacatccatc    75720
tacaaactat actcccgaac agcaacacga aaaattaaaa cattatgttt taatccctaa   75780
acacctttgg tcttatatta aatacggaac gcatgtccgg tactacacca cacaaaatgt   75840
tttccgagtc ggtggctttg tgcttcaaaa tccctacgaa gccgttataa aaatgaggt    75900 aaaaacagca ataagactgc aaaatagttt taacacaaaa gcgaaagggc atgtaacgtg   75960
ggccgtccca tatgataata ttagcaagct atatgccaaa ccagatgcaa ttatgcttac   76020
catacaagaa aatgttgaaa aagctcttca tgctttaaac caaaacgtac tgacgctcgc   76080
atcaaaaata cgttaaatat aattttttgta gaggataaaa agctatttta gctaaaaaat   76140
aattcatata cgtttatgca gaggaagaac ggtggctttc aaattcagat tgcatccacg    76200
tagaccgtag cgttttttt gcttctggtt tatatcgtaa accgtaataa acatcatcat    76260
ttgtatccgt tggatctttt tcccactccg gataaaaaat cggttttctt tttttggtc    76320 gttttttgca gtaagctgta aattaaggga atatagctta tcgaaaagtt gttcctgatc   76380
catataaata gcagcatata ttaaaaaaaa taaaaaaaga cgcttcaacg agtcagtacc    76440
actgcttgcc aacgatttac gttggttggt gcattatggt gatatagtaa tgagtgcctg    76500
cacaagtgct tgcacaagtg cctgcacaag tgcttgcaca agtgcttgca caagtgctta    76560
cacaagtgct tgcacaagtg cctgtacaca ttactgcatc gccaaagcac ctgcaatgcc    76620
tacttcctca acagagtacg ataactaaat gcttttaagc accgcttgcg tcgatgtgtc    76680
cttcggggca atcgggttca attggatcca atattattag tcataattac ctaatactta    76740 ttcaattta tctttttac cttgtaagat ttaaacagcg ttttagcttg tttaaagcaa     76800
cgtttaaaac aagctaaaat gctgtttaaa acaacgtttt aaacaagtta aacaaataa    76860 gcttataaat ataccatgac aaaattagcc caatggatgt ttgagcagta tgtcaaagat   76920
ttaaacctaa aaaatcgagg gtcccccctcg ttccgcaaat ggctcacatt gcaaccctca   76980
ctgctgcgct attcgggtgt gatgcgtgct aacgcctttg acatcctaaa atatggctat   77040
cctatgcagc agtcaggtta tacggttgct acgcttgaaa tccactttaa aaatattagg   77100
tcttcctttg ccaacattta ctggaaccgt gatagcgagg agcctgagta cgtctgctgt   77160
tgtgccacct atcaatcgca cgatggcgaa taccggtatc gatttgtttg gtaccaaccc   77220
ttcatagagg cttataatgc catagaggcg ccctggatc ccctggaaac cattatcctg    77280
aacctcattg cggcacgaga tctagacttc gttgttcaca tatttcctta taataagggc   77340
catgaagact attttggcctc cacgcaactt attctcaaaa tctttattgc gacgctttta   77400
atggacattt taagaattaa agacaacacg ttggacgttc acttaaattc cgactatatt    77460
attgtgatgg agcggctttg gcctcacata aaggatgcca tagaacactt ttttgaagcc   77520
cataaggact tactagggta cttaattgcc tttcgcaatg ggggaactt tgcaggaagt    77580 cttagacccct cctgtgggca aaagattgtt ccctaacga ttcgagaggt cctacaaatg    77640
aatgatatta atttagccgt atggcgggag gtgttatta tgcaggaatg ttccgactta    77700
```

```
gtcatcaatg ggatagcgcc ctgtttcccc attttaaca cgtggacgta tttgcaaggt    77760
attaaccaga tttttttga aaacacgtct ttgcaggaga aatttaaaaa agattttatt    77820
gcccgagagc tttccaaaga aattatcaag ggccaaaaaa cgttgaatga caaggagttt    77880
aaaaagttaa gcctacatca aatccagtac atggaatcct ttctacttat gtcggatgtt    77940
gccattatga ttaccacaga gtatgttggc tataccttc  aatccctgcc gggtattatt    78000
tcgcgatcca gctatttatc ccccatcgtg aaaacattt  tgatggacga agactctttt    78060
atgtccctac tatttgacct atgctatggc gcctacgtgt tgcataaaaa agaaaatgtg    78120
attcacgcgg atttgcacct gaataacatg acctactacc atttcaaccc aaccagtttt    78180
acagatcgca acaaccagg  aaaatacacc ttaaggtca  agaatcctgt gattgccttt    78240
ataaccgggc ccaaagtcga aaccgaaacg tacgtgttca agcacataga tgggttcggc    78300
tgcatcattg actttagcag agccattatg gggccaaacc atgcaatcaa gcttgagcgg    78360
cagtacggcc tcgcttttgt aaacaccttt taccgcaatc aaagtgagca tattttaaag    78420
gtattacggt actatttcc  tgaaatgcta accaatcgcg aaaacgaaat acaggggtg     78480 attttatcaa actttaattt ctttttcaat agcattactg ccattgattt ttacgccatt    78540
gctagaaacc tacgtagtat gctttctttg gactatttac acacctctga ggtgaaacga    78600
aacgtagaaa tttcgcaaac attttggat  acatgtcaat ttttggagga aaaggccgtg    78660 gaattttgt  ttaaaaatct tcatactgtc ttatctggca agccggtcga aaaacggcc     78720 ggggatgtgc ttttacccat cgtatttaaa aaatttttat acccaaatat tcctaaaaat    78780
atattacggt ctttaccgt  aatagatgta tacaattata ataatataaa gcgttattct    78840
gggaaagcta tacaaacgtt tccacccctgg gctcaaacca aagaaatctt gacgcacgcc    78900
gagggtcgta catttgaaga tattttttcct agaggagaat tagttttaa  aaaggcttac    78960 gcagaaaaca accatttgga caaaatttta cagcgtattc gtgagcagct tgctaatgaa    79020
aatttgtaag gcttgcagtt cttgtatggt cagaacctat gtcgatggaa acattatttt    79080
tcgctgcagc tgcggcgaaa gcgttcaagg ggatagtcag aacttgctcg tctctagcaa    79140
ggtgtaccac accggggaaa tggaagataa gtacaagatt tttattaaaa atgcaccctt    79200 tgacccacg  aattgccaaa taaaaaagga ttgcccaaat tgtcatttag actatttgac    79260
acaaatctgt attggaagcc aaaaaatcat tatattggtg tgccgctgtg gctatatgag    79320
caacagagga taaccatat  catcccaccg aattatgaca ttcctttaaa accgtccgcc    79380
taaatagttt tcacacctttt ggtggcagac tattttataa aaagtaatgt tggttcatga    79440
agataaagtg tgccaaagaa acttttataa acaaatgatt aatgtaggtg ctagtcgtgt    79500
gtacttaaac agggtattct atagccaagt attttctata gccaagtatt ttctatagcc    79560
agtattagtc aagtatttag atgtcagggt attttatag  ccagtatttt tctatatgta    79620
caaactattc cagtaaacat atgtgtgttc tttattgagc agcatcatgg cattaacaag    79680
tttattaaac tgctctaatg ggcattaaat gacaactcgg tgcttagcaa aagtgcctat    79740 acctttaac  aattagggcc gggaggcatt cccagctttt ttctataatc agccatacag    79800 taccccctgag cctcatacac gggaataagg tccttccatt ccttgttggg atcggcgggc    79860
cagctctcaa atgaggtgtg aatgtaaggg tcctgttctt tttccttaat gaagcgttta    79920
atctccattt gatgttgttt acttttttgt ttgcggcgga gcgtgttccg caccaatacg    79980
taaaaaatac caagaatcac acataaaaga attattaaaa aaaatatcat catcgcgggg    80040
```

```
tttaaaaaac gatcccatgc aacaggaatc gttcttaaaa ccttgtctgg cagggctgta   80100
aacatgaagt ctcctcctat aatcggggtg ggactgtagc ctaacagttc aaggtcctgt   80160
cgttctagat acttattggc gaactgccca cccttttgccc ccgttttttt attaatcaag   80220
cagcgctgca ttttccacca ttctaaatct tcaggagaaa gctcaatgcc atatatcaac   80280
tttaacgtta ttgcatcttt ttcaatatcc ttatcaattt ggctgagctt ttgagcttta   80340
agcgggtcta gtgtgtactt ccatttaaac ttagtgtcct gtagtttggc tacatgaaat   80400
acggaacatt tcggcggggc ctttgtgacg cccttacact gcggaagttt atcattagga   80460
caggcgcata gatgagactg cgccacagca tcgcgaacta catcgcagac ggagtacatt   80520
ttcctcctat gttaaacaat aaatttttt catagctgaa atttgtgggc ctatcttttc   80580
ccttgcccgg ataataatta aagggagtg ttgaaacatc tgggagagaa ttgcttaaaa   80640
aatgggtttt tgggaggggt aactgcgact gttgtacgtc gttggccagg gagattctat   80700
atgccgggct aaaggtgcaa cgttcctgtg aacaacttag tacgcgcgtt gttaatacaa   80760
atggactggt attagcaaac ctcgtaaact cttccggact tgtttgtttt tgtatgatgt   80820
ttagcaggga gtctgccttt tcgagaatcc aaagcgtcgc attgtagtaa aataaaaata   80880
gcgacttatc ggcaggcgtt gcaaaagcgc cgtatagaaa ataaagcagt aagtactggg   80940
gagacaccac aataaggtta tcttgaatga tagatatcgc tagctctttA aacatagtgc   81000
taaaaaaatg tatgtcgttc gtcttgaata taggggggact atagtccatg tagggctcac   81060
atatctcagt caggtgaagg cccatttctt ttatgacttc ttccggggttg tacgtcgcta   81120 acaccagcgc gggataggct ttgggcatat ccacggtaag tgttatgttt ttatcattct   81180
tatggtagga gtaagatggt tgtggaaatt ctgttttcca ctccgggact ttgcaggtaa   81240
ttctcagctc atttagagtc tggtacagga gggcgtatgc cgcaaagccg tgtatggcca   81300 cttgttaaa gggaattgaa aacgtttttac tttcgtatgt cgacttcaca ggaacaacgg   81360
gaatggggta atattttct atgaggttat accgctgcaa atccttttta aacctgctaa   81420
aaacatcttc ccttggtggg ttatcaaaag gaaagcaaaa tgctaggtgt agccccggccc   81480 gctggtaatc ggggtgaatg atttttaaggt ttttatacgt taatgtgggt atggtgttaa   81540
agatattggg gggcatatat gaaagatcag caacccacac aaagtccgtg cgcacccgca   81600
tggtctgcac atggatggcg cgcaccgtgc ccacctgctt gaagccctttt tcatacaaaa   81660 tgtcagcaag ttcgtaggcg tcctcaacgt ggttggggga aaacatatca aagtcgggtc   81720
tttctccctc gggataaaatt gagctgcctt taagatgcag ggcataatca atggcaatcc   81780
ccccgtacaa aataagcttt ttctttatga taaattcgcg gaccacctcc aaagccgcct   81840
caatctccac ggcatttgcc tcacgtttttt gagcaatgag ccggtactta gaaacattaa   81900
aatcagtctt tagtaaagac gtcataaata gtgtttaata tatattaaag gtttgaataa   81960
aatactaaat agtaaaaatg gatgccctat taaggaaat agaaaagtta tcgcagccat   82020
ccttgcagaa agaaaacaat gatgtatgcg atctctgttt tatgcaaatg aaaaaaattt   82080
ctaactatca gcttttatgc gaagagtgcg gtcagctgaa ggactggttt gaacctgaat   82140
ataatgaaaa attcacggta tattctcgtc taaagatcgt gggtgccaat agttcctatc   82200
accagcgcga tttggacaag gccaactcaa gtgactatag ctccttgcaa tttcatcaca   82260
ttttagagga gctcaaatcc ctaaatgtta agtatatgga tgcggggcaa aagcccttc   82320 ctattccaggt gttaaaagaa actgctcaca gttataacca agtacaacaa catcgggtca   82380
tacgcagcat tacaaagctt cagatcttag ccagtattct acgtagcatt tgtttaaaat   82440
```

```
taaacattgc ttgtacggtg gcagacgccg cgaggtttac tcaacttaat accaaaggga   82500
tctcaagggg catggatctt ctgcgctccc tatttgtaga caataaaatt actttaaacg   82560
ttgatttaaa ccctatagac agctttatta atagtaccta cagtgcctta caaattaaac   82620
aaatccacca agaactgcag gaggaaaatg tttataattt aaaagaaatt gttaagagct   82680
ttatattata cgcggatgag aagaacatcg gcgtcgatct taacaggaga accgttgtga   82740
ttgctacgat gtataatgtt ttacgccgtg cctactaccc catagaaatt gatacggtgg   82800
tgtatcaatg taaaatacga aaaaatacaa ttacacgtgc tcttaaaatg tatgaggatt   82860
actactccca ctttaagtct ctttatgagc agtatcattt aaacgcggca aaaaaattaa   82920
tttaaactaa acgtttaaac taaatgttta aactaaacgt taaaactaaa catttcgact   82980
aaagtttaaa acctagtcta acagcgggat gcccatttcc ctggggttcc atatttcaac   83040
aattttttga ccttcgggtg ttaccttgat gcagcgcatg acgagcagtg aattttcct    83100 attaaagagt tcttgcttag ctatatcaat aggactgcta tattttttt taagcattgt    83160 agatccatta attgccaatt gttgcgctct aacggcgacc aaccttgtgg cctcaaaggt   83220
ggttaaaacg ttggaggtaa tgcgctcgtt atcgggtata atgaccaatg tttgcgacga   83280
ggcctgcaca aagccctcgc agatggacgg agactccacg atctcgtcct tgtcctcgga   83340
ctcctcctca ctgtcgacga ggttctcctc ttccgtttcc acatattcct ccacgaggtc   83400
atccatgata agatcctcgt tgtcattatc agccatatta cactgttatc aaatgtactg   83460
tttaatacgc aaatggattt actacgtttt aattgtatgt cttcatgtgc aggctctagt   83520
ggaaagtaat tttctcacaa tttttggcac cgttacactt gtgcccacaa aaacccgcga   83580
tttttttatt ttatattact tttgaagta cgagtttaac cagtcgcttt caaaccttat    83640
gcgtctatct cgccaaaaaa cgctcacagc ggtgttggat attacctta aaaaaataac    83700 attaatttt accacagagg gcgtattgcg tatggattct acgaataagc caggcgtgcc    83760
actcgatata gaccccagt tcattgacct tgatagtatt ttaatggaac tggatcatta    83820
ggacctctcc cgcccattta aatttttagt ttctacaata ataaaatgcg cgaggaatca   83880
tgggaagacc acgataccat tcagctcacc gctcagcgca aatacctcgc cgaggtgcaa   83940
gctctagaga cccttttgac tcgagagctt tcagtctttc tcacagagcc aggcagcaaa   84000 aaacaaata ttattaatag aatcacagga aaaacctacg cacttcccag cacagagcta    84060
ctaagactct acgagcatct cgagcaatgt cgcaagcaag gcgccctcat gtatttttg    84120 gaaagacagg ggacctactc gggtctcatg ttggactatg accttaaact caatacaaat   84180
gctgttcccc cgctggaacc ccccgcgcta tcacggcttt gccatcgaat atttgtgcat   84240
ataaaaaaca gcagtgtgct gcctgagggc agccataaaa tccacttctt ttttacatta   84300
aaacctgaag tggttcaggg caaatatggg ttccatgtgc tcattcctgg tctcaagctg   84360
gcggcttcta ccaaaaaaag cattatagga tccctacagc acgatgccac cgtacaaaaa   84420
attctacacg agcagggcgt tacaaatcct gagtcctgtc tggacccca ctccgcctcc    84480 gttccctcgc tcctctacgg ctcctccaaa ctaaaccaca agccctacca actgaaaacc   84540
ggctttgagt tagtctttga tagctctgat cccgactaca ttcccattca tcaaataaaa   84600
aatttagaat cttataattt agtttctgag ttgagcctta cgaatgaaca gggaagcctt   84660
gtaagacctg tctattgcgc ggcagacatt gccgctgaga aggaggaaga gatcccgacc   84720
gaggatcact cgctctccat attaatgcta catgatcccg aagcccggta tttacataaa   84780
```

```
attttaaatc tgcttcctcc ggagtattat gtagagtacc ccctatggag caacgtcgta   84840
ttcgctttgg ccaatacatc cgctaactat cggcccctcg ccgaatggtt ttcgcaaaaa   84900
tgccctgaaa aatggaatac gggaggaaaa gagaaactag aaaaactttg gaatgatgcc   84960
tcgcaccaca ctgaaaagaa aatcaccaag cggtccatta tgtactgggc ccacaaacat   85020
gccccccagc aatacaaaga aattgtagaa caaggctact tttccattct cgctgaatat   85080
gtgtatagct ataacggcat gcttgagcac tacatgatcg ccaaagtcat ctatgctatg   85140
atgggcaaca agtttgtagt ggacgtggat tcaaacggga agtacgtttg gttcgaattt   85200
gtgctaccgg gccagccaat gaatcaggga gaaatatgga agtggcgcaa ggaggtaaac   85260
ccggatgagc tgcacatcta tatttccgaa aacttttcaa gggtgatgga ccgaatcacg   85320
gagcacatca ataccacct cagtcaaccc catgaaagca atattttaaa ttattataaa   85380
aaactattaa aagcctttga acgctctaaa agtaaaatct ttaatgacag ctttaaaaag   85440
ggagttatca gcaagctga gttttttattt cgccaaagaa gctttattca aactctggat   85500
accaatcccc acctactggg ggttggcaac ggggttctct ccattgagac catcccggct   85560
aagctcatta atcatttca cgagcatccc attcatcagt acacacacat atgttatgtg   85620
ccctttaatc ccgaaaaccc ctggacaaaa ctattattga atgcactcca agacatcatc   85680
ccagaacttg atgctaggct gtggatcatg ttctacctaa gcacggccat atttcgcggc   85740
ctgaaggagg ctctgatgct tttgtggctt ggaggcggct gcaatggaaa aacttttcta   85800
atgcgacttg tggccatggt attgggcgat cactatgcct ccaagctcaa catcagcctt   85860
cttacaagct gcagagaaac cgcggaaaaa cccaacagtg cctttatgcg gcttaagggg   85920
cggggatatg ggtactttga ggaaaccaac aaaagcgagg ttctaaatac gtcgcggctg   85980
aaggaaatgg taaatccggg cgatgtcacc gctcgagagc ttaatcaaaa acaggaaagc   86040
tttcagatga cggccaccat ggtcgccgcg tccaactata acttcatcat tgacacgacg   86100
gaccacggca catggagaag actgcggcat tatcggtcaa aggtgaaatt ctgccataac   86160
cccgacccca gtaaccccta cgagaaaaag gaagatcctc gctttattca cgagtacatc   86220
atggatccag actgccaaaa cgcattcttc agcatactcg tctattttg ggagaagcta   86280 cagaaggaat acaacgggca gattaaaaaa gtgttttgtc ccaccattga gagcgaaacg   86340
gaggcgtaca gaaagtcaca agatacgcta cataggttta tcacagaaag agtcgtggag   86400
tcgccctccg cagaaactgt gtacaaccta tccgaggtcg tgacggccta cgcggaatgg   86460
tacaacacca acattaacgt aaagcgccat attgccctcg agctatccca ggagttagaa   86520
aactctgtgc tagaaaaata ccttcagtgg tctcccaaca aaacgcgaat tctaaagggt   86580
tgccgtattt tgcataaatt tgaaacgctg cagcccggcg aatcctacat tggggtgtcc   86640
acggccggca cactcctaaa cacacccata tgcgagccaa aaataaatg gtgggaatgg   86700 tccctaatc cctctgcccc tcctgagaaa gaagcgtctg caccaactcc ttagggaata   86760
tccttagaag catgtctttc ggcagagcca ttaccggtag caaaaaagca acattgagta   86820
tattatatgc cttagcctgc tcataagcgt ccttttttt catggtattt tatgttttta   86880
aatattttta attattttt aaatacgatg aacagttcgt gctccgaagg ctgtttacta   86940
aaaatcggtg tgaatccgca ttcttttaaat atggtttccc attcggggat ggtatggaaa   87000
tccatgtctc tacgaatagt atggtgccca agtgcgtcct gcaggctgtg aagccagaag   87060
gcctcctgac cttgatgaag gtcgtacatg ataagaaaac catcagggttt caacagatgg   87120 taaagcttgt taaaatcgtt tatcgtaaga tgatgcgccg ccataggtaa ccctatgagc   87180
```

```
tccacagagt tttcatgctg gacatcgtcc atatcggtat aaaacgtttc acagtaaatg   87240
agacgcttaa acgagtatcg atgacaaaca tttatttcca agtaggtttg cactacgttt   87300
ttaggtatat cgggaatcat gttgattaag gttgtttcgg gaaacttaat catctgacta   87360
ggcttcattt tcaactcttt aaaggatttc ccggagaagt gaaaatgggt ctttacgtat   87420
ttatgtaaaa atacctgaat gggcagaggg ggctcctcct cttcgttctc gacgcctccc   87480
aaaatatttg gaatttcctg acgtggcaaa agaaagttta tgtccacgtt tacgaatcca   87540
tcgaggacgg acacaaagct tggctctaat ctccattcca tatactgttt agaaacggga   87600
gatagcataa tcctaggcgt cacaatgcac gaagggtttt taatcaccgc atcgtggtaa   87660
gaaaagtgta ttccatttct tccagtataa agaagcctat gttcgtcgta gcagaaacaa   87720
ttaaggcggt atgcctcata catacactgt ttcaaagtac aaaacacgttt taaaaaggtt   87780 tctgcattgg cggaggccaa gcggttttgc cattggtgga aggggttcaa tcctacaatg   87840
gccagctcgt ttaaaatatc ttcgcggcgc gctaaaatct gcaccataga agaatacttt   87900 agcattttt tttcgcacca ttcgcgaaga tgtttagcta cattattaac cttattattg   87960
ataaagtata cgatggcatg ttggaagcct tcaaaaataa agagcccctc caaaagatca   88020
tctgccaata gaagatggat gttggtgtaa gcattgtcaa tattttgtag aaacggcgga   88080
atgcctgcca aaaccgcttc agcaagcata gctccgttcc gttgtttact gtccaataga   88140
ttcgtaagtt ttttgtccgc aacagacacg acggctagga tggttgcaat gtcagaaatg   88200
gcggcttgcc agaaataacc cgaaaagcac atgcgcgctt cttctataga taaaaacgaa   88260
aagcgagagg caatgtctcc gagctgcgtg agttgaagac cttttctcc tctggttaaa    88320 aggcctgcca caatggcccg ctcaatggct gatgccagcg catccgtggg gggaggatcc   88380
agcatatcaa tctcctctgc cttaaacacg ccttccttat tttttttaat cgtttctacg   88440
acaatgctaa gaaaaatggc cccagggcct tccgtaatga tttcaggata ctgctgcact   88500
ggtatttgct caaagacgtg ttttgtgtaa agcgggtaaa agtgcccagg aaatactctc   88560
cctacacgcc ccttcttttg ctcgatacgg ctttgagccg cggggcgcgt aataagccct   88620
cccgcccatt cgggatagta ggtttcaatg cttctgttcc acccgggatc tatgacgtac   88680
ttcagcgttt caatggtaag gcccgttttc gcaacaaccg tggaaacaat gacccttctt   88740
aaaggttttt ccactttagc ggttaaggga ttttcaccc acagattctt aatttccgct     88800
ttcaggccaa ggtaggcctc atttcctgc gcaatcgcct cactatcgat cggcaaaatc    88860
aacattaacg gcagctttc tttggcaagg tccatatttg cattattcag caacatcgaa   88920
aggaagcgta tttcagccat accgggcatg aaaattaaaa tatctgcttc cgtgggacga   88980
tcatgaatgt tttcttttatg aatagtgaga gccgtttcgc aggcggtctt aatgtagttg    89040
ttggtgttat acagcggcca gtgggtttcc acaccgtact gtcgtccttc caccaaaata   89100
atgttttctt ttccgatacc aaaataggtt gagtatttat gggtatcaat ggtggcgag    89160 gttaaaatta caaagggaat acgcagcgcc cctatgcttc ctctttgcaa catgcgctga   89220
agcatacttt taatatacat gagcataagg tcgatgccta gggctcgctc atgggcctca   89280
tctataatca taaaggcata gcgggaagct atctcatcat ccgtcattgt atgtagctgc   89340
gccaacagaa cccccgcggt tgcataaata aggccccgat tgggtttttc cgtcagaggc    89400
ttcgtttggt agcccactgt ttggcctaat atcatgtcgg ggtagtgggt tgaggcgccg    89460
atgtctttgg cgagggtcac cgcggttagg actcttggct gggtacaaat aaccgagcgt    89520
```

```
cccaagtatt tttggaaaga atgcgtgttt tcatttctca gaattctgaa cacgtgtacg   89580
ggtaaggccg tggattttcc ggaaccagtg cgtgacttta taatgagcac ccggtctgcg   89640
agggaggttg aatggcccc tccaaactcc gggagacgtt gttttatcca agtgatgatg    89700
taatgaatag aacatcatt cttgtgctca gcgggcacgt tatagagatg accaggctcc    89760
aataaagtcg gttttcccat attctattgt tttaaggatt gattgttcat aaatatttt    89820 atactctgac caagaaatta ttttttttatt aagccggtta tttacgttgt tatggaacgc  89880
gaaggtccag tactgaaagt cctccgagtt gtttaatgtc aagggatttt tgtaagata    89940 cgaaaaggcg tggtgctggc acctggtgca tggcagagac tcgataaagt tcagtatcca   90000
ttggatggct tcatatttt ctttccagct aggagcgtct gaaaaaaga tagcatatag     90060 atgcaaggat cgccagtatt taggtcccca atgcaacatt tataacctt tgaaaaatct    90120 cattccatat agaggtaaat atttttttc catggagaat tttttttgcac tcttgaaggg   90180 attgcgccac atcgtcaaat gttttttgtt ttccatgtat tttggcgtaa ttccagccag   90240
tatctgtgtc atggtcctta atgtcatccg ctaactgaaa ggcatgtcca aaacaatggg   90300 cagcccttc aatcatccca atgtcttcaa cggatccagt tcctaaaacc cagcccataa    90360
taaacgcgat cttaaaaaag ggaatggttt tttctggagt gtctactaac tgaccggaac   90420
ccgcgctgtt tagagagtgg cttacaaagg tacacagcag cgctcccagt tggttgggat   90480
ccggaaacct tggacagtgt tccttaatcc agtcgatttg ccggcaaata ttttgaaatc   90540
cttgcatggt tagcgccaga gcgctcatct gcgccttggc tacgccaaag cgggcccaca   90600 ctgtatctt atttcgccgc ttcacatcgt tgtcaaagga gggcatatca tcgataatca    90660
aagaagctac gtgaaagtac tccgctgcta gggcggcctc tgccggataa ataggcgccc   90720
caaaggaatg ttgcaactga caggcccgaa caatttccat caggataatg ggacggatat   90780
acttcccacc tcttagagcg taagagcaag gctctgttag ttgtccctta aagtccccat   90840
cttcaatagc attatttaag atggtctcaa actcttcact aaaggtttta taattttag    90900 gattcagtgg atgtattcca tgaaaaagcg cgacactacg cggtgctgtg attctaaaat   90960
acttaggttt gcgcgtatag gatattaaaa taataataag aactacaatg atggagatat   91020
agatgagatg caacatgctg agttgtctcc ccgcagggaa tggtccttt ccgcgcttgt    91080 taacggtacc gaggaggcgt tgaaatcttt aggaaggtg ctgtctagtt tggaatctcc    91140
aattcctccc gtatatttag gtatataatt attgtgtcta gaaattgttt gctttgaggt   91200
atcaaaatat tcagcctgac cgctatttct tttagaataa ttcggtatag ggcttgagta   91260
gttggcaata ctcttaaacc ggggcaccaa ggtaacaata ttttccatat aatgggtttg   91320
atacgctttg tttaaaaatg ggcttaccgg ctttatgctt gttagttgtg cattgagtac   91380
cggtatgtct tctaggattt gtggctttat agaatgatta gcaaacacag aatgtagtat   91440
attagatact tgtagcatat gtctattgc ggaaaattcc tggtattctc tgccgtgttg    91500
cgaatctttg ggcggaaggg gaccaagcat cggcacgtcc gtgtaggtac tggtggattt   91560
tatgagttcc tgctctatgt tcggtttgac atgtggattt cctaaaggaa tacctctacc   91620
tgcaatccct ttttctaccg acgcaggtag attgtgcgct aaacacaaaa tattgtacac   91680
gtctttgtgc ggaatatatc cgttatagtg ctggcccggc atctgatcgc caaggtgctg   91740
ctcatgctta atggtaccct ttgttctgag tttaggaaga tcctcgtacg aaaaaaattt   91800
tgtgtgctcc ctgaacctcg tagaaggaac cgaactattt tttgggtttt ttaaggaagg   91860
caatgaggaa ggctgggtca gacaattttt ctgtgtgccc tttaagctag ccacctgcgg   91920
```

```
aaatgttttt ttttccgtac gaacaacatt gcgcctaatt aggttttccg tatgggttga   91980
aaaagcagga cgatgatttt taaaatgatt aaaaagttta ttttttggaa tggagctgta   92040
cggctccaga tcttgcgcat cgccgtaacc aatgtttttg tgctgagggt tcagcataaa   92100
agaaaagtta cgtagatcac tgagttgcaa tccctttttca gccttttcag gactattagt   92160
gtattcattg tatacaggcg cggctccatt tttgttgccg cagtaccggg aatttagtat   92220
attatcagaa taccggttat gacgcggcaa atcgcttttcc caagaggtg gatctgacct   92280 ataatcggct aacagctttg aagcataatc atgatacatt gtatataaaa gttaattatt   92340
atattgagaa ggcataatta cttcttgtag gggtacaaga ggctttgaat caggcaaact   92400
gacgggtttt gaatcggccg gctttggacc ggcaggtatc ttttaggtt gatcttcttc   92460 tagctcatta gacacggatg ggggagaaat aggaggaata atttcatctc cgcccttata   92520
tttgtcatgg atagaagaaa caattacatc catgtttgat ttattataaa tgtcgtttaa   92580
ctggtgattt aaaacataat aatgcaaaaa taatagggct acaatgcata tatatacgta   92640
aatagccgtc ttcgtttttc gttttttatc caccggcgga ttacaaattg caaaaaatac   92700
aactaatacc accgctgtaa tgattaaggc cacaatgaaa ggattttgaa aggatgttt    92760 gaacggttcg cacgtataaa ttttttctcc taaattattg atacccgcaa taaaatctac   92820
attcatttta tatatttata aattatgaaa aatttagagt tacatctccg ccggaccaat   92880
cattgctaaa atttgaagat tcttcaaaaa ggcccgactg gttgaatgtc ttctgctcag   92940
gtttccaaaa atttttccaag aatggatttt gaacataggg ctcatcttga ttttcttctt   93000
caaggatatt ttctttgata tcaagaacag cttctttaaa ctcaggtgta tcttgattaa   93060
actcaggttt atcctgatca atcgcaaaaa tattatcttc ttcagatata tcctgtttaa   93120
tcgcaagaat agtttcttcc tcaggtttat cctgatcaat cgcaagaata ttttcttctt   93180
caggtttatc ctgaccaaac tcaacaatat cttttctcgct aaatccgttt ttagtgtgaa   93240
gctcttggtt ttgaagagaa ttatcaaaat ctattttagt tgttgtccta daccgtggca   93300
cgggatagtt atctaatggt ttacttacta tagtcctcga atgtggcacg ggataattgt   93360
ttggtgactt gctggttagc tcttggcttg ttaatagttc ttgttttctc aataattcca   93420
tctctactac ttcttttttga tccgctggtg tctcttttttg gtattcttca ttagaaaaat   93480
gttcagaggg taatgtttca ataaactttg tgagtggata gctgctcttt gatgtagaag   93540
agcgttgaat ttgctgataa aggagttgaa caagtcgccg gtattcactc tgtcttttt    93600 catatttttt acgtagcgtg gagagatctg ctaagagcga cttgttttca gatgttaatt   93660
cttcaatttg atgaagaagg ctgcgattgt atgaactaag tcttgcatac gtttcttcta   93720
attctgtctc cggctccaca taggcctgtt ttcgcagaaa tttattgtat agttccattc   93780 ttttttttgag cagaaaggta agactataat cttgcatttc tttcgtaact ttatggtagt   93840 tttcttccg gttttttgata ataaagggca gcattttttc tgttgtgata aaggtgccca   93900
gattgctaat gtagtcgcac agtagcaatt ccaagataga ttctttcttt tcaaggctta   93960
tagattggct gtattcttta ggtatgaaag aatcaacaat cgttgttacg aagtttgaaa   94020
agtttaatgt tttgctgtta atttgggtaa tgttacaaaa atatttgtaa aaactatcta   94080 gcatttttc ataaagtttt ttattttgtt taacccctaa aatatagccc tttacttgat   94140
actgatattc cgtaacaatg gaatgtttttt tgtatagtgc atttttgtat aaaaagttat   94200
aaaaaatgtt gataaaatac gcaccaaggg tttcaaaaat acttataacg tgggattctt   94260
```

```
cctgatccat tatatcatat gtaatattat tttaataaaa aattactgac gaataacatg    94320
caaaaaaaat atgtttaaac ttattttaag ctagcactta tttaaaagtg ttttaaacac    94380
gttttaaatt gtatgttaat acacttaaaa attaagccga aatttgctcc aataaggatt    94440
acttttatca atgaccacct ctttactata aacggcttta cataatttta ataatgcttt    94500
agagccaaag ctgaaggcag tgggaagcgg cactgtacta tggtaaaaat gttgccgatg    94560
ttcatcctcg cggatgtaca caagtttcct atatccttta aacacaatat ggctaatttc    94620
ttccacatac tccttatcct gtttggaata gcggttgctt tgacgggaaa aattcgacat    94680
acaaatagag gcatttgtaa aaatggaaac aaatgcgttt ttacgaagat tggcgggtaa    94740
atcggtatca tcttggcagc aaataatcat cgaaataaaa cagtgacgat tttggtaaaa    94800
aaacttttta aaaatttctt ttgtaaataa tgggtgcagt tcggccgcgc agtcgtctaa    94860
tattaaaagt aaacgaggat taagattgat atagtttaac gtaaactttt catcctctgt    94920
aaggcataag ttttttataca tatgaatgtt ctgtataata atttttttta aaagttgctg    94980
ataaagcgat gtaatctttt cttctttttt ttggtccgtt tgttcagcct ttaagcactc    95040
cacttttgca atattttttgt tttccttttg ctgtatatcg atcggaagtt tatgatacaa    95100 tgttttagc atatcgatgt tgtttactcg actgtagatg gaggacatca tagtttgccg    95160
ctgccagatg gcctccaaaa agcgttcagc gcccttgttg tcattttttt tttgcttatc    95220
ggcgagccac aagcggtagt gtattagagt tggatgtaca aaaccctcat atgaacgatt    95280
tgagggttcc gaggggggcaa ccactaaaat ttgttcaata tggggttgca ggattttcat    95340
aatatgttta acgtacacgg ttttgcctgt ttttgagggg ccatatagca cagttgtttt    95400
atctataaaa tgatgtgctt tgaactgtag ttcaggaatt agcttccctg aatgggtcgt    95460
tagggccatc tctatattat tacaattctg cttttgtata taaatttct ttttcgagtt    95520 tattattatt gttgacccac atatctaccc gtatcgtatc atcaggcaca ttgagcattt    95580
caagcgcatt atctaactgt ttttttgttt ttatcagctc gctttcttca tcggggggtta    95640 aattttcttt actaagcagt tgcttaattt tttcttcgca gtcgtctata aaatcatact    95700
ctcgagcttt tttgatattt ccagatgctt tttctaggtt ttttagctcc ttaaaggaaa    95760
gcagtccctt aatcccgcta tccgtgtgaa aggttgaatt atagatggag agccccggag    95820
catccgggcc agtttcttgt atattttttg cttttttgtg gtaaatagta tttcgtaaaa    95880 tctctttttcc tatctttagg tcttcctcat gacggtccaa aatccgtttt attatttcat    95940
tattttgatt aaaataattg tagcgctctc tgttggcctt aaagcttccc aggagtgtcc    96000
agttgcctaa ttgaatggat gaaacctctg agaaaatctg gtctttatat ttataataaa    96060
attcatcaac cttttgttgg ttgctgctat ccaccacatc ataaataatg aaggcaaact    96120
ctaggtcggg ttttttctggg tagatgcttt ccgtagcggc ccgcaactct tcgtaattat    96180
cctcaatgta ataattccac ttataaaaag tatcctgagg tggaatatgc tgcgaaagat    96240
atctagtaat ttttgtgtta aagagaatgg gtttaaacgc cctcggattt tcaagcatat    96300
gtttaatgct ttggtgaagt tctatatttt gtaatatgtg ggctgctgcc ctatagccct    96360
gtggggtttg ggtgattgca tcaatatcgg cctgaagctc attaggcaca tttaatgttt    96420
tttgcatgat gtgtaaaggg atgcgctcag gatctgctaa atcggtgtat tctgtgcttg    96480
tacaagtgct tgcacaggta tctacattgg tatctgcaca catgcttgca caggtgtcta    96540
cattggtatc tgcacacatg cttgcacaag tgtctacatt ggtatctgca caagtatacg    96600
cactttgagc atgaagatta ggatcaaaca caaaatgttc tcgtaaaaag ctatcgatcg    96660
```

```
ttgttttagc ttccttgctt ttctgcgtct gggttttgca gctatctgct atagataaaa    96720
ttgtatttac taccgattca gagggaacat cattagtttc ctgtttcaaa gtatcaacta    96780
acgttattag ctcactgaga agagttttgg tcgtgtgggt aggttttgaa taggaaggca    96840
tccattcctg cagagctttg aagacatatc caataaagct agtcattata agacgtcgaa    96900
tatactgctc ccgcaaattt gtaaagagc aaaaggccac cctgctatca ttttgaact     96960 gtttgtaagg gttcgtcctt tggtaaagct gtttaagcgt ttcttcggat atttcagtag    97020
agggatcctc caatacgttt ttgagaagct catcaatatt aaattctgcc atatcttaga    97080
gtttattata tacatattaa agctttaata taaggggggt ataacaatgg acgaaatcat    97140
caataaatac caagctgttg aaaaactttt taaggaaatt cagcaaggat tggccgcgta    97200
tgatcaatac aagaccttaa ttagtgaaat gatgcactat aataatcata tcaagcagga    97260
gtattttaac ttttaatga ttatttcacc ttatcttatt agggcgcata gcggagaaac      97320
gctgcgaaac aaagtaaata atgaaattaa acgtcttatt ttggttgaaa atatcaatac    97380
caaaatatct aaaacgctgg taagtgttaa tttttacta cagaaaaaac tttcaacgga     97440
cggggtgaaa acgaaaaaca tgtggtgcac caataatccc atgctgcagg taaaaacagc    97500
ccacaacctt tttaagcaac tatgcgacac acagtccaaa actcaatggg tacaaacttt    97560
aaaatataag gaatgcaagt attgtcatac cgacatggtg tttaacacca cgcagtttgg    97620
gctgcaatgt cctaactgcg gttgtattca agaattgatg ggaaccattt ttgatgaaac    97680
acatttttac aaccatgatg ggcagaaagc aaagtcaggt atctttaacc ctaaccgtca    97740
ctatcggttt tggatagaac atattcttgg tagaaatcca gaacaagagt tggggaccaa    97800
acaagatccc tgcggaacca aggtgttgca acaactaaaa aaaattatta gcgcgataa     97860 taaatgcatc gcgcttttga cggtcgaaaa tattcgaaaa atgttaaaag agataaaccg    97920
cacagactta ataattgtg tttctcttat attgcgtaaa cttaccggag tagggccgcc     97980
tcaaatatca gagtcgattt tactacgagg cgaatacata tttacagagg caattaagat    98040
acggaaaaaa gtgtgtaaaa aagggcgtat taataggaat tattatccgt attatatata    98100 taaaatttt gacgccattt tgcctccaaa tgataccacg aatcgacgca ttttacaata     98160
tattcatttg caaggaaatg atacgctagc taataatgat agtgagtggg aatctatctg    98220 tatgagctc cctgaaataa aatggaagcc cacagatcga acccattgtg ttcattttt      98280 ttaaagatga agattttta gatgattttt tttagttttt taaaagacga aaaaattttt     98340 taaagatga atattcttaa accccgcaaa ttacttttt ttaggtactg taacgcagca      98400
cagctgaacc gttctgaaga agaagaaagt taatagcaga tgccgatacc acaagatcag    98460
ccgtagtgat agaccccacg taatccgtgt cccaactaat ataaaattct cttgctctgg    98520
atacgttaat atgaccactg ggttggtatt cctcccgtgg cttcaaagca aggtaatca     98580 tcatcgcacc cggatcatcg ggggttttaa tcgcattgcc tccgtagtgg aagggtatgt    98640
aagagctgca gaactttgat ggaaatttat cgataagatt gataccatga gcagttacgg    98700
aaatgttttt aataataggt aatgtgatcg gatacgtaac ggggctaata tcagatatag    98760
atgaacatgc gtctgaaga gctgtatctc tatcctgaaa gcttatctct gcgtggtgag     98820
tgggctgcat aatggcgtta acaacatgtc cgaacttgtg ccaatctcgg tgttgatgag    98880
gattttgatc ggagatgttc caggtaggtt ttaatcctat aaacatatat tcaatgggcc    98940
atttaagagc agacattagt ttttcatcgt ggtggttatt gttggtgtgg gtcacctgcg    99000
```

```
ttttatggac acgtatcagc gaaaagcgaa cgcgttttac aaaaaggttg tgtatttcag   99060
gggttacaaa caggttattg atgtaaagtt cattattcgt gagcgagatt tcattaatga   99120
ctcctgggat aaaccatggt ttaaagcgta tattgcgtct actgggcgt ccagctataa    99180
aacgtgactg gcgtacaaaa agtccaggaa attcattcac caaatccttt tgcgatgcaa   99240
gctttatggt gataaagcgc tcgccgaagg gaatggatac tgagggaata gcaaggttca   99300
cgttctcatt aaaccaaaag cgcaacttaa tccagagcgc aagaggggc tgatagtatt    99360
taggggtttg aggtccatta cagctgtaat gaacattacg tcttatgtcc agatacgttg   99420
cgtccgtgat aggagtaata tcttgtttac ctgctgtttg gatattgtga gagttctcgg   99480
gaaaatgctg tgaaagaaat tcgggttgg tatggctaca cgttcgctgc gtatcatttt    99540
catcggtaag aataggtttg ctttggtgcg gcttgtgcaa atcatgaatg ttgcatagga   99600
gagggccact ggttccctcc accgatacct cctggccaac caagtgctta tatccagtca   99660
ttttatcccc tgggatgcaa aatttgcgca caagcgttgt gacatccgaa ctatattcgt   99720
ctagggaatt tccatttaca tcgaatctta cgttttcata aagtcgttct ccggggtatt   99780
cgcagtagta aaccaagttt cggtacgcat tctttgtgcc gggtacaatg ggtcttccaa   99840
aaggatctac aagcgtgtaa acggcgccct ctaagggtgt ttggttgtcc cagtcatatc   99900
cgttgcgagg aaacgtttga agctgcccat gggcccccat ctgggacgtg ccctgaatcg   99960
gagcatcctg ccaggatgaa tgacatgcac ccaatatatg atggcccacc atatcatgga  100020
aaaagtctcc gtactgggga ataccaaagg taagcttgtt tcccaaggtg ggggtacccg  100080
tatgcgggcg tactttattg tattcaaacc ctactggaac ataaggctta aaatgcgcat  100140
taaaatgcac caaatgtgtt tcttcgattt gactcaaagt gggttcggga tcgggtttcc  100200
cataactttt gttcacattt ttaatgttag agatcctgct attcagcaag tcttgggcca  100260
atataatctt gtcggccttc ccatcgttag caataagaca aaaagctcct cctgatgcca  100320
tatataatgt tataaaaata atttattgtt tttattaaat atggcggttt atgcgaagga  100380
tcttgataat aacaaagagt taaaccaaaa attaattaac gatcagctta aaattattga  100440
cacgctcttg ctggcagaaa aaaaaaactt tttggtgtat gaactacctg ccccttttga  100500
cttttcctcc ggcgacccct tggccagtca gcgcgacata tactatgcca tcataaaaag  100560
cctcgaggag cgcgggttta ctgtcaaaat atgtatgaaa ggggatcgtg ccctcctttt  100620
catcacctgg aaaaaaatac aatccattga gataaacaaa aagaagaat atctgcgcat   100680
gcacttcata caagacgaag agaaagcatt ttattgtaaa ttttttagagt ctagatgagc  100740
ttttacgcaa tgttgtacag tgttgtatat atgtcttgta agcatttgtt gtagagtaat  100800
aagtaaaaga taaataaaaa tgactattaa aataaagccc aaaccattaa aaatattttt  100860
atctgttaga tttaatttaa taaatggctc atggaatgtg tggtgcgccg ctgcatgagg  100920
tgtggccgca tgggatgtgg tcgcataaga tgtagctaca tgggatgtgg catttgcttg  100980
catgtaagga tcatgatgtg ttgggtcttc atcccagcaa taatcgccat ctttatctag  101040
ctgaattgta tacccccatta tatatcactt attatttttt tttaatgttt catgaatttc   101100
attataggcg gtgaaagggt cctcaggccc cttctgtaaa agattataga gatcttcgga  101160
cgctttatgt ttcgtgcgaa ttaaggcggg atataacaaa agagagggcc ccagttccaa  101220
acaaatttta cttagcgggc tcatattttg caccaagttt cccactactt gcgatgtttc  101280
ataacgcatt ttaaagagct ttatcataaa agtgttatgc aggccggtgt agtctggcct  101340
atagttaagg aaggggattt ctctggtacc gtcaaacacg atctcaagtc ctctagcaag  101400
```

```
cccgatcaaa atttcttcag caatggatga gtatctaatt cctacattac gaagcgtaag    101460
catttctata acatcatcta tttcctgcat agaggaatct attgtaggaa ttttaatatc    101520
atctgtgctg atttgttcat tcccaagata ggtaagcagc atattaattt tttctagctt    101580
tactagctta gtcttacgct cataatcatg atctttttta taaaaagagt tgggatcacc    101640
gttggaccgt agatgattaa taaggcggtc tacttgcttt gtactaggtt taatactttt    101700
ttcactatac tcgctttcag catagtggtt tttacgatct cttttagaaa tagctgtttt    101760
ttgagatgcc tcagactctg catattttt tctatgcgta gaaagagaat aaccgcggtc    101820
attacgtgaa ctactgttgc atgcaaggcc tcggcgcgtc ttaccgctgc gcacactgcc    101880
attgcgtata ctgccatcgc gcacactgcc gctgcgtata ctgccattgc gtatactgcc    101940
gctgcgtatg ctgccgctgc gtatgctgcc gctacataca ctatcactac atatgctgtc    102000
agtacatacg ctatcgcggc gtatgccgcc gtgtaccttg tcgccgcccc tacccgaggg    102060
ttttttagat ataatactgt gtggggagtc aagcgaaaat tcagggtcat taagttaat    102120
gcccaatgac tttgccaatc cattaagctc ttcatcaaaa tgatcggtag gaaaactttg    102180
ttgcttgccc atgacctgtt tttcaagttc ctccaaattg gcttgctcat ttatatggag    102240
attattcata agcgtcgtaa ttccagcaag atttgctcct tctaaaaatg tggtgtcctc    102300
catcggatat actatactat ttaaaagctt ttaaataaaa atgtgtttgg aagaaatgct    102360
ctcttcaagc gtgtgtagct cagatataaa tgcctcctca gaaagctttc caccatactc    102420
ctttctcatc gtataggagg gcgccggttt aatgtaggaa atccactggg aggtaaaaaa    102480
ccggtacaac atatttagca gctcgcgggc ctcccaccct ttgggctccg tatagtgcac    102540
atcaacataa gaggcggcgc atgaaaagct gcaaaagttg ccgagaacgc ccatctcaat    102600
ctctcctcgc tcattttcac gcatataggt gggcacgaat tttgggacag tcttgaaata    102660
gagatgacat gtccagcatt taaagctaga atgggtaacc catttggaaa cagtggtgaa    102720
tacggagggt agcttttttt cgacctcggc ttcatcgtca ttcgtattta acgtatcggt    102780
ggcagttttt ttggattgca agcattcttc aatggtaatc ccggataagt ataaaatatt    102840
aggacaatta gtttccataa ttttgatagt tatttttata caacatggat ttaattaaag    102900
ataaatggag gacgaaacgg aactgtgttt tcggtcaaac aaggtgacga ggcttgaaat    102960
gtttgtctgc acatacgggg gaaaattac cagccttgca tgttcgcata tggagttaat    103020
taaaatgttg caaattgctg agccggtgaa ggcattgaac tgcaactttg ccaccagtg    103080
cctaccgggc tacgaatctt taataaagac tccgaaaaaa actaaaaaca tgttgcgccg    103140
tccgcgcaaa acagaaggcg atgggacttg cttcaatagt gccattgaag cctccatttt    103200
gtttaaggac aagatgtata aattaaaatg ttttcctagt accggggaaa ttcaggtccc    103260
gggcgtcatt tttccggatt ttgaagacgg aaaaaacatt atacagcagt gggtagactt    103320
cttgcaacat caacccattg aaaaaaaaat ccagattatt gaatttaaaa cgattatgat    103380
taattttaag tttcaaataa acccagtgtc tccccgcgtc atcattcatt taaaaaaatt    103440
tgcagctttg ttggaacaca tccctactcc atatcccata cgtgaaataa agcctccatt    103500
agaagactca aaagtatccg caaaatttat ggtcagtccg ggaaaaaaag tacgcattaa    103560
tgttttcttt aaaggtaaga taaatatttt aggctgcaac acaaaggaat ccgcggagac    103620
catttatacg ttttgaaag atcttatcag cgtacattgg caagaaattt tgtgcgtgtt    103680
accggtaccc gattaaagaa tgttttcatt aataaggtaa tcgactatgc taaaaagaat    103740
```

```
aacaagaaaa ataccttgaa gaactatacc aaagtaggta ggttttctgc atgtcacggc   103800
atggttaaaa ttgctaataa tgtagtccac aaaagcattg ctcaatacga ctaaaaatag   103860
taaaaaaagg ataagtgctc tttttatatc catatacttt aaaacttatt ttttacacta   103920
ataatttcct gcggccgcaa tataaactgt aggtcatcta taacgcccag acctgttaaa   103980
agtagagtac tatgttttaa gggatttaaa atatccgccg caagaatgtg aatataattt   104040
tcaaagtggt ttacaggaat gcgtaagcgt ttttttttgc actgcggttg gtttagggtc   104100
gaatactggc aggaggtata tatattaata agaccgcggt cgatggtttc aatatcttca   104160
tagaattcaa tgcgcggcgt caaaagtttt ttaagatgtt gacataactc atcatacgtg   104220
taggactgga ggggggaaag aagggtgtag tcaaagttaa aaatgttttt ttgaagaacc   104280
tttaaagcat gttccgcgtc cgtggtttcc aaaatatgtt ttatggtatg aatgtcattt   104340
aaatctacaa agtctgacag cttttgtgtag aactcggtga cggaggttat tttctggaaa   104400
tcggtttttt gaaaaagatt ttcaatgtgt ttgcgggttg agttgctttg cagtccatac   104460
aagacatcaa aaaattcaat cagcaaaaac ttatacaaat ggttaatata aaaagctttg   104520
ttggccttat tctgctgagg atatggttcc tctagggat atagaatggc ttggtctata   104580
tccctaggat caatagtcaa tgttgcgatg ggaagctttt ccagcgtagc gggaagagtt   104640
tgggttggag cgtagtaaaa gtatagcccg ttttttccct ctgaaagaaa gcccacaaat   104700 tctttttta tattttgcag caccgctgag ggtacgattt cgtactgttt atactgtttg   104760
ttgaaaaggg taataaattt ccaggtttct tcaaagcttg caatctgggt gggccgcaga   104820
tcaaagtcga tgggaatgtc gtcatgaatg taggatgata gtcttatagg aaaataaata   104880
gggcgatcgg tgtctgaatc gataagtaaa gcataacaaa agttatgcct gttgataagt   104940
tttttaccaa ccgtgtagcc gggaatgttt ttcacgtcat ggatatccca ccagttatcc   105000
ttgcacataa actcgctcat agactggatg acctccatca cagggtcatc ttcggtaaaa   105060
atatactggg cctcactgtt tttcagaaat ctttttttgct gggtgatggc cattgggtag   105120
atcccttcgt ccgtgtcaaa gataatggct atcttcttcg atgggctaag aattttttgt   105180
attgtgctgg gggacacctc aaacccgatg tcgccctgtt tatctttaaa aaagacacag   105240
tgaaggtcgt agcatatggc aacaaggtcc agaaagatgt cctgccatgt ggtgtcccat   105300
tgaagcagtt ggttttttg ttcaacaaag gtttgtaaga taaggtttgc cagctccgcg   105360
ccgctggaaa acatgttgcc ggccccattc cccaaaatat agtactgcgg tgtgttggcc   105420
gcctttgcaa tttcaatggc aagggccttg ggggcaagat ccaaaattcg agcaaggga   105480 taaaaaagcc cggcattgct aattccaagc atggtttgct ccaccccac aatgcaaaaa   105540 atgtcgggct cttttatcgt atttaaaaac agttcatctg ctatctggtg gggtagaaag   105600
gcaatccggt tcaccggtat ttttttcca taggacaagg tatgacgcga tgtttgtgta   105660
ttaagatcct ccaggtcttg ttctacaaac gtgtgcttgg tgaggcaggt attgttaata   105720
tagaaccgct ttgtgcccag cagggccttc gtctttggc agcacggcag acagtaattt   105780
agggggtggc ggccttctag taggcttaga tgagggtagt caggatgcgg gcagctatag   105840
taggcaggta ccccctccgt gaaattccaa tactttacta gctccttgcg cttggctggc   105900
ggcatggact tcacctcggc ctctgagtaa atgacgggtg gccgtgggtg ctggcatagg   105960
acggagtaaa ccgttgcctg cgtgtcgtac ttgcgcaggt catacaggtc ggggtcctgt   106020
tcttgaagcg cacgtagctg agaggctccc tttccttgtt gttatcgtg cagttgagag   106080 agtttattaa ccaaaatttt gtcaggcccg gtgatcaagt tatctaaaaa cacaaatagg   106140
```

```
taaacccaaa gatagttaaa ctcttcctgg gtaatgttaa acatttctat tttgatatct   106200
gtaaccctat ggtagatgcg aatgttgcgg ccgccgtaga ttgttttccca ccgggccgca  106260
acatttgtgt caaagaggta cgcatacgtg ttttggagca acgcaacatt gatgtccatt   106320
ttgcgccccg gaccggagga aataatgatc atccgttcga tttcgtgggg atcatacgaa   106380
taaatcccct ttttaaataa aaaattgtag accccggttt gctggaggcc ccgcacggaa   106440
ataatccctg cttgctcgta ttcccgccaa cgacttttga gctcggtaaa tcccttgcta   106500
gaaagcgtat agggccaaaa ggtggacacc gacatggagc tgatagaaat ttggatgtcc   106560
tcgttggagg gaaggggcag actccctcca cgaggaaacg cggcaggccc catatcatta   106620
attgtatgaa taataggatt tatgaaatta tttagggtgg acaccacgga gttaaagtcg   106680
tggcgctcgt tttctgacca attgctttcg ataaagtagt gcccattatt ttgtatggta   106740
agaataaagg cctttttatt gataaagcgt attaaaataa tagtgggtac acggaatgtt   106800
ttattgctga attttttcagg ctccgtggaa gttatgtggt gtttggaaac cacggtggga  106860
cctgttttac tataaaagaa caccaccagc tgaggaatat cgggagtagc tggaaatagg   106920
tcgaaaacat tgcgcacatt aatttgaata tttacgaggg gtgaaatttt aatcattgcc   106980
gaggtgacgg ccaacgtgcc gcgtgttagt ctattcccct cgtacttggc aatgacttgt   107040
tgtgctctgg catacgtaaa gtttattagt ttttgctcta ggagaagcct ctttttaaga   107100
ctggtcaagg atggagaaag agcaggatac tgttttttcca tttgtaaggg agattgtacc   107160
aatagtttaa aggcatcggg ggaaagaaga ggccaatact tcataataag gccgtaatag   107220
agtaagtcaa attggtaatt atcctctatg gcaatggaga tttggcgccg catggggggcc  107280
actagcgtgt tgaggtctgc tacaaagatg tgatgaatgt ttttttatgag ctggaagctg  107340
tcgagcgctt ccacatagag ctcatctttt tgactttcca tagatgcgtc gatgttcacc   107400
ccacccacct gttgaaactc cttttttgtag tcgcgaatgt ctaacgccac cccgctaccg   107460
cttaacaata ggcgatacgt tacctgaagc gcattgtttt gaaaaaagaa aatgtgttgt   107520
ctataagggg ggatccctgt ggcaacgtaa atttttttctc gaatgtctttt aaaagtgtct  107580
tcagggaaaa tactatactc gctatacatc gtctcaattt ctggcatcat cacgtttgtc   107640
tcctcgccac gatcctccac aaaaagtttt tcaaactcat ctaaatcatc gctatctcca   107700
cccaccacgt attgggaaag cttttttctcc caatcctcgc cgtaaaaatt ttgtaaaatt   107760
tctttgtcct taggggttcg ctgcaggtct ttgcggcagg cctgtaacac gtttgcagga   107820
acggatccca aaaaaataaa cgtcttcgtg tactcatttt ccacaggatt ataaagtaga   107880
actcgtagag gatttgttaa aaagtcattt tggaaatcca ttatacccgg tatagaaaat   107940
aaaatttaaa ataaaaacgg atgatatcta tcatggaccg ttctgagatt gttgcacggg   108000
agaacccggt gattacccaa cgagttacaa atctcctaca aaccaatgct cctctactat   108060
tcatgcccat tgatatccat gaagtacgat atggagccta cacactttt atgtatggtt    108120
ccctcgaaaa cggttacaaa gcagaagtaa ggattgaaaa catcccagtt ttctttgacg   108180
tacagattga gttcaatgat acaaaccagc ttttttttaaa gtcgctactg acggctgaaa   108240
atattgtgta tgaacggctg gagacgctca cccagcgtcc tgtaatgggg taccgcgaga   108300
aggaaaaaga gtttgcacca tacattcgaa tattttttaa aagcctgtat gagcgacgaa   108360
aagccattac ttacttaaat aatatgggct acaacacggc cgcggacgac acaacctgtt   108420
attaccgaat ggtttcccga gaattaaaac tacctcttac aagttggata cagcttcagc   108480
```

```
actattccta cgagcctcgc ggcttggtac acaggttttc cgtaaccccc gaggatcttg    108540
tttcctatca gaatgatggc cccacagacc acagcatcgt tatggcctac gatatagaga    108600
cctatagccc tgttaaggga accgttccgg acccaaatca ggcaaacgac gtggtgttca    108660
tgatatgcat gcgcattttt tggattcact ccacagagcc tctagcgagc acgtgcatca    108720
ccatggcacc ctgcaaaaag tcctcagagt ggaccaccat tctatgctcc tctgaaaaaa    108780
atttgttgtt aagctttgct gaacagttta gccgctgggc tcctgatata tgcacagggt    108840
tcaatgattc tcggtacgac tggccctttta tcgttgaaaa atctatgcag cacggtattc    108900
tagaagaaat ctttaacaaa atgagccttt tctggcacca aaagctggat accattctaa    108960
aatgctatta cgtaaaggaa aagagagtca aaatctcggc cgaaaaatcg atcatttcct    109020
cctttttgca tacccctgga tgcctaccca ttgatgtccg caacatgtgt atgcagcttt    109080
accctaaagc cgaaaaaaca agcttgaaag cgttttttaga aaattgtggg ttagattcga    109140
aggtagacct gccgtaccat ctcatgtgga agtattatga acacgagac agcgaaaaaa    109200 tagccgacgt ggcctattac tgcattatag atgcccagcg ctgtcaggac cttctggtgc    109260
gccacaatgt tatccccgat cgcagagagg taggaattct gtcatacacc tcgctgtatg    109320
actgtatcta ctacgcggga ggacacaagg tatgcaatat gctcattgcc tatgccatcc    109380
atgatgaata cggccgtatt gcttgcagta ccattgcccg aggtaagcgg gaacacggaa    109440
aatatcccgg cgcctttgtg atagaccccg ttaaagggct tgaacaggat aaacccacca    109500
caggtctcga ctttgcgtcg ctgtaccccct cactcatcat ggcctacaac ttttcgccag    109560
aaaaatttgt agcctctcgg gatgaggcaa atagcctcat ggccaagggt gaatctcttc    109620
actacgtctc ctttcacttt aacaatcgtc tcgtggaagg atggtttgtg cggcataata    109680
acgttcctga taaatgggga ttgtacccaa agtactcat cgatctactt aacaaacgga    109740
ccgcccttaa acaagagctt aaaaaactag gtgagaaaaa agaatgtatc catgaatccc    109800
atcctgggtt taaggaacta cagtttcgcc atgccatggt agacgcgaag caaaaggcgt    109860
tgaaaatttt catgaacacg ttttacggcg aggcaggtaa caatttgtcg cccttctttc    109920
tgcttcctct agccggagga gtcaccagtt cgggtcaata taatcttaaa cttgtctata    109980
actttgttat caataaaggt tacggcatca agtacggtga caccgactca ttatacatta    110040
catgcccaga tagtctttat acagaggtaa cagacgcata tttaaacagc caaaaaacga    110100
taaaacatta tgagcaactc tgccacgaaa aagtgcttct gtctatgaaa gccatgtcta    110160
cactatgcgc cgaggtgaat gaatacctgc gacaagataa tggcaccagt tacctacgta    110220
tggcctacga ggaagtactc tttcctgtgt gctttacagg caagaaaaag tattatggta    110280
ttgctcatgt aaacacaccc aatttttaata caaaagaatt attcatccgc ggaatagata    110340
tcattaagca gggtcaaaca aaactcacca aaacgatagg aacgcgaatt atggaagaat    110400
ccatgaaact acgccgccct gaggaccatc gccccctct tattgaaatc gttaaacgg    110460 ttttgaagga tgctgtggtt aacatgaagc agtggaattt tgaagacttc atccaaacag    110520
atgcgtggag accggacaaa gacaacaaag cagtccaaat ctttatgtct cgcatgcacg    110580
ctcggcgtga gcaactaaaa aaacacgcg ctgcagcatc gcaatttgct gagcccgagc    110640
cgggagaacg cttctcctac gttatcgtgg aaaaacaggt acagtttgat atccagggcc    110700
accgcacaga ttcctccaga aaggggggaca agatggaata cgtctctgaa gcaaaggcta    110760
aaaatcttcc tattgatata ttgttttata tcaacaacta tgttctaggc ttgtgcgcga    110820
gattcattaa tgaaaatgaa gaatttcaac cccctgacaa cgtcagcaat aaggatgaat    110880
```

```
acgctcagcg ccgagctaaa tcctacctac aaaaattcgt gcaatccatt caccctaaag    110940
acaagtctgt cattaagcaa ggcaatgttc atcgacagtg ctacaaatac attcaccaag    111000
aaattaaaaa aaaaataggc atctttgccg acctttataa ggaatttttt aacaacacca    111060
caaaccccat cgaaagcttt attcaaagca ctcagtttat gatacaatac tttgatggag    111120
aacaaaaagt aaaccattct atgaaaaaaa tggttgaaca gcatgctacg gctagtaatc    111180
gagctggtaa gcccgctggt aatccagccg gcaatgcgct gatgcgggct atatttacgc    111240
agctgattac ggaagaaaaa aaaattgtac aagccttata caataagggg gatgcaatac    111300
acgatcttct cacctatatc attaacaata taaattacaa aattgccacg tttcagacga    111360
aacagatgtt gacgttcgag ttttccagta ctcatgtaga actgctatta aagctgaata    111420
aaacgtggct tattttggct ggaattcatg tggcaaaaaa acatctgcaa gcttttttgg    111480
attcatataa caatgaatcg ccgtctagaa cattcattca gcaggctata gaggaagaat    111540
gtggcagtat taaaccatct tgctacgact ttatttccta atacttctta agaaactctt    111600
taaacaagga cttcgcatgg tcaaaggttc taaacccatg gcccttatga ttcgccaaaa    111660
aagcggtttc atcaagattt tctaaccctt tcacggatga agaaataagg tgttcggcct    111720
cgtttgccca ttttctatga ttttttttca cctcgggttc tagatctgtt ttctccatat    111780
actcattgtg gtcatatttt tttttgggag gaggcgtggg tggaggaatg ggtgaggaa    111840 gtacacccga ctttcccgct tcaaccgttt tataaaaaaa tagaagcata atacaaagaa    111900
taaggactat cgcaaatatg ataaccagtg tcccagtcga gggcattttg ttatataagt    111960 aacgttttt ttatttttta taattcgaat gaagaaccat gttgaatagt cttctactca    112020
aagacatttt gttatacggt aaatgagaat ttataaaatc cgaatatcac tatcatactg    112080
tttatctgag aaggtctcac tgggtcctgt gatggagaac ccatactctg taatgctggg    112140
gtttataatg tggtcaggac tgacaagcac atttctgaac tgcgagagtt ctaggtttag    112200
acgcagtcgt aatagtcgct gtatatttgt aataaatatt agattgcgta tgaggcgagt    112260
gtcaaagcga tccttttccaa tttgtactaa ggtgggcttt tgtattccaa ctcccacttg    112320
tttaacgatg gaccagggtc cttcttcccg attttgttcc gtgatatagg tcagcacact    112380
attttctgta tatgaggtat gatgtcgcat attaatacct ggtgccattc caactggcgg    112440
ttgtgcaatt cgggctgtac cgggacccaa ccatcgtgga gttttataaa catatcgttc    112500
tagcgtattt aaaaattcct taaggttatt tacgagtagc atgaagggtg ctattaaaac    112560
aggtggatgt tttataacca ttgtcataaa ccattgcatt gcttcaatat cattttgtaa    112620
tgcttgacgg ggaggcgggg caggtaatcc acgtatgttg aataaagcgg ttaattgtgc    112680
accggctgtt tggggcgtaa tattttgtat taaatttatc atcgaattgg cttgcccggc    112740
atttcctata agatcgatta aattggttat ttgacctcga tattgttgta cccagttttg    112800
aatggcagcg atgatctcag gggttggatt gttttgaatt tcaggtgttt gtattagatt    112860
attcacttct cttcgtgtat cttcaagctg agtcctaaat gcatttaact cgcctataat    112920
ttggtttcta tcaataacat ttcttaaacc tcgaactgtt tcagccaatc gtatagtacg    112980
cacaatttca tgtaaggcct ggtttatgta tattgacatg gatggcccc accgctcacg    113040 tccacgttga atacctgcgg ccaaactagg acctgcctcg tcataatcaa attgtgtagg    113100
ataaaggctt ccaaatagca ctttattgaa aatttggtca gaaagaaatt tagggcggcc    113160
catatttagc gcgttgtccc ctctaaagat gcgtgacatg tatccggcgt tgcctttgga    113220
```

```
tagtaactca ttcccatatt gagtaataga gaccgagaca taggggttta taagaagttt    113280
tagcataaat tctcgagtat ttatgggggg acgattcgga atgtttaata cctctgcaac    113340
atctggttga ggagccgtgg tgtccagaga tcgtactttt tcagccgaaa tgccgtacat    113400
aagacaagca atttcttcaa aactatagtc atagttgtaa atattggcaa gtggtataga    113460
tcgcatcagc gcatttacat tgataggtat aatattcata tcaaacaagt taaatatgcg    113520
ctcgcgctct ctattagagc caagagtgcg tgtttgacct ttcggcgaca ctattttgtg    113580
aatatgattg atttgctcct cttggtaaga gctttccacg aaggaaatta cgtcttgcaa    113640
tgttttacga agcgaataca ctgcattcat ccctattccc gctgttataa tgggtttatc    113700
gtctctgttc tcgctaataa gattaactcc accaaaagta ttttcattgt acatcatcac    113760
tgttttaaaa ctacggatat ttatgataaa tcggagagcc tgaatggcgt gggtataaaa    113820
gtgttcaaat cgcgtgggag taatttgttc gcgagcaact accgtttcat tatagttttt    113880
catgataagc tgtactccgg gcatatctga gagctgtacc ggatcatttc ccagtaattt    113940
tcttgtgccg tatagtagtt taaactcggg ggagccgctt tcaaggttcg ggtaagaag     114000 aggatcatat acctcattat tttctattct taggtcatgt aaataataga gcgaaagtga    114060
aaatggcata agaggctcct tattgtaccg ggacatatag ttttgaatga agtgttcttc    114120
tgtttcaaga tagatgggat gatcggtaag ctcgtgcagg acctccatgg cagaatctgc    114180
cagagtgtga gagcctctaa tgatcccgtc gatcactgcg accagtcgct ttcgcacaac    114240
atcgctcgta ttattttgtg cgtctcctag gggcataagc gtaacattgg gacgaaatac    114300
gccgccaatt ccccgcaggg ccgcctgacc gacggatagt cctgtcgcag gaacattgtt    114360
attattataa taaataacgg aatcattatt ggctcccaag agtgccgtca gattagggcg    114420
agctagttgg acatttgtgt attgtataaa ttgttttaga agctctccct ggctaataag    114480
aatattaaac attttgttaa atagtggaag attggctcta taattttctt taaggtaaat    114540
gggaatttct gttaaagtag aaataagatg ctgactcagg ccctggcgat tggtatcctt    114600
aataagccgc tgaagtataa gtcccaaaga cagaagaagc accgactgct ctgtggggtc    114660
gcctctatga ccaaagacgt tgttattgcg tgctaagtca gggtgagcat atcccatctc    114720
catcactgct tggctaaagt tcccattagc gaatgcatta ataagattta gatatatttt    114780
tccgctggga gcatcataaa atcgggtaat atatgaagct atgagctggt taaacaccat    114840
catcatacta cgattatttt gaataccata gtctgatccg tataggcgat aacgtcgaag    114900
gttgtttgcg gcatcattga cattggcata ggttctgagc gctatgttgt cccagtagct    114960
aagagtattt tcctcctggg cgttgttggt acgaataaga ttggagagtc taaagtctcc    115020
tagtgccacc tgctctacac gaagtccaga gttattctcc aaagcatcgt aaaatacgag    115080
tctactgaat actcttccgt attgttcaaa gcgttcagag gattggggat tgttatttat    115140
ttgaatatta gccgcgtccc ttctttgcgc cccacctcga agttgcagta cattataagg    115200
ctttgtaagc aaggtgtagg ttttattaat gatttggtta accccctcca ggcccaattc    115260
accgccagga agcggccttc ctccggcatc ggtaggtggt ttaataagtt tgtcaattaa    115320
atgttcttcc aaccagtaaa atgagccagg attagatcta ttttcatagt attgaataat    115380 gttttatca atatgcgggc gtagaagatc aagaaaatac ttcgtgtcgg ccatcaaaga    115440
atcaattaag gaaataagac ctgtaaaatc taaatgcact tgagcggtgc tggtttcagg    115500
gaagcgaact tgaaccattt tgttaaaact ggaggtcatt tcgaagatat tggtcaacag    115560
gagctgcatg attcgctgat tatctactaa ataccttgcg gccaactctt gctccggacg    115620
```

```
aactcctcca ccagcaggaa tacccacata tggtacaatc caagcaaaaa gagtttctgt   115680
ggttaaattt cggtcttggg ctgctgcagc cgcttcggta gtgggatcag ggtacaccat   115740
agaaagccgc atattgattt ctttaatgac taatcctgga tttctaatct cagagatggc   115800
cccgtgtttt cttccgagcc agtcaataag attggcgcgg ttcacgttgg cagcttgtgt   115860
ctctcgtaac cattcgataa tgcttttttg aatcgtatct aggtctaaac ctttaatgtt   115920
attacgaaag ttattaagaa gtacgtaaat agcactcaat aagttaagac ctgtaataac   115980
ggtttcatga aacagaaata ttttgttaac atctgtatct gccagtgact cagagccttg   116040
aataagtttt gaaacgattt gaattttatc ggtatgctcc tttttgagtt cattgatagc   116100
ctggcgaatg agttcttggt aggaaatttt gcccaattct tgttgcagac tgggatcttc   116160
aaacatctca ctaagctgtt tcctaaattt ttgtaccaaa tcccactggg agttgggctg   116220
cagcattcct gtttggacat ccacagagtc tatattgtat agtgccgggc gccacttggg   116280
ggtaggctgg gttgaaggac taataaacct atcggaggga agtaattgtg aggattgtgt   116340
atagccatcc tcatcaggaa gaatggagta gttggtttga ttcatcattc caaaatcatt   116400
catagttcgc gcttcctgaa caatgcgttg aaattttttcc cattcggtgc gtgtaatgac   116460
accgaatctg cggtttattt catttacaaa atggataagc gcttttttgg ttgcttcttg   116520
ttcaccatac tctaagttaa agtgttggta aatgacgttt atttctttga taagctgacg   116580
aatttcggtt tctgagtagt caccaatgtt aataagctca ataggacgca taaagataat   116640
gcgaataagt cctgagaaga ttccttccag ctcaggaagc atcgagatct gtacattttc   116700
atctctaaag gaaaacaact tttgataaaa ttcggcgagg cggggaaggc ggaagtaaag   116760
ctctgctgcc tcgggaatta cctcgggctc tagctcatcg gcaccccca atatcatacg   116820 cgtgggtata agtttgtaca cgggctcagg ccgttcaaac atgtcgtaaa tccctaatac   116880
aataaaaatc ttggcggcca tacttttcag catgaaggtg aagaagacgt cctcggtttc   116940
ccagcgggtt gatagggcgt cgttaactct cacagtagag aggtagaccc gctgagccgc   117000
ttcctcggca gtctgtgcaa gcgccatcct ttgtcctcca atttctgatt gatttagatt   117060
tttaagtccc acggaaagcg cagaatgttg aagatattca agcaaggttt tatagatttg   117120
caggggcgac atgggcacca tttgccgcag ctcctctccc ccaagcatgt ccccaatccg   117180
ggcaaaggca ttgatgatat ttttaagcgc ctgaaagtta gaaagagagc gcccgataag   117240
gtcgcgaatg ttttttagcct ggcttgctct gacgggacgg agggtaccaa cgcttcggcc   117300
ttgttggatt tcagccgcaa cttttttcgta gtagtggccc gcaggagcat tatccgtaaa   117360
gacgttggag tcgttgcctg tggaggtggg aaaactttca aagacttgtg caagcgtgtc   117420
ccctgttgtc tcggtgaacc atcgtccat aatgcgcacg ccatccagca tctgttggac   117480
tgtttgaata gaatctatgt tgtttacaaa cgttttggta atgtttttaa gataaagatc   117540
tagcccttcc agagctcgat agaatcggcg ttttacatca tactccagct cgatggcgct   117600
tacggttgcc ttccagtcta cttcctgggc acctccagga tttgggccca cgtgtcctct   117660
ggcaagatct acagccggag aattaatgcg cgcattttttt tccgtatcca actgcatgag   117720
gcgtcccgca atagcatctc cgagaatagt ggcatagttt tcctcgtagg attgaaactc   117780
ctgtttgtta tgcgttaaat tggagtaaat ctgggccaca taatagtaat acataaaggt   117840
gttaattgcc tggttgaggt caacctgcga tcgcgcggcc ttgctgagcc caagctcttc   117900
aactgttagg gcagcaccgc ctacccttgt acactcgcag tcctcctcgc ctccatactt   117960
```

```
tttttgcaca atatcggtat aaaaatcaat aatctgtagc aagcgagagc aggagtcata   118020
aagattttta aaattagggt cggttttaga tatctcctcc aaaacatttt taacaagcgt   118080
aagctgtgtt aagaaggttt cgcgttcttc tcgtgcggcc gcattggtgt aaaagccgat   118140
aagacttaga tcaagtgcga tggtgcccat atcattaatg cgcgaaagag catctcgaag   118200
cctcgttatg ttcggcgtca aggcaatttc tttaacaagt ttgatgccta ttttttttcac  118260 attttccaaa aagtcgttat aggcttgtgt gctttttattc aaaaattcca tgaggatgtg   118320
ctttctatcc agtctttgcg cttcaatcct cctatctagt ggcgttttct cctcatcgcc   118380 ccccttttg gcacaactgt tctcaaggat tttgtggcgt tcattaaagg tctgtcgcaa   118440
caggttcacg gctttttcaa actcagcaat gttttctgcg gagacaagac cactaaacct   118500
tttgaggtca agctccttgt caaactccgc ccagttttg ctttgaaggt actgttcaac   118560
cttgagtcct actttctgga gagccttatt aattttattc gcaacagacg cagcaatacc   118620
tagattacaa agtgtgtacg aaagtacttt tccaaaattt ttggttccca agacactatt   118680
tgtatcattt aaaagtttaa taatatccac ctcatccgtc tgcagtttat caagttcctt   118740
ttgggtggga gttaaaatat tgtcaataaa attcgttaaa atgttgattt gcaggttttg   118800
ttcatttaaa agtcgacgat atactgcttc aatcatggtg actgcattaa tgacttcctc   118860 attggggggct gctttggtta cctccgtcac catgcgctcg tgaagttgct taatggcgtc   118920
gtttaacagc ttgatatttt caagtgtatt ttctatactg ccgtgtacat caagatactc   118980
tgcgcgcagt ccatgagtta gggagttaat gtacagaact atttgtcgac atatactggc   119040
ggccccttcg gtggtatcta taagcttatc ctgacctaaa tcaataaatt cctggttaat   119100
ggcgtctgca atcattttac agacggtctc ctgttttttcc gcattttta caaaggtgga   119160 accggctcga ggatcgggca gttgttttt gatatcttta agaatatctt cgatgggctg   119220
ctttgtgtct actttgaacc ctattttggc aatcgccctg ataattcctt ctataatccg   119280
cagctttgct ttactcgata cggagtctat gtgataatct ttaatgtgtt gtacaggatt   119340
tttgtccccc ccgccattaa aatatcctcc ccctgaaaaa ggacgagttt gtctttgtat   119400
atgatcctgt aacttcgcat atatatttgc ttctgatgaa ggcagtggtc tactagaggt   119460
tgaagatcca cggttaccca ttataataaa aaaaataaag atttaaaact acaaatattt   119520
tgctgtttat aaacccaatc atataagact aactaaaaca ttaaatgtag gtgagataaa   119580
agcttatttt ttttaaaagt ttaataacca tgagtcttac cacctctttt tcttcttcct   119640
ttagaggggt tccataaatg gtttgaataa aatttatgtgc tctaataacc ttgttaaaat   119700
caggtgcctt tccatattgt tcaatatgtt gcacagtctt ttgtgcaagc atatacagct   119760 tggagtctttt aggtacctcc gatgagggct cttgctcaaa caacgtttca aggaggatg   119820 tgcattcatt ggtttcatta tcatttttt catgaatgtt ctccgaagat gctgaggatt   119880
ccgtctcctc ttcaaacagc acatgcgaaa tcatattcca ttcttcttga gcctgatgtt   119940
cagtataccc ttgccctgca tatatacgag cagatttcac aatatcatac ttaacagtac   120000
taagcaatgt ttttatagcg gtcgtaacaa ttctaccgct attgataatc tcaacagaaa   120060
accaattata caggctaccc gcatgaaaca caacttgtga agatgatctt aaatccgttt   120120
tgaagatgac ctccattttc atggatatat ttaaaataaa atccattcaa ttttaaaatt   120180
ataaaataat aagaagatgc cctctaatat gaaacagttt tgcaagattt ctgtatggct   120240
acagcagcac gatccagatt tattagaaat tatcaacaac ttatgtatgc ttggcaattt   120300
atccgcggca aagtacaaac acggagttac cttcatttac cccaaacagg caaagatccg   120360
```

```
cgatgaaata aaaaaacatg cctactccaa tgacccttca caagccataa agaccttaga    120420
atcactcatc cttccatttt acattcccac tccagcggag ttcaccgggg aaatcggctc    120480
ctacaccgga gtgaaattag aggttgaaaa aacggaggcg aataaagtta ttttaaaaaa    120540
tggagaagcg gtcctagtac cggcggccga ttttaagccc tttcctgatc gccgactagc    120600
ggtctggatc atggagtcag gctctatgcc cctggagggt ccccctata agcggaaaaa    120660 ggagggtggg gggaatgacc cgccggttcc taagcatatc tcgccgtata ctccgcgcac    120720
gcgtattgcc attgaggtgg aaaaggcctt tgatgactgt atgcgtcaaa actggtgtag    120780
tgtcaataat ccctatcttg ccaagtcggt ctccttgctg tctttcttgt cgctcaacca    120840
tcccaccgag tttattaagg tactgccgct tatagacttt gacccctcgg tgaccttta    120900 tctacttctt gagccctata aaacgcatgg ggatgacttt ttaattccgg aaaccattt    120960 attcggccct accggatgga atggtacaga tctgtatcaa agtgccatgc tggagtttaa    121020 aaagttttt acccagatta ctcgccaaac ctttatggac atagccgatt cggctactaa    121080
ggaggtagat gttcccatat gttactcgga tcccgaaacc gtacattcct atgccaatca    121140
cgtgcgtact gaaattttgc atcacaatgc cgtcaataag gttacaacac ctaacctcgt    121200
cgtgcaggcc tataatgagc tcgagcaaac caataccata cgacattacg ccctatttt    121260 cccggaaagt accatcaacg cactgcgttt ttggaaaaag ctgtggcagg atgaacagcg    121320
atttgttatc cacggcctgc accgcacgtt gatggatcaa cccacctatg aaacctctga    121380
gtttgcagag atcgttagaa atttacggtt ttcgcgtccc ggcaataact atataaacga    121440
gcttaatatt acaagtcccg ctatgtacgg cgacaagcat accaccggag atattgcgcc    121500
caatgataga tttgccatgt tggtggcctt tatcaacagt actgactttt tatacaccgc    121560
gattcccgag gaaaaggtag gggggaatga aacccaaacc agtagcctta cagacctagt    121620
tccaacacgg ctacactctt ttttaaatca taatctaagc aaacttaaaa tcttaaaccg    121680
cgcgcagcaa acggttagaa atattctttc aaatgattgt cttaatcaac tgaaacatta    121740
tgttaaacac acgggaaaaa atgaaatact aaagttactt caagaataag tatgttgata    121800
cctgtggtgt gttttacctg tgggtttcct attggaacct acgcggcaat ttttgacaag    121860
gctcgtaccg agtatattaa accaaaatg gcggaacat tgccgcaaaa tatcccatta    121920
gatgcttctc tccagattga gttaaaagac ctcattacag ctctgggaat cccaatgcgg    121980
gtgtgttgtc gcactcattt aattactacg ttggattatc gtaaatatta ttaatatcta    122040
aaattgaaaa aatattttta atgttactag taaaaatgac tacacacatc tttcacgcag    122100
atgatctcct acaagcattg caacaagcaa aagcagaaaa aaattttca tctgtattt    122160 ctttagattg ggataaatta cgcacagcga agcgtaatac aacggttaaa tatgttacgg    122220
tcaatgtcat agtaaaaggc aaaaaagctc cgctaatgtt taactttcaa aatgaaaaac    122280
atgtaggaac cattcctccc agtaccgatg aagaggttat acggatgaat gctgaaaatc    122340
caaagttttt ggtgaaaaaa cgtgacaggg atccctgttt gcagttcaac aaatacaaaa    122400
tctcgccgcc attggaagat gatggtctca ctgttaaaaa gaatgagcag ggtgaagaaa    122460 tatacccgg cgacgaagaa aaatctaagt tgtttcaaat tattgaactg ttagaagaag    122520
cctttgaaga cgctgtgcaa aaaggtcctg aagccatgaa acgaaacat gttataaaat    122580 taattcaaag aaaaatttct aatagcgcgg ttaaaaacgc agacaaacct ttgccgaatc    122640
ctatcgcacg cattcgtatt aaaatcaatc ccgctacaag tatactaaca ccaatattgc    122700
```

```
ttgataaaaa taagcccatt actttacaga atggtaaaac aagctttgaa gagttaaaag   122760
atgaagacgg cgttaaggcc aatccggata atattcataa gcttatagaa tcgcattcta   122820
tacatgatgg catcattaat gctagatcta tttgcatcag caatatgggc atttcatttc   122880
cgctttgctt ggaaatggga gttgtaaaag tttttgaaaa aaataatggg attgatgtga   122940
actccattta tggctcagac gatatttcaa ctcttgttaa tcagattgct attgcttaaa   123000
caatttgctc aaaacaagct tataaacgtt tcttaggtat gcgatacgta aatcctaatt   123060
ctttaataag ttcttttttca gtagtgattt ttagaggtac taaagtttga ttttttaaata  123120
atccatactg atttagctta taattctttt tttttaacgc agctcgaatt cttattaaat   123180
aagaaacggg acccgtaaaa tgaagtactg cgtatggctt ttcctcggct aaggccgtaa   123240
aaagatcaag ttgatatgtg ttttttttcc attcaataaa aagtacacac tttcgttctc   123300
cgcagacttt tacagaaaaa gaaagatcct ttatgcgaat gttgggcagg acgtgtttta   123360
aaagttttt ttctggaaca ataataagaa gatccacgtc attaagcatt ttctcttcgc    123420
gtcttaagct accaacagca acgatgtttt ttgataaaat ttttataagt tgtccattat   123480
attcaaacgc aagtcgggag cgtaagtcat ttacaatttt ttttccttga ataagcgtta   123540
acattttata tttaatatta aaatcttttc attttatata ttatatacgc aaaatggcac   123600
ttgatggttc aagtggtgga ggctctaatg tagaaacatt acttatagta gcaatcattg   123660
tggttattat ggcaatcatg ctttactatt tttggtggat gccccgccag caaaaaaaat   123720
gtagcaaggc tgaagaatgc acatgtaata acggaagctg ttccctaaaa acaagttaaa   123780
acatgcaatt atatgcatgc atataaacgc atgcatataa acgcatacat ataaaatgcg   123840
taaatactat ataaaaaact ataacatatc aatcaaggaa tcaacacttt tataattttc   123900
cgtaatatat ttttcatcca taatgatgtc agagtacatg gtccctatgc gaggaacaga   123960
gcccataagg gtaggcgcgg caataccgta aatgggattc acggcggagt caaccgcagc   124020
atctgtcaag acctggactg gagacgacaa ggccattcgc aacaacacgt tggaaggctc   124080
tcttgcatta agccctgcct tttctagaga ggtaacctgt cccgttcttg tcatgagatc   124140
tgcgtacatg agtaaatgac gatggttggg acccttgtcc cccataaccg ttctaatttc   124200
actaataatt ttttgccgtg ccgcttctat gccgtaaagc tccatggtgt ctcctataga   124260
ggacgatacg atggtgtatg ggtcgatgtt atcatcaagc attgcgccaa aaatattagt   124320
cccgtttgtt ttgatggcgt agatattgtc tagtcttacc agtttcccct gggcatccac   124380
acggtggcgc ataagcttaa caacattcgc atttttgatg cctggtattc ctctaatcgt   124440
gctatttaat agtttatcca ccacatttac ggcaatttt tcatccgtag ccattcgggt   124500
attggtactg cgtctaaagg cgcttcccg taggtatatg cgaataatga tgggaatccc   124560
tgaggccgtg ttttccacag aatgcatgat gtaggtgttg gggtgtttag ctcttagact   124620
attaataata ctttctagac taatgctttt taatatcatg gttgttttgt ttaattccaa   124680
gcggatacac cagtttgcaa tatcctctgg gggctgtagt agaggatggt tttccagaaa   124740
atccgtcatc cattccacat cacttgcaaa atcggggtac atcacatttt tttttgtgct   124800
tgaatacgtt tcgtacaata ggtgccactg caatatcaac cgttcgaacg ttataagctc   124860
tatgctgtta gcaatttctt gcgcatatgt tttatttgtt tccacttccg ggttctttag   124920
acgtaaaagc atttcagagg attgttcagc ctctacgggc ttcgcgctaa agatctcctg   124980
gggccgcaca attcccgact tgttggttcc cccggccacg gaccggtggt gggagtccag   125040
catatattgt gtcaagggct ctgatacgga ctgcgccgcc aggattccca ctgcctcacc   125100
```

```
gtagttaata agactttgag tatattgtag ccttatgagg tccaggatgg cactcatctg   125160
ctcgcaggta atgtttaatg ttttaacggt tgccagttcg atgcgaataa gcatgcgcat   125220
cagagaggca gcccgtttaa gataaacggg tatgggcgtt tgtagtcgtt cctgaatgtt   125280
gttaataaac acgtatggaa gatttttgca aaacgttttg accatcgcgt attttttgtag  125340 aatactttt  tcgtcgaagg gaagcacgcc actggtggag ctcagtagaa tgttttttac   125400
gatgctggcc acgtttaccg gcacctgtct aacatctgta agcagctgac tgaaattaaa   125460 atttttcgacg tttaggaaga tctgtcgata tttatctcta tcctttttaa ggcgtgaaaa  125520
ttcttcttca aacaagggcg attgtatccc ggtgtacttg aatttgtctt caagttcctg   125580
gtccgacagc atgatggttt caaaccgtac ggtttcaagc tggcgcgcat caaggccgtc   125640
ctctccgtac aactgctgca caagacgcgt atcgatggaa acccgtcggt aataatccac   125700
aatacaggat tgaaggccaa agatggcttt acggttggca tagcctgtgg atgatgtcga   125760
taatgctttg ttgatcaagt cgaatcttcc attcatttcc ccaaagataa attcagggga   125820
ggtaaggccc gcaatatagc tgttgcagat gaacccgtag gcctgcgcct ccagggcaaa   125880
cctggggtag tacaccaggg tcctaccgaa ggaaaactgg ggttgaatgc gttgtgtatt   125940
aatttcaatt tggccgatgc ccgccatgat gtgaatcata ttggggtttg agcccttggc   126000
gccagtggcc accatctgaa aaagcccatt ggtttccgga ttaatggaat tcataatcgg   126060
ctttaaaatt ctatcgggaa attaagcgc  attcagctgc aattttttcgt agaagtcatg   126120 cgttgtcagg cctataggcg gcatgatgtc tccatgaagc agccggttgt ttatttcctc   126180
cgactcaagc agcagttcat tgataatttc ttggacctcc tgatgtgcct ccgggggttag  126240 gagcatgtcg gccgtggaca ctgtgaatcc ggcgttgcgc acgtagttta gggcgagctg   126300
ctgggtcgca aatatcattt tcaaggcctg ctgcggccca tacctacgcg aaataaggtg   126360
atagattcca ccggaggaac ccgctccgac ggccttttg  tcaaggacgc cttcaatgag   126420
ttcgccgttg cgtatttgtg tagagatgtc ctgcttgtta taatgcatgt agggtgcata   126480
cacttctgag taccatgtgg gggctcgttg ataattgatg ggggtctgcc tcagtagcat   126540
agatacaacc gatttgccat ccagcaggtc agttggggag tagttggcaa aacaaggtgg   126600
gtcggtttgg gttgtttgaa acaaccccat ggcgtgcagc ttgttcatca cattttttccc  126660 catgggggtg ttcgtgcgtg taagcaaaaa gcttcccacc gtggagtcct gcacctgccc   126720
attaacggga cccgagctct ttgtggaaat gaaccagttt cgcacagaac aaagtagttc   126780
ggcctcaacg cggctcatga cgctccaggg aacccagaga ttcatctgat ccccgtcaaa   126840
gtccgcatta taccaggcac atgcgctgac attcatttga aacgtagaaa ttttttgggtt  126900 ttcaagaacg acaatccggt gaaccccctat gctgcttcgt tcgagagaag gctggcgatt   126960
aaaaaacgcg acgtcgccag tgacgacgtc acggtaaagg atgtctccta cctccagcct   127020
aaagtcttgt ttgagaccct caatgtcgtg aacggattgt gttatttgct tatacactct   127080
tgaacaacca gggtactggc gctttccatt taaaaaatag ggcattaatc tattaatatt   127140
ataatgttgc actgtttccg caacttgcag cgttcgtgca aaggaaatgg gatagccaac   127200
ctcgtccagg tgaaggtctg agttcccgca gatggtggac cggctgatcg accatacctg   127260
gctgcccagt agggatttac gaattcttcc ctccttgcga ggaagtcttc gcatgatgga   127320
gggagcaggg cgtgccccca tgacgatccc acgctttccc gtgcctccct gggttgcggt   127380
ggtggaaacg gaatccaaca aaaagttata gtaaagttgc tgtatggttt gcaaattgcg   127440
```

```
gtcaatattt aaaggtattt tttggccgcg cacgatttgt aggtccttcg ggatcagcag   127500
attctttcga accagatact gaatcacgtt gttaatgtcg tgaaagcttt gggggcctga   127560
cccgattccc aatctgatgc caggtcgtat gctgatgggg gggatctgaa tggccttaag   127620
cacaagtttt tcgggatggg agttttact tcgccccagt tttacaacgg tgtcgtaggt   127680
tacgcgcgaa aaatctctc tgatgatctg cgggtacagt ttgtcaatct tgccctgctg   127740
atccgcccaa aaggtaaaat aatcttccga gtccttaaca attttggggt gtactgcctt   127800
acagacgtag cactgctttc cttcggtttg gcttgaagcc gcttcaataa gacgcttagg   127860
cctaataagg tgctcgtacc tctttaggtc aacgatggga gccccgcagt tgagacatat   127920
aacccttaac catcgtcgta tttcggcgat gaagagcggc tgaagcaccg gagcatgcat   127980
ctgcagtatc ccagggtgtc ccatacattg cttgcgctgg tgtgagcaag tgatgcattt   128040
ataatggtga tcggtggttc ccattcgcgc atcatagata cccccttcgg cgggaagggt   128100
gccctcaaat aaattagaaa tggtaacctc cataacgcct tgcctcttat gatcattgtc   128160
accggcaata ttgaactgaa cggcggctat ttcggcatat ccagcctcca tattttgct   128220 aaatacataa taaaacttca aatgttaaaa aaataacat cggttggcat atttttttgt    128280
taaaaccaag tgttaaatga tttctaaaac atttatcggt tcacgaaaac ctaccgcacg   128340
ggcctgaaga ggaatgccag ttttggggga agctcggca tattccacgg taagctcttt    128400
tccataaaga tgttttttaa ataaggcggg cgtgagtttt tgaaaagag cataacgatc    128460 cgcgtacgtc aaatgcttag gagtgactac aaaccgcttt tgtttggca attcgcaaac    128520 ccataaaatg gcgcctaagt cctttccctt ttttccctga gtatagtcca ctaaaataaa   128580
ttcagcgtct agcagcggtt tcagcttggc aagatgcgct gagtggtagt tgttgtatcc    128640
cggctcatag ggcccattgg cattgcgtac gatggctccc tcgtagccct ccttaataaa    128700
ctgcgcctta agcctaaggg cctcatccac attcttcacg ctaaattttt caacttggtg   128760
gataaaggta agatcttcct tctgtttaaa aatatttgtt aatagctgtt gtctcttgtt    128820
ggaaggcatt tgaagctgat cactccaaaa acagtcaaac acgtaaaagt gcagctcgga   128880
ggaatctgtc ttcgcattcg cctgccccgc gatccattgc agaggtttgc ggtgtaaata    128940
aagctcacca tccaaatata ctctcacgtc tataaataaa taaagctgtt tgagctcttt    129000
tttaatattg tcaagaccta aaaattcctt tttcgtgcgc gaatacaaga gaatgctacc    129060
atcgccctgc tggcaggcca cagctcgaac gccattacgc ttgcgctgca cgatgggatc    129120 tgttcttct tcaaaaaatg tcttaggaat tatattaaaa tattttacca gcataggggg    129180
gataattcct ctatttgtgt gggctccccg cttttgtctg gcatggcgat tatatttact    129240
aagggcgtcc ttgaatgcct gatggactac cgttgtggca ttttttttac ccaagttttt    129300
tccctcggta acacgtgtca tttttgatat ccgcaccgcc ccttcttcca caaaaatt     129360 tgtgaaaatt tcagcaacgg cgtctttac atctgtggaa acatctcat ctgtgatggg      129420 aatgatcgtg ttgtgctgca ccacttgcac acaaataatc catgaggcct tttttccgct    129480
tttcgtttca gactcaatcg gaggaaaaca aaaaatgttg tttgaatatt gcccaggaaa    129540
ttgatttagc atggttttaa caataaaata agcctatcaa ttttttttata atttgaatag   129600 ttattccaaa ttcaatatgg cttctttaga taatttagtg gcacgatatc agaggtgctt    129660
taatgaccag tctcttaaaa atagtactat tgaacttgaa atacgttttc aacagataaa    129720
ttttttatta ttcaaaaccg tatatgaggc acttgtggca caagagatcc ctagcaccat    129780
ctcccacagc atccgctgca tcaaaaaagt tcaccatgaa aaccactgcc gggaaaaaat    129840
```

```
tttgccgtcg gaaaatcttt acttcaaaaa acagcctctc atgttttta agttttcaga   129900
gcctgcatct ctgggctgta aggtctcgct ggccatcgag cagcccattc gtaaatttat   129960
cttggactcc tccattctcg ttcggctcaa aaatcgtacg acctttcggg tatctgaact   130020
ttggaaaata gagcttacca ttgtaaagca gctgatggga agcgaggtct ctgcaaaact   130080
tgccgctttc aaaacgcttc tgtttgacac cccagagcaa caaacgacaa aaatatgat   130140
gacgttaata aacccagatg acgaatatct ttacgaaata gaaatagagt atacaggaaa   130200
gcccgaatcc ctaacggcgg cagatgttat aaaaattaaa aacacggtgt tgacacttat   130260
ttctccaaac catttaatgc taacagccta ccaccaggcc attgaattca ttgcctccca   130320
tatactgtcc tcagaaatcc ttcttgctcg tattaagagc gggaagtggg ggcttaaacg   130380
cctcctcccc caggtgaaat ccatgaccaa agcggattac atgaaatttt atccgcccgt   130440
tggctactat gtaacggaca aagcagatgg aattagaggc atcgccgtca ttcaggacac   130500
gcaaatttat gtggttgcag accagttata cagcctaggt accaccggca ttgaacccct   130560
taaaccaacc attttggacg gtgaatttat gcctgaaaaa aaagaatttt atgggtttga   130620
cgtcatcatg tatgagggca atctattgac gcaacagggg tttgaaacaa gaattgagtc   130680
tttaagcaag ggcattaaag tcttacaagc gtttaacata aaagcagaaa tgaagccctt   130740
tatttcgcta acaagtgcag atcccaacgt gctcctcaaa aactttgaaa gcattttaa   130800
gaaaaaaact cgcccatatt ctattgatgg catcatttta gtagaacctg caattctta   130860
tctaaataca aacaccttta agtggaagcc cacctgggat aacacattag acttttggt   130920
gcgaaaatgt ccggagagtt taaacgtacc agagtacgcg cccaaaaaag ggttttccct   130980
gcatctacta tttgtaggca ctccggaga gcttttaaa aaattagcgc taaattggtg   131040
tccaggatat acgaaactat tccccgttac acagcgcaac caaaactact ttccagtaca   131100
gttccagcca tcggattttc cattggcatt tctttattac cacccagata cctcgtcatt   131160
ttctaatata gatggaaagg tccttgaaat gcgttgtctt aagagagaaa tcaatcacgt   131220
cagctgggaa attgtaaaaa tccgggagga taggcagcag gatcttaaaa ccggcgggta   131280
ttttggcaat gatttcaaaa cagccgaact cacatggctt aactatatgg atccctttttc   131340
ctttgaggag ctggcaaagg gccctttctgg aatgtacttc gccggtgcca aaaccggcat   131400
ataccgcgct caaacagcac ttatttcctt tattaaacaa gaaatcatcc aaaaaataag   131460
tcaccaatcc tgggttatcg atcttggaat aggaaaaggg caggacctag gacgttacct   131520
ggacgcaggg ataaggcatc ttgttgggat cgataaggat caaaccgcgc ttgcggagct   131580
tgtttatcga aaattttcgc atgctacgac ccgacagcac aagcacgcta ccaacattta   131640
cgtgttgcat caagacctcg cagagcctgc gaaagaaatc agcgaaaagg tacaccaaat   131700
ttacgggttt cccaaggagg gagcttcttc cattgttagc aacctgttta ttcactatct   131760
tatgaaaaac acgcagcagg tggaaaacct ggccgttctg tgccataagc ttcttcagcc   131820
gggggaatg gtgtggttta ccaccatgtt gggagaacag gtcttagaat tacttcatga   131880
aaatagaata gagctcaatg aagtatggga ggctcgtgaa aacgaagtgg tcaaatttgc   131940
tattaaacgt ctcttaaag aggatatatt acaggaaact gggcaagaaa ttggagtcct   132000
gttacccttc agcaatggcg acttctacaa tgaatatctt gtgaacacag cgttttaat   132060
taaaatattt aaacatcacg gcttttccct agttcaaaag cagtccttta aggactggat   132120
tccagaattt caaaacttta gtaaaagttt gtataaaatt cttacagaag ccgataaaac   132180
```

```
ttggacaagc ctttttgggt ttatttgtct gcgcaaaaat taaatatttt ttcataagaa    132240
gtactaccca ggttttaaag aaatagctaa aaatatcata tggatactgc catgcagctt    132300
aaaacgtcta ttggtttaat tacatgtcgt atgaacaccc aaaataacca aatagaaact    132360
attctggttc aaaaacgtta cagccttgct ttttcagaat ttattcattg tcattactct    132420
ataaatgcta atcaaggtca tctgattaaa atgtttaata acatgacaat taatgaacga    132480
ctgcttgtca aaacactgga ttttgaccgc atgtggtatc atatttggat tgaaactcca    132540
gtctacgaac tataccacaa aaaataccaa aaatttagga aaaattggct tctcccggat    132600
aatgggaaaa agcttatttc attaatcaac caagcaaagg gctcaggaac acttctatgg    132660
gaaatcccta agggtaagcc gaaggaagac gagtcggacc ttacctgtgc catacgggag    132720
tttgaagaag aaaccgggat tacccgcgaa tattaccaga ttctcccaga gtttaaaaaa    132780
tctatgtcat actttgacgg taaaacagaa tataagcata tctacttcct tgcaatgtta    132840
tgtaagtcgt tggaggaacc caatatgaat ctttctttac aatacgaaaa ccgaattgcc    132900
gaaatttcta aaatttcttg gcaaaatatg gaggctgtac gttttattag caaacgccag    132960
tcattaaacc tggagcctat catcgggcct gcatttaatt ttattaaaaa ctatttacga    133020
tacaagcact aggatgccgc attaaaatgc cacataaggt aatacactag gaatgtcgca    133080
cacgcacaag aatacaacgt cgccggagat ttattatcta gtacacgttt tatgtatgta    133140
caatccgcct tcatttaata tattgagcgg atgtactatg tatttatttt aacaaaaaac    133200
attattttt ttaatcttca tcatctgttt ttataaactc agtaatatca aaagtagctt     133260
gtggggtttc agagggttca ccttggttat cctccgtgag gataacatgt tcttcaggtt    133320
cgtcgtcact ggagaaccca tcatttaatt cctcttcact caacatctgt aaaaaatctt    133380
ccaagctttc gctatcgtta aaatcctcat catccataag aataatggta ccttcctcat    133440
cgtttcctcc ttgtttcgtg tctaaatagg cctgcatggc atttgcaaaa gtatcaaaat    133500
aggctgagtc agattgctgt tccaaaatat ggccttgcgt attaaatgtg gttgcatcgt    133560
tgttaaatgc ttgcaaatac agtaagggat ttatatccat tattattaag caaaaaaaat    133620
ttaaattatt tttcgaccga tgttaggtaa aattaaacaa ttgctatagg tgttaagcaa    133680
tgtttattga ttttaagtac tcaacaacca tgatgtaaat actatacagc acttttggat    133740
ttttaatcaa atccagatta atactaactt cttttgtgat acagttcgta ataatagtat    133800
cctgctcatc gttttgtaag atttctttta atatatttt ttttaccggg atactaagca     133860
attgattatt ttcttttaaa aactccttt gatattcaat cgtcttattc attgaatatt     133920
tgtatataac tataattaca aatgttcaat gaattgttat tcatgtcggg agatggctat    133980
ttaaaaatca tgtcctattt ttctttgctc aataagcatc caaatatttt catggcgttt    134040
tattaattgt tcattattga acgtatcaca aagatcattt ataaattgca gatagtttat    134100
tatttctttc aagagagtaa caaacattac ttcagcagaa catataatag gtaattcagt    134160
ggcgttaaaa gaattttgat cttgttgata cgccaatggc gaggacttaa ggagatttgg    134220
gggtcttgcc caaaccccta ggctgctgtt cttgtttttt agggcgtcat aaagaaatga    134280
aagcacattg caaggcttaa gccgcgacat ctccttcccc ttgggccctt tccatatttt    134340
tagatctaag atctcatccg agcttataga gtaggtatag taaagttttt caaaaaagca    134400
tatctgcttg aagtcttttt tagaacgact ttcaagaagc atttctataa tgttaacaag    134460
ttttgttagg tttaaggcct gttcctgtgt aagctcctct tgcacgtgat agactgaaaa    134520
agtgtgctta ggaatgaaaa tactccccgt ggcactggcc tgttgtctgc caggtatata    134580
```

```
gtacacgctg ctgttagcaa gctgtaccgg cacaatttgc cccacttctg caacattatt    134640
ttgcgattcg gacgagggta tgacaatagt tacgggttca gtcaataggc tttcgccgag    134700
aataatatta ctgtcatttt taataatttt aacggccgct attaaatcaa aggcatttaa    134760
gtaagaaaca acagcagaaa atcttacatg catatatcct cttccgctat tattcgtacg    134820
cataataaaa caaggggagc gttgtataac gccagtaata ttaagaataa aactgttttt    134880
gaaacactta cccacataaa tgttttcaag ctccttcaaa agatgagcct ccacatttgt    134940
acaaaaattg gtaggatcat caatattcaa cgttgtctca aaaatttttt ggtcgatcat    135000
atctataata tattctgtct atttcaattt aaataatata cgaataaata acgagattat    135060
tttattaaat aagcaatggt gtatacactt tgtatttact ttgagatata ctttgtgtat    135120
cacaacgtgc cctaagatgt gtgcacaagt gacggcattt tgtcgttaaa aaggtaaaac    135180
cagcggattc catcctgcat tccatttggt tgattacgag cctccatttc tttttgcaaa    135240
aggttattgc gaatgagtaa gcagagcttg atggcactaa tctttgtaag gtttaaactt    135300
atgcccaatt ggtcagcaat tttttgttgc tcctcccgtc cgcgtgtttc gcatacggct    135360
ccccggttta gcatgcgaat atcagtaatc tcattctttt ttaaaacctg ataggtgggg    135420
cggattttaa atttaagggc ctttcccttg ctttccatat agcctatgac gatgtcgttt    135480
tcttttcgtt taacattaat attaagcata taaagcggaa tttcatgcca ggttttatct    135540
tctcgcgagg taataagtcg cacggagtcc tccgtggcat agcccactag agtgttgtca    135600
tccccaggca cgtggcttat aattttaaaa atgtccggaa atggctgaat atctttttt     135660 gaaaaagcga tgaaaaactt tttataaacc tcgacaaggg cccccatacc tgcaagatta    135720
tctataataa gtgcttctag catcgtatag tgaaatgaag cggggtagtg gatgagtacc    135780
tgctccattg gctcatcctg aaaatccttc tgaaactttt catacaatac ttgaaagggt    135840
tctttggtct gcgagtgttc gaggtatttg gtaatacgga tgctgtgcat cgcgggaggc    135900
tgaaaatccc gaatatatgt ttcaatatct aataccggtt ccttttatg gttaagcacc     135960 gcagcgacgt acaaatgctc aggctttgcc ggcacatgca taatggtgca aagacgattc    136020
tgtatccata attccttgca ctggtttttt gagtagcata gagaaatgag cgccagcgcg    136080
aagttgtcct ctgagaagag tttattatcg atggtaattc cctgtatgag cttgggagtg    136140
gaaacagcct tccatagctc ggagtacgtc cacacggggc gtgccataaa caaagatata    136200
ataatattag aaattgtttt tacctcttgc tccccgtatc cataggcctc aaaggtattg    136260
aggacggtgg ctccgacgtt tgccggcgtg atggatggac taaggggcag actttccaac    136320
ataggcttat caatcttaat ctggttggtg aacccatcaa tggcgtgctt tcgcagcgcc    136380
ttatccccct cctgtattaa aatgtattct tttaattttt gtgcgtactt agcgagctct    136440
ggccctccat cgggtgttgt cgatacgtac aaataaattg tcacgttgcg ctcactgggg    136500
gggagctcca tgtgtgaatt ttttcgcacc accctcccaa atacctgaat aagccgggga    136560
atatcaaggg gcaatgacat aatcatctcg taccgcacgg cctgaaagtt caaaccctcc    136620
acaatcacct tggacccgat gagaatacgc agctggtggc cttccaggtt ggacgaggcg    136680
ttaaaaagag ccaggcttcg ttcgcgtaca gcgggctcta tttcgctgtg cagaatggtg    136740
aaccgtactg gaataaactg atggtcgcta tgtgtgtgct catcgcgaat cgcggcgcag    136800
atggagcagc gggtcgttcc cacaggggac gaaacttcat ttaaaatgcc attactttgt    136860
aaaatttctt gcaagataag aaccccccgac atgcggaccc gattgtggta aattaaaatt    136920
```

```
ttcccccggc cttgccgaat aatggaaaga atgtctttca tcatttgagt gtattttccg    136980
ctataaaagg ccaatcccga gatgtgcgtt ggtggctgca gcgacaaaaa gctgccactc    137040
acattaaagg gggctctacg cgaaggctca ataatctgta ccccgttttc cagaagccag    137100
tctgtgcttg ccatagaaag ggcggtgggg gtttccgtcg agttaaacag gccgtaagcc    137160
ttgggttccg tttgttttga aaattttggg ttgggaaaca ccatgtcata aatgctgtac    137220
gcattactcg agattttagg gtcagggccc agctgtttaa gcgtttcaag ctgatactca    137280
gacatggggc attcgatgaa atgtaagtac ggcaatgttt cgtctttata ggacaacatc    137340
tttccggcaa atattctttc ggggtaaaaa ttggtgttgg tatccaacaa aaagatacc     137400
cttccggtgc tcagtctttc cacaagagct agggcgtcct ttttccattt aacgaatgc     137460
ccactgctgt caaacagttg ctggcgctgg aggggctggc cgttgggcag ctcatgccgc    137520
ggaaccaaaa ggtttaacag gtcgacgtat tccatgacac tcccggttac gggcgttgcc    137580
gacatgaaga cggccctggg ggcctggtga ggtggaaagg catccaggac atactgtaaa    137640
gcgatgccat aattatttcg ttcctggata ttgtacacgt tgtgtatttc atccgcaatg    137700
agcagtcctc ccctaagttg ctccatgatt ttttgattca cccggatgag gccgtttgtc    137760
tcggcctcgc taattttttg cacgaactga gatatatcgt tctcattcaa tgtatcttct    137820
gcttcgtcag aacgatgaaa cagagaaagc acatcaaagt ttttctcttc acccttactc    137880
gtaatattga aaagcttgga tgcaaattcc ttatagccgt aaaactgaaa aaagcctccg    137940
cggtttctat cggttaaacg gcgctttaac gtactaacga acccatttag atgccgtgat    138000
tcgaccgacg tggtgctgcc agactgcttt gcaatgtgaa gaagccggtg tagctcagcg    138060
acctccttgt aagaaacaaa tcccagctca ggacgtctta gcatttctgt ttgaatgatg    138120
gcgcgtgtaa agcctaccac aaaaatccag ggcgcatttt caataaaatt catgtagtgg    138180
ttcataaatt gacgcgcgat ggcaatcgcg gcaatgcttt ttcccgtccc ggtctgccag    138240
tttaataaaa gacgcgagta gggcgtgttg ggattttgaa agttttggac gaaaagctgg    138300
gcattatgca attggagacc cttgatggaa ggaaagggcg acgcgtaggg gtcacacgga    138360
aaaaacgctc gcccccccct ctcgcagcca ggcccaccga tctggacaaa atgagcccgc    138420
agatcacgaa tgagctcttt ttggtcgaca ggagggggaaa tcaacgattt aaactccttt    138480
cttcgcgcca actgctgcaa aaagtctgcg gcatccaatt cgggatacgc catattatca    138540
taaaaaaata aaccttttta tgaaaacttt tatgtgattc tgtattgcaa ttgttttta     138600
tgaatactgt aaataagcgt atcaacttgt ttttctaacg aagaggcgtt attcttttt     138660
tctggatata aaataataat aagtataata attaagacta acagcaggc aatcactatc     138720
aaactcatat tatacttact tttttataaa agtattata tcttatgaat gcgcaagttc     138780
agctaattgt tcgtcgcttg gaatgtggga ctgcaggag gtggagtttt tccttttttct    138840
aaagaatacc gggaaatggt ggtgaggctc aggttgttgt acatagtagc taggaggagg    138900
tttaggtatg ctcgacttgc agtcaatagt ccggttatag taaacgatgg caacgatgat    138960
aagaataata atgagcaaaa tcaaaatgcc caggagaatc gcagttgttc cgggatattt    139020
ggcgattgta tgggctaaaa ggccttgggt gctttgttta attccctcgc gggttgacag    139080
gttatgagaa agcagtggag acgtttcagt gtccattat tacaattgaa cagttatatt     139140
aatctcaaat aaaatataac acaaaattaa ttatggccat gcaaaagtta tttacgtata    139200
tttacgagtt tattgaatat cgtaagatgg tgctgttgga agaaaggta ccatatgata     139260
agtttgttca aatggtactt aatacaggat ttttttcgtat taacgcggag acgctgaatc    139320
```

```
acggaatcgt atccgtgttt atctttggag caaatggcaa gtacgttcac cacggaggcg    139380
acatgagaac gcttttaacg aatacgctta atgaaaaaaa acattatgaa gaattaattt    139440
taatcgttga taagcccgtt ttaagcaaaa aaaatatttt agatataatc gtcgagcagc    139500
gcgctgcaaa tcccacgatt gtaataaaca tatatcccta ccacctgttc tgcattaaca    139560
ttcccaaggt gagtgccatt cctaaacata aactaattac tcaggaggag gcgcaggagt    139620
ttttaggtcg cgaatatctg caaccgcagg acctcatgca aattagcgcg tcagacccc    139680
cggtggtctg gctgggagga agaccgggag actttgtgca aattgagcgg ccctcagaga    139740
cagctatgca cgctgttgtt atccgcttta tcaccaagtc caaaatttga gtcccgtgtt    139800
taaagatgac agacagctaa gtaagcatat ctgtaaaatt gtcgatgtcc tctgtggata    139860
gagcgctttc ctctgagcag caaattttt catacatctc catgggggat ggcgaggctt    139920
taatagtatg taggtcacgt aagaactgtt gtatgatggg atatttgtct tttaaaaact    139980
ggggatgttt cataactgga attatttgaa agataaagac cttccatcca aagtagccaa    140040
ccacatttgg catttcggga cacgcggttt cataaggcat agaatagtga atagtgtact    140100
gatcttttg atacagcgtt tcaagtagtt ggcgaaatgt ttccgcgtcg agcgtgccaa    140160
aatcttgagg agcctcggtg tgctcctgtg tagagcagat cgtgatgatt ccccaggcaa    140220
gcgggagcat ggactctgga gggtggatat ccgtattggt ctcattattc gatcccagct    140280
gatgaatgcc gcacacgcga acatggcct cgacgtagat gcccatagag ataggcggcg    140340
aaagggcaag accggattgt atttgcggca tatagtagga gggcaccgag ttttttattt    140400
ttcggttgaa tggggacttt atttctacca gcacggggat gcgtttcgtg gcctcatagc    140460
gtacgttgtt aaaaattgtt ttgatttccc aggactgttg agtgtatccc agcgttaggt    140520
gacaaaaccc atcggggcta ttactatgtc cggggtatcc caaataggtc ccatcaatat    140580
gaatattgtc acctatgacg gtggtttggc agaacaactc aagcagatct ttactaacac    140640
gctcaaaaag ggttccccag ctacaagcag cgcggttcaa attcttctta aaagatttg    140700
cttttttccgc caaggttata taatagcttt tgtaagggtt taaacctaaa acgctggcaa    140760
ggtcagagcc acccacctga gtgcgacgaa tagcatgcca ggcatcggag cgctgctgag    140820
gagagtcttt aaacaggcgt acaaaggttt ccattatact tgttttaaca ggaattcaat    140880
ataaaaagtc aacacagttt gcaatttttc caatctcaag atatagccat acattttttt    140940
ttccaattgg cgaatatgtt taagctcatg tgtttcaata ttagcatccg gaaatttaaa    141000
tgcataaaga tgttcaaagg cctgattttat acacgtatca aaggatctgt ggtatgttat    141060
tagcttcagc atgtgtgcca gatcttcaag atggtctaaa tttatacggt tttccacgtg    141120
gtggatcatg tctgccacat cttgagcccc catccagggg atcacaaggt actccccctt    141180
aaagatgatt cgtcgttttt ttaaaaaatc atgaaaacgt tttaaagctt caagaaaggg    141240
gcagttgggc tttgaccca aaatgctgac gacgatatcc tcgggcatga tgtattcgca    141300
gtgaggatag tagtttacgg actctaattc agcggcccgc cgttttattt cgtatcttgc    141360
ccagttattc agagagtact ccacgcctcc gaccacaaca gacatcctat ctattaaaaa    141420
ataacaataa aaaccttatg aaatctatgt atagtggccg ctaaaatgtc tatattagaa    141480
aaaattacgt caagtccctc tgaatgcgca gagcatctta caaacaaaga tagctgttta    141540
agtaaaaaaa tacaaaaaga gctcacctct tttttggaaa aaaagagac actccggttgc    141600
gattcggagt cctgcgtaat tacccacccc gccgtgaagg cctatgcgca acaaaaggga    141660
```

```
ctggacctct ccaaagaact ggagactcgg tttaaagcgc caggacccag aaacaacacg 141720
ggtcttctta caaacttcaa tattgatgaa acgctgcaga ggtgggccat aaaatacacc 141780
aagttttca actgtcctt ttccatgatg gactttgaga gggtccatta taaatttaat 141840
caagtggata tggtaaaggt atataaggga gaagagctac aatatgtaga aggcaaagtg 141900
gtcaagcgtc cttgtaacac cttcggatgc gttttaaaca cggactttc aacgggcact 141960
ggaaaacact gggtagccat cttgtggat atgcggggcg actgctggag catcgaatat 142020
tttaattcga cgggaaattc tcctccaggt cccgttattc gttggatgga acgggtcaaa 142080
cagcagctat taaaatacaa ccacaccgtg aaaacgcttg cagttaccaa cattcgtcac 142140
caacggtcgc agaccgagtg cggcccctac agcctgtttt acatcagggc acgcctcgac 142200
aacgtgtcat acgcccattt tatatccgct aggattaccg acgaagacat gtataagttt 142260
agaacccatc tgtttcgcat cgcataaact aataaagttt gaattcttta taggaataaa 142320
aatggaagcg tttgaaatca gcgatttcaa agagcatgcg aagaaaaaaa gcatgtgggc 142380
tggcgccctc aacaaagtca ctatttcggg tcttatgggg gtctttaccg aagatgagga 142440
ccttatggcg ttacccattc acagagacca ctgccccgct ttgttaaaaa ttttgacga 142500
gatcatcgta aatgccacgg atcatgaaag agcttgccat aacaaacaa aaaggtaac 142560
ttacattaaa atttcgtttg ataaaggtgt gttttcttgc gaaaacgatg gcccgggaat 142620
ccccattgca aagcatgagc aagccagtct tatcgccaag cgcgatgtgt atgttcccga 142680
ggtggcttca tgtcactttt tagccggaac gaacatcaat aaggccaagg actgtatcaa 142740
ggggggaacc aacggcgtcg ggctgaagct cgccatggtg cattcgcagt gggccattct 142800
taccaccgcc gacggcgcgc aaaagtatgt tcaacatatc aaccaacgcc tagatatcat 142860
tgagcctcct accattacac cctccaggga aatgtttaca cgtatcgagc tcatgcccgt 142920
ataccaggaa ctagggtacg cggagcctct gtctgaaaca gagcaggcgg atctttccgc 142980
ctggatttac cttcgcgcct gccaatgcgc ggcctacgtg ggaaaaggca ccaccattta 143040
ttacaatgat aagccttgcc gcacgggctc tgtgatggcg ctagccaaaa tgtacaccct 143100
gttgagcgcg cctaatagca cgatacatac ggcgaccatt aaggccgacg caaagcccta 143160
tagcctgcac cccctgcagg ttgcggcggt cgtgtccccc aagtttaaaa aatttgaaca 143220
cgtgtccgtt atcaacgggg taaattgcgt aaaaggagaa catgtcacct ttttgaaaaa 143280
gactattaat gaaatggtcg ttaaaaaatt tcaacaaacg attaaagata aaaaccgcaa 143340
aacaacatta cgagacagct gttcaaacat ctttatcgtt atagtgggtt ccattccagg 143400
aatagaatgg accggccagc ggaaggatga acttagcatc gcggaaaatg ttttaaaac 143460
gcattactcc attccttcta gttttttaac aagtatgaca aagtctatcg tggatattct 143520
tctgcaatcc atttctaaaa aagataacca taaacaggtc gacgtagaca aatatacgcg 143580
tgcccgcaat gcgggaggaa aaagggcgca ggactgcatg ctactcgcgg cggaagggga 143640
tagcgcactt tccctgctgc gcacgggact aaccctggga aagtccaacc caagcgggcc 143700
ctcctttgac ttctgcggca tgatctccct gggaggagtc atcatgaatg cctgcaaaaa 143760
ggtgacaaac attacaacgg actctggaga accattatg gtgcgcaacg aacagcttac 143820
caataataaa gtgttgcagg gaatcgtgca ggtattgggt ctagacttca actgccatta 143880
caaaacacag gaagagcgag caaagctgag atacggctgc attgttgcgt gcgttgatca 143940
agatctggat gggtgtggaa aaatccttgg actgctgctg gcctactttc acctgttttg 144000
gcctcagctt attatccatg gtttcgtaaa acgactgctt accccgctga tacgtgtgta 144060
```

```
tgaaaagggt aagaccatgc ccgtggaatt ttactatgaa caagagtttg atgcctgggc   144120
aaaaaagcag accagcttag ccaaccatac cgtaaaatat tacaagggat tggcggcgca   144180
tgacacccat gaagtaaaaa gcatgttcaa acattttgac aacatggtgt acacgtttac   144240
cctggatgac tcagcaaagg agttgtttca tatttatttt ggcggggagt cggagttgcg   144300
aaaaagagag ctttgcaccg gcgtggtgcc gctcaccgaa acccagacgc agtccattca   144360
tagtgtccga cgaattcctt gcagcctgca tctgcaagta gataccaagg cttacaagct   144420
ggatgccatc gagcggcaga ttcccaactt cttagacggg atgacgcggg cgcggcgcaa   144480
aattttagcc gggggggtga aatgcttcgc ctccaacaac cgtgaacgaa aggtttttca   144540 gttcggggc tacgttgcag atcacatgtt ttatcaccat ggcgacatgt cgttaaacac   144600
aagtattata aaagccgccc agtattaccc aggctcctcc cacctctatc cggtattcat   144660
aggcatagga agttttggct ccaggcacct gggaggaaag gatgcaggat ccccaagata   144720
catcagtgtg cagcttgcgt ctgaatttat taaaacaatg ttccccgcgg aggactcatg   144780
gcttctcccc tacgtctttg aggacggcca gcgggcggaa ccagagtact acgtgcctgt   144840
gttgccgctt gctattatgg agtacggcgc caacccatcg gagggctgga agtacaccac   144900
ttgggcccgg caactggaag acattttggc cttggtgagg gcctacgtcg acaaagacaa   144960
cccaaaacac gagctactgc actatgcaat aaaacataag attactatac tcccgctgcg   145020
gccctccaat tacaatttca agggccattt gaagcggttt ggccaatact actacagcta   145080
cggcacgtac gtcatctcag agcagcgaaa tataattact attacggagc ttcctctgcg   145140
tgttcctacg gttgcataca tcgaaagtat aaaaaaatcg agtaaccgca tgacatttat   145200
tgaagaaatc atcgactaca gtagttcaga aactattgaa attctggtga aattaaagcc   145260
aaatagtctt aaccgtatcg tggaagaatt taaggagact gaagagcaag attccataga   145320
aaattttctg cgcctgcgca attgtttaca ttcacatcta aactttgtaa aacctaaagg   145380
tggcattatc gagtttaaca cgtattatga aatttgtat gcgtggctac cttacaggcg   145440
tgagctttac caaaagcgtc ttatgcgtga gcacgcggtg cttaagctgc gcattatcat   145500
ggaaactgct attgtacgct acatcaatga gtctgcagag ctaaatcttt cccattatga   145560
ggatgaaaag gaggcaagcc gcattctaag cgagcatgga tttcccccgc tgaaccacac   145620
gctgatcatt tcccctgagt ttgcctctat agaggaactc aatcaaaaag cactgcaggg   145680
ctgttatacc tatatactat ctttgcaggc tcgagaattg cttatcgcag ccaaaactcg   145740
tcgggtggaa aaaataaaaa aaatgcaagc tcgtcttgat aaggttgagc agcttttgca   145800
agagtctccc tttcccggcg ccagcgtatg gctggaggaa attgatgcgg tggaaaaggc   145860
tattataaaa ggaagaaata ctcagtggaa atttcattaa acgctaccgg ttttatgatg   145920
tccaataggt gttaagcaat cagttcatca acatttttt caagaatttg aaaagtttgg   145980
ataatgttct gaatacttt ttctaaaaga gttatcaaat cttcttgtga ggccttatga   146040
ataattgtta ataccatttc ttgcttatgg ggaacacact gatacccac aaagctaata   146100 tcaggaatca tttcataaat atatgttttt agcagatttc cgatggtatg ggtttcatct   146160
tttatcgtga taatggcctt tgttttttcc tcatccatgg aaaacagcac aagttccggc   146220
tgcggctctt caaagttttc ataaattttt tgaatgcttt ggattcggcc aataatgatc   146280
cggcaggcgt tttttaaata cgtgcgaacg gcctggttga tatgtggcag cggcaccgct   146340
ggaaagcaaa gccccaggcg gtggtgacgc gggtctgagg tcatagagct ttgcttgtaa   146400
```

```
ccgctaagcg ccatatattc tttttttatcc gttgggtact gttcaatgtc aaggtgggaa 146460
aaatgtgttt taacggcaag attaaaggcg gcatgctttc gtcctatgcc cttttttaata 146520 tagatatcct ctataatcaa cgattttccg ggttgtagga agccaatctc aaaggtagga 146580
ttaaaaatcg ggtatttaag cttagggcct gccacctgga tgagatcgcg gctatagatg 146640
gttttaacct cacagctatt gtttaaactc cgcagagcaa ataccagtgt ctcgttttc 146700 gcataaatcg gaatgaaatt aatgcggttt ctaataaatt gttccgtcat aaacaggtcc 146760
gtggaatcct cgatcttata cccaccgggc ttaatatcta gcatataatt gggaatttca 146820
tcttgcaaga cccgcgacag gccgtggacc gcggctctgc taatgcccctt aaagtccata 146880 acaacattga ccgggacgag gggcaactgc tcctcgagct gaaatagttt tttggccgca 146940
tttttaataa agaggttgga aaagtctatc aaaaacggtt tgatttccac gttttggaaa 147000
attttttcca tttgtattat aaatatatct atatatattc aaattatggt agtttatgac 147060
ttgctcgttt ctttaagtaa ggaatccata gatgtgctac ggtttgtaga ggcaaacctt 147120
gcggcgttta accagcagta tatttttttc aatatccaaa gaaaaactc gatcacgaca 147180 cccccttctca ttacgccgca gcaggaaaaa atttcgcaaa ttgttgagtt tttaatggat 147240
gaatataata agaacaatag aaggccctcc gggccgccgc gtgagcagcc catgcaccca 147300
ttattgccgt atcaacaatc ctcggacgaa cagcccatga tgccgtatca acagcccccg 147360
gggaatgatg atcagccata tgagcaaata taccataaaa aacacgcgtc gcagcaagta 147420
aatactgaac tgaacgatta ttatcaacat attcttgcat taggcgatga agacaaaggt 147480
atggacagca tgttaaaact tccagaaaag gcaaaaaggg atagcgatga tgaggacgac 147540
atgttttcta taaaaaacta acgacgtaac aattaaacaa aaataaaaat cattataaaa 147600
tgaatcttga atacgtccaa gttgttcaaa aatttaatca agtactccta gaacttacca 147660
aaaaagtatg taccgttgtg ggcgggagca aacccaccta ttggtatcac cacattagaa 147720
gggtttgctc agaatgtcca tccatgccga tgagtatgat aggtccgtat ctgaatgtct 147780
ataaagccca aattctaaca agggacaaga atttttttat gaatttcgat cccgcgcata 147840
atgagtacac cttatcatt caaaaactaa aagaagcagc ccgaaatatg ccggaagacg 147900
aattagaaca gtactgggta aaacttttat ttttacttaa aagctacata aaatgtaagc 147960
cctttattaa ttaagaatt gatgcataac taataaatgg ccggtcgtgt taaaataaaa 148020
cagaaagagc tcatagactc tactgtaaaa aacaaaaatg tgatgaatct gttccatgaa 148080
attataggct caaaaggcaa tattaatttt agcgttgtct ggcccaagtt taaaaaaatc 148140
aaacagagcg tttatgacta catttccact cttttctgtgc tggaaaaagc aaacgttatg 148200
caaaactttg aagctgataa gaaactgttg gaactttttg tacaaaagct gtgggctgcc 148260
tatgaaggct atttcaaata tcccgagatt gaaaaatatg aggtggaagg ccaggtaaat 148320
ttcaatctcg tacctcagtg cgtcctcgaa aagtttagcc agttgtatag gataagaatc 148380
aattcagagc ttgtcacact catcctaaac agctgtgcct ttatgagtaa atataacgat 148440
tatattctca aaaagatcc ctacatacta accataaccc ccggcctatg ctttccccc 148500 attcccaact tcgaggacct aaattttaaa catctttaca acagtgataa aaattctcag 148560
catgacaaag agtttatcat gtttatatta tataagcttt atacggctgc cctaggagtg 148620
tacaatgcca tctcgattcc agacatcgac gtagaagacc ttgaaaatat catcctatcc 148680
tcggtgagcc agattaaaaa acaaattccg cgctgcaaag acgccttcaa caaaattgaa 148740
tcttcggtac acctgttgcg caaaaatttt aacacatatt acagtgacta tgtgggctca 148800
```

```
ggctacaacc caaccatcat tatggaacag tacattaaag acatatcaca ggattccaag  148860
aacatatcac cacgcatttc ctaccagttt agaaccatca tcaagtatta ccgcgacatg  148920
attgccacca ggcatcaaac gatggacccc caggtattaa acctcgtaaa gcacgtcgaa  148980
aagaaattag atatgcttga tagagaaaaa aattagtata tatagttatg gtgaatcttt  149040
ttcctgtttt taccttaatt gtgattatta caatttttaat tacgactcga gaactatcca  149100
ccacgatgct tattgtttct cttgtaacag attatattat tattaataca cagtatacgg  149160
aacagcagca tgaaaacaat acattttca tgccgcaaaa aaattctttt aacgaatctt  149220
ataataaaga caaaaaatct aatatacata ttccctacca gtggctggcg cctgaactga  149280
aggaagctga gagcaagtac tggtggggca attatgatcc tcatagcgag cccgttctcg  149340
ctggcgcatc ttgaatatct tcatacgtgg cacgtcacca tcaaaaacat gcccaacag   149400 cacgggcttg atataaaggt ggccattgtg gtctcaacat cgcatttaaa taatttttg   149460 ccaatttccg gggcgcttaa catcgaatgt ataaccttcc ccagttgcgg catcaaggag  149520
atagacctcc tatgggcgcg cattaaacta tttcaacatt actgcgccat cggtgcccgt  149580
cttttatggc tggtaagtgc tgacatcagg cccctgttt cagcgtggcc agccatcgcc   149640
gacagtctaa aaagggagc agatgcggtc gttattccct accctcccg atggaacaat   149700 cttataccta ccgtcatcaa agaaatagtt gtccaccaaa aaatgcct tgtggcggtg    149760 gatgcacgcc accttgatac agatacccag attgtagggg ccgggatggg ctgcatcgtc  149820 ctaacccta aggccttat ggtgcgccta agtattggca aacagccgt taagatactg     149880 tggcccgacc ttcacggcac tgccgagggc attcctctgg aggggtgga ggttggctgg   149940 tttttaaacg cttatgcgca taaattaaat atacgctgcc taggggctga tcatattgcg  150000
cagcacttaa cttaattctt tatttaaaaa gtccacgcat ccagtggcgg cctacattaa  150060
gggcctacgc acataaatat acactggcta gaagtacgcc ttcatttaaa ccattgaatt  150120
atttatataa tggctgcaaa cattattgca acaagagccg tgccaaagat ggccagcaaa  150180
aaagagcatc aatactgtct gctagactcc caggaaaagc gtcatgggca ttatccctt   150240 tcatttgaat taaagcctta tgggcaaaca ggcgcaaata tcataggagt acagggctca  150300
cttacccatg ttatcaaaat gacagtattt ccatttatga ttccttttcc tttacaaaaa  150360
actcatatag atgatttat tggtggacgc atttattat tttttaagga actggacatg    150420
caagcagttt ctgatgtaaa tggaatgcaa taccacttcg agttcaaggt tgttcctgta  150480
agccccaacc aagtagagct tcttcctgtg aataataaat ataaatttac atatgctata  150540
ccggtagtgc aataccttac cccaatcttt tatgatcttt cgggaccgct agatttccca  150600
ttagatactc tttcggtcca tgtggatatc ctctccaatc atatacagct tcctatccaa  150660
aaccataacc taacaacggg tgatcgtgtt tttatttctg gatataaaca cctgcaaacg  150720
attgaattat gtaaaaataa caagattttt atcaaaaata taccgccgct ttcatccgaa  150780
aaaataaaac tatatatact aaaaaatcga atcagaattc cgctatactt taaatcttta  150840
aaaacgtcta agtaataaca tttttatagt ctactcctag ttccgaaata ggctgaattt  150900
cttttttaag tccttttaaac caaggatgtg atacaagact cttaaaggaa agccgcttat  150960
tttcattaat tgttaaacat tccgtgataa actgttttcc cgtctctgaa atgttctcgg  151020
gaatataatt ttcccgtttc aggatatcat ttaaataaaa attttctgca cgaaatctaa  151080
aaagattaac cgcgaccata cctatcgtcc acacggttaa aggaagctgg tagtaataac  151140
```

```
cataataata aaattctgga cacacgtatt cccatgttcc aaacatatta tattggggac 151200
gggtttcgtc taatctaaca gcgcttccaa agtcaatgac cttaatgatc ttttgattta 151260
tgtctataat aaggttctca tccttaatat ccccatggat aaagcccttc tcataaatgt 151320
tttgtataat aagaataagc tggaatatta ttttttttggc ttcggtttcc tcaagttttt 151380
taaagtaatg ataatgaagt agatcaacac tatttggaat atattctatg attagtatat 151440
gatacatagc atttttcggta tattcgataa gcttaataac accggagta tcttgcaggg 151500 cttttcaacac gatgacttca tttcctggaa tttctttttt agaaacgtac ttaaatataa 151560
tgggttgccc tacttgatga cccaaaaaga cgttatttct gccaccctca aacatgggtc 151620
tcgtcgcaat gaaatacatg tgctgcgttg tggagatcct ttccaccttt gctgtaggat 151680
aaaacgcata ttgtgcctgg ggattttta acatttttt aagctgttgt tccggcctgg 151740
acatgtttta ttagctttat atataaaggg ttagaaggtt taatttcaat atgccctta 151800 atgatgggat tatattcgta aaaggtatag cctaatccta cgtctttgtt ttttggtaa 151860 aaaaactgtt tgccctcgta ggatatgcta taggcttta cttcggcttt tacaagcggt 151920
tggcagggat tgggcaaacg taaatcgcgt tcaaagttt catgaaaaag caaagcattt 151980
gtgggctgac acatcagaca gccgcttcg ccattgaagg cacattcaat ggccgcccct 152040
tttagtaaat cgcggaaagc agaattaaga tggctctttt caagccccct ttcgtgaaaa 152100
cgctcatcaa tcgttttttg ttcctgactg ccttcgggaa tactataaaa cattttttga 152160
ttagccaccg cgatgtacaa aaaaggctgt acggttttct cctcgggcgg tagcgcatcg 152220
tggctaccaa tgcgtataat gcgcgccttc acttgatcct ctcgggcctt atcccagtac 152280
ggctctagga tatgaacctg ccgcccgtat ttgagatcca atccctcagc tcctgtttta 152340
gagacgagta aaattttaat aacctctccg tgtatattca gcggcgaatt ccaaagctgc 152400
tggatcatgt cgcgctcttt agataaaatt ttccctgtaa taagcgtaaa tcgtgttatt 152460
ttggaggaca ggactaacgt atgggtcggc ccatcttccg caaagttttt caccataaga 152520
tctttcccat ccttatgaag gaggatggtg ttgtgcccct cttccaatac ttttagggc 152580 tgaaggcact ggtagccctc tatttctaaa aagcgggcca cgacgtgaag gcccaattcc 152640
acaaactgtg agtaaatgag cacagggccc ggagacgttt taatatttt tagcatgcgt 152700 actattttgg gactagaatt ttctgtgaag gcctctttgg gcagctgctg aacagcctct 152760
gataattttt catcctcctt tactgttagc atttcggacg cgaagatgct gatcatacgg 152820
gaacgcacat agtaggagga gcctgactct tgctccgatc ctggcaggca gagggcggcg 152880
gcatttattt tttcatacat tcctgagctg gcgtgctttt ccgcgttttc aacgtctcgg 152940
gccagcagat attgcctata ctgctcgggt gacatttcaa ccttttctat aataagagga 153000
agctctgtgg ggaatagctt gttgagctca ttctggtttc cagcgtagct tatcataccc 153060 actaggcgt ttagtagttt gtccgcgttt aaagggctat tcgttgtttt attgacataa 153120
gcggtgtaga atctttcata gtgaagaggt aataagattc gcccgcttag catattaaaa 153180
cagggcacca tttcaaaggg gtccttcgaa cacggggtgc ctgttaaaaa cagaatacga 153240 atattttag cttgcataat attattgtac agctggcggg catttgtttt atcattggcg 153300
ctattgataa ttcctctaaa gaggttgtgt gcctcgtcaa cgatgagcag gcatccattt 153360
agggaccctc ccgcctttat gatctgctgc cccatgttgt aagcgtctag gacacaaac 153420 ctgaagcgcc gcgagatttt ttgtagctct ttggagtgat ccgtcgtttc cggatataaa 153480
agtttaataa gctttaacaa agactgttgg aagtttgagt gcaacgactt gggtgcgatc 153540
```

```
agaatcgggt tgtaaatatg tgaaagtgag atggcaagcg acaggctcaa aatggttttc 153600
cccatgccca tctggtgata gatgaggagg ccccgtgtgt tttccccctg gcctatccca 153660
aatttaggat ccgaaaaggc ggtgtaaatt aaaaactggt agtatttcag ggctcgtgca 153720
aagcgggcag tgagtgaggt gtctttgctt tcctgaagct ctttatattt ttcatatacc 153780
tcttttaggt atgcttctat ttggacgggg aaggaggtgt tgttgtgcac gcaagacatg 153840
actcgttata aggatcccat attaaaactt cattagaaga atagggctgc tgatagctag 153900
cgctgcactt aaaaatgggg tagccctttt tcttgtaaat ccggtgcctg tcgtagacct 153960
ggctagaaag cgggcttagt gtatctttaa tgtccacaac gatgcgtacc ttttttttcat 154020 ccgatccctg ccgggtaata cgtcccaaga tttgctccat gttgtttctg cggggcgttg 154080
ccatgatgat cgatgtcata tgcttgaagg aaatgcctct acgcccgtag ccataggtca 154140
gcaagataat ggaagcgctg tgtgcctgag aaagagcggt atttgaaacc ccgccgcata 154200
ggagcgccac ctccggaacg ataatttgaa catctttgaa ttctttggaa agcgcctgat 154260
aaaaaatttc taaaagtttg cgaaattcca cgaaaatgat gatgccatac ggctcatcgg 154320
tcccccattt gtgaggctca gcggtatgca gggagtaaag ccgctttgcc tcatttacga 154380
caagttgtat acgcgaagga tcttgaagta gtttatcaat ggtggcaatg gccgatacct 154440
tttcattaat atacacaggg ctaacgaagt caggatgtcc ctgatattcg atttccctca 154500
cgtacccgga aaaggttgtg gtgggactta cagtcctctg gggctgtcct agatggtgaa 154560
taataatctt gtccatacca tcgggccggt ccagggtgt agcggacagt cctaatatcc 154620
gactaagttg tattttccaa aaaattttgt aattctccgg cgagtgtaat tcatgtgcct 154680
catctaacac gactagacca aagggctcaa agaactgctc aggcttcttg cgcagggtat 154740
taatgattcc cacgatgacg tcgtactctt tgctcgtcat gtcctttttc ttgcacgctg 154800
cattattgta agcagctaca cgtaggtggg gcaggagcaa tgttagctcg tcgatccact 154860
gtatttgaat cgccttggtg ggcacgatga ccagggtagg gtacaaaagt ttttgaataa 154920
tgctgatcgc aatacgcgtt ttccccaaac cggtatttag atgtaggtaa aagcgcccat 154980 aggggggacag gagcttttta tgaatctttat cgaccatttc ttgctggtag ttaaatagtg 155040
gaaattctgt ttcaacgcat gggagggccc gcagcgacac ggggcgcgtc gtgtaaacca 155100
tgttaaacat ttcaaactgc ttttgcagca atatgggaaa ataaatgtat tccccctgca 155160
gcgtgaaggc agtttcctgt cttatggcta tgtgctttgg ctgcccgggt aatgcccgcg 155220
ccgtaacggt gagcgcctta agaacgcgcc cgaaatcatg ttgtaattta ctttgtagct 155280
tcttataatt tattcctatt ccagcaaagg atataatggc ctccattctc acgctggacg 155340
ggttatatgc agaggttcca aaattcttac cagaggcgtt acgagagggc tgtgctggca 155400
agaatcctct aagctttat attcaacaaa ttttaaattt aatgggatgt gacggtaacg 155460
agtaccatgt tcttttttacc agcagctccg aggaagcaaa tactcatatg atcatggccg 155520
ccgtgcgtcg ccatttgctg cggacgcagc aaaggcctca tgtcattatc ggagcagccg 155580 agcccccctag cgtcaccgaa tgtgtgaagg cattggcgca ggaaaaacgc tgcgtataca 155640
ccatcatccc cctaaaaaat tttgaaatag atcctgttgc ggtatacgat gccatacaaa 155700
gcaatacctg cttagcgtgc atttcaggca ctaatgctgt tgtcaaaacg ttcaacaaac 155760
tccaggacat cagcaacgtg ttaaaaggta ttccccctgca ctcagaagtg agtgatcttg 155820
tttatcaagg atgtattcaa caaaatccgc ccgctgatag tttttcaata aatagtctct 155880
```

```
acggcttcct gggagtcggt gttttgggaa tgaagaaaaa ggtcatgcaa ggattggggc   155940
cgctcatttt tggaggaggg ctgagaggcg gaagccctaa tatacccgga attcatgcca   156000
tgtataaaac gctaacccag caaaggcctt ctatgaaaaa aataaatac aatacatacg    156060 ctgttcatga aaactttaaa aaacatcagc atgtatatct acccataggg ggcgtgtctg   156120
cagaggacac gtctgcagaa acatatcta caaaagacat gcctgttgaa ggcccgaagg    156180
gactcccggg ctatatttta tttagcgttg gccgtcgcgc cgaggagcta caaaaaaaaa   156240
ttttcactaa atttaatata aaggttggcc gtgttgttga cttacaagag atactgtttc   156300
gtatcaaaat accccaaaaa tactgggaga cattattgtt catccaatta agagataatt    156360
tgaccaaaga ggacataaaa agagttatgg ttgttttgat gcatttagat accatcactc   156420
ctcgtggctc tcttcctcct ccgagccact cttcttcttt ttcttaatcg tttttgtttg    156480
ttctataata agggaaaaga actccgtggg atcttgttcc ccgtacaggt tatctgcgac    156540
cataaggatg cttagaatgg taaacaggtg agaatacata agggtttgcg ttttaagaaa    156600
accctgacgt tgaatcataa ttgaaaacac cttgcaaagc cgactcatca gttgttctgt    156660
aatggcgtta agcattttct ggaattttc ttggtttttcg ggtgtgattt tatattcatg    156720
tagaaagtgt ttcacacctg aggagaagaa tctttcctcc ttcgagagcc catctttgat    156780
gatgggaagt tccttgatca gggcaaacca ttcctcctct tgggcttgcg gattctgaag    156840
atactgatgg cagatatggt ttagaatggt gcacacgtag ctaataagct ctgagctgat   156900
tctttggttg gttttcaaat gttggcgaaa gtagttttc accgaagtgc atgtaataaa    156960
cgtcttcatt ttcttataat atacaacagt atgttgagtc tttaatttaa aattacaagg   157020
agttttctag gtctttatgc gtataggtgt ttctttgtcg taaattttca atagccgaca    157080
ttgtttgtga agcagtgttc tgagtagtga ctgtcgtgta aggctcagcc ggatgagcag    157140
gagcactcgc ggccgcaggt gcggccgccg gcccgccagt tgccatgact agtctgtccg    157200
taactgggtt gtccgtaact ggtttgtttg ttgctggtct gtttgttgcc ggtctgcccg    157260
tgactggctt gcctacactt gctgtagtcg ctccagctgg tttagaggta cctggttgtg    157320
gagtgacttc tacccactgc tgatcttgat aaggatttat aaactgtata tcttcctcct    157380
caatagcagc agctttttc tttcttgaag agaatagata gattagaacg atgataatga    157440
tgactaagac cacgatagca atgagaatag tatacatatg tgtggagaag aagcttggtg   157500
tagtgactgg tgacaaacac tcaccataat gccgcggata aaccggttga aaaaattcag    157560 aatccatttta agatactatt ataaataata tataaaaatg ttgtggcgca atgaaattac   157620
agaatttatg gaccaacttt ccaagtattc tcaagaaatc ttaaaaacgt ttaagcaatt    157680
gcgtcctagt gaatataaac aatacaatga attttttaaca caagttacac cgttgctgca   157740
aaaaacccct gaaaaaattc cagagttggt tgaccatata ttcaattacc tagacaacgt    157800
tgaaaaaatt tgtgagctcc tcgtgaatgc tagctcaatt attattagtt caaaaatacg    157860
agaacaagta aaacacggaa tgagcttcag ctataaagcc gacctcgact ccttggcgga   157920
cattctctct caaaaacagt acgtgcttat gcatctttca aaaatattg cggccgagta     157980 ttttaatacg tgtttaaacc aagggaaatc caagttagat ctcaaagctg cctctgtatt   158040
ttatagtagt cgttcccgaa cggcaagctc agcagaactc tatagaaaaa tgctatacgc    158100
ctatggttca ccgcaggaaa ttaattatta tactgaaaaa gcccgaaata agacgttgga    158160
tgtggaggag agcgacagca tggccatcat cgaacgaacg gccgacaca accttttccct   158220 tatgcacccg ctagaagcca tggggcttac ctttggggca accaacacgg acgccgaccc   158280
```

```
ggaggatctg aaggacaaaa cggtgataaa tttaacgctc ccgcaggcaa cagaaagcat    158340
cacctaccat cttaaatccc taatgcagct aaaaaaagta agtacggctt caggactaaa    158400
tacaaacatt ttgaaagcat ttgataatat tatttccacc cctgtgaaaa aaaataaaat    158460
ggcctccaag ttggcgcccg ggatggatgt cgtgttcact agcgataacg gaaaacatt     158520 ttttactaaa aacattttaa gcaaaaacat gctagcgggg cccaaagagc gggtgtttgc    158580
atataataat ctcattagta atttaaataa ctcctgtttc atacaaaatc acaacgattt    158640
tttaagacag caggactctt ggcccttcta tgacgcgcac aatttttacca acaagttttt   158700 aatgcagcct attttttcgg ggcagacccg tcctcggctt cagggagcca tggaggcggc    158760
gcatgtggaa acgcatctca cggcattttt acaaagtatt cagccctcta ggccacaaga    158820
tccctctgtt ttggcttccc ccaagttatc tgctctaatc ttgaactaaa aacagccttt    158880
cttggactta aatgatggtc taccagtttt tgaaataact tagagaacta tgaagatttt    158940
catgaaattt aaattagaga tttgcaaagg ttacttgcgg tcattttctg ttgaattaaa    159000
taattattcg aatagtataa tgtctgaaga tattcgtcgt ggtcctggca gaccgccaaa    159060
gaaaagggtt gttcccaact ttgagcgcaa gggcattctg gaaaaccag ttcggccaca     159120 aagccgtctc gagttttcct atgataaccc gctgatattt aaaaatcttt ttatttactt    159180
taaaaacctt aaaagtaaaa atattttggt gcgatgtacc cccaccgaga ttaccttttt    159240
ttcacgtgac cagtcgcagg caagctttgt tattgccacc atcgacggaa aaaacgtgaa    159300
ccattattac gccagtgatg tcttttggct aggcatcaac agagagctcg ttgaaaaaat    159360
gtttaacagc attgatcgct cttttttaaa aattaccatc gttcaccgct atgacaagcc    159420
tgaaaccctg tttttatct ttacggattt tgacattgac aaggagtgca cgtatcagat     159480
tacggtctcg gagcccgagc tcgatatgga ccttatcgaa atggaaaaaa gcatcagtga    159540
agaaagactc aagaactatc ctctgcgctg ggagtttacc tccaagcagc tcaagaaaac    159600
atttagcgac ttatcaaact acaccgagct cgtgaccatt gaaaaactcg gcggcgatac    159660
gccgctgcac ctgtatttcc aaaagtttaa ctccatctca taccacgaga tgtataaatc    159720
ttccaacaag atcaacctga cctcgaccat tcctaagtcg caggtgttcc agataaatgt    159780
taaaattgct cacatcaagt cgctggcctc ggctatggtc accgacaaga tccgcattct    159840
gtgcgaagaa aatgggaacc taatctttca atcggaaatg gatgcccctta tgttaaatac    159900 gattaccttg aacaccacga tatagttcgg taacattaga tgttctaata tttagcatct    159960
aaataatacg ctgtagtccg gtcagggttg cgtcacagtt ttcccatttt tttgcctcgt    160020
cggcggtggc caccgttgcc ctatcattta cgcccggtaa gacaaagcta aaggcgttca    160080
gcggggcttg gcaatgcccg cccagcgtga aggagctcgg aggattttgc gcatcccgaa    160140
atcccttagc catgttgttt aacacttcgg ttacgtcaat cgagtgaagg gatcccttgg    160200
gatccgtgaa tgtaaagacg cagtttctaa agcgcatgta tgcgatggac gattcatcgg    160260
gggttttgaa ggtaacagtg ttccccttgc tgtacttaaa gggggaccat ccggtaaaat    160320
tataccaaat gaaagcaata ataattaaaa taaccaacac aatagttata gacaacacaa    160380
agtctgtagt gccgcccatt attaaataaa atatttttag accgccggct taaaatttac    160440
ttattgctca tagcttaagt ctatttttatt catagcttaa gtttattgct catggcttaa    160500
gtctattgct tatagcttaa gtctatttta ttcatagcct aagtctattg ttcatggctt    160560
aagtttgttg ctcatagctt aactccatta ctgatagctt actgatcatg acttaaataa    160620
```

```
aaatattttg cccgcttaaa aattgtttag gtttgaaaaa ataagagatg gaggggggcaa   160680 cttatcgtca ttgtgtttac ccccactgga agacatcaaa cggtaaataa ttataagaat   160740
caaaatgatt aatataaggg ttaaaaaagg atgattcatc acattaatta aaaacgtatt   160800
tataacgctg ttgcagttga aattttggta taggtcggaa atattgcccg agcctccgta   160860
ttctgcaatg ttctgacata tggtgagtcc ggagggggcac tgcttgttgg tcaaaatatt   160920
tctttgctcc gttgttttat aggcattttt atttccatta cacggagcaa acgcacattc   160980
aggccatagg gtgccggagt tcacacaggc acaatactgg ctatacgcat actcatcctt   161040
tgagcacaat ccctgtttat cgcatatgct cccaataata ttgtcatcct ccgccgtttg   161100
ttgatttgta tgcgagcgta aaatagcggc ccaggccttg ggctcctttt tttgcagctc   161160
ggaaatcgaa gggcctgtac agctaaagtc gacccaaata tcattgcatt tcgtggaaac   161220
tggcatgcaa gacataattg aaataattaa taagtatata tcatggcaac aaattttttt   161280
attcaaccta tcaccgaaga agctgaagca tactacccac cttccgtgat aacgaataaa   161340
cggaaggacc tgggggtaga cgtatactgt tgctccgacc tagtgcttca acctggacta   161400
aatattgttc gcctgcatat taaagtagca tgcgaacaca tgggcaaaaa atgcggtttt   161460
aaaatcatgg cgagaagcag tatgtgcacc catgaacggc tgctcatcct tgcaaacgga   161520
attggtttaa tagacccggg ttatgtgggc gagctcatgc tcaagatcat taatcttggc   161580
gacaccccgg tccaaatatg ggccaaagaa tgtttggtgc agttggtggc ccaaggtgac   161640
catgtgcctg accatatcaa catcctaaaa agaaaccaaa tatttccgct gtttgcgcct   161700
accccaagag gcgagggtag atttgggagc acgggcgagg ccgggattat gagaacttaa   161760
tttttatttt tttcttaaca taatgggagg ctctacaagc aaaaattcct ttaaaaatac   161820
gaccaacatt atcagcaatt ccattttcaa tcagatgcaa agttgtattt ccatgttgga   161880
tggcaaaaat tacataggcg tattcggtga tggaaatatt ttaaaccacg ttttccagga   161940
tttaaactta tcattaaaca caagttgcgt gcaaaagcac gtaaacgagg aaaatttcat   162000
tacaaatctt tcgaaccaaa ttactcaaaa tttaaaagac caagaagttg cgttaaccca   162060
atggatggac gcaggaactc acgatcagaa aacggatata aagaaaaata taaggtaaa   162120 cttaacaacc acacttattc aaaactgcgt ttcatccctg tcgggtatga acgtgctggt   162180
ggtgaagggg aatggcaaca ttgttgaaaa cgcaactcag aagcagtcgc agcaaatcat   162240
ctctaactgc ttgcagggga gcaagcaggc catagacacc acaaccggca tcactaacac   162300
ggtaaatcag tactcacact acacctcaaa aaacttttttt gacttcattg cagacgcaat   162360
ttcggctgtt tttaaaaaca tcatggtcgc ggctgtagtt atcgttctaa tcatcgtagg   162420
gtttatagcc gtcttttact ttttgcattc acggcaccgc catgaggagg aagaagaagc   162480
tgaaccactc ataagcaaca aggtattaaa aaatgctgcc gtttcgtaat aatttaatta   162540
aaagtaaaaa aaaaggtatt gttatagtga tggcagattt taattctcca atccagtatt   162600
tgaaagaaga ttcgagggac cggacctcta taggttctct agaatacgat gaaaatgccg   162660
acacgatgat accgagcttc gcagcaggct tggaagagtt tgaacccatt cccgactatg   162720
accctaccac atcaacttcc ctgtattcac aattgaccca caacatggaa aaaatcgcag   162780
aggaagagga tagtaatttt ctacacgata ctagggagtt tacttcactg gtccccgatg   162840
aggcagacaa taaaccggaa gatgacgaag aaagcggtgc aaaacctaaa aagaaaaaac   162900
atttgtttcc aaaattaagc tcgcataaat cgaagtaaaa attgaagcga aaaaagtag   162960 aaaaaaaatg tttggagctt ttgtaagcca ccgtttgtgg tcagatagtg gttgtacgac   163020
```

```
cacctgcatc acaaacagca ttgctaatta tgtagccttc ggcgaacaaa ttggatttcc  163080
ctttaaatca gctcaggtat ttattgccgg ccctagaaag gctgtgataa atattcagga  163140
agatgataaa gttgagcttt taaagatgat tgttaagcac aatctttggg ttgttgctca  163200
tggaacctac ttagatgtgc cctggtcccg taagagtgcg tttgttacac attttataca  163260
acaagaacta cttatatgca aggaagtcgg tattaaaggg ttagttttac acctaggcgc  163320
tgtggagcct gaacttatta tggaaggact aaaaaaaatt aagccggttg aggggggttgt  163380 catttacctg gaaaccccgc ataacaaaca tcatacatat aaatacagta caattgagca  163440
gatcaaagaa ttgttttttac ggatacgaaa taccaggttg aaacagattg gtttatgcat  163500
tgatacggct cacatctggt cttccggtgt caacatctcc agctataatg acgcggggca  163560
atggctgcgc tcgctggaaa acattcattc cgtgatccca ccaagccaca ttatgttcca  163620
cctaaatgat gccgccacag aatgcggaag cggtatagac cgacatgcaa gtcttttga   163680 aggaatgatt tggaaatcat atagccataa aataaagcaa agcggtttat attgttttgt  163740
tgaatacgtt acgcgacacc agtgtccggc tatattggag agaaacctcg ggtcttccat  163800
gcaattacaa accgctttaa ccgcagaatt tactacatta aaatcgttat taaaataagg  163860 atgagttta gcgaatgtcc cttagttatt agtgcatgca aaaaattct acaaaagcgt   163920 attacaatag agaatgaagc acttataaat gccttaataa ccgctttagc gcagaccagc  163980
acgttgaatg atctttgttt attacctatt caaacctatt tgcttagtta taaaaatgct  164040
tttgagtgga tacacttcgt atgtattgca atcaccacta ttttggataa taagtataac  164100
tggaaggact gtacggtaga tattaattat attttttctcc atgtaaccta tatttacaat  164160
attaaaacca aggaatacct agactactgt tcttaaactt tattttttct atatttacgc  164220
caaagagaat atttaaagtt tttttgaaaa aaataatata tgtagataaa attcagttac  164280
atgatatatg tgtaaacatg tgtggtaaac aacatatggt tatgctttat aagataaatg  164340
cgcataatat atgtaaacaa aatatggtta tgtgttaaat gcatataaat gtattttaac  164400
gtatatcttg tgataatgga tatatgcatt tattaaaaga ggctgtattt attataaatc  164460
ttgctaagga tgccattgtc aacatatatc ccatgttgga caaattgcgt tgcgatccag  164520 ttctttttt ttgattttgt ttaatgctat ccttttgaa gggatggttg tccaccatat  164580
ttattcgatg ttcaatgaat aggtctgctt tttcgtaagg cagtgaaggt cgttccaaga  164640
ctccttgaac gatggacgtg ttttcttgga tccacttaaa aagcacgtgg cattcaaaaa  164700
caggacagtg attggatcct tggatatgct ttggacagcc aatgcttgaa gagatgtagt  164760
cccttttctt taggacaagc ttctccacgc tggggcaaca gagatcgttc aagttctgga  164820
cggtcgcatt tggaatgttg aaacttcgta tccattcacc ctcgggtcct cccttatgaa  164880
gaaggagtat ttgctcatgg tccttagtaa tcttaaccaa atgttggaag atcatttttt  164940
tacctgcttt aaaggcctga agggtgtcag ttggcaaagc tattgaattc gggagtgggc  165000
tttcatcaag cgtgaaatgg tgaatgtgac gcgactggaa agaaaacgac cgttgattta  165060
ttttttcaaa gattgggtcg attccgccat gaaagaacag ctgcaagatt ttagaaggcg  165120
tatttttttc ccaataaaaa atgaccactt ctcgtgggat taaaatcgtc tgtgtcccat  165180
tttcattata taattggccc ataaagccat caacgtcaat caacaccaaa agcatggtat  165240
agagagcttt tagaaccgga gttcgttaaa aaaatacaaa gttcgtttaa aacgtgtaat  165300
gttactaaaa aaatgtaatg tttaaatgat aatgatacca catgcattaa tgaaaaaaac  165360
```

```
ttttaaattt tgtttaaat atttgcatga aaatggaaac attttagtc tgtttatttc   165420 acaatgcaga tggtttacat caacagattc aggaaatttt gtatttattg cggatgcata   165480
tttacgaaac aaatctttac ttaaagcagg aactatcacg gcttatatat ccaaataggc   165540
aactttcttt tgtgttactt atgccccttt cccttctaag aaactgggat gacattgaat   165600
atttaacgga cgttgtagat gataagcaga ctctacatta cgcggcaaat ttgctgacaa   165660
actacgttct acatctatcc atgtttcaaa agctgacaaa accatacttc cttttagcgg   165720
tcaagcgggt cagcgaaaaa ctcaacaaaa agcagcgaca ttcattttac gaggtattgg   165780
taacctccga aaccttgaat aattatgaaa acctatctaa aaacatttta aatacgttga   165840
tgtttgccgt gcgctacgta tttaaaccta cgccgaacta ttcagaaatt ctcgcagagt   165900
tggaaaaaaa aaataaaatt caccatatta tttttaatat ggtaattacg gattttgcgc   165960
aaatccgtga acaacaaatg gataaacatc tgtgtgaaac aaataatgag cttcgtcagg   166020
aatgtaaaga aactatttt gatttaaagg tggtaggaaa tgtttagcca ataaactcat   166080
gcccgcattt tttacaggta caaaatatcg tggatggctc atcgagggcg cgtgtttgta   166140
cttctctgta ggtacacata cgctgcttgc agttgggaca cttataaagt tgtgacgtct   166200
tttcggcgac cttttgctgc gaacgtagag taattctgt cttctccttt aaggcggcag   166260
aggggcaaag ctcggcgaac gtcatgctac caattgcctc cggttttagc tcgccagaaa   166320
ttagcttatt aagggcatcg ttatcctgtt gttggtgact ttttttttcg cagttaataa   166380
tatgattgat cgtcccacaa cgggttgaat attcttctaa aaaggttttt tcttgttgct   166440
ggtacgtata atgataacac gaggcctcga ttttttgcgc gtattcggtg cataaatcag   166500
tatgttcctt aaaaaacata tgttttgaa gcgttctaaa aaacatcatt tggatgatat   166560
cacgcatttc caaaataata tagggttcta gtcttttgga atctttcata actagatcgg   166620
tggtaatatt cttagtcata caatttatta aaaatggttt aatatattgt aaatattttt   166680
taggcgtgtc agcctgtaaa aaacattctt gttcaatctt atttgtaagg atagtatttt   166740
gcaaatactt atttagcaaa aatacgatag aatcgcgggc tatatgcatt ttcatataat   166800
ttttttttaa aatttaatac aaaaaaaaga agtatagact cttcttctag tccggttagt   166860
tcgttggttg cctcaacatg gagactcaga agttgatttc catggttaag gaagccttag   166920
aaaaatatca atccctctt actgctaaaa atattaaagt agtgatacaa aaagagcaca   166980
atgtcgtctt acctacagga tctataaata gcatactgta cagtaactca gaacttttg   167040 agaagattga taagacaaat accatttatc ccccgctttg gatacggaaa actaattgt   167100 aaccagtagt acatttaagg atagtttaag cagtaaatgt agaataacac agttaagcaa   167160
taaataacaa gtatataggg atatataggg atatatagaa atatatagaa atagctaagc   167220
ttaatactaa ttcagctttt tttttaacta aaacctgaat agatgcgaag tagcggacat   167280
atacatacta aaataagcca tacatttact ttcttcttga acatgaaacc ttttttttctt   167340 ctgttgttgg tatataaaca ataggactgt ttgctgaggt tgtatgatct tctacaactg   167400
ctgtctcagg atgacgatgt tttttaaac taaagtgta ggatggaatg agtggaatat   167460
agttatggct cgactatcc tgtttcgtac aggaatattt tttacaaata gaacgcaaca   167520
agcatatgaa taaaaacaga atgatatac aggagcataa aatagatatg aacactaagg   167580
ggtagcagct tttataacgt tccgtatttt tcttagctat caattgattt accgtaatat   167640
ttatctcggg aaactttgtt ctacaatatt ttgtttggta ttccagaaac tcatgtcctg   167700
gcttattccc gcagcttaaa aaatgataca aaatgtgtt attgttacta aaattaattc   167760
```

```
ttcttaagaa aaactgcgga agacgcttta ggtacgtctg ttcctgtttt agtaggaagt   167820
agtataaggg acaatttctt tttccacaca ttagattatt gtaatatagg taggttgggg   167880
tgttggagcg aataagtttt ctgagtatgt tataatctat gacttgtaaa tcgttatacc   167940
ttaggtccaa aaacttgagt tctttaccaa agccacctgc aatttcagaa atattttttca  168000 tcccgcagcg gataatacgg atgtcctgaa acgtctttaa aatacttgta ttgtagtgaa   168060
tacttatgtt attttttttgt aaataatcta tgtcatgaca agtgcatgaa atgccagcag  168120
cattgcttgg tatagtatta tatgcaggaa gaactatact actattgaga atagtcacat   168180
tgtacttata ccatgtatta ttttctgata taaagtattt gcaggtgacc tgtggtttaa   168240
tcctacctgt taagccactt cctaaaaaaa caaaaatat gaaaacccctt agcatcctgt    168300 atatactatt aaaatttat aaaatttct gtttaaattt catttagaca aaaaaataat     168360
atatatacat cagcaagaaa ttatatacag attatataat tttctgattt ttttttgcca   168420
caataagcat cattatatgc attaaaatct caatactaaa cactaaaatc taaattctaa   168480
gcattaaatt ctaagcatta aattctatgc actaaactgt aagcactaaa atctaagtaa   168540
ctaaaatcaa cactaaatgt atgcaaccta aaatgtaaag cattactcat catcctcctc   168600
ttcttcatcc tcatcatcat aggttaagat atatgtgtca tcctccattt cttcacattc   168660
atcttcataa gcatcactgg gtattggtgg aacattggat gcagcatttt taaaatattc   168720
tatgtcttct ggtgaacact catctaatga ttttttgaca gtccttttaa cttccatggg   168780
atatgattcc aaatcctctt tatataagag tttacggtag cttttagctg catccacatt   168840
tgctggagaa tctggatttg gctcattgag cagtgaaatt acactaagaa gaatggtatc   168900
aatcttttga gccggagacc aagtcattcc ctgttcttca gcattgtctc cgtgtaagat   168960
agagatacat agttttccat cagagtaaat attaggatgc cacatttcag aggtgaatgt   169020
taatctgggt ggtgcatatg ggtattctgg aggaaaggcg attttttgcct tgaataagcc   169080 tccctcataa aaagtgtcag gtgggcccct taagatcaca tcccattcag tcatatcctt   169140
ctcattcacc gaaattttga aattctcaga gggattctct atcaggtgtc tgtactctgc   169200
tattaaaaac ctggaaacca tggttatta atattaatta aattccctgg tttattcctc    169260
cttaaaagta gatgaaccctc ttttgttttt tattgggttc attttttacta aatttatgaa  169320 ctggaaaaaa ctttaacggc ataattatca aatgcgaagg gggatccgta taaaatccta   169380
gcttgccggt aatggctatt aagttaaatt tggtaccagt aacactaata tttaaaaagc   169440
cctgatcatt aactttccac attaaaagat tattatattc gaatgtttgt ccaatatgga   169500
caactttgtc accagatgtt acatttgatt tggttgttag tggctgaagc ttggcacaat   169560
caaaaataag cccattaaca ctaagatata gaggagtggg ttgatctatt ttctcatagt   169620
ttaatattcc atcttttccac gtaatagctt gataattatc cgcagcaatg agttgaaatt  169680
ttataaatag tacaggggtt ttagttgtcg ttatacattt aaagggtgtt ttataaaaat   169740
aaaaataata attgttaaaa gtatgataat aatcgccaaa ataatttcat acatttttta   169800
taagaattat acatagtatg gtatttaaaa tattagctaa atttaaaaaa acttcatgat   169860
ttttaaaaca gggaaaaagg ggattaggtt gaataaaaaa ggtaagcact tgtctatata   169920
ttttttttac aatgttgcct tgagtcgcat ttttaactgg ctggggagta tcagagtgga   169980
atatcactgt agtaggtcta taaggtcttg ttaaaatatg atcggtcatt gttttcgtac    170040
tagtgtcatt tagggtcgac ctgatagctc gatataaagt tataggggat aacctatcaa   170100
```

```
atacagtctt atctgtgctg aaatgtatat cgtcttcttt atcactaata atattaggaa   170160
tggctgtcat taaataatta ctacttgttg ttgtgggtga aatagttgta ctggtattat   170220
tggaaatggc tgtcattaaa taattactac ttgttgttgt gggtgaaata gttgtactag   170280
tattattaga aatggctgtc gttaaataat tactacctat tacaagtaaa ctaatgctaa   170340
ctacattttt aacctcaata aacctaaaaa gccatactaa ataccctaaac aacatcctgt   170400 tataatatga gcagaaaaaa aaataagtat aattagggaa ttattcttat tcgcttacta   170460
ttaagaataa ttcagaatct tatttagtta gaaactatca taaagtgaat aggactcatc   170520
gtcggatgaa gattccgttt cagagatagt ttctttttct tcctcagaat aatctgttcc   170580
tacaatagaa tcggtgtcat cctcagaaag agaagtattt aaatatggac tatctatagc   170640
aatatcctct tctatctcgc aatcctcctc ctccatttcc atagtgtgta ggagaatatt   170700
tttatcatca tgctcacttc tttttttgtt gaaagatgaa ccgtcctcaa tacggttcat   170760
gttaagttcc ttcatcttat gtataatttc cgtaatccgt gatgttttg acatgtaaga    170820 tggttttaag gttatatcca caataacagg agaatctcta tcattttcat ttgataaact   170880
ttgatctttg atttcttcgt ctaaaattct tgtctttttt tgggtactag atgaaataga   170940
ggaattcata ttctgaaacg atatatcaag gggagctgga cgcttttttc caattaaacc   171000 gttttcgag atactatgat tagatgaatg atctttagcc aagctgtcct tggatatact    171060
atagttagat attttacctt taaataatat tcttctatac aagttattct taggtaaaga   171120
attagtatgg attcctatat ttttatctga aggagtgtcc atatcggaga acgtcctctt   171180
acgaatattt tgaccacgag ccatttcatc cactataggc agtattttgg ctggctatgg   171240
ttctttgttg tgacaattct atgagatttg attgcaaatc aatttttagt tttaaatata   171300
ttggtaccta ggacaaagaa agtatatata gccataatt attccactaa attgatttcc    171360
agactgatgg gtatggagcc atgttgtctc tgcagacgat cgcaaaaatg gccgtagcaa   171420
caaacaccta ctccaagtat cactatccaa tactgaaggt cttgggctg tggtggaaaa    171480 acaatacgct aaatggccct attaaaatat gtaaccattg caacaacata tggtaggag    171540 aatatcctat gtgttacaat catggaatga gtctggatat agctttgatt cgggcagtaa   171600
aggagcgtaa tatatcctta gtccagcttt tcaccgaatg gggggaaat attgactatg    171660 gggcactttg tgctaacact ccatctatgc aaagattatg taaagtttg ggagccaaac    171720 caccaaaggg ccgaatgtat atggatgctc ttatacatct ttcagatacc ttgaatgata   171780
atgatctgat taggggggtat gagattttg atgataatag cgtgttggat tgtgtcaatc    171840
tcatacgact caaaataatg cttaccttga aggcccgtat acctctcatg gaacaactag   171900
accaaattgc cttaaaacaa cttctgcagc gatactggta tgccatggct gtacaacaca   171960
acttaacaat cgctatccac tattttgata atcatattcc taatataaag ccatttagtc   172020
tgcgctgtgc tttgtatttt aatgatccct ttaaaatcca tgatgcttgc agaactgtaa   172080
atatggatcc taatgagatg atgaacattg cttgtcaaca ggatttaaac tttcaaagca   172140
tttactattg ttatcttta ggggctgata ttaatcaggc tatgctaatg tctttaaagt    172200
atggtcatct ttctaatatg tggttttgca tagatttggg gcggatgcc tttaaagagg    172260 caggggcgct tgctgagaaa aaaataaaag agtgttacaa cacatattag gtcttaatat   172320
ctttaagcga gagttgattc cccctgtaa agatcctgat ccttatcaaa tccaaattct    172380
gttaaaaaac tacattctaa aaaatgtctc aactgttttt acatattatt gccagtagcc   172440
attgtttata tcagaaaata acccatttgt ttatcttttt ttgtggggca accattaaga   172500
```

```
cccgacgcaa aaaaagatta atcttttatc agatacctaa aacgttctat aagggagtct 172560
atgagatgga tcatattttg atggtcatag taagaagcaa gcttttttggc gaaaacaacg 172620 gagttaaaga atttaacccg ctcatgtttg gataggactt ttaacagcga gccaaaacag 172680
tatttaaaaa tttggcaata gttttttttgg gatgcaataa acaaacactt gatcagtgcc 172740
cgcttcactt tctgatcaga catgtttgcc gcataacagg cctttttaaa cttagtaata 172800
taattatgtt ccgcaagcac cattaacaag ggaacgatgg gaagctgctt ttcttggtga 172860
aatttacgta aatattcgat ggccaccgct tggacgactg tgtaatttac taagttagaa 172920
atgatagctt tcatggttgt aaaaatatac ataggatttt cttttttctgt atacagtttg 172980 aaaagcttat gattacgtga aatgatggcc attttttaata caagatggta tagtgtatct 173040
ttaggtaaaa atgccttgca agccgcgatg atgtcgatgt tgtctccatg aacagcgata 173100
gaaactaatg tttccaatct aaatgttttt atctgcatta atagaagaat gcagtcaatg 173160
ttattatact taataatact gtaatacacc gaatcaatga ccgtcatctg agaatcaagc 173220
tgacttatta gtaaatttaa cgttttttttg gaggcatgac ctttgatcgc ggcactaagt 173280
gcacacagta tagcaaaatt gttaaataca ttttgattta ggagaaggag taatattttc 173340
cttcggttat agtacgcagc atctgtgatg attattggcc gataaatgtt aaaatgtgtt 173400
aacagctttt taaaaaaacg gaagtaattt ttttggatcg ctgtttgcat catcgaaata 173460
atgagataat cagggtatat aatgggtagg tcacatgcta cctctaacaa agaatagtcg 173520
cccaatctaa aggctgtgtt gaaaagcgta ctatcatcat acgtatcgag tacccctgct 173580
gttacaaacc aagcgataag atgaatgtgc cgttccttgc aagctatcgc aaatagggag 173640
tttcctatgg aatgtcgaat aatgtactcc ctatttttt ccaaaatgtt tggaaaattg 173700
tatagcgttg cggcatacag tagacactcc attctggcgt tataatttttt actttttacat 173760 atgaataggt ggaagaactc gaataattct tgagaacttg ttaaatgcat aatatggtga 173820
tattttggtg tcgttaaatg gtatgagaaa atgcattcta atacatcttt tcggttatgc 173880
tttagcgcct gagctaaggc atattcaggc tcgacccata ggactagtgt ttctataatt 173940
gagatattcg cctgctttgc cagggcatac tttaagacgc tccggttaga aaaaatgttg 174000
ttatgaagat ggataaccgt atccattttt acgatgggac cattccagta tagtcctaaa 174060
tgctgtagca gatcttttgt tagttgtgaa gcgttctcgg tgtcatata aatatgttgc 174120 agggcttttt tctgtaagga gaacatttcg tcgtaatcgt acaaaaaaaa ttaaatttg 174180 ggcatggatg attcaaacat aacaaaatca agatttttata acagtttgca ttaacctata 174240
catatatgca agtaaatgag atattatcta tcataacgaa tcaagggata tttgtatata 174300
tcaggagttt ctgaaataaa gatatgaaga ttatcatagt agtatccatc aatcacaatg 174360
caacttcctt taaggcataa tttagtaaac tcagcactcc catcttctgg atgctttaca 174420
actaacatta aaaactcctc agtcatatta tctgtaataa aataagatcc tcctggagcc 174480
atttgtagca tgtctcttat tcctacaaaa tcttttttgg gatggtaaaa actcagcagt 174540
ttcaaactct tttttagttt ttttttcctgg tatttaagcc atttgttata aaacagtttt 174600
cttatgaaaa tgcatttgaa aatattggga atgtttaacc atgcttcttc cgagcacatc 174660
tccagatact tactttcttt gtttcccatg tctaatttat tgctcactaa gttagtaatg 174720
aatctatttt aataatctac tttactaatc tatcttaata acctatctta taatctatct 174780
taataaccta attataaccct atttataatt ggctaatgct gccggcattt catgcctatc 174840
```

```
taaacaactc ctactaagca atctactatt acatatatag attcactttt tatatttgta    174900
aatcatgaga attataaaat cattactcat ttttattgta aattagtggg tatttgtaaa    174960
aatcttcaaa cgttttaaga tagttttcta gagagaagta atctttgcca tcaatatata    175020
atgcttttcc tttaaactcc agttttgcta tgtttagtga gccgtttcta gatcttttg     175080
ggcaataaat agattttcat tggttgcatc gtccgtaagc agaaaggtac cactaggcac    175140
gttaaaaaac atacgttcta tttcatggtc ggatttttga aatagaaaa atctaatt       175200
tttaatccgc gttaactctt ttttatcaat cttttccagac tgttttatat atactttatt  175260
gcaaatctta caatcctcta tggcttcatt atacttattt tgcttatcct ctattgacat   175320
gtccgtattt gataggtaac ttccgttaag gcggttcccc atggttttag atagattttt   175380
aattcagttg tatactttta ttatgaggct aaaatataga agtttgatcc taaaaaaata   175440
aaaagatttt gtacatttat ttatggttta tagcggtata gaggccgata aaaggtatcc   175500
gggtagtctc ctatgatatc gtcaatttg tataataac agttgttatg gtagtattgt     175560
ccaaaccgag tatgtatgcg ccggtgaagc gtccgcccgc taatggtaca gttccaggtt  175620
aagacaatca tatcacaccc aaaaagagag gaaacagcat aggtgcccaa aggttcatta   175680
tataacatac gccgcatata ttttagtttt ttttctccat ggtaataatc acaggttttc   175740
atgtcctgct aataggatg attcccatg tatgataata tataaataat ttagttttta    175800
gcttttcaa aaattgggc gctcgaaact aaattttcct tatcacagcg tttggagaaa     175860
gcgtatttaa agatatatct tcttctaaca agactgcaaa aaaatctta cccttatt      175920
ttataatgtt catcatagcg tttgaagata tcagaaggtg ccaggtttta taaaaatatc   175980
ctttaggatt tataacgata caagggtcta taaaatatat gcgggtataa tcttataaaa   176040
tcatcgattt tttcataata ttctccgttt atacaataaa gatcataaca gatattgatg   176100
cgtagatgca ttattcgcgt gttcgttggg cagctaaagg atatcacaac gtagttttt    176160
ttaagaaag cgaaactac ataagtccct aagggttcat tgaatagtaa acgccatatt    176220
tgttttaaat tttgttgttc accatagtag tattcgcact ttttcaagtc tttttaata   176280
agcctattcc ccatgtatgc ttataaataa aaatttagaa atgtgctata ttattggttg  176340
atgaatcatg aacacgtctt tatatgttgat atgttacttt aaaaacattt gtatttcaa   176400
cagacgcgtt ctattcttat taagaatgat gccgtcttta ttttaaacct tggtttaaaa   176460
tttaaagaag tatttataaa ctataatcat gggaactttt tcagtaactg cctctgcaaa   176520
aagtgacgat gctgtttgta agtatttaga agaaccaata gatgaaaatt acagaaacat   176580
attaagaaat gagcatgtta aaaaaatttt aaatgaggct ctgaatcgac atattactac   176640
ctataatcca gtagttgatt ggtgtaataa ctattcaaca ttttcatctc aggatttcga  176700
tgaatataaa atttatatac atagcgatct tatggatgga cgacctcgtc caaaaaaaac   176760
atggtgtgtc atcatgtaat gtttgttagt tttatataaa cgcaaaaata ttcttctagg   176820
agatgttgat atactaccta ttgaattcaa tatattaaag tacatttctg gctattccca   176880
ttacggtatt attattacta tttttaagag ctagatgtgg atttaagtaa taataacatt  176940
ctcccgttcc tcctagagac acctcatcaa attcccatcc tatgcaacct ttatgttgta  177000
aacataatga ttgacagcat tcatcttctt ttgaccaagt cgtccaaatc ctaccaagat   177060
ctatacgtgt ttttccaaat ggagattgaa gatcagcagt agtggcatta aacctataaa   177120
aaccaggtgc ataatcacat gaacggatcg taggatctaa tttaatatct tttatatctt   177180
gttttactgc ttctagacaa cttttatcag tacatgttcc acgtacacag tggtgtcctt   177240
```

```
tatccttaca atccgtatct gtcttacatt ttttttttcgg cggtttatgt ttcagatggt   177300
aaaaacccag tattaaaata atcacaagaa taattcctat aagtacttga acaacaggat   177360
aaaacatttt aatattaaat atatttttta attaaatgaa tagatttaat ccaagtagta   177420 ttaaatttt ttagaaatag tgttctacaa ataatgaaat gaatggtcca aaaaaaataa   177480
ggtgtacaat aatgtaatat attgttaggc taagtaaatt taatatttta aagtatttgg   177540
aaaaatattt tttaacatat gatgtctagg aatattttt agacatttaa aaccatatag    177600
ttactttatt tattacactg aacttgaaaa gacttattac ctaaaatatt aatagatgaa   177660
gtaatattgt gtaattgagt ccataacatg ggtgggaaac aaaaatctcg taatatgaaa   177720
aataaacatc ctaaaagag tgcaattgtt ataagtttat gtaactttat tttaaagtaa    177780
gaatataaaa atatgagtac aagaggaata ggggccatta ctaacattgg ctccaacatc   177840
ctgttgtcta caaaaaaaaa tatttttttt agcaaaaaaa aatccatgga aggatattaa   177900
tacacataat tatttgacat cacattagtg tacttaccaa atagtaatat acaaccatcc   177960
taatattcac ctttatgaaa tgatcccaac ctatacggta aaatagtata ggttttaata   178020
aagaaaaaag atattctgtg gtttttattt ttgtatagtg tgtgaataca aaataaaatc   178080 ccaaattta acctttttctt ttttttctat acaggatgtt agaaatagta ttggcaacgc   178140
tgctaggcga cctgcagcgg ctccgggttc ttacccctca gcagcgggca gttgccttct    178200
ttcgagccaa tactaaggag ctagaggact tcttatgctc agatgggcag tctgaggagg   178260
tactgtctgg cccccttctt aaccgtctac tagaaccctc aggccctctt gatattttaa   178320
ccggatatca cctatttcgt cagaatccca aggcaggtca gttgcgcggc cttgaggtca   178380
agatgcttga acggttatac gatgctaata tttacaatat actgtctcgg ctgcggcctg   178440
aaaaagttcg caacaaggct attgagctat actgggtttt ccgagctatc catatttgtc   178500
atgctccttt agttttagat attgtacgat atgaggaacc ggactttgct gaactggcct   178560
ttatttgtgc tgcttacttt ggtgaacctc aggtaatgta tttgctctac aaatatatgc   178620
ctctgacccg cgcagttctt acggatgcca tccggataag tcttgagagc aacaaccagg   178680
tagggatttg ctatgcttac ttgatgggag gcagcctcaa gggactagtc tccgccccac   178740
tgcgtaaacg tctgcgcgcc aaactacgct cgcagcgcaa aaagaaggac gttctttcac   178800
cccacgactt cttactgctg ctccagtagc tttttttgcc gcaggagcac cgcggatagg   178860
agctcctcca cgctcgcgat ccggcgctgg aagcggaacc gatcgaccgc cacctgctcc   178920 cagggacccct tgcgctcgat gtcgtcggct tcccacacct cgacggctgt ggcaaaatgg   178980
acatgcttcg cgtcgttcgt ccgttttttg cgccgcctcc ccattattct tcctgtaaga   179040
ttagtgttta atacctataa taacataatt ttaagatttaa atataccaaa acttaaacta   179100
tttttgtata gtaactatta gcatgtctac acatgattgt tctctaaaag agaaaccggt   179160
tgatatgaac gatatatctg agaaatcagt tgtcgtggat aatgcacccg agaaaccagc   179220
tggagcgaat catatacctg agaagtcggc ccgcgaaatg acatcatcag aatggattgc   179280
tgaatattgg aaaggtataa aacgtggaaa tgacgtgcca tgttgttgtc caagaaaat    179340 gaccagtgca gacaaaaagt tttcagtatt tggtaaggga tccctaatgc gctccatcca   179400
gaagaataat taaaaaaaat attttttta gcaagttttt aaactatta aataaatgtg      179460 gtaaaaaaat tcacataata attaaagtga acgtgttaga attaatatttt ttttataatc   179520 ggatataata tccattaaat caataaatga tagtgttgct accacactaa acaataacaa   179580
```

```
acagaaacgc acgatacctt tcctcatgat ttataatagc gtgttatcta aagattttt   179640
tgaaaaaaat attaaattt  agttgattat ttttttcagt tacaacattg ctttagaaaa   179700
aatacctaat tactacatag caaataaagc gagcgcattg ttacaaacaa catttttttt   179760
gcgcctggat actcctatat atgagaacta taatacggta tattaatcct attaccaaca   179820
ttgtcaataa tagtatgtag gcaatgacat actttaaata ccaaatatcc atggttattt   179880
ctaaaaatct tgaaaaaacg ttaaatttta gatcggtcac ctacgacagt aatactaatt   179940
ttaataattg atgactgaaa tcataatata atgccgtgcg aaaataatt  attttcggt    180000
taaagatacc attacataaa aaatatgcca tctactctac aagtgcttgc taaaaaggta   180060
ttggccttag gggagcataa agaaaatgaa catatatcta gagaatatta ttatcatata   180120
ttaaagtgtt gcggtttatg gtggcatgaa gctccgatta tactttgtta tgatgggagt   180180
gagcaaatga tgataaagac tccaatcttt gaagaaggca tattacttaa tactgcatta   180240
atgaaagctg tacaggagaa taattatgaa ttaataaagt tgtttactga atggggagca   180300
aacatcaatt atggattaat ttccattaat accgagcatg cccgggatct atgtcgaaaa   180360
ttaggagcta aagaaatgct tgaaggaaat gaatttatac aaattatatt caaaacatta   180420
gatgatacca ccagtagtaa tataaattta tgtcatgaat tattcaccaa caatcctctt   180480
ttagagaatg taaatatggg ggaaatgagg atgataattt attggaggat gaaaaattta   180540
acgaacctat tattaaataa tgactctatt agtgaaatat taactaaatt ctggtatggt   180600
atagcagtaa aatataatct taaggatgcg atccaatatt tttaccagag attcatggac   180660
ttcaacgagt ggcgagtaac atgtgctctt tcttttaata atgtgaatga tcttcataag   180720
atgtatataa cagagaaggt tcatatgaat aatgacgaaa tgatgaatct agcctgcagc   180780
attcaagaca gaaatttatc aaccatttac tattgttttc tattgggggg ctaacatcaa   180840
tcaagcaatg ttaacctcag tattaaatta taatattttt aacttattct tttgtataga   180900
cttaggggct gatgcctttg aagagggtaa gaccctggcg aaacaaaagg ggtataatga   180960
aatagtggaa atcttatcat tagatatcat ttatagtcca aatactgact tctcatcaaa   181020
aatagaacct gaacatatta gttctttgtt aaaaaacttt tatccaaaaa atctgttcgc   181080
ttttgatcgt tgcaaccccg gtttatatta ttcttagagg accgctacaa aaattatttt   181140
ttttcttgat caaagctcca aaataattat tagattaaag tcgcctatag cagcagccca   181200
ctccaaaaaa agtatttat  agtacaaaaa acacgaaaaa tagtttgcgg ccggcggcaa   181260
actatttgtt gttgtctaaa acttaatgtt tttttaatat ttttaaatgc aaccatggat   181320
tgttggacta tcagggagaa gaactatagc tacatcatat tgtcaatact ggtaatacta   181380
ttaatatggt atcttatact taactattgt cgatcgaaaa aaaatgcagt tacaaacaac   181440
atgccgccac catacacggt gtcaagtagc tgttctcaat aatagggttg attgacgctc   181500
ttcgtaataa tatgttgatt gacgcatcat aaaaatgctgt ggttgattaa tatgttgatt   181560
gtcgcctact ttattatata agtaatgatt tttgtataaa atacgggttt gtgagggctt   181620
tatttttttct tattagaaca aagcatgcaa tttaaggcct acagcaagag taatttaaca   181680
cctacaacag taattttaag gtcagtaata atgtttaatt aaggcctgac cactaaaact   181740
taaacgattt tgtaaaaaaa aatgtctact ccactttctc tacagactct tgttaaaaaa   181800
gtgctggcca cacagcacat atctaaagaa cactacttta ttttgaaata ttgtggttta   181860
tggtggcatg aagcgccgat tacgatttgc attgatgagg atagccaaat attgataaaa   181920
tcggcaagct tcaaagaagg cttatcttta gatatcgcat taatgaaagt cgtgcaagaa   181980
```

-continued

```
aataaccatg atttaataga gttgtttacc aagtggggtg cagatatcaa ctctagctta    182040
gttactgtta atacggagta tacccggaac ctttgtcaga aattaggcgc aaaggaagct    182100
ttgaatgaaa gggatatttt acaaatattt tataaaacac gtcatcttaa aactagcagt    182160
aatattattt tatataatga aattgttttct aataatctcc ttttccaaaa tatagagaga    182220
ttgagtttaa tagtttatag gggcttgaaa aacttatcaa tcaactttat attggatgat    182280
atttcattta gcgaaatgtt aactagatac tggtatagta tggcgatatt atataacctt    182340
actgaagcca tccaatattt ttatcaacga tataggcatt ttaaagattg gcggcttata    182400
tgtgggcttt cttttaacaa tttgtctgac cttcatgaag tatataactt agagaagacg    182460
gatatagaca ttgatgaaat gatgaagttg acctgtagta cgtatgatgg taattattcg    182520
actatttatt attgttttat gttgggggct gacatcaatc gggcaatgtt aacctcggta    182580
ataaactttc atattggtaa cttgttcctt tgtatagatt taggagctga tgctttcgaa    182640
gacagcatgg aactagcaaa acaaaagaat aataatatat tagtagaaat attatcattt    182700
aaaaattatt atagttcaaa tacctctctt ttatcaataa aaacgacaga tccggaaaaa    182760
attaatgcct tattagatga agaaaagtat gagtcaaaaa atatgttaat gtatgaagaa    182820
ttatctcatt gatacaaaat tatttttttat aacagaactc tctgatggtg acaaatctcc    182880
gataggaata tatgacgtaa cataattatt ttttttcgccc agaaaaaaat tataaatgtt    182940
attattgcca gcacttttat caactatacg tacaaaaagg tgttgaccaa aaaaataatt    183000
ttttttcttg atcaaagtat gtaaacgccc gcttacagca aggatcttaa gtgagagcca    183060
ttaaatttta ttgatagctg cttgccacca gtagaatacg gccaaaccac ctaacaggaa    183120
atacaaggcg gcccttcggc caataaggtg gataaaaatc acgcataaga cggttgtaac    183180
atagcacttt agtgcgaata tcaggaatgc caatagcatg tagataaggc accaaacatc    183240
gcagctatac atggctaaag atcaaccaga aaaggtttaa attttaacgc cggcccaaaa    183300
cttaaacttt ttttgatatt tttaagtgca gccatggatt ggtccggcca taggatgacc    183360
tatgcctacg tggcattctc attgatggca atagcaataa tatggtatat tctacttatc    183420
tattgccgat cgaaaaaaaa tgttgttaca agcggtaata cgctcgcttt agcgccaata    183480
tcgcatatgt gaaaaatgtt cgccgaaaaa aacattaaaa tttagaaccg ccgcggcatc    183540
tcaggggcgg caacattttt ttttatatgg atattgtcac acaccacctc atctatgacg    183600
caatatatta ctgctaatat caggttcccc aatagtatgt agagaaacca cacaagatag    183660
atattcatgg cgattttgta cgaaaaaaca ttaagtttta gcttctttga cgcctgtgta    183720
ctaataatgt ttaacgcctg tagtataata attgatacct acagcagtaa ttgataccta    183780
cggcgataat gtctctctgg ccgccccaaa aaaagtatt tacggtaggg tttattaccg    183840
gcggcgtaac accagttatg gtcaattttg tctggcccgc cgcccagccg caaaaaaaaa    183900
tcaattacaa ccgcaaaaaa aaatatttcc ggccgcggcg tttcaaaaaa taatctttgc    183960
gaaataattc cgcatcttgt gaaatgaacg cctacagtaa taattttaat ctttgacacc    184020
tacagcagta gtaataattt taatctttaa cgcctgcagc agtactaata ttttaatctt    184080
taacgcctac agcagtagta ataattttaa tgtttaacgc ctacagcagt agtaat        184136
```

<210> SEQ ID NO 3
<211> LENGTH: 24
<212> TYPE: DNA
<213> ORGANISM: Artificial Sequence
<220> FEATURE:

<223> OTHER INFORMATION: Chemically Synthesized

<400> SEQUENCE: 3
catggaacta ttcaacgagc agga                                          24

<210> SEQ ID NO 4
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 4
cgctgatcaa ttccacagtt                                               20

<210> SEQ ID NO 5
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 5
gacggcctgt gggcatt                                                  17

<210> SEQ ID NO 6
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 6
gcgatggatt ccggcat                                                  17

<210> SEQ ID NO 7
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 7
gtcttattgc taacgatggg aag                                           23

<210> SEQ ID NO 8
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 8
ccaaaggtaa gcttgtttcc caa                                           23

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 9
gtaagatacg aaaaggcgtg                                               20

```
<210> SEQ ID NO 10
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 10
gacgctccta gctggaa                                                  17

<210> SEQ ID NO 11
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 11
gttgttatgg aacgcgaag                                                19

<210> SEQ ID NO 12
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 12
gggtttctac aggacgtaac a                                             21

<210> SEQ ID NO 13
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 13
ctgttgaatt acgttaagca tg                                            22

<210> SEQ ID NO 14
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 14
cattggggac ctaaatactg                                               20
```